(12) United States Patent
Tanaka

(10) Patent No.: US 9,347,003 B2
(45) Date of Patent: *May 24, 2016

(54) LIQUID CRYSTAL COMPOUND HAVING TETRAFLUOROPROPENYL, LIQUID CRYSTAL COMPOSITION, AND LIQUID CRYSTAL DISPLAY ELEMENT

(71) Applicants: JNC CORPORATION, Tokyo (JP); JNC PETROCHEMICAL CORPORATION, Tokyo (JP)

(72) Inventor: Hiroyuki Tanaka, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/379,752

(22) PCT Filed: Feb. 7, 2013

(86) PCT No.: PCT/JP2013/052814
§ 371 (c)(1),
(2) Date: Oct. 13, 2014

(87) PCT Pub. No.: WO2013/125356
PCT Pub. Date: Aug. 29, 2013

(65) Prior Publication Data
US 2015/0069297 A1 Mar. 12, 2015

(30) Foreign Application Priority Data
Feb. 23, 2012 (JP) ................................. 2012-037697

(51) Int. Cl.
*G02F 1/1333* (2006.01)
*C09K 19/34* (2006.01)
(Continued)

(52) U.S. Cl.
CPC ............. *C09K 19/3402* (2013.01); *C07C 22/00* (2013.01); *C07C 43/192* (2013.01); *C07C 321/22* (2013.01); *C07D 239/26* (2013.01); *C07D 309/04* (2013.01); *C07D 319/06* (2013.01); *C07D 407/04* (2013.01); *C09K 19/0403* (2013.01); *C09K 19/20* (2013.01); *C09K 19/3003* (2013.01); *C09K 19/3028* (2013.01); *C09K 19/3048* (2013.01);
(Continued)

(58) Field of Classification Search
CPC ........... C09K 19/3402; C09K 19/0403; C09K 19/3003; C09K 19/3028; C09K 19/3048; C09K 19/3059; C09K 19/3068; C09K 19/20; C09K 19/3066; C09K 19/42; C09K 19/46; C09K 2019/0444; C09K 2019/3004; C09K 2019/3009; C09K 2019/301; C09K 2019/3016; C09K 2019/3042; C09K 2019/305; C09K 2019/308; C09K 2019/3083; C09K 2019/3422; C09K 2019/0466; C09K 2019/181; C09K 2019/3019; C07C 22/00; C07C 43/192; C07C 321/22; C07D 239/26; C07D 309/04; C07D 319/06; C07D 407/04
USPC ............... 252/299.01, 299.6, 299.61, 299.63, 252/299.66; 428/1.1; 349/182, 183
See application file for complete search history.

(56) References Cited

U.S. PATENT DOCUMENTS 8,889,035 B2 * 11/2014 Furusato ............... C09K 19/08
252/299.01
2014/0306158 A1 * 10/2014 Saito ....................... 252/299.61

FOREIGN PATENT DOCUMENTS

CN 101616883 12/2009
EP 480217 4/1992
(Continued)

OTHER PUBLICATIONS

Kirsch et al., "Liquid crystals based on hypervalent sulfur fluorides Part 4. [1] Pentafluorosulfanyl alkanes and olefins", Journal of Fluorine Chemistry, Jan. 24, 2006, p. 610-619, vol. 127.
(Continued)

*Primary Examiner* — Geraldina Visconti
(74) *Attorney, Agent, or Firm* — Jianq Chyun IP Office

(57) ABSTRACT

A liquid crystal compound having high stability to heat and light, etc., a high clearing point, a low minimum temperature of liquid crystal phase, a low viscosity, a suitable optical anisotropy, a large dielectric anisotropy, a suitable elastic constant, and good compatibility with other liquid crystal compounds, a liquid crystal composition containing the compound, and a LCD element using the composition are described. The compound is represented by formula (1):

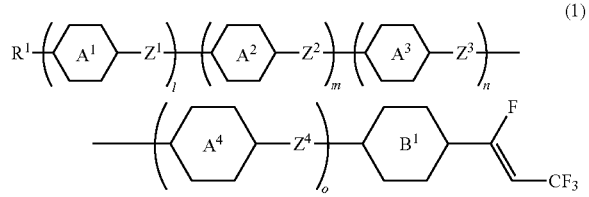

wherein, for example, $R^1$ is $C_{1-10}$ alkyl, ring $A^1$, ring $A^2$, ring $A^3$, ring $A^4$ and ring $B^1$ are independently 1,4-cyclohexylene, 1,4-phenylene, 1,4-phenylene in which at least one hydrogen is substituted with halogen, 1,3-dioxane-2,5-diyl, or tetrahydropyran-2,5-diyl, $Z^1$, $Z^2$, $Z^3$ and $Z^4$ are single bonds, l, m, n and o are independently 0 or 1, and $1+m+n+o \geq 1$.

22 Claims, No Drawings

(51) Int. Cl.
*C09K 19/04* (2006.01)
*C07C 22/00* (2006.01)
*C07C 43/192* (2006.01)
*C07C 321/22* (2006.01)
*C07D 239/26* (2006.01)
*C07D 309/04* (2006.01)
*C07D 319/06* (2006.01)
*C07D 407/04* (2006.01)
*C09K 19/30* (2006.01)
*C09K 19/20* (2006.01)
*C09K 19/42* (2006.01)
*C09K 19/46* (2006.01)
*C09K 19/18* (2006.01)

(52) U.S. Cl.
CPC ......... *C09K19/3059* (2013.01); *C09K 19/3066* (2013.01); *C09K 19/3068* (2013.01); *C09K 19/42* (2013.01); *C09K 19/46* (2013.01); *C09K 2019/0444* (2013.01); *C09K 2019/0466* (2013.01); *C09K 2019/181* (2013.01); *C09K 2019/301* (2013.01); *C09K 2019/3004* (2013.01); *C09K 2019/305* (2013.01); *C09K 2019/308* (2013.01); *C09K 2019/3009* (2013.01); *C09K 2019/3016* (2013.01); *C09K 2019/3019* (2013.01); *C09K 2019/3021* (2013.01); *C09K 2019/3042* (2013.01); *C09K 2019/3054* (2013.01); *C09K 2019/3077* (2013.01); *C09K 2019/3083* (2013.01); *C09K 2019/3422* (2013.01)

(56) References Cited

FOREIGN PATENT DOCUMENTS

| | | |
|---|---|---|
| JP | H06-500343 | 1/1994 |
| JP | H08-040952 | 2/1996 |
| JP | H08-059525 | 3/1996 |
| JP | H08-176033 | 7/1996 |
| JP | H10-504032 | 4/1998 |
| JP | 2005-298466 | 10/2005 |

OTHER PUBLICATIONS

"International Search Report (Form PCT/ISA/210) of PCT application", mailed on Apr. 9, 2013, with English translation thereof, p. 1-p. 6.

"Office Action of China Counterpart Application", issued on Jul. 1, 2015, with English translation thereof, pp. 1-14.

\* cited by examiner

LIQUID CRYSTAL COMPOUND HAVING TETRAFLUOROPROPENYL, LIQUID CRYSTAL COMPOSITION, AND LIQUID CRYSTAL DISPLAY ELEMENT

CROSS-REFERENCE TO RELATED APPLICATION

This application is a 371 application of the International PCT application serial no. PCT/JP2013/052814, filed on Feb. 7, 2013, which claims the priority benefits of Japan Patent Application No. 2012-037697 filed on Feb. 23, 2012. The entirety of each of the above-mentioned patent applications is hereby incorporated by reference herein and made a part of this specification.

TECHNICAL FIELD

The invention relates to a liquid crystal compound, a liquid crystal composition, and a liquid crystal display (LCD) element, and more specifically relates to a liquid crystal compound having tetrafluoropropenyl, a composition containing the compound and having a nematic phase, and a LCD element using the composition.

BACKGROUND ART

Liquid crystal display elements are widely used for displaying of personal computers and televisions, etc. The elements utilize the optical anisotropy, dielectric anisotropy and so on of liquid crystal coumpouns. Operating modes of LCD elements include the phase change (PC) mode, the twisted nematic (TN) mode, the super twisted nematic (STN) mode, the bistable twisted nematic (BTN) mode, the electrically controlled birefringence (ECB) mode, the optically compensated bend (OCB) mode, the in-plane switching (IPS) mode, the vertical alignment (VA) mode, and the polymer sustained alignment (PSA) mode, etc.

Such LCD element uses a liquid crystal composition having suitable physical properties. In order to improve the characteristics of the LCD element, the liquid crystal compounds contained in the composition preferably have the physical properties described in items 1) to 8):
1) high stability to heat and light, etc,
2) a high clearing point,
3) a low minimum temperature of liquid crystal phase,
4) a low viscosity (η),
5) a suitable optical anisotropy (Δn),
6) a large dielectric anisotropy (Δ∈),
7) a suitable elastic constant (K), and
8) good compatibility with other liquid crystal compounds.

Effects of the physical properties of the liquid crystal compound on the characteristics of the element are described below.

A compound having high stability to heat and light, etc. as described in 1) increases the voltage holding ratio of the element. Thus, the service life of the element becomes longer. A compound having a high clearing point as described in 2) broadens the temperature range in which the element can be used. A compound having a low minimum temperature of a liquid crystal phase such as a nematic phase or a smectic phase, especially a low minimum temperature of a nematic phase, as described in 3) also broadens the temperature range in which the element can be used. A compound having a low viscosity as described in 4) decreases the response time of the element.

A compound having a suitable optical anisotropy as described in 5) improves the contrast of the element. In accordance with the design of the element, a compound having a large optical anisotropy or a small optical anisotropy, namely a suitable optical anisotropy, is required. When the response time is decreased by decreasing the cell gap of the element, a compound having a large optical anisotropy is suitable. A compound having a large dielectric anisotropy as described in 6) decreases the threshold voltage of the element. Thereby, the electric power consumption of the element is decreased.

With regard to 7), a compound having a large elastic constant decreases the response time of the element. A compound having a small elastic constant decreases the threshold voltage of the element. Therefore, a suitable elastic constant is required according to the characteristics to be improved. A compound having an good compatibility with other liquid crystal compounds as described in 8) is preferred because physical properties of the composition can be easily adjusted by mixing liquid crystal compounds having different physical properties.

A variety of liquid crystal compounds having large dielectric anisotropy have so far been prepared. Patent Document 1 and Non-Patent Document 1 have described a compound (S-1) having trifluoropropenyl. However, the compound does not have a sufficiently large dielectric anisotropy, so a liquid crystal composition containing the compound seems to be quite difficult to have a threshold voltage required by a commercially available element.

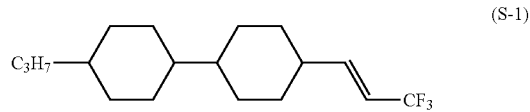

(S-1)

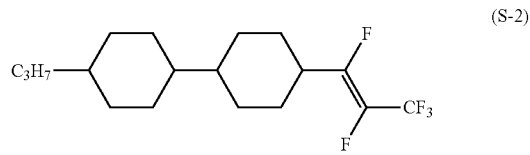

(S-2)

Patent Document 2 describes a compound (S-2) having pentafluoropropenyl. However, the compound does not have a sufficiently large dielectric anisotropy.

Moreover, Patent Document 3 also describes compounds (S-3) and (S-4) having pentafluoropropenyl or difluoroethyleneoxy. However, the compounds either do not have sufficiently large dielectric anisotropy, and additionally do not have sufficiently high stability to heat and light, etc. as described in 1).

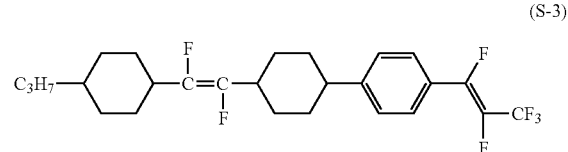

(S-3)

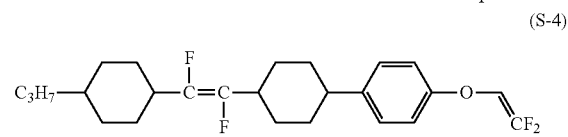

(S-4)

Under such circumstance, development of a compound having good properties with regard to the above characteristics 1) to 8) is desired.

PRIOR-ART DOCUMENTS

Patent Documents

Patent Document 1: EP 0480217 A2.
Patent Document 2: JP 2005-298466 A.
Patent Document 3: JPH 0840952 A.

Non-Patent Documents

Non-Patent Document 1: *Journal of Fluorine Chemistry*, 2006, 127, 610.

SUMMARY OF INVENTION

Technical Problem

The first object of the invention is to provide a liquid crystal compound having high stability to heat and light, etc., a high clearing point, a low minimum temperature of liquid crystal phase, a low viscosity, a suitable optical anisotropy, a large dielectric anisotropy, a suitable elastic constant, and good compatibility with other liquid crystal compounds. This object is for providing a compound having a particularly large dielectric anisotropy.

The second object is to provide a liquid crystal composition containing the compound and having a high maximum temperature of nematic phase, a low minimum temperature of nematic phase, a low viscosity, a suitable optical anisotropy, a large dielectric anisotropy, and a suitable elastic constant. This object is for providing a liquid crystal composition having a good balance between these characteristics.

The third object is to provide a LCD element containing the composition and having a broad temperature range for use of the element, a short response time, a large voltage holding ratio, a large contrast ratio, and a long service life.

Solution to Problem

This invention relates to a compound represented by formula (1), a liquid crystal composition containing the compound, and a LCD element using the composition.

Advantageous Effects of Invention

The liquid crystal compound of the invention has high stability to heat and light, etc., a high clearing point, a low minimum temperature of liquid crystal phase, a low viscosity, a suitable optical anisotropy, a large dielectric anisotropy, a suitable elastic constant, and good compatibility with other liquid crystal compounds. The compound has a particularly large dielectric anisotropy.

The liquid crystal composition of the invention contains the compound and has a high maximum temperature of nematic phase, a low minimum temperature of nematic phase, a low viscosity, a suitable optical anisotropy, a large dielectric anisotropy, and a suitable elastic constant. This liquid crystal composition has a good balance between these characteristics.

The LCD element of the invention contains the composition and has a broad temperature range for use of the element, a short response time, a large voltage holding ratio, a large contrast ratio, and a long service life.

DESCRIPTION OF EMBODIMENTS

Usage of terms in the specification and claims is as described below. "Liquid crystal compound" means a compound having a liquid crystal phase such as a nematic phase or a smectic phase, or a compound having no liquid crystal phase but being useful as a component of a liquid crystal composition. "Liquid crystal compound", "liquid crystal composition" and "LCD element" may be abbreviated as "compound", "composition" and "element," respectively. "LCD element" is a generic term for LCD panels and LCD modules. A clearing point is a transition temperature of a liquid crystal compound from a liquid crystal phase to an isotropic phase. The minimum temperature of a liquid crystal phase is the transition temperature of a liquid crystal compound form a solid to a liquid crystal phase such as a nematic phase or a smectic phase. The maximum temperature of a nematic phase is the transition temperature of a liquid crystal composition form the nematic phase to the isotropic phase, and may be

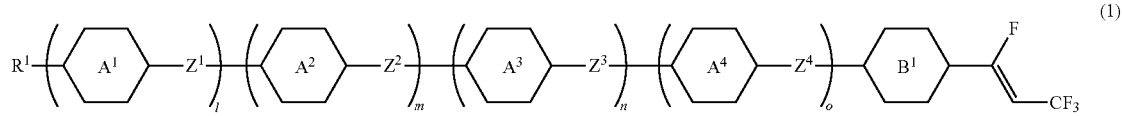

(1)

In formula (1), $R^1$ is $C_{1-15}$ alkyl, and in the alkyl, at least one —$CH_2$— is optionally replaced by —O— or —S—, at least one —$(CH_2)_2$— is optionally replaced by —CH=CH—, and at least one hydrogen is optionally substituted with halogen;

ring $A^1$, ring $A^2$, ring $A^3$, ring $A^4$ and ring $B^1$ are independently 1,4-cyclohexylene, 1,4-phenylene, 1,4-phenylene in which at least one hydrogen is substituted with halogen, 1,3-dioxane-2,5-diyl, tetrahydropyran-2,5-diyl, pyrimidine-2,5-diyl, or pyridine-2,5-diyl;

$Z^1$, $Z^2$, $Z^3$ and $Z^4$ are independently a single bond, —$(CH_2)_2$—, —CH=CH—, —C≡C—, —COO—, —OCO—, —$CF_2O$—, —$OCF_2$—, —$CH_2O$—, —$OCH_2$—, or —CF=CF—; and l, m, n and o are independently 0 or 1, and l+m+n+o≥1.

abbreviated as "maximum temperature." The minimum temperature of the nematic phase may be abbreviated as "minimum temperature." A compound represented by formula (1) may be abbreviated as "compound (1)." The same rule applies to the compounds represented by formulae (2) and so on. In formulae (1) to (14), the symbols of $A^1$, $B^1$, $C^1$ and so on enclosed in hexagons represent ring $A^1$, ring $B^1$, ring $C^1$ and so on, respectively. The amount of a compound expressed by a percent is a weight percent (wt %) based on the total weight of the composition. The symbol $R^1$ is used for different formulae. In these compounds, two groups represented by arbitrary two $R^1$ may be identical be different from each other. The same rule also applies to other symbols such as ring $A^1$ and $Z^1$, etc.

The expression "at least one of 'A' is optionally replaced by 'B'" means that the position of 'A' is arbitrary when the number of 'A' is 1, and positions thereof can also be selected without restriction when the number of 'A' is 2 or more. The expression "at least one of A is optionally replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one —CH$_2$— is optionally replaced by —O— or —CH=CH— includes alkyl, alkenyl, alkoxy, alkoxyalkyl, alkoxyalkenyl and alkenyloxyalkyl. In addition, a case where two successive —CH$_2$— are replaced by —O— to form —O—O— is not preferred. In alkyl and so on, a case where —CH$_2$— of a methyl moiety (—CH$_2$—H) is replaced by —O— to form —O—H is either not preferred.

This invention includes the following items.

Item 1 is a compound represented by formula (1):

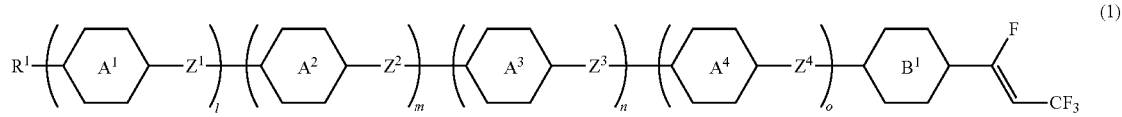

(1)

In formula (1), $R^1$ is $C_{1-15}$ alkyl, and in the alkyl, at least one —CH$_2$— is optionally replaced by —O— or —S—, at least one —(CH$_2$)$_2$— is optionally replaced by —CH=CH—, and at least one hydrogen is optionally substituted with halogen;

ring $A^1$, ring $A^2$, ring $A^3$, ring $A^4$ and ring $B^1$ are independently 1,4-cyclohexylene, 1,4-phenylene, 1,4-phenylene in which at least one hydrogen is substituted with halogen, 1,3-dioxane-2,5-diyl, tetrahydropyran-2,5-diyl, pyrimidine-2,5-diyl, or pyridine-2,5-diyl;

$Z^1$, $Z^2$, $Z^3$ and $Z^4$ are independently a single bond, —(CH$_2$)$_2$—, —CH=CH—, —C≡C—, —COO—, —OCO—, —CF$_2$O—, —OCF$_2$—, —CH$_2$O—, —OCH$_2$— or —CF=CF—; and l, m, n and o are independently 0 or 1, and l+m+n+o≥1.

Item 2 is the compound of Item 1 in which ring $B^1$ in formula (1) is 1,4-cyclohexylene, 1,4-phenylene, or 1,4-phenylene in which at least one hydrogen is substituted with halogen.

Item 3 is the compound of Item 1 in which in formula (1), $R^1$ is $C_{1-15}$ alkyl, $C_{2-15}$ alkenyl, $C_{1-14}$ alkoxy or $C_{2-14}$ alkenyloxy, and $Z^1$, $Z^2$, $Z^3$ and $Z^4$ are independently a single bond, —(CH$_2$)$_2$—, —CH=CH—, —COO—, —OCO—, —CF$_2$O—, —OCF$_2$—, or —CF=CF—.

Item 4 is the compound of Item 1 in which in formula (1), $R^1$ is $C_{1-15}$ alkyl or $C_{2-15}$ alkenyl, and $Z^1$, $Z^2$, $Z^3$ and $Z^4$ are independently a single bond, —(CH$_2$)$_2$—, —CH=CH—, —COO— or —CF$_2$O—.

Item 5 is the compound of Item 1 in which in formula (1), $R^1$ is $C_{1-10}$ alkyl or $C_{2-10}$ alkenyl, ring $A^1$, ring $A^2$, ring $A^3$ and ring $A^4$ are independently 1,4-cyclohexylene, 1,4-phenylene, 1,4-phenylene in which at least one hydrogen is substituted with halogen, 1,3-dioxane-2,5-diyl or tetrahydropyran-2,5-diyl, ring $B^1$ is 1,4-cyclohexylene, 1,4-phenylene, or 1,4-phenylene in which at least one hydrogen is substituted with halogen, and $Z^1$, $Z^2$, $Z^3$ and $Z^4$ are independently a single bond, —(CH$_2$)$_2$— or —CH=CH—.

Item 6 is the compound of Item 1 which is represented by any one of formulae (1-1) to (1-3).

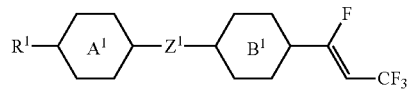

(1-1)

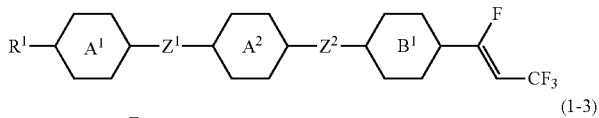

(1-2)

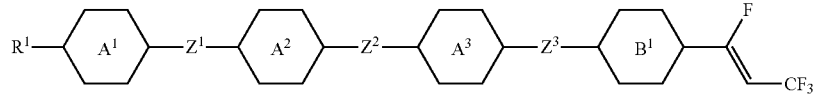

(1-3)

In formulae (1-1) to (1-3), $R^1$ is $C_{1-10}$ alkyl or $C_{2-10}$ alkenyl;

ring $A^1$, ring $A^2$ and ring $A^3$ are independently 1,4-cyclohexylene, 1,4-phenylene, 1,4-phenylene in which at least one hydrogen is substituted with halogen, 1,3-dioxane-2,5-diyl, or tetrahydropyran-2,5-diyl;

ring $B^1$ is 1,4-cyclohexylene, 1,4-phenylene, or 1,4-phenylene in which at least one hydrogen is substituted with halogen; and $Z^1$, $Z^2$ and $Z^3$ are independently a single bond, —(CH$_2$)$_2$— or —CH=CH—.

Item 7 is the compound of Item 1 which is represented by any one of formulae (1-4) to (1-19).

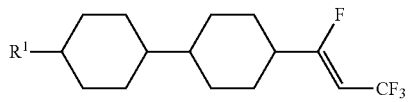

(1-4)

(1-5)
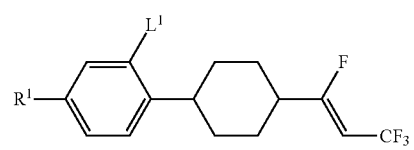
(1-6)
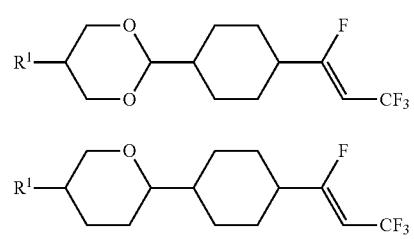
(1-7)
(1-8)
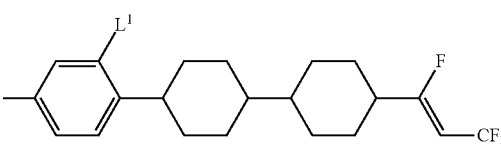
(1-9)
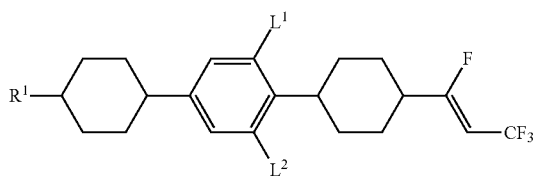
(1-10)
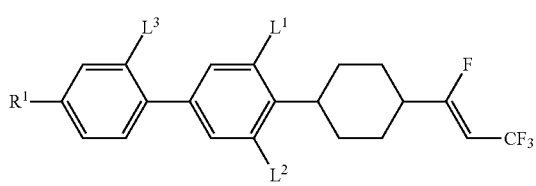
(1-11)
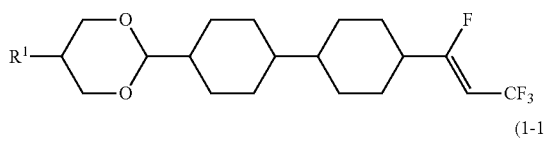
(1-12)
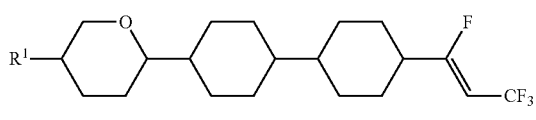
(1-13)
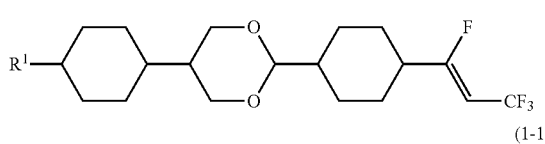
(1-14)
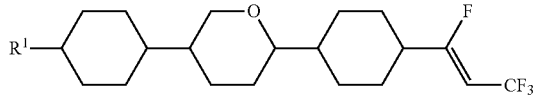
(1-15)
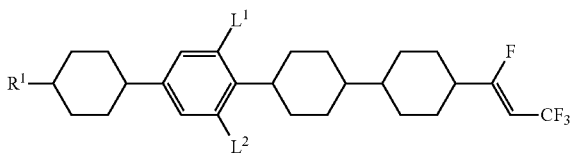
(1-16)
(1-17)
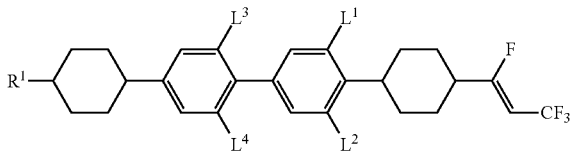
(1-18)
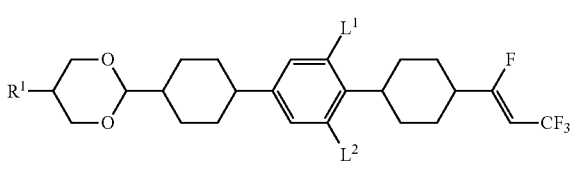
(1-19)
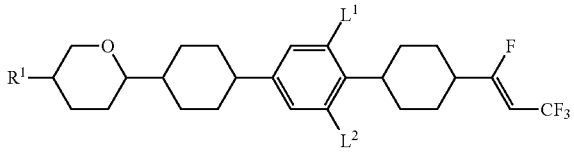
In formulae (1-4) to (1-19), $R^1$ is $C_{1-10}$ alkyl or $C_{2-10}$ alkenyl, and $L^1$, $L^2$, $L^3$ and $L^4$ are hydrogen or fluorine.
Item 8 is the compound of Item 1 which is represented by any one of formulae (1-20) to (1-31).
(1-20)
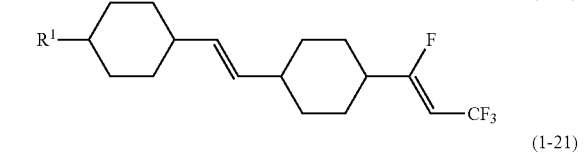
(1-21)
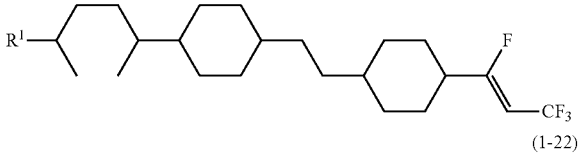
(1-22)
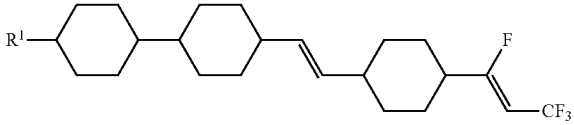

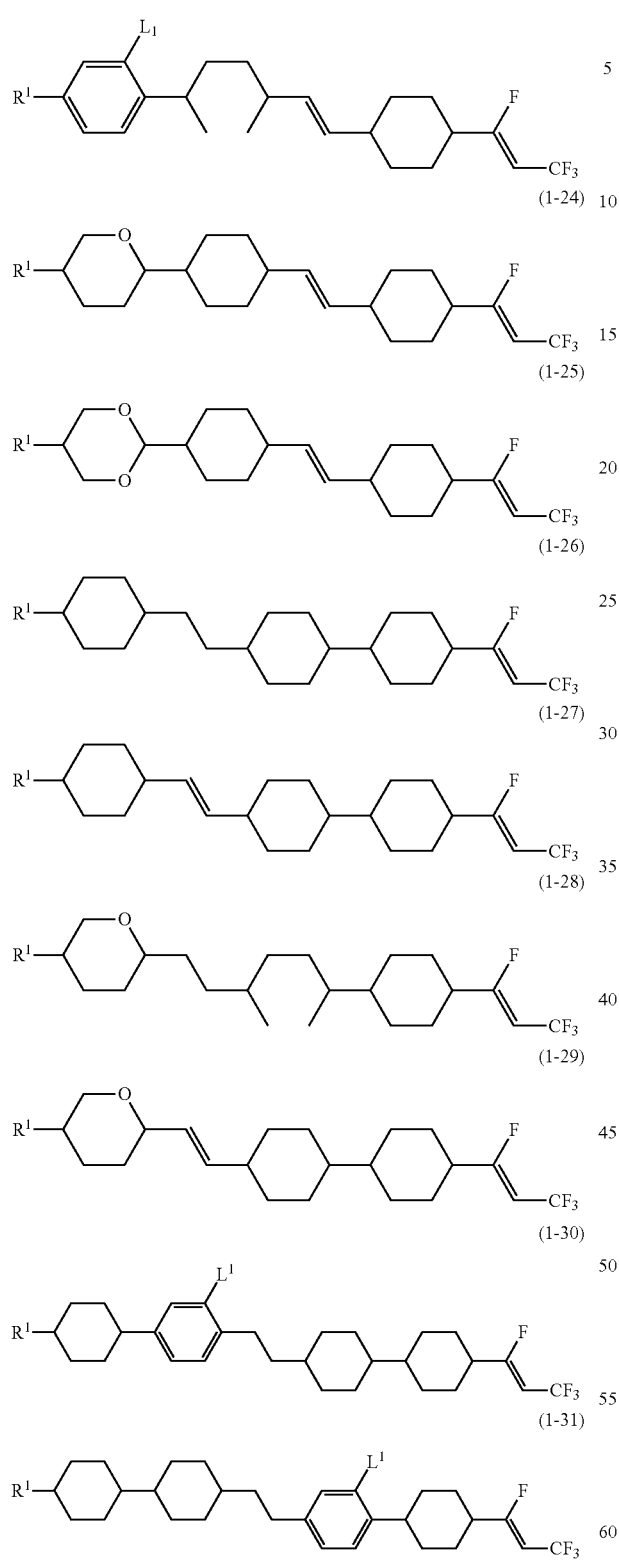
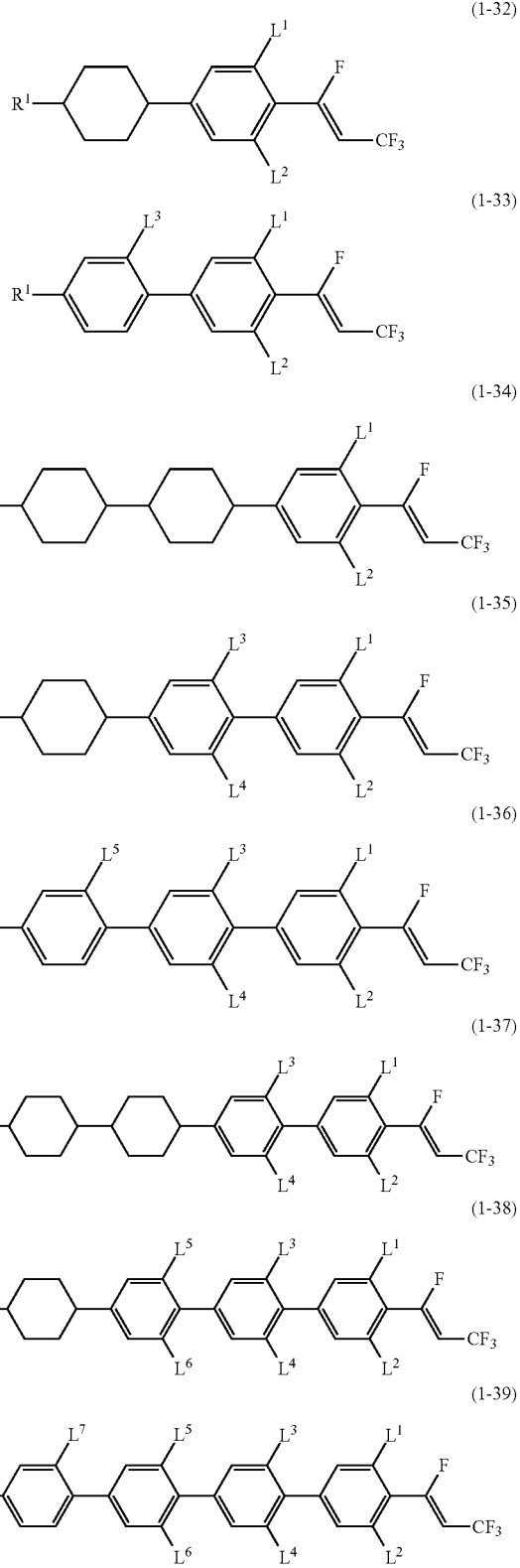
In formulae (1-20) to (1-31), $R^1$ is $C_{1-10}$ alkyl or $C_{2-10}$ alkenyl, and $L^1$ is hydrogen or fluorine.
Item 9 is the compound of Item 1 which is represented by any one of formulae (1-32) to (1-39).
In formulae (1-32) to (1-39), $R^1$ is $C_{1-10}$ alkyl or $C_{2-10}$ alkenyl, and $L^1$, $L^2$, $L^3$, $L^4$, $L^5$, $L^6$ and $L^7$ are independently hydrogen or fluorine.
Item 10 is the compound of Item 1 which is represented by any one of formulae (1-40) to (1-47).

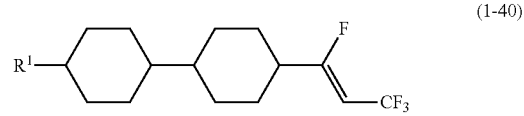
(1-40)

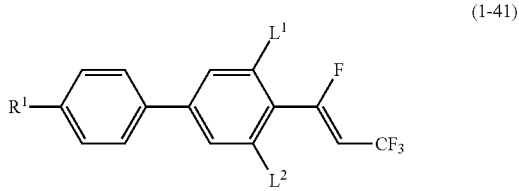
(1-41)

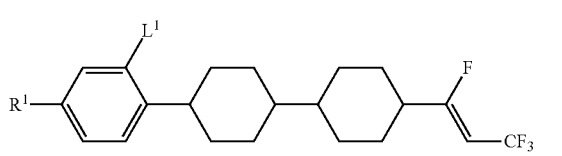
(1-42)

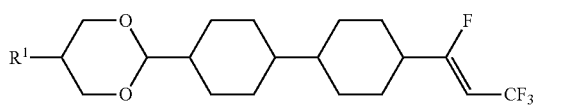
(1-43)

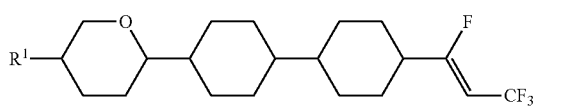
(1-44)

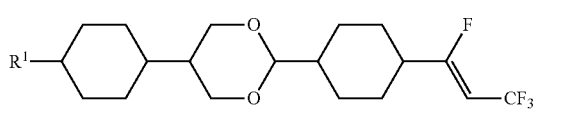
(1-45)

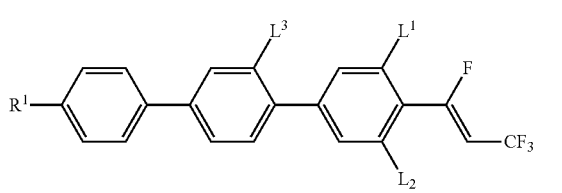
(1-46)

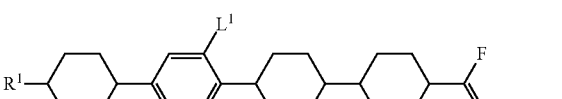
(1-47)

In formulae (1-40) to (1-47), $R^1$ is $C_{1-10}$ alkyl, and $L^1$, $L^2$ and $L^3$ are independently hydrogen or fluorine.

Item 11 is a liquid crystal composition containing at least one compound of any one of Items 1 to 10.

Item 12 is the liquid crystal composition of Item 11 which further contains at least one compound selected from the group consisting of compounds represented by formulae (2) to (4).

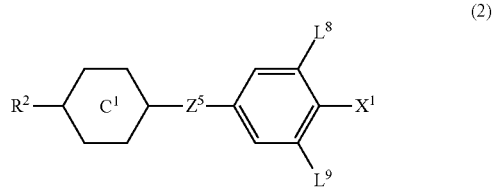
(2)

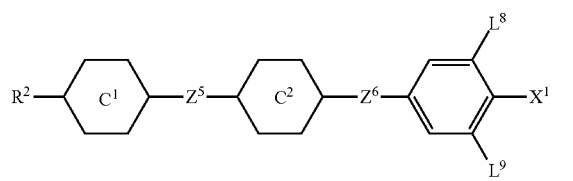
(3)

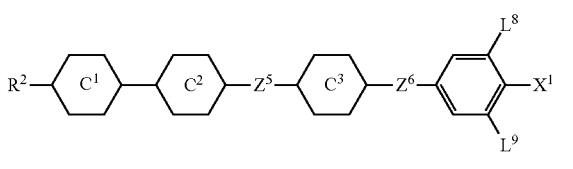
(4)

In formulae (2) to (4), each $R^2$ is independently $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;

$X^1$ is fluorine, chlorine, —$OCF_3$, —$OCHF_2$, —$CF_3$, —$CHF_2$, —$CH_2F$, —$CF=F_2$, —$OCF_2CHF_2$, or —$OCF_2CHFCF_3$;

ring $C^1$, ring $C^2$ and ring $C^3$ are independently 1,4-cyclohexylene, 1,4-phenylene, 2-fluoro-1,4-phenylene, 2,6-difluoro-1,4-phenylene, 1,3-dioxane-2,5-diyl, tetrahydropyran-2,5-diyl, or pyrimidine-2,5-diyl;

$Z^5$ and $Z^6$ are independently a single bond, —$(CH_2)_2$—, —CH=CH—, —C≡C—, —COO—, —$CF_2O$—, —$OCF_2$—, —$CH_2O$—, or —$(CH_2)_4$—; and $L^8$ and $L^9$ are independently hydrogen or fluorine.

Item 13 is the liquid crystal composition of Item 11 which further contains at least one compound selected from the group consisting of compounds represented by formula (5).

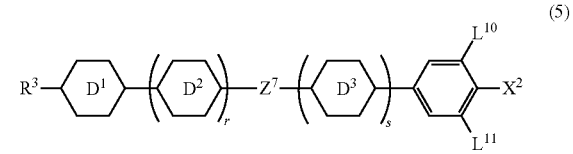
(5)

In formula (5), $R^3$ is $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;

$X^2$ is or —C≡N or —C≡C—C≡N;

ring $D^1$, ring $D^2$ and ring $D^3$ are independently 1,4-cyclohexylene, 1,4-phenylene in which at least one hydrogen is optionally substituted with fluorine, 1,3-dioxane-2,5-diyl, tetrahydropyran-2,5-diyl, or pyrimidine-2,5-diyl;

$Z^7$ is a single bond, —(CH$_2$)$_2$—, —C≡C—, —COO—, —CF$_2$O—, —OCF$_2$—, or —CH$_2$O—;

$L^{10}$ and $L^{11}$ are independently hydrogen or fluorine; and r is 0, 1 or 2, s is 0 or 1, and r+s is 0, 1, 2 or 3.

Item 14 is the liquid crystal composition of Item 11 which further contains at least one compound selected from the group consisting of compounds represented by formulae (6) to (11).

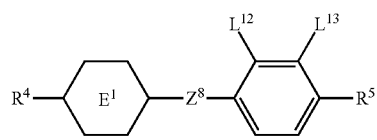
(6)

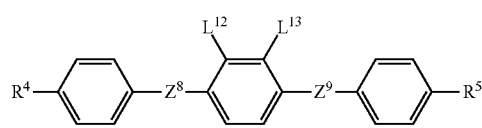
(8)

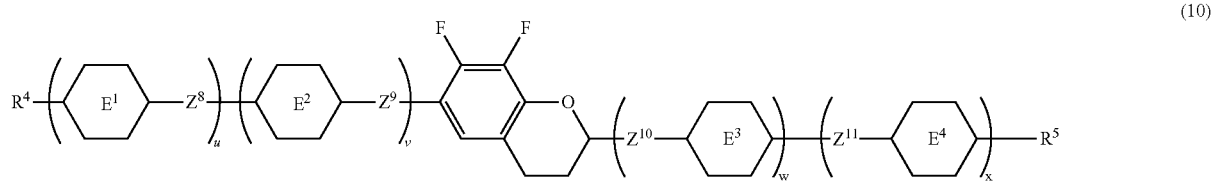
(10)

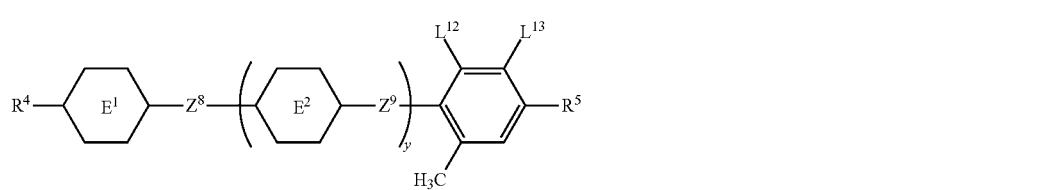
(11)

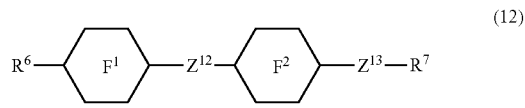
(12)

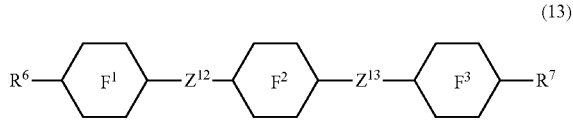
(13)

In formulae (6) to (11), $R^4$ and $R^5$ are independently $C_{1-10}$ alkyl or $C_{2-10}$ alkenyl, and in the alkyl and the alkenyl, at least one hydrogen is optionally substituted with fluorine, and at least one —CH$_2$— is optionally replaced by —O—;

ring $E^1$, ring $E^2$, ring $E^3$ and ring $E^4$ are independently 1,4-cyclohexylene, 1,4-cyclohexenylene, 1,4-phenylene in which at least one hydrogen is optionally substituted with fluorine, tetrahydropyran-2,5-diyl, or decahydronaphthalene-2,6-diyl;

$Z^8$, $Z^9$, $Z^{10}$ and $Z^{11}$ are independently a single bond, —(CH$_2$)$_2$—, —COO—, —CH$_2$O—, —OCF$_2$—, or —OCF$_2$(CH$_2$)$_2$—;

$L^{12}$ and $L^{13}$ are independently fluorine or chlorine; and t, u, v, w, x and y are independently 0 or 1, and u+v+w+x is 1 or 2.

Item 15 is the liquid crystal composition of Item 11 which further contains at least one compound selected from the group consisting of compounds represented by formulae (12) to (14).

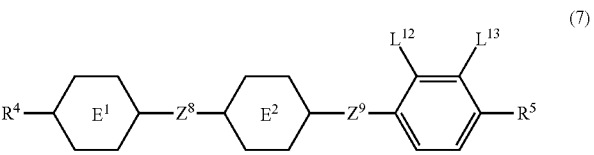
(7)

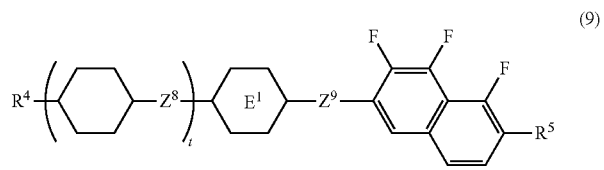
(9)

-continued

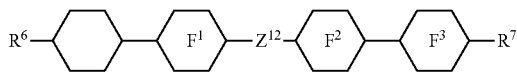
(14)

In formulae (12) to (14), $R^6$ and $R^7$ are independently $C_{1-10}$ alkyl or $C_{2-10}$ alkenyl, and in the alkyl and the alkenyl, at least one —CH$_2$— is optionally replaced by —O—;

ring $F^1$, ring $F^2$ and ring $F^3$ are independently 1,4-cyclohexylene, 1,4-phenylene, 2-fluoro-1,4-phenylene, 2,5-difluoro-1,4-phenylene, or pyrimidine-2,5-diyl; and $Z^{12}$ and $Z^{13}$ are independently a single bond, —(CH$_2$)$_2$—, —CH=CH—, —C≡C—, or —COO—.

Item 16 is the liquid crystal composition of Item 12 which further contains at least one compound selected from the group consisting of compounds represented by formula (5) of Item 13.

Item 17 is the liquid crystal composition of Item 12 which further contains at least one compound selected from the group consisting of compounds represented by formulae (12) to (14) of Item 15.

Item 18 is the liquid crystal composition of Item 13 which further contains at least one compound selected from the group consisting of compounds represented by formulae (12) to (14) of Item 15.

Item 19 is the liquid crystal composition of Item 14 which further contains at least one compound selected from the group consisting of compounds represented by formulae (12) to (14) of Item 15.

Item 20 is the liquid crystal composition of any one of Items 11 to 19 which further contains at least one optically active compound and/or at least one polymerizable compound.

Item 21 is the liquid crystal composition of any one of Items 11 to 20 which further contains at least one antioxidant and/or at least one UV absorbent.

Item 22 is a LCD element containing the liquid crystal composition of any one of Items 11 to 21.

The compound, the liquid crystal composition and the LCD element of this invention will be described in sequence as follows.

1-1. Compound of this Invention

Compound (1) of this invention and its preferred examples are described below. Preferred examples of the terminal groups, ring structures, linking groups and substituents of compound (1) are also applied to the subordinate formulae of compound (1).

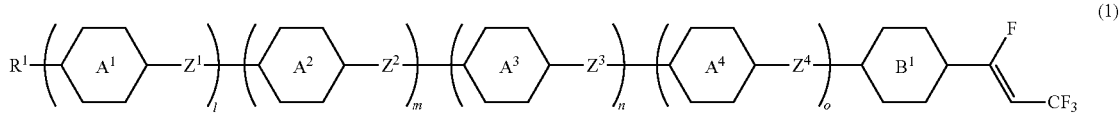

(1)

In formula (1), $R^1$ is $C_{1-15}$ alkyl, and in the alkyl, at least one $-CH_2-$ is optionally replaced by $-O-$ or $-S-$, at least one $-(CH_2)_2-$ is optionally replaced by $-CH=CH-$. In these groups, at least one hydrogen is optionally substituted with halogen.

Examples of such $R^1$ are alkyl, alkoxy, alkoxyalkyl, alkoxyalkoxy, alkylthio, alkylthioalkoxy, alkenyl, alkenyloxy, alkenyloxyalkyl, alkoxyalkenyl and alkenylthio. Among these groups, the straight ones are preferred to the branched ones. However, when optical activity is required, $R^1$ is preferably a branched group.

The preferred configuration of $-CH=CH-$ in the alkenyl depends on the position of the double bond. The trans configuration is preferred for alkenyl having a double bond at an odd-number position, such as $-CH=CHCH_3$, $-CH=CHC_2H_5$, $-CH=CHC_3H_7$, $-CH=CHC_4H_9$, $-C_2H_4CH=CHCH_3$ and $-C_2H_4CH=CHC_2H_5$. The cis configuration is preferred for alkenyl having a double bond at an even-number position, such as $-CH_2CH=CHCH_3$, $-CH_2CH=CHC_2H_5$ and $-CH_2CH=CHC_3H_7$. An alkenyl compound having a preferred steric configuration has a higher clearing point or a broad temperature range of liquid crystal phase. These are described in details in *Mol. Cryst. Liq. Cryst.*, 1985, 131, 109 and *Mol. Cryst. Liq. Cryst.*, 1985, 131, 327.

Examples of the alkyl are $-CH_3$, $-C_2H_5$, $-C_3H_7$, $-C_4H_9$, $-C_5H_{11}$, $-C_6H_{13}$, $-C_7H_{15}$, $-C_8H_{17}$, $-C_9H_{19}$, $-C_{10}H_{21}$, $-C_{11}H_{23}$, $-C_{12}H_{25}$, $-C_{13}H_{27}$, $-C_{14}H_{29}$, and $-C_{15}H_{31}$.

Examples of the alkoxy are $-OCH_3$, $-OC_2H_5$, $-OC_3H_7$, $-OC_4H_9$, $-OC_5H_{11}$, $-OC_6H_{13}$ and $-OC_7H_{15}$, $-OC_8H_{17}$, $-OC_9H_{19}$, $-OC_{10}H_{21}$, $-OC_{11}H_{23}$, $-OC_{12}H_{25}$, $-OC_{13}H_{27}$, and $-OC_{14}H_{29}$.

Examples of the alkoxyalkyl are $-CH_2OCH_3$, $-CH_2OC_2H_5$, $-CH_2OC_3H_7$, $-(CH_2)_2-OCH_3$, $-(CH_2)_2-OC_2H_5$, $-(CH_2)_2-OC_3H_7$, $-(CH_2)_3-OCH_3$, $-(CH_2)_4-OCH_3$, and $-(CH_2)_5-OCH_3$.

Examples of the alkenyl are $-CH=CH_2$, $-CH=CHCH_3$, $-CH_2CH=CH_2$, $-CH=CHC_2H_5$, $-CH_2CH=CHCH_3$, $-(CH_2)_2-CH=CH_2$, $-CH=CHC_3H_7$, $-CH_2CH=CHC_2H_5$, $-(CH_2)_2-CH=CHCH_3$, and $-(CH_2)_3-CH=CH_2$.

Examples of the alkenyloxy are $-OCH_2CH=CH_2$, $-OCH_2CH=CHCH_3$, and $-OCH_2CH=CHC_2H_5$.

Examples of the alkyl in which at least one hydrogen is substituted with halogen are $-CH_2F$, $-CHF_2$, $-CF_3$, $-(CH_2)_2-F$, $-CF_2CH_2F$, $-CF_2CHF_2$, $-CH_2CF_3$, $-CF_2CF_3$, $-(CH_2)_3-F$, $-(CF_2)_3-F$, $-CF_2CHFCF_3$, $-CHFCF_2CF_3$, $-(CH_2)_4-F$, $-(CF_2)_4-F$, $-(CH_2)_5-F$, $-(CF_2)_5-F$, $-CH_2Cl$, $-CHCl_2$, $-CCl_3$, $-(CH_2)_2-Cl$, $-CCl_2CH_2Cl$, $-CCl_2CHCl_2$, $-CH_2CCl_3$, $-CCl_2CCl_3$, $-(CH_2)_3-Cl$, $-(CCl_2)_3-Cl$, $-CCl_2CHClCCl_3$, $-CHClCCl_2CCl_3$, $-(CH_2)_4-Cl$, $-(CCl_2)_4-Cl$, $-(CH_2)_5-Cl$, and $-(CCl_2)_5-Cl$.

Examples of the alkoxy in which at least one hydrogen is substituted with halogen are $-OCH_2F$, $-OCHF_2$, $-OCF_3$, $-O-(CH_2)_2-F$, $-OCF_2CH_2F$, $-OCF_2CHF_2$, $-OCH_2CF_3$, $-O-(CH_2)_3-F$, $-O-(CF_2)_3-F$, $-OCF_2CHFCF_3$, $-OCHFCF_2CF_3$, $-O(CH_2)_4-F$, $-O-(CF_2)_4-F$, $-O-(CH_2)_5-F$, $-O-(CF_2)_5-F$, $-OCH_2Cl$, $-OCHCl_2$, $-OCCl_3$, $-O-(CH_2)_2-Cl$, $-OCCl_2CH_2Cl$, $-OCCl_2CHCl_2$, $-OCH_2CCl_3$, $-O-(CH_2)_3-Cl$, $-O-(CCl_2)_3-Cl$, $-OCCl_2CHClCCl_3$, $-OCHClCCl_2CCl_3$, $-O(CH_2)_4-Cl$, $-O-(CCl_2)_4-Cl$, $-O-(CH_2)_5-Cl$, and $-O-(CCl_2)_5-Cl$.

Examples of the alkenyl in which at least one hydrogen is substituted with halogen are $-CH=CHF$, $-CH=CF_2$, $-CF=CHF$, $-CH=CHCH_2F$, $-CH=CHCF_3$, $-(CH_2)_2-CH=CF_2$, $-CH_2CH=CHCF_3$, $-CH=CHCF_2CF_3$, $-CH=CHCl$, $-CH=CCl_2$, $-CCl=CHCl$, $-CH=CHCH_2Cl$, $-CH=CHCCl_3$, $-(CH_2)_2-CH=CCl_2$, $-CH_2CH=CHCCl_3$, and $-CH=CHCCl_2CCl_3$.

$R^1$ is preferably $C_{1-15}$ alkyl, $C_{2-15}$ alkenyl, $C_{1-14}$ alkoxy or $C_{2-14}$ alkenyloxy, more preferably $C_{1-15}$ alkyl or $C_{2-15}$ alkenyl, and particularly preferably $C_{1-10}$ alkyl or $C_{2-10}$ alkenyl.

More preferred examples of $R^1$ are $-CH_3$, $-C_2H_5$, $-C_3H_7$, $-C_5H_{11}$, $-C_6H_{13}$, $-C_7H_{15}$, $-C_8H_{17}$, $-C_9H_{19}$, $-C_{10}H_{21}$, $-CH=CH_2$, $-CH=CHCH_3$, $-CH_2CH=CH_2$, $-CH=CHC_2H_5$, $-CH_2CH=CHCH_3$, $-(CH_2)_2-CH=CH_2$, $-CH=CHC_3H_7$, $-CH_2CH=CHC_2H_5$, $-(CH_2)_2-CH=CHCH_3$, and $-(CH_2)_3-CH=CH_2$.

In formula (1), ring $A^1$, ring $A^2$, ring $A^3$, ring $A^4$ and ring $B^1$ are independently 1,4-cyclohexylene, 1,4-phenylene, 1,4-phenylene in which at least one hydrogen is substituted with halogen, 1,3-dioxane-2,5-diyl, tetrahydropyran-2,5-diyl, pyrimidine-2,5-diyl, or pyridine-2,5-diyl.

Preferred examples of ring $A^1$, ring $A^2$, ring $A^3$ and ring $A^4$ are 1,4-cyclohexylene, 1,4-phenylene, 1,4-phenylene in which at least one hydrogen is substituted with halogen, 1,3-dioxane-2,5-diyl, and tetrahydropyran-2,5-diyl. Preferred examples of the 1,4-phenylene in which at least one hydrogen is substituted with halogen are groups (15-1) to (15-18).

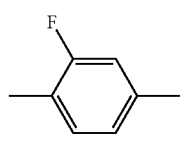
(15-1)

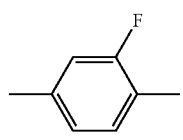
(15-2)

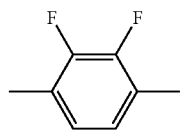
(15-3)

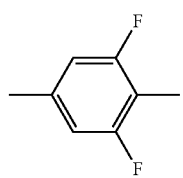
(15-4)

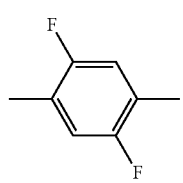
(15-5)

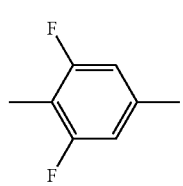
(15-6)

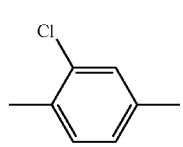
(15-7)

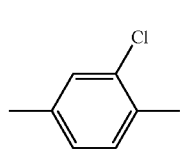
(15-8)

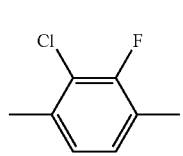
(15-9)

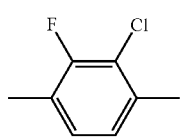
(15-10)

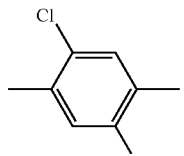
(15-11)

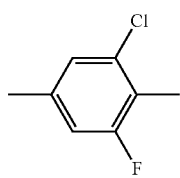
(15-12)

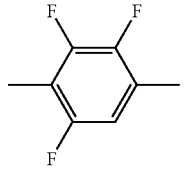
(15-13)

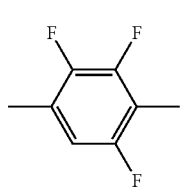
(15-14)

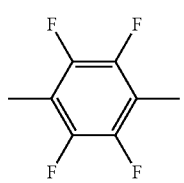
(15-15)

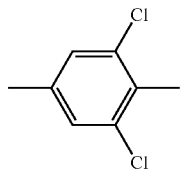
(15-16)

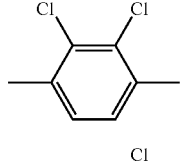
(15-17)

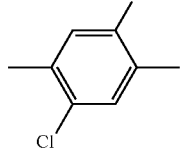
(15-18)

2-fluoro-1,4-phenylene is not left-right symmetric, including the left facing one (15-1) in which the fluorine at the lateral position is positioned at the side of the left terminal group, and the right facing one (15-2) in which the fluorine is positioned at the side of the right terminal group. The preferred 2-fluoro-1,4-phenylene is the right facing one (15-2). 2,6-difluoro-1,4-phenylene (15-4 and 15-6) is either not left-right symmetric. The preferred 2,6-difluoro-1,4-phenylene is the right facing one (15-4). Even for other groups not being left-right symmetric, the right facing ones are preferred.

More preferred examples of the 1,4-phenylene in which at least one hydrogen is substituted with halogen are 2-fluoro-1,4-phenylene, and 2,6-difluoro-1,4-phenylene.

1,3-dioxane-2,5-diyl is not left-right symmetric, including the left facing one (15-19) in which the —O— groups are positioned at the side of the left terminal group, and the right facing one (15-20) in which the —O— groups are positioned at the side of the right terminal group. The preferred 1,3-dioxane-2,5-diyl is the right facing one (15-20). Tetrahydropyran-2,5-diy (15-21 or 15-22) is either not left-right symmetric. The preferred tetrahydropyran-2,5-diyl is the right facing one (15-22). Pyrimidine-2,5-diyl and pyridine-2,5-diyl are also preferably right facing ones (15-24 and 15-26). That is, the —O— or —N— group(s) is at the side of the tetrafluoropropenyl in each right facing ring.

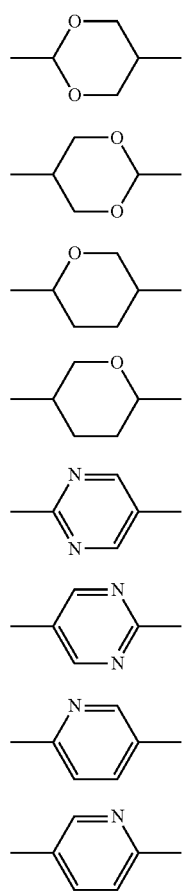

More preferred examples of ring $A^1$, ring $A^2$, ring $A^3$ and ring $A^4$ are 1,4-cyclohexylene, 1,4-phenylene, 2-fluoro-1,4-phenylene, 2,6-difluoro-1,4-phenylene, 1,3-dioxane-2,5-diyl, and tetrahydropyran-2,5-diyl.

Preferred examples of ring $B^1$ are 1,4-cyclohexylene, 1,4-phenylene, and halogen substituted 1,4-phenylene as mentioned above in the case of ring $A^1$, ring $A^2$, ring $A^3$ and ring $A^4$.

In formula (1), $Z^1$, $Z^2$, $Z^3$ and $Z^4$ are independently a single bond, —$(CH_2)_2$—, —CH=CH—, —C≡C—, —COO—, —OCO—, —$CF_2O$—, —$OCF_2$—, —$CH_2O$—, —$OCH_2$— or —CF=CF—.

Preferred examples of $Z^1$, $Z^2$, $Z^3$ and $Z^4$ are a single bond, —$(CH_2)_2$—, —CH=CH—, —COO—, and —$CF_2O$—. More preferred examples of $Z^1$, $Z^2$, $Z^3$ and $Z^4$ are a single bond, —$(CH_2)_2$—, and —CH=CH—. It is particularly preferred that $Z^1$, $Z^2$, $Z^3$ and $Z^4$ are all single bonds or are a combination of single bonds and one —$(CH_2)_2$— or —CH=CH—.

In formula (1), l, m, n and o are independently 0 or 1, and l+m+n+o≥1. Preferred examples of l+m+n+o are 1, 2 and 3. More preferred examples of l+m+n+o are 1 and 2.

1-2. Physical Properties of Compound (1) and Adjustments Thereof

By suitably combining the species of $R^1$, ring $A^1$, ring $A^2$, ring $A^3$, ring $A^4$, ring $B^1$, $Z^2$, $Z^3$ and $Z^4$ and the value of l+m+n+o in compound (1), physical properties such as the clearing point, optical anisotropy and dielectric anisotropy can be adjusted as required. Compound (1) may contain isotopes such as $^2H$ (deuterium) and $^{13}C$ in an amount over the natural abundance, since there are little differences in physical properties of the compound. Main effects of the species of $R^1$ and so forth on the physical properties of the compound (1) will be described below.

When the left terminal group $R^1$ is a straight chain, the temperature range of the liquid crystal phase is broad, and the viscosity is low. When $R^1$ is a branched chain, the compatibility with other liquid crystal compounds is good. A compound having optically active $R^1$ is useful as a chiral dopant. By adding the compound in the composition, generation of a reverse twisted domain in the LCD element can be prevented. A compound having non-optically active $R^1$ is useful as a component of the composition. When $R^1$ is alkenyl, its preferred steric configuration depends on the position of the double bond, as mentioned above. An alkenyl compound having a preferred steric configuration has a high maximum temperature or a broad temperature range of liquid crystal phase.

When ring $A^1$, ring $A^2$, ring $A^3$ and ring $A^4$ are all 1,4-cyclohexylene, the clearing point is high, and the viscosity is low. When at least one of ring $A^1$, ring $A^2$, ring $A^3$ and ring $A^4$ is 1,4-phenylene or 1,4-phenylene in which at least one hydrogen is substituted with halogen, the optical anisotropy is relatively larger, and the orientational order parameter is relatively larger. When ring $A^1$, ring $A^2$, ring $A^3$ and ring $A^4$ are all 1,4-phenylene or 1,4-phenylene in which at least one hydrogen is substituted with halogen, or a combination of the two kinds of groups, the optical anisotropy is particularly large. When at least one of ring $A^1$, ring $A^2$, ring $A^3$ and ring $A^4$ is 1,3-dioxane-2,5-diyl, the dielectric anisotropy is large. When at least one of ring $A^1$, ring $A^2$, ring $A^3$ and ring $A^4$ is tetrahydropyran-2,5-diyl, the compatibility with other liquid crystal compounds is good.

When ring $B^1$ is 1,4-cyclohexylene, the stability to heat and light, etc. is high, and the viscosity is low. When ring $B^1$ is 1,4-phenylene or 1,4-phenylene in which at least one hydrogen is substituted with halogen, the clearing point is high, the optical anisotropy is large, and the dielectric anisotropy is large.

When the linking group $Z^1$, $Z^2$, $Z^3$ or $Z^4$ is a single bond, —$(CH_2)_2$—, —CH=CH—, —$CF_2O$—, —$OCF_2$— or —CF=CF—, the viscosity is low. When the linking group is a single bond, —$(CH_2)_2$— or —CH=CH—, the viscosity is even lower. When the linking group is —CH=CH—, the temperature range of liquid crystal phase is broad, and the elastic constant (K) is large. When the linking group is —C≡C—, the optical anisotropy is large. Particularly, when the linking group is —CF$_2$O— or —COO—, the dielectric anisotropy is large.

When l+m+n+o is 1, the viscosity is low, and the compatibility with other liquid crystal compounds is good. When l+m+n+o is 2, the viscosity is low, and the clearing point is high. When l+m+n+o is 3 or 4, the viscosity is low, and the clearing point is particularly high.

As mentioned above, by suitably selecting the species of the ring structures, terminal groups, linking group and so on and the number of the ring structures, a compound having target physical properties can be obtained. Therefore, compound (1) is useful as a component of a liquid crystal composition used in a LCD element having a mode such as the PC, TN, STN, ECB, OCB, IPS or VA mode.

1-3. Example of Compound (1)

Preferred examples of compound (1) are compounds (1-1) to (1-3). More preferred examples of the same are compounds (1-4) to (1-19), (1-20) to (1-31) and (1-32) to (1-39). Most preferred examples of the same are compound (1-40) to (1-47).

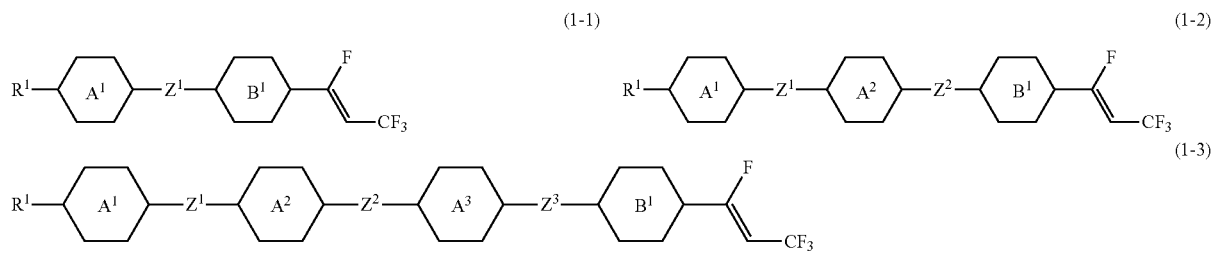

In formulae (1-1) to (1-3), R$^1$ is C$_{1-10}$ alkyl or C$_{2-10}$ alkenyl, ring A$^1$, ring A$^2$ and ring A$^3$ are independently 1,4-cyclohexylene, 1,4-phenylene, 1,4-phenylene in which at least one hydrogen is substituted with halogen, 1,3-dioxane-2,5-diyl or tetrahydropyran-2,5-diyl, ring B$^1$ is 1,4-cyclohexylene, 1,4-phenylene, or 1,4-phenylene in which at least one hydrogen is substituted with halogen, and Z$^1$, Z$^2$ and Z$^3$ are independently a single bond, —(CH$_2$)$_2$— or —CH=CH—.

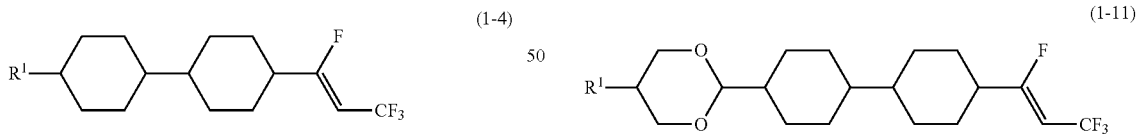
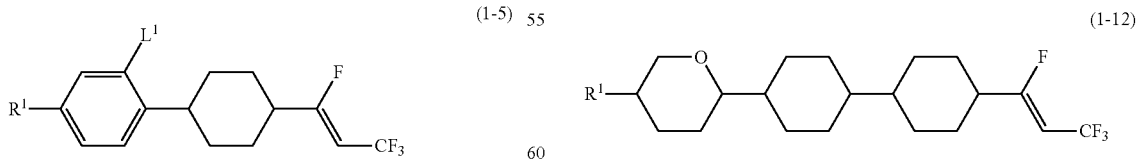
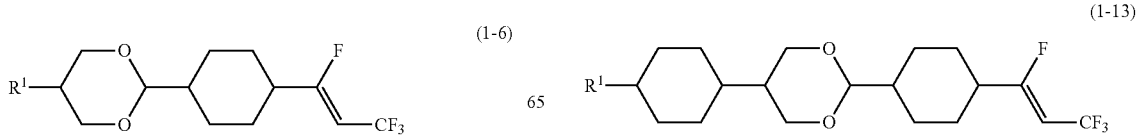

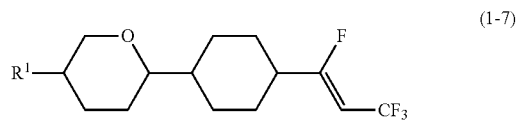
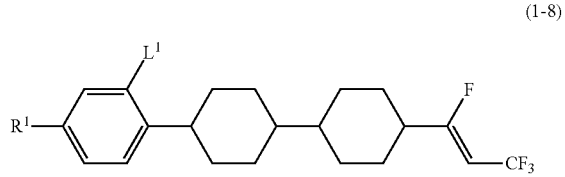
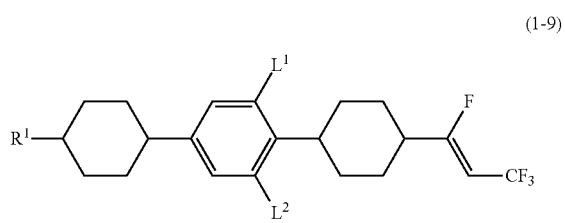
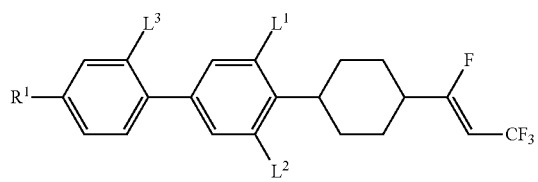
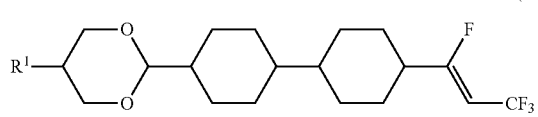
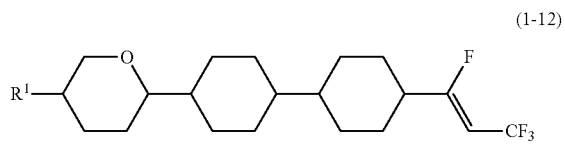

(1-14)
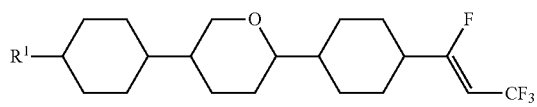
(1-15)
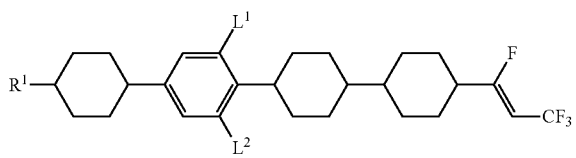
(1-16)
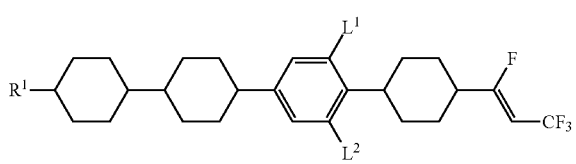
(1-17)
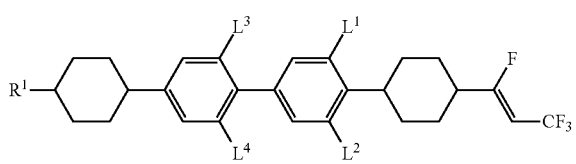
(1-18)
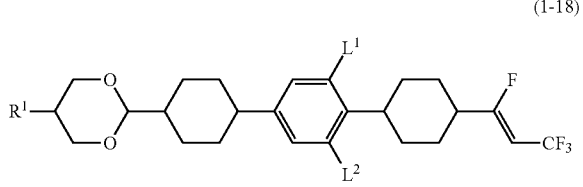
(1-19)
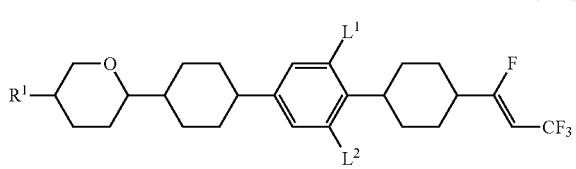
In formulae (1-4) to (1-19), $R^1$ is $C_{1-10}$ alkyl or $C_{2-10}$ alkenyl, and $L^1$, $L^2$, $L^3$ or $L^4$ is hydrogen or fluorine.
(1-20)
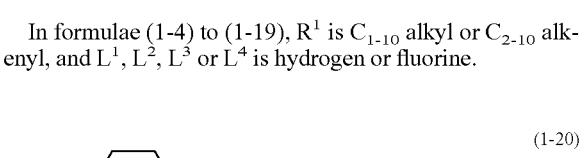
(1-21)
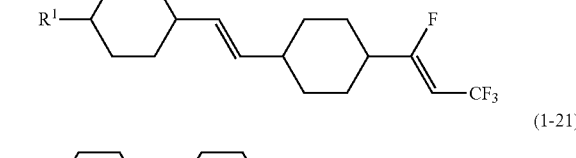
(1-22)
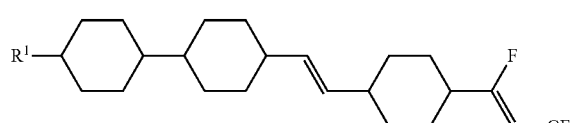
(1-23)
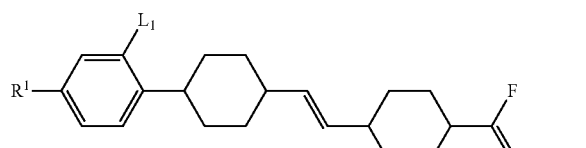
(1-24)
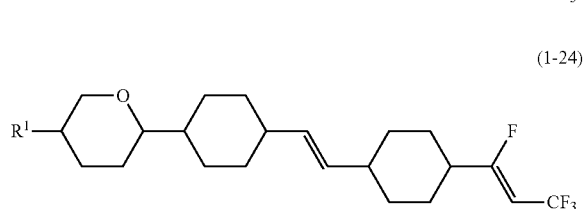
(1-25)
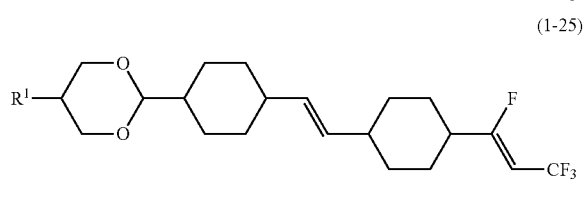
(1-26)
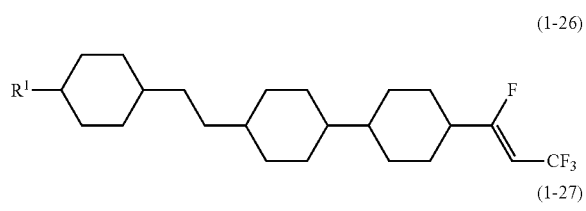
(1-27)
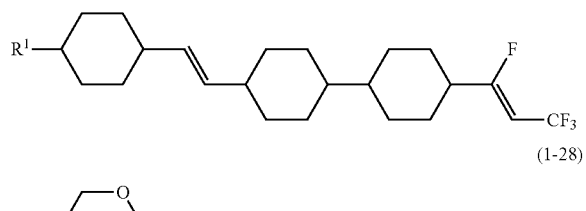
(1-28)
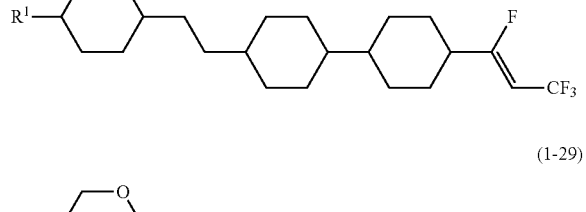
(1-29)
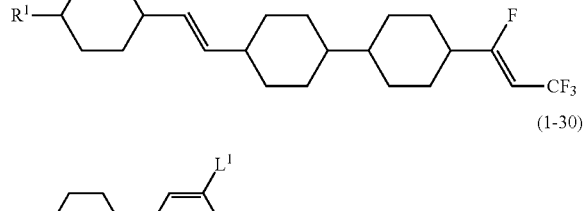
(1-30)
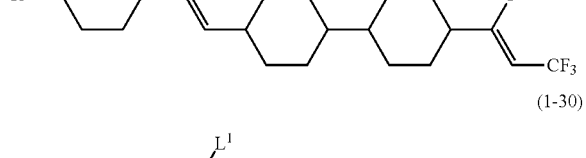

(1-31)
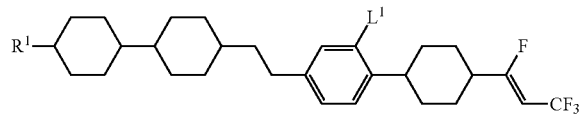

In formulae (1-20) to (1-31), $R^1$ is $C_{1-10}$ alkyl or $C_{2-10}$ alkenyl, and $L^1$ is hydrogen or fluorine.

(1-32)
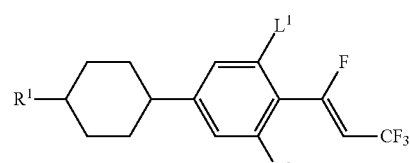

(1-33)
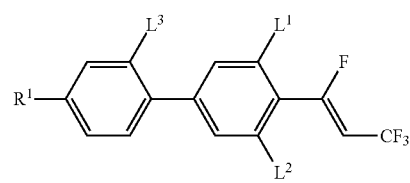

(1-34)
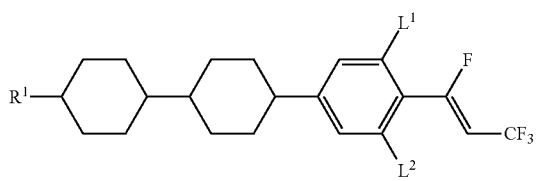

(1-35)
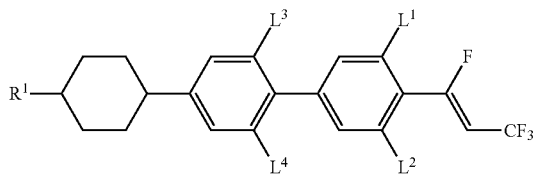

(1-36)
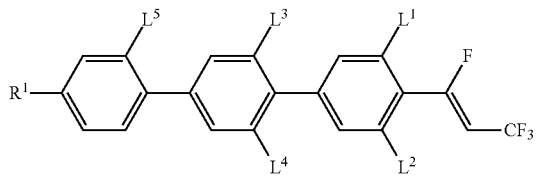

(1-37)
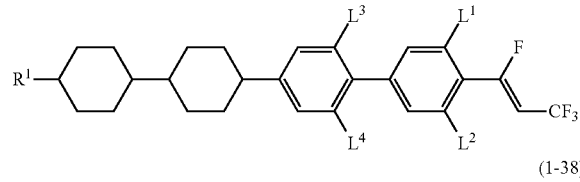

(1-38)
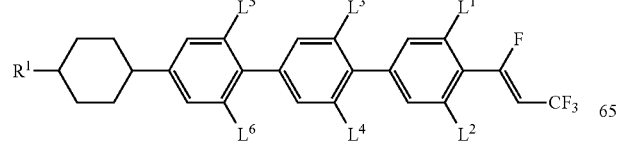

(1-39)
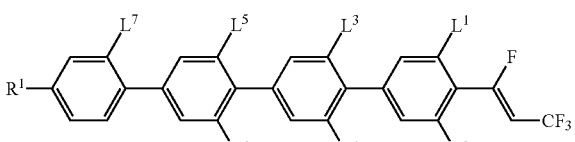

In formulae (1-32) to (1-39), $R^1$ is $C_{1-10}$ alkyl or $C_{2-10}$ alkenyl, and $L^1$, $L^2$, $L^3$, $L^4$, $L^5$, $L^6$ or $L^7$ is hydrogen or fluorine.

Because the liquid crystal compound of this invention has the aforementioned $R^1$, ring $A^1$, ring $A^2$, ring $A^3$, ring $A^4$, ring $B^1$, $Z^1$, $Z^2$, $Z^3$ and $Z^4$, and tetrafluoropropenyl, it has a better balance between characteristics such as a high stability to heat and light etc, a high clearing point, a low minimum temperature of liquid crystal phase, a low viscosity, a suitable optical anisotropy, a large dielectric anisotropy, a suitable elastic constant and good compatibility with other liquid crystal compound, and has a particularly large dielectric anisotropy.

In view of a high stability to heat and light, etc., a high clearing point, and a low viscosity, compounds (1-4) to (1-19) are preferred. In view of a high clearing point and good compatibility, compounds (1-20) to (1-31) are preferred. In view of a high clearing point, a large optical anisotropy and a large dielectric anisotropy, compounds (1-32) to (1-39) are preferred.

(1-40)
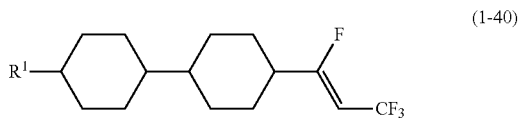

(1-41)
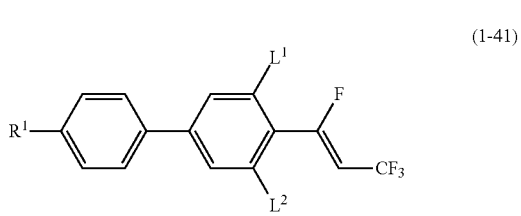

(1-42)
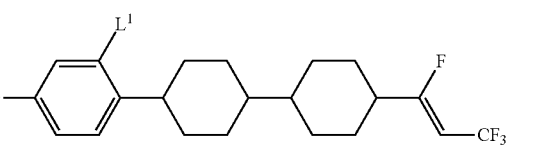

(1-43)
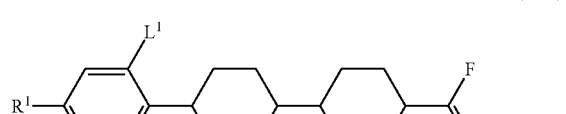

(1-44)
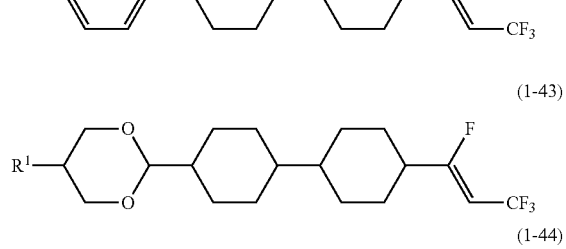

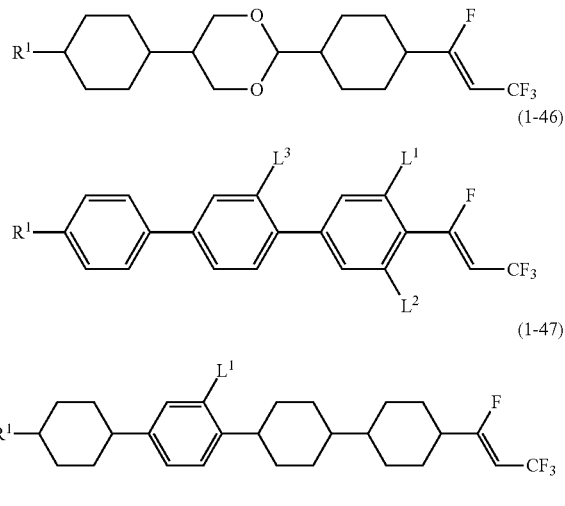

In these formulae, $R^1$ is $C_{1\text{-}10}$ alkyl, and $L^1$, $L^2$ and $L^3$ are independently hydrogen or fluorine.

1-4. Synthesis of Compound (1)

Methods for synthesizing compound (1) are described. Compound (1) can be synthesized by a suitable combination of methods of organic synthetic chemistry. Methods for introducing target terminal groups, rings and linking groups to a starting compound are described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Maruzen Co.).

1-4-1. Formation of Linking Groups

Examples of the methods for forming the linking groups in compound (1) are shown by the following schemes. In these schemes, $MSG^1$ (or $MSG^2$) is a monovalent organic group having at least one ring. Monovalent organic group represented by a plurality of $MSG^1$ (or $MSG^2$) may be the same, or may be different from each other.

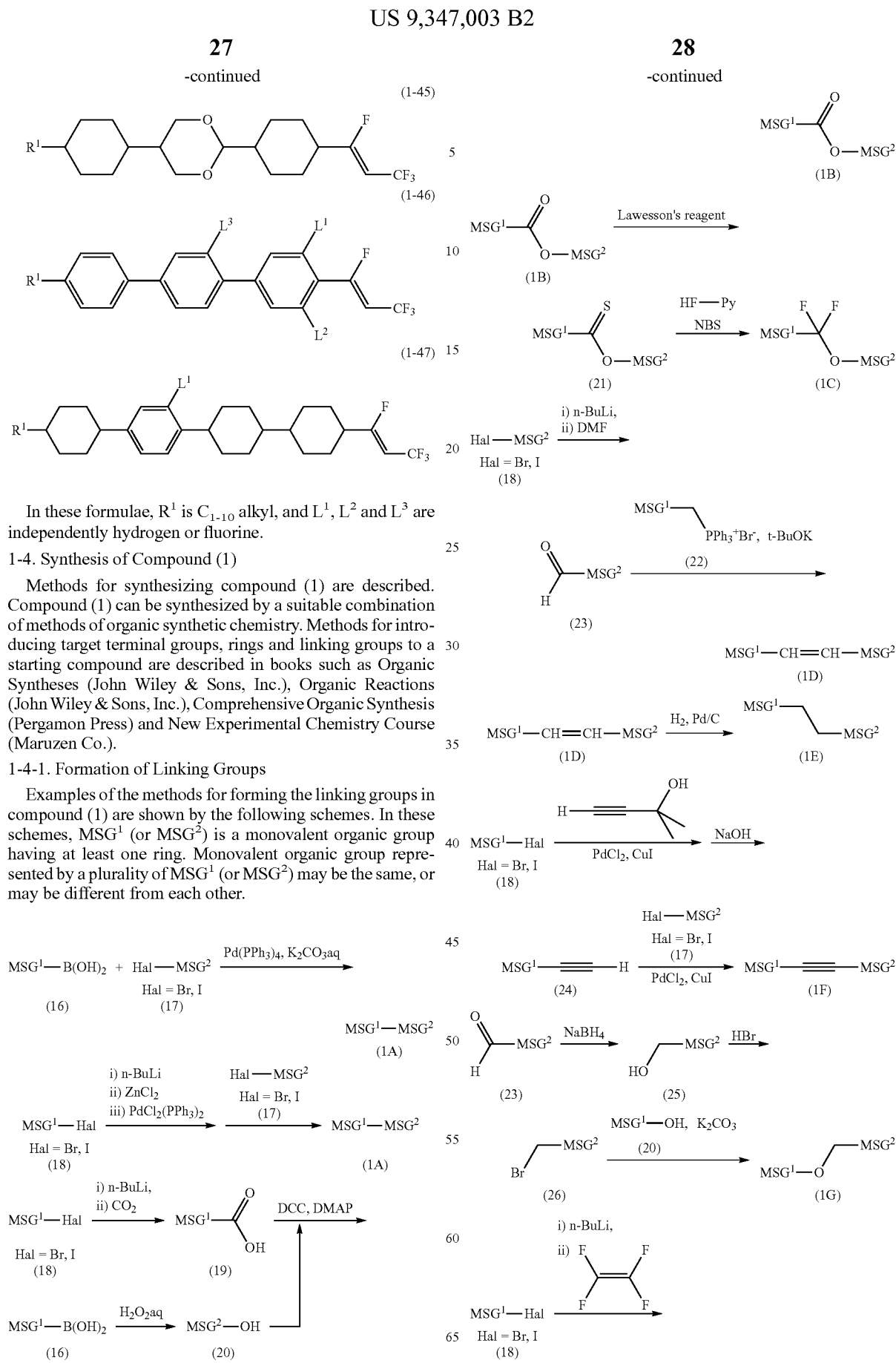

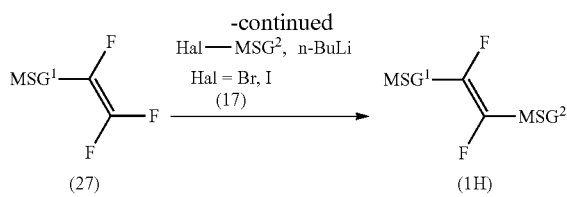

(I) Formation of Single Bond

Boric acid (16) having a predetermined ring is reacted with halogenated compound (17) synthesized with a well-known method, in the presence of an aqueous carbonate solution and a catalyst such as tetrakis(triphenylphosphine)palladium, to synthesize compound (1A). Compound (1A) may alternatively be synthesized by reacting n-butyl lithium with compound (18) synthesized by a well-known method, with zinc chloride, and then with compound (17) in the presence of a catalyst such as bis(triphenylphosphine)palladium dichloride.

(II) Formation of —COO— and —OCO—

Compound (18) is reacted with n-butyl lithium and then with carbon dioxide to produce carboxylic acid (19). Next, compound (19), and phenol compound (20) synthesized with a well-known method are subjected to dehydration in the presence of N,N'-dicyclohexyl-carbodiimide (DCC) and 4-dimethylaminopyridine (DMAP) to synthesize compound (1B) having —COO—. A compound having —OCO— could also be synthesized through this process.

(III) Formation of —CF$_2$O— and —OCF$_2$—

Compound (1B) is treated with a vulcanizing agent such as Lawesson's reagent to form compound (21). Compound (21) is fluorinated by hydrogen fluoride pyridine complex and N-bromosuccinimide (NBS) to synthesize compound (1C) having —CF$_2$O—, as described in M. Kuroboshi et al., *Chem. Lett.*, 1992, 827. Compound (1C) could alternatively be synthesized by fluorinating the compound (21) with (diethylamino)sulfur trifluoride (DAST), as described in W. H. Bunnelle et al., *J. Org. Chem.* 1990, 55, 768. A compound having —OCF$_2$— could also be synthesized with this process. These linking groups could alternatively be formed through the process described in Peer. Kirsch et al., *Angew. Chem. Int. Ed.* 2001, 40, 1480.

(IV) Formation of —CH=CH—

Compound (18) is treated with n-butyl lithium and then reacted with a formamide such as N,N-dimethylformamide (DMF) to produce aldehyde (23). Then, phosphosium salt (22) synthesized with a well-known method is treated with a base such as potassium t-butoxide, so as to produce a phosphorus ylide, which is then reacted with aldehyde (23) to form compound (1D). A cis-compound is produced under the reaction conditions, and, if necessary, may be isomerized to a trans-compound by a well-known method.

(V) Formation of —(CH$_2$)$_2$—

Compound (1D) is hydrogenated in the presence of a catalyst, such as Pd/C, to produce compound (1E).

(VI) Formation of —C≡C—

2-methyl-3-butyn-2-ol is reacted with compound (18) in presence of a catalyst containing palladium dichloride and copper halide, and then deprotected under a basic condition to form compound (24). Compound (24) is reacted with the compound (17), in presence of a catalyst containing bis(triphenylphosphine)palladium dichloride and copper halide, to produce compound (1F).

(VII) Formation of —CH$_2$O— or —OCH$_2$—

Compound (23) is reduced with a reductant like sodium borohydride to form compound (25), which is halogenated with, e.g., hydrobromic acid, to form compound (26). Compound (26) is reacted with compound (20) in presence of potassium carbonate and so on to form compound (1G).

(VIII) Formation of —CF=CF—

Compound (18) is treated with n-butyl lithium and then reacted with tetrafluoroethylene to produce compound (27). Compound (17) is treated with n-butyl lithium and then reacted with compound (27) to produce compound (1H).

By combining the above methods, a brominated compound (28) can be synthesized.

1-4-2. Formation of ring A$^1$, ring A$^2$, ring A$^3$, ring A$^4$ and ring B$^1$ For rings such as 1,4-cyclohexylene, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5,6-tetrafluoro-1,4-phenylene, 1,3-dioxane-2,5-diyl, tetrahydropyran-2,5-diyl, pyrimidine-2,5-diyl, and pyridine-2,5-diyl, related starting compounds are commercially available or can be synthesized with well-known methods. The MSG compounds (16) to (18) having such rings are used here.

1-4-3. Method for Synthesizing Compound (1)

An exemplary method for synthesizing compound (1) is described below. The brominated compound (28) synthesized with a well-known method is reacted with mercaptophenyltetrazole (29) in presence of a base such as KOH to obtain sulfide (30). The sulfide (30) is oxidized by an oxidant such as MCPBA (m-chloroperoxybenzoic acid) to obtain sulfone (31). The sulfone (31) is reacted with lithium diisopropylamide (LDA) and then with N-fluorobenzenesulfonimide (NFSI) to obtain fluorinated sulfone (32). The fluorinated sulfone (32) is then reacted with trifluoroacetaldehyde (33) in presence of potassium hexamethyldisilazide (KHMDS) to obtain compound (1). The trifluoroacetaldehyde (33) used in this reaction is obtained by heating ethyl hemiacetal (34) in concentrated sulfuric acid.

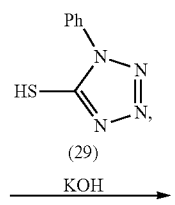

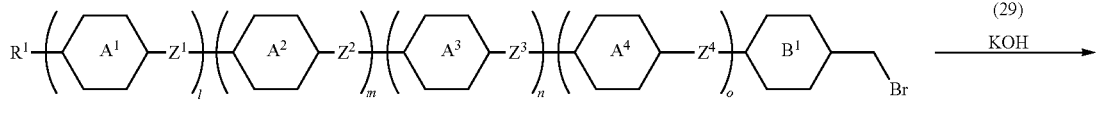

(28)

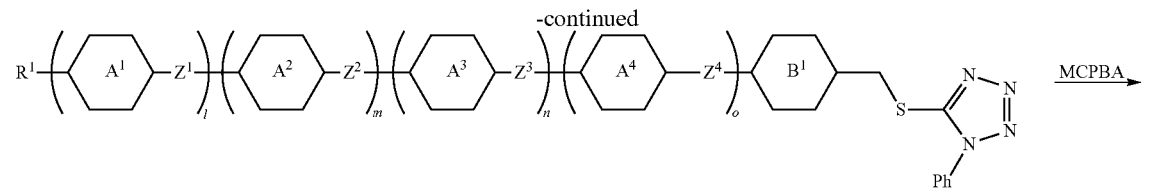

(30)

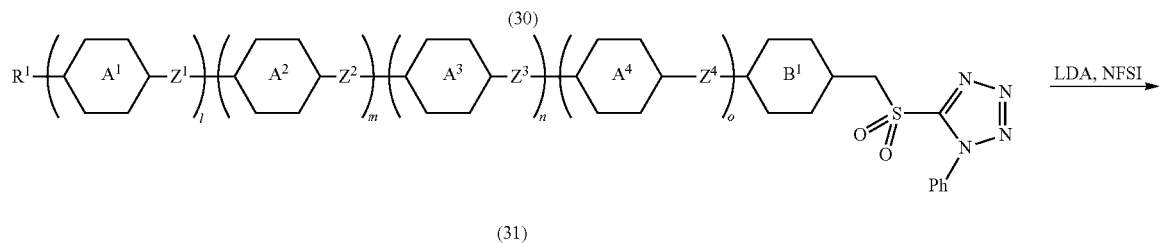

(31)

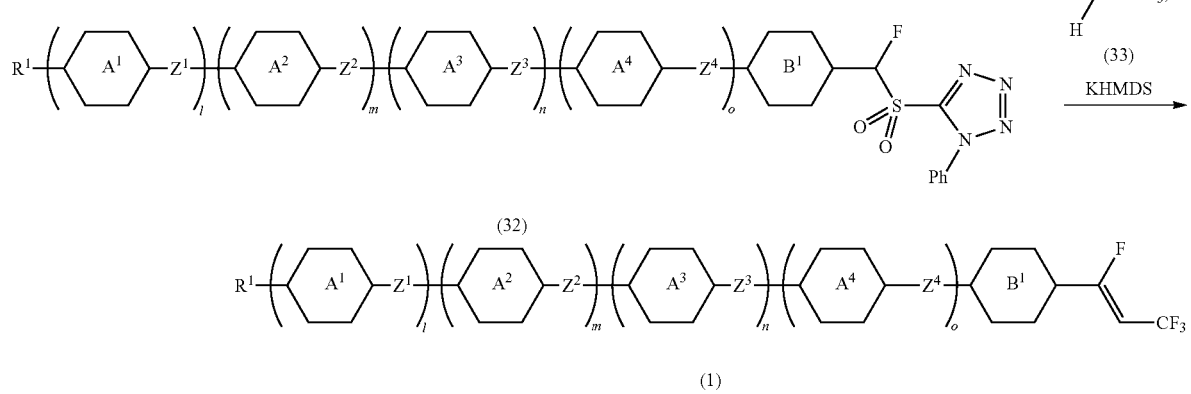

(32)

(1)

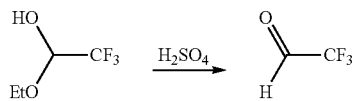

(34)     (33)

In these compounds, $R^1$, ring $A^1$, ring $A^2$, ring $A^3$, ring $A^4$, ring $B^1$, $Z^1$, $Z^2$, $Z^3$, $Z^4$, l, m, n and o are defined as above.

2. Composition (1)

Liquid crystal composition (1) of this invention is described below. The composition (1) contains at least one compound (1) as a component. The composition (1) may contain two or more compounds (1). The component of the liquid crystal compound may include compound(s) (1) only, but it is preferred that composition (1) contains at least one compound (1) in an amount within the range of 1 to 99 wt % in order to exhibit good characteristics. More preferred proportion is in the range of 5 to 60 wt %. It is also possible that composition (1) contains compound (1) and various liquid crystal compounds other than compound (1).

A preferred composition contains compounds selected from the following components B, C, D and E. In preparing composition (1), for example, the component can be selected also in consideration of the dielectric anisotropy of compound (1). A composition whose components have been suitably selected has a high maximum temperature of nematic phase, a low minimum temperature of nematic phase, a low viscosity, a suitable optical anisotropy, a large dielectric anisotropy, and a suitable elastic constant.

Component B includes compounds (2), (3) and (4). Component C includes compounds (5). Component D includes compounds (6), (7), (8), (9), (10) and (11).

Component E includes compounds (12), (13) and (14). These components are described below in sequence.

Component B includes compounds of formulae (2) to (4) having a halogen- or fluorine-containing group at the right terminal (one of the terminals has a fluorine-containing group bonded to the benzene ring). Preferred examples of component B may include compounds (2-1) to (2-16), compounds (3-1) to (3-112), and compounds (4-1) to (4-54).

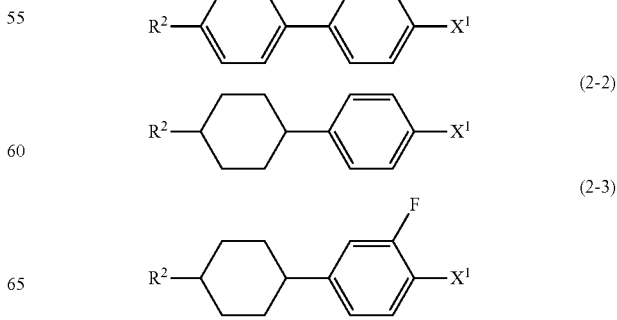

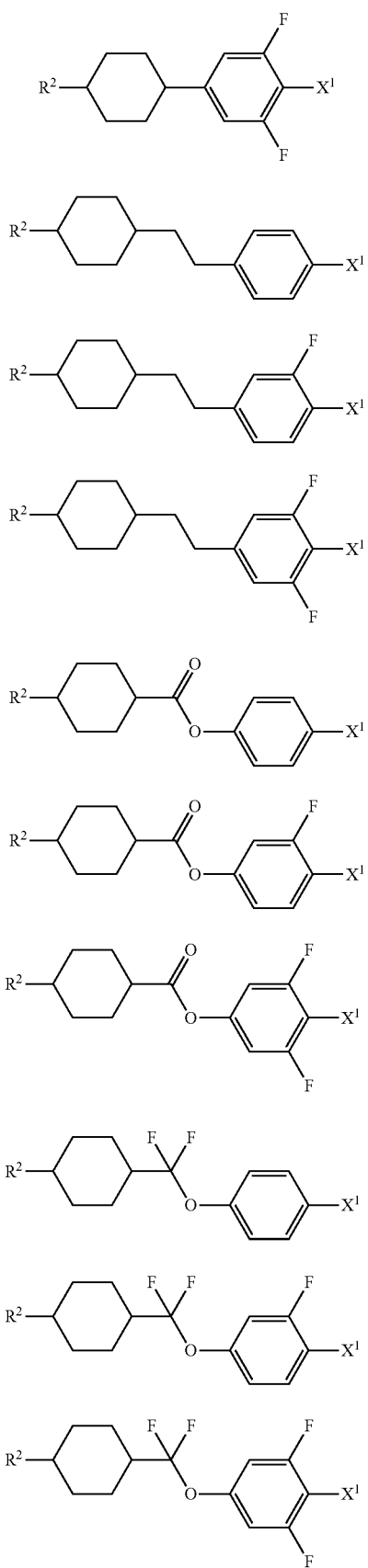
(2-4)
(2-5)
(2-6)
(2-7)
(2-8)
(2-9)
(2-10)
(2-11)
(2-12)
(2-13)
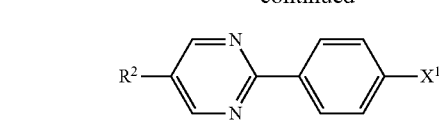
(2-14)
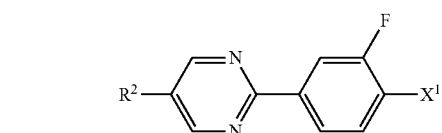
(2-15)
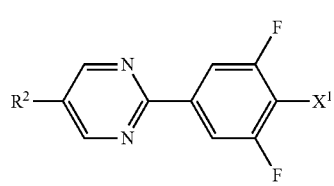
(2-16)
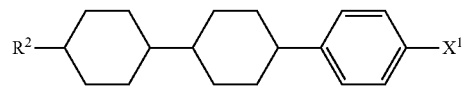
(3-1)
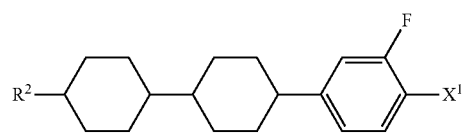
(3-2)
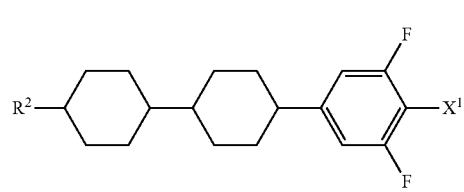
(3-3)
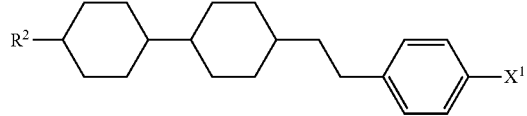
(3-4)
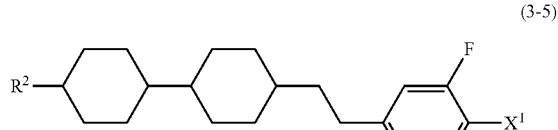
(3-5)
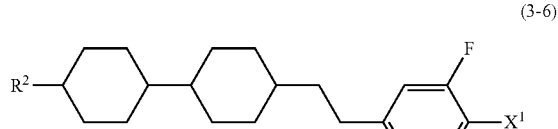
(3-6)
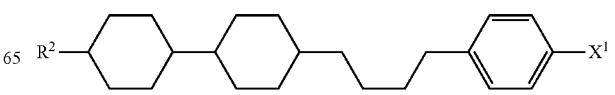
(3-7)

(3-8)
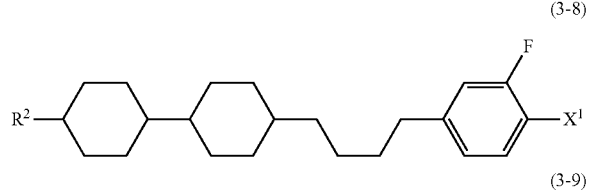
(3-9)
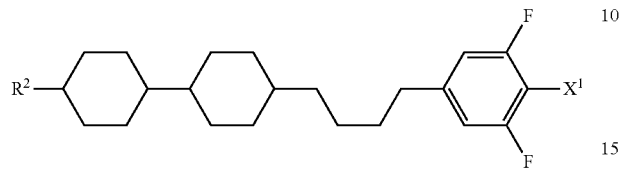
(3-10)
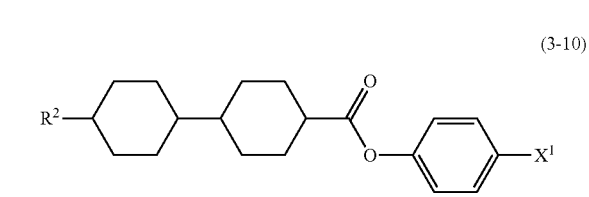
(3-11)
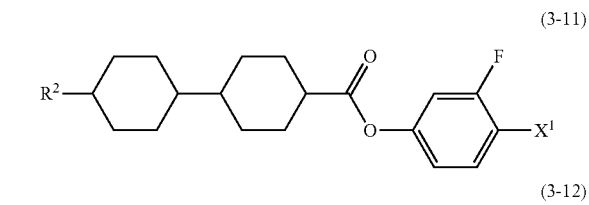
(3-12)
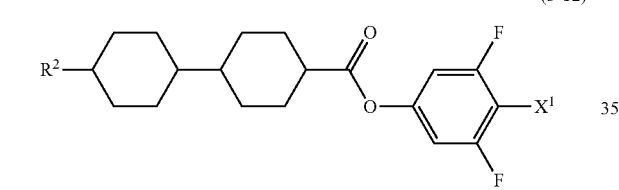
(3-13)
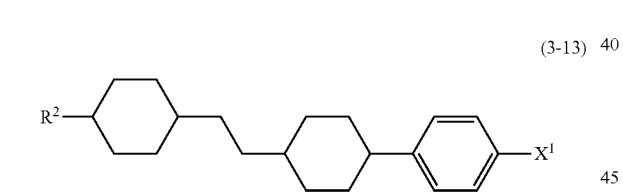
(3-14)
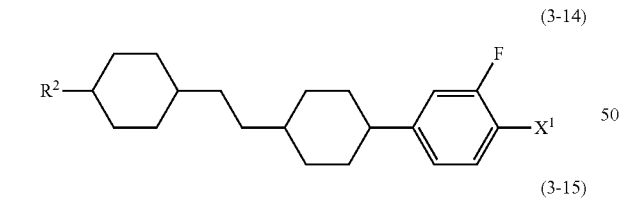
(3-15)
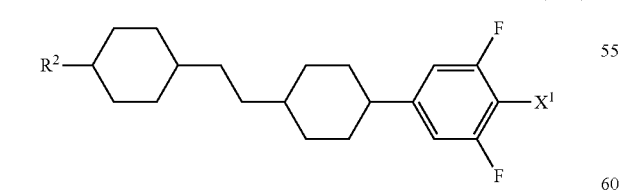
(3-16)
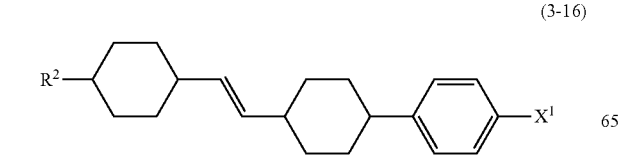
(3-17)
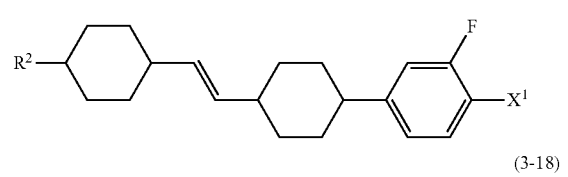
(3-18)
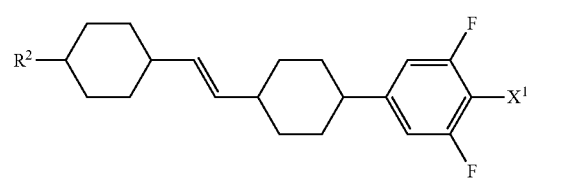
(3-19)
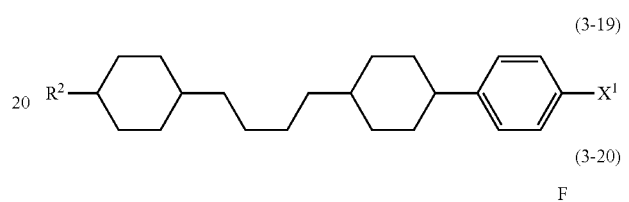
(3-20)
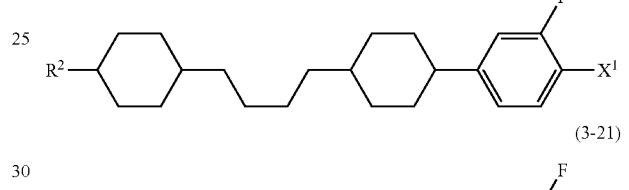
(3-21)
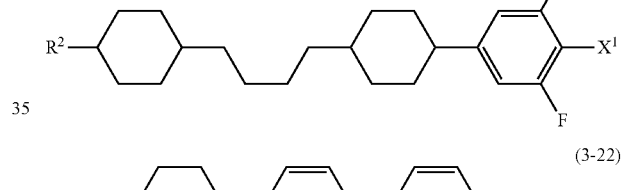
(3-22)
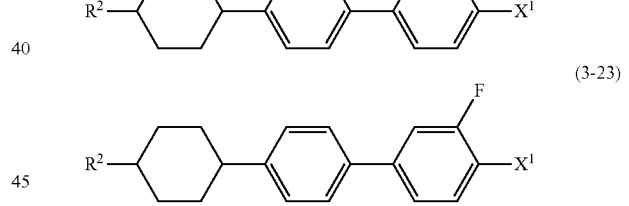
(3-23)
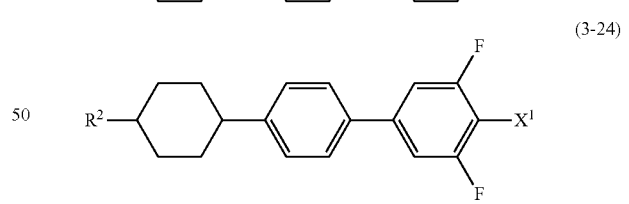
(3-24)
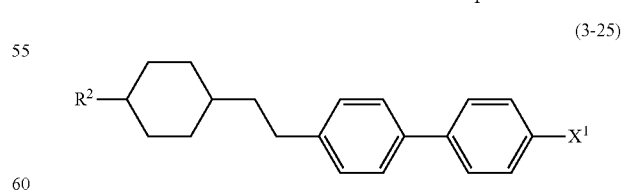
(3-25)
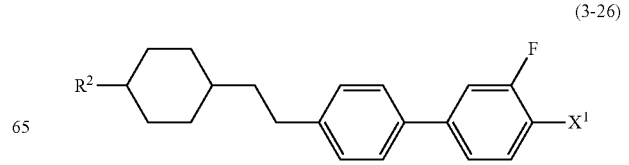
(3-26)

(3-27) 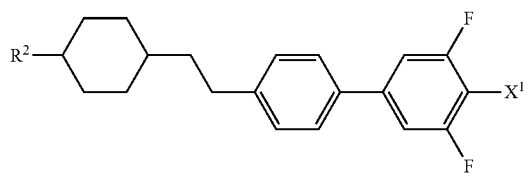
(3-28) 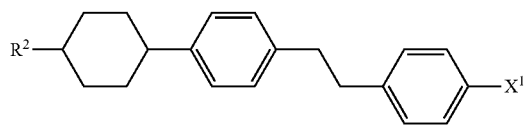
(3-29) 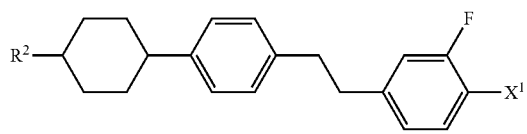
(3-30) 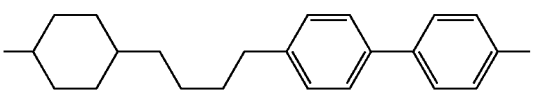
(3-31)
(3-32)
(3-33)
(3-34) 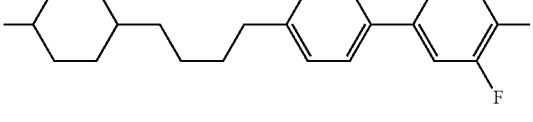
(3-35) 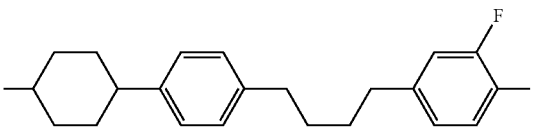
(3-36) 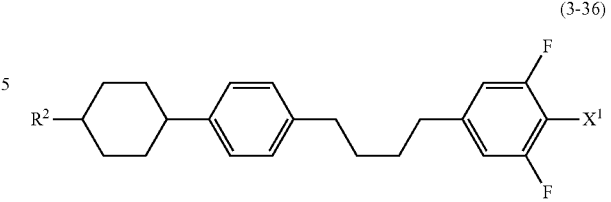
(3-37) 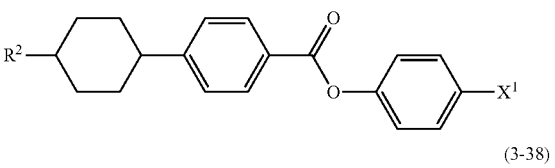
(3-38) 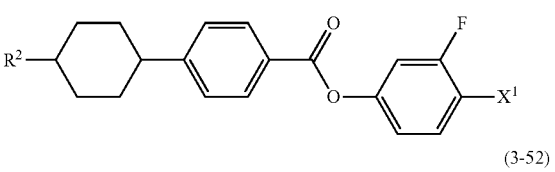
(3-52) 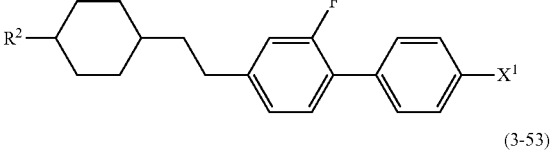
(3-53) 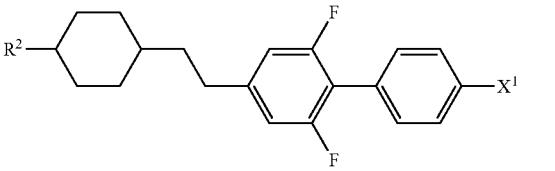
(3-39) 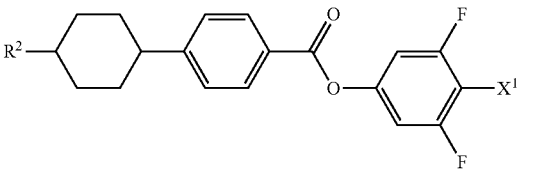
(3-40) 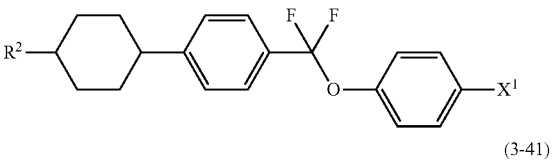
(3-41) 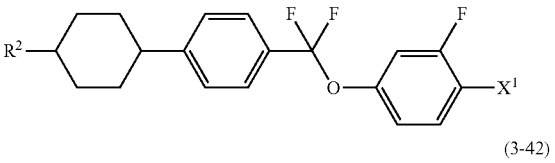
(3-42) 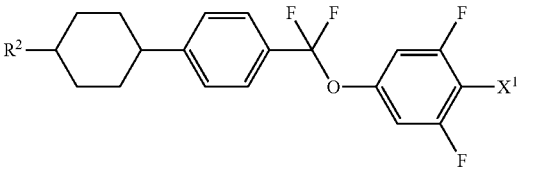

-continued
(3-43)
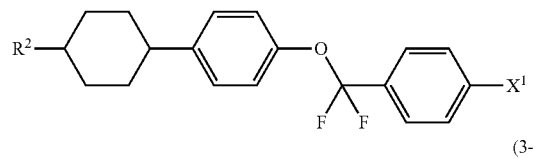
(3-44)
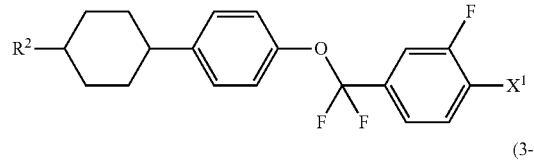
(3-45)
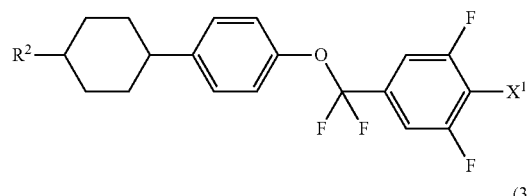
(3-46)
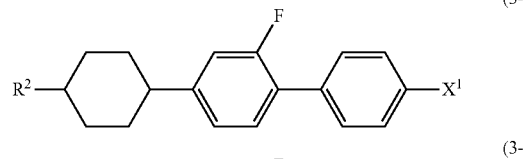
(3-47)
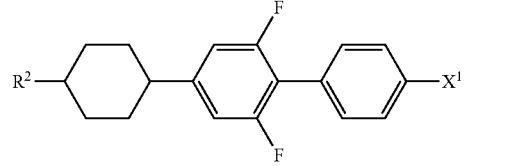
(3-48)
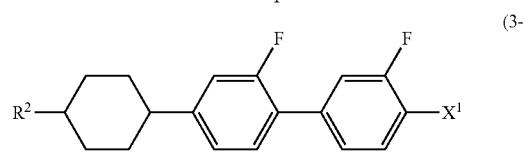
(3-49)
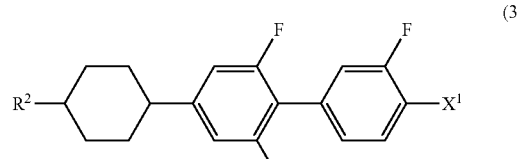
(3-50)
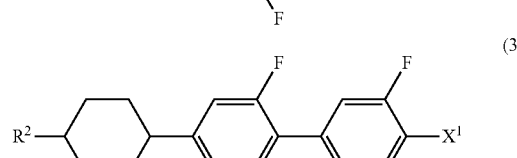
(3-51)
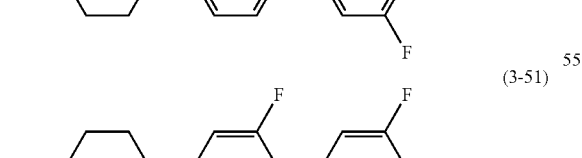
(3-64)
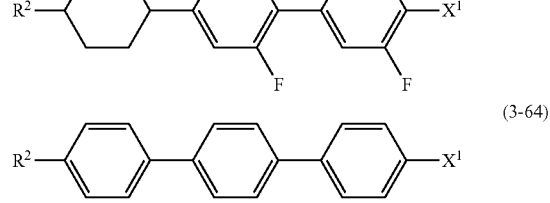
-continued
(3-65)
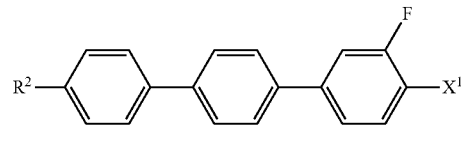
(3-54)
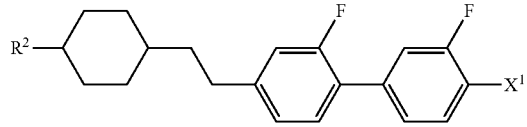
(3-55)
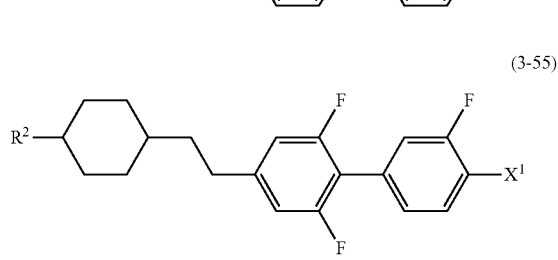
(3-56)
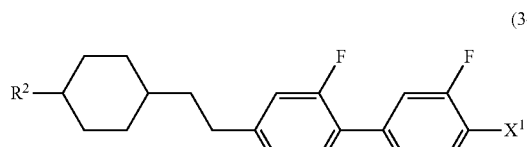
(3-57)
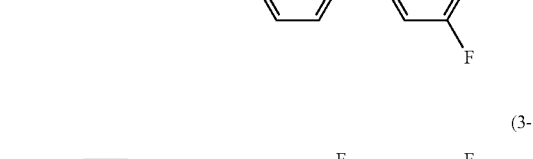
(3-58)
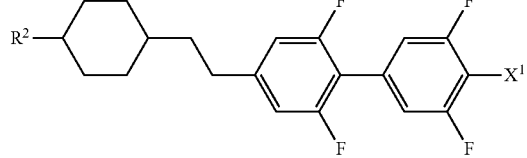
(3-59)
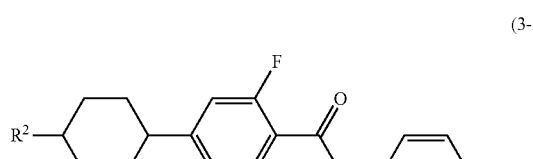
(3-60)
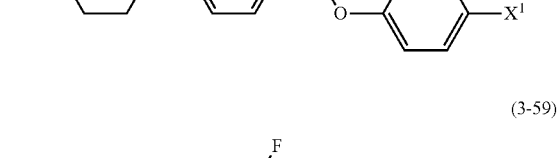

(3-61)
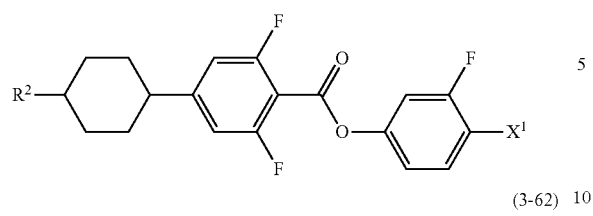
(3-62)
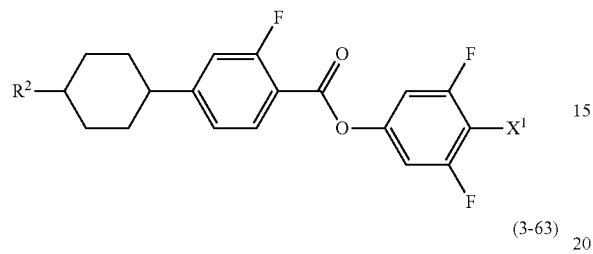
(3-63)
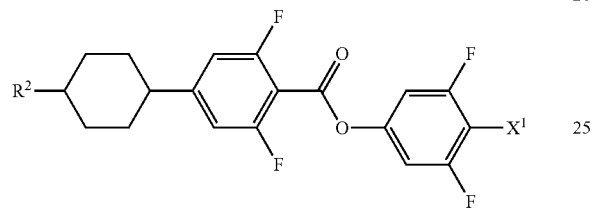
(3-77)
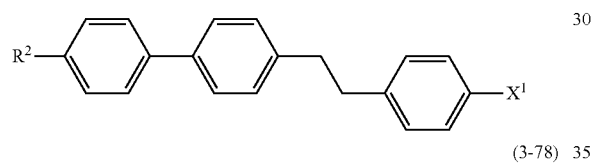
(3-78)
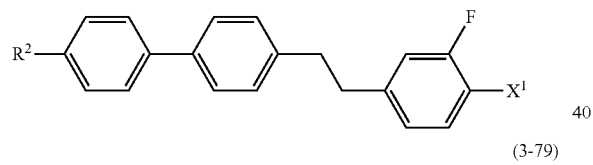
(3-79)
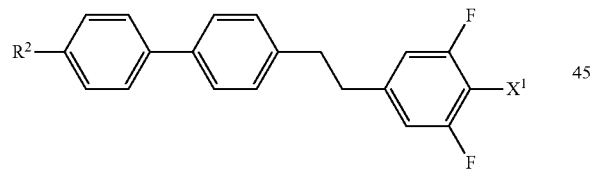
(3-80)
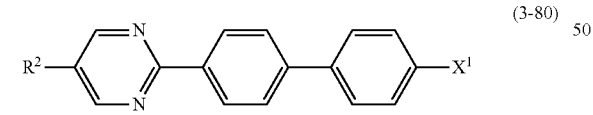
(3-81)
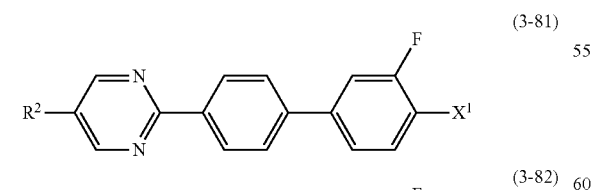
(3-82)
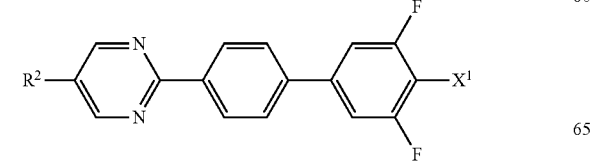
(3-83)
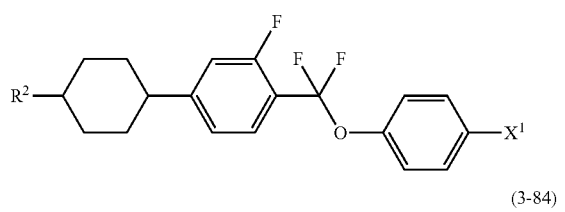
(3-84)
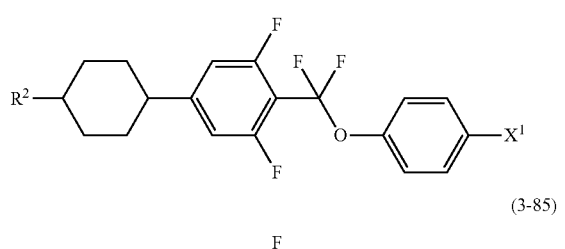
(3-85)
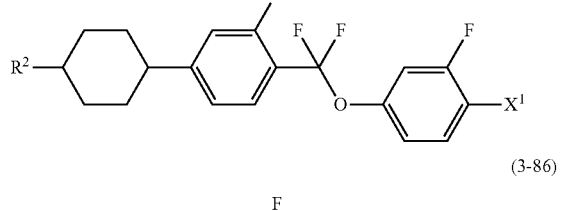
(3-86)
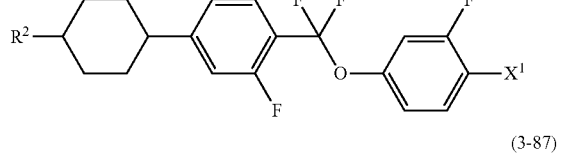
(3-87)
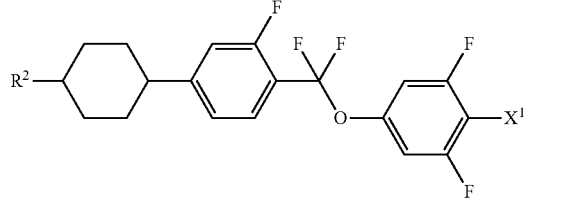
(3-88)
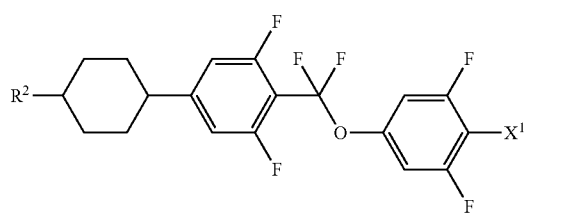
(3-66)
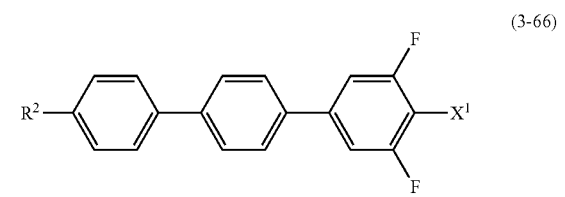
(3-67)
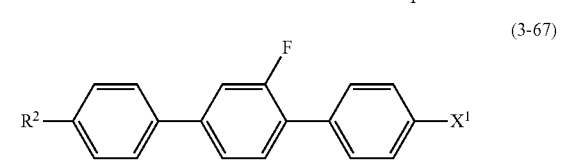

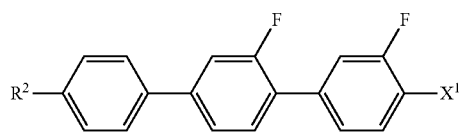
(3-68)
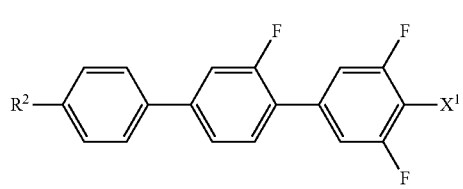
(3-69)
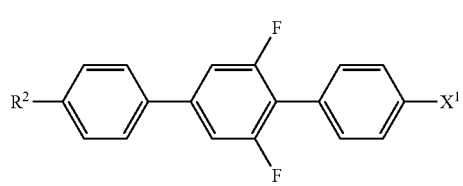
(3-70)
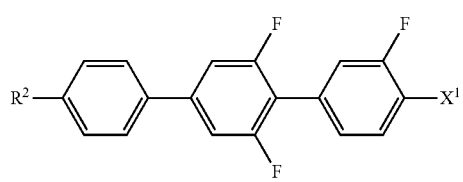
(3-71)
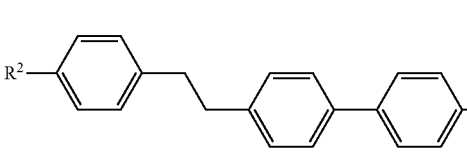
(3-72)
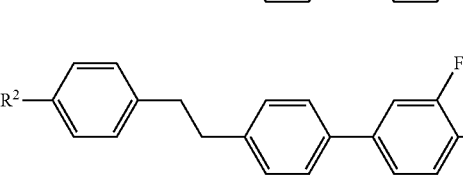
(3-73)
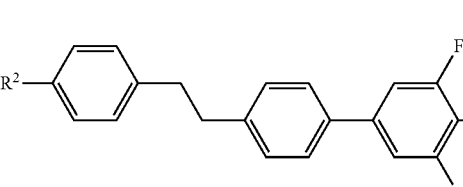
(3-74)
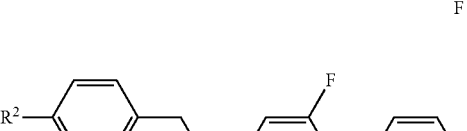
(3-75)
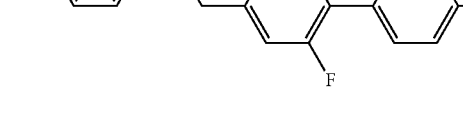
(3-76)
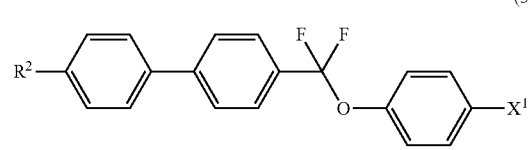
(3-89)
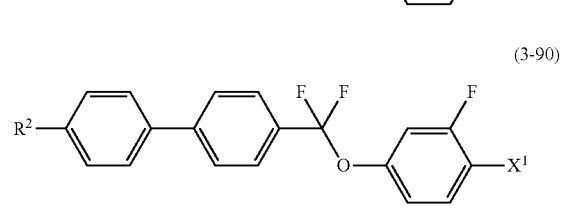
(3-90)
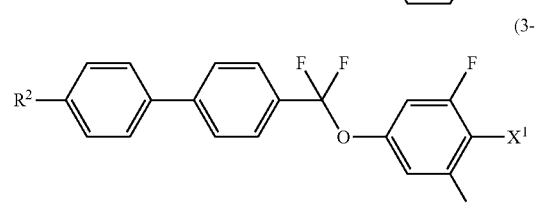
(3-91)
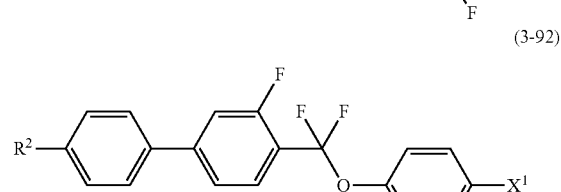
(3-92)
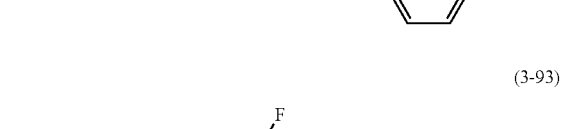
(3-93)
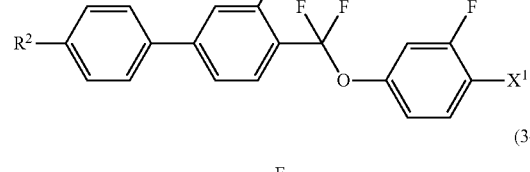
(3-94)
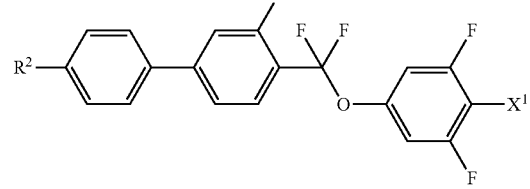
(3-95)
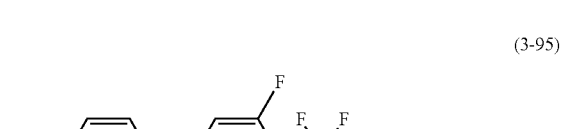
(3-96)
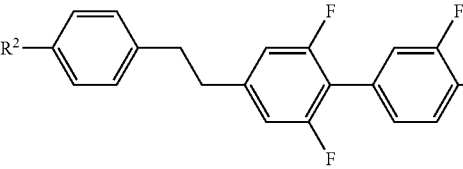

(3-97) 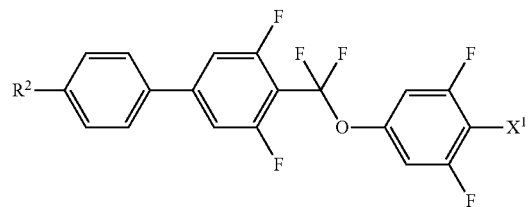
(3-98) 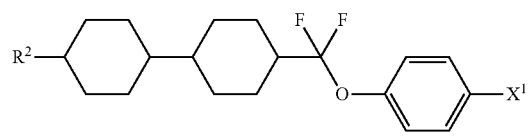
(3-99) 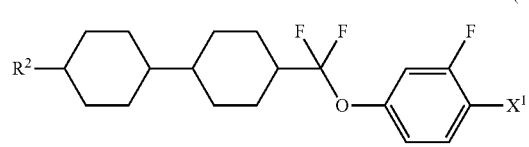
(3-100) 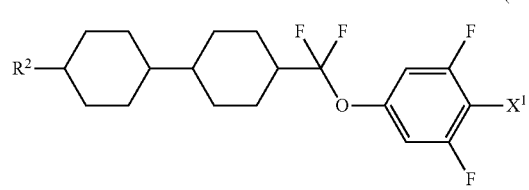
(3-101) 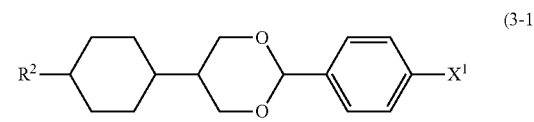
(3-102) 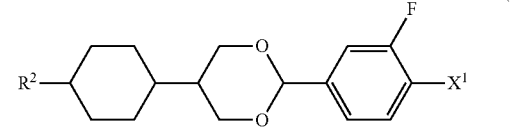
(3-103) 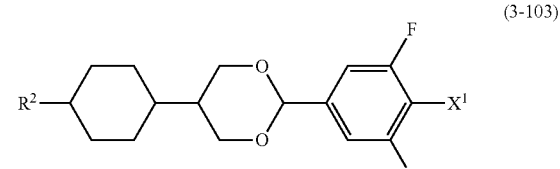
(3-104) 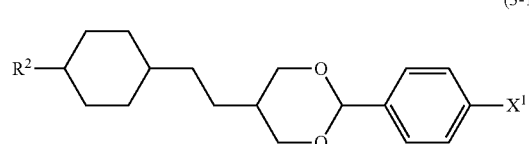
(3-105) 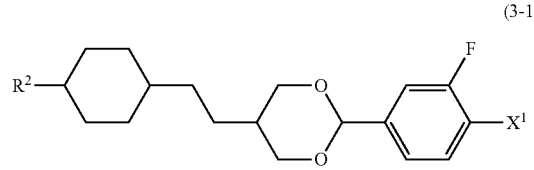
(3-106) 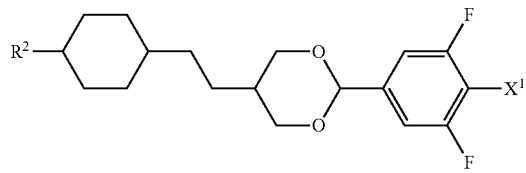
(3-107) 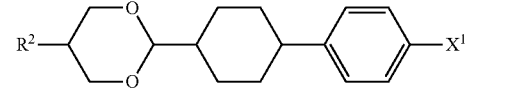
(3-108) 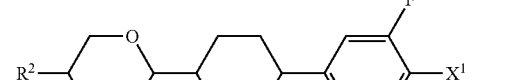
(3-109) 
(3-110) 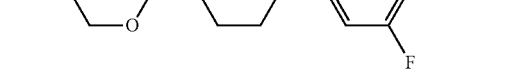
(3-111) 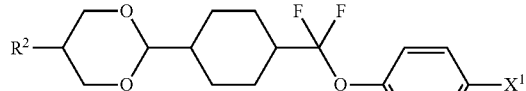
(3-112) 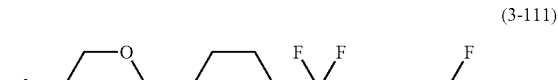
(4-1) 
(4-2) 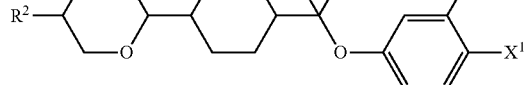
(4-3) 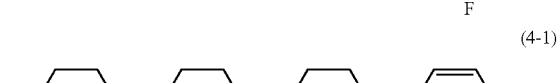

(4-4)
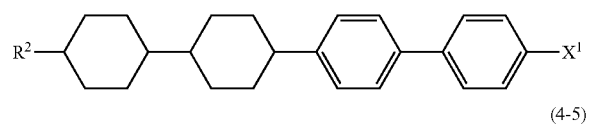
(4-5)
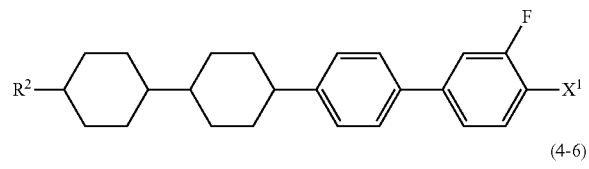
(4-6)
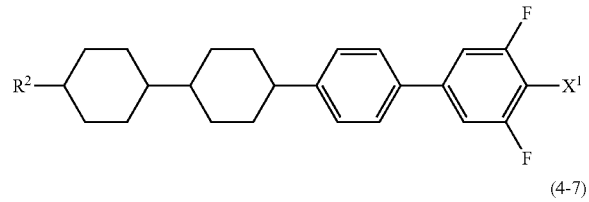
(4-7)
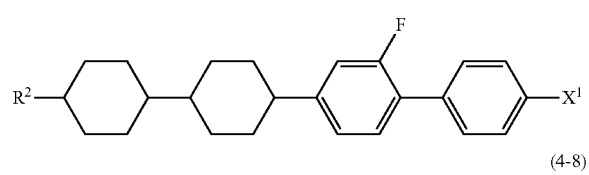
(4-8)
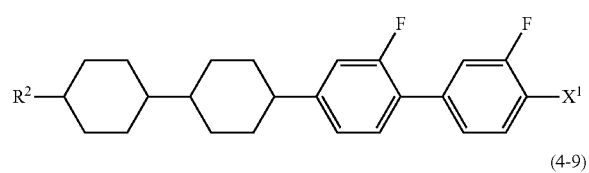
(4-9)
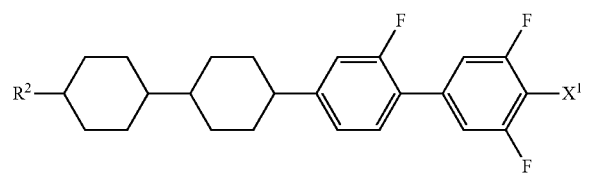
(4-10)
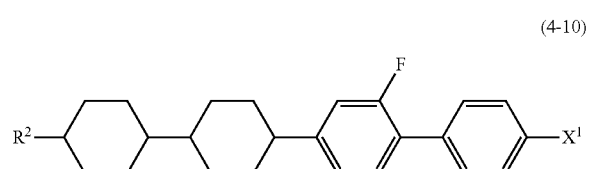
(4-11)
(4-12)
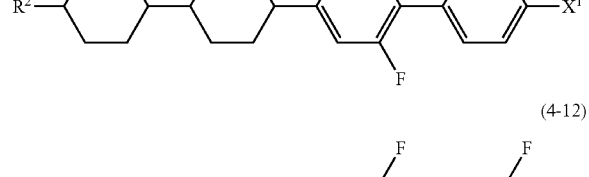
(4-13)
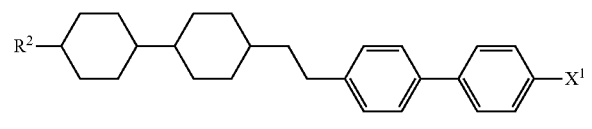
(4-14)
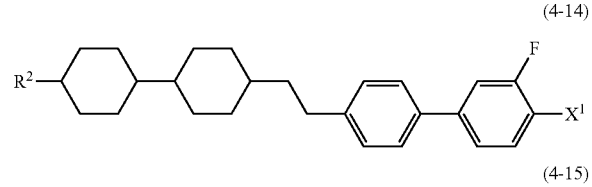
(4-15)
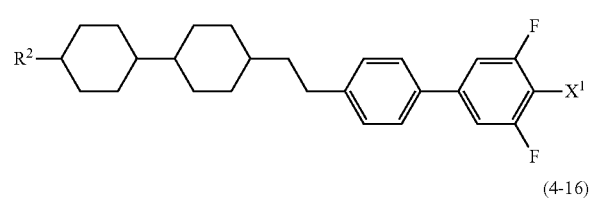
(4-16)
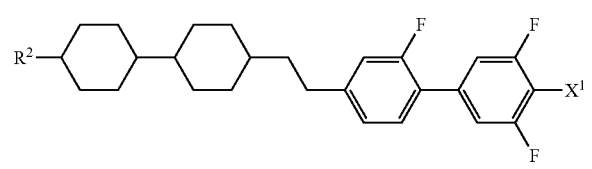
(4-17)
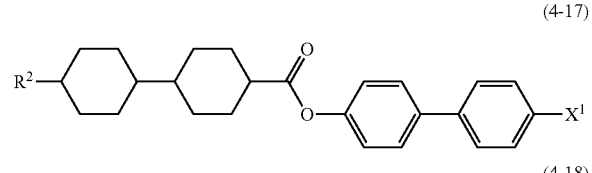
(4-18)
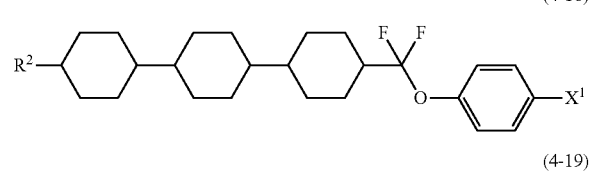
(4-19)
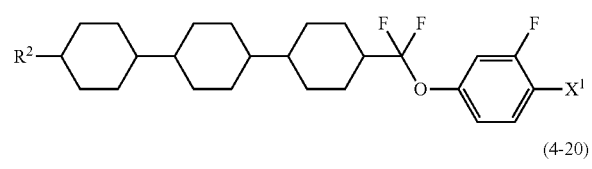
(4-20)
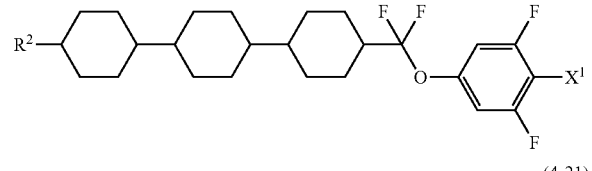
(4-21)
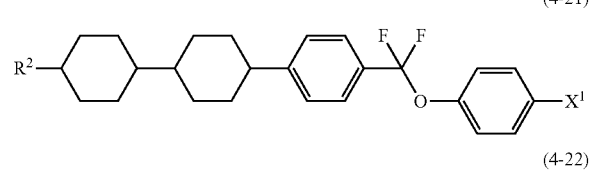
(4-22)
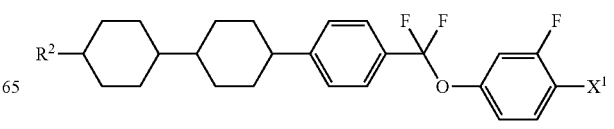

(4-23) 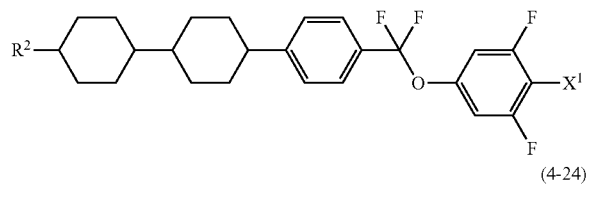
(4-24) 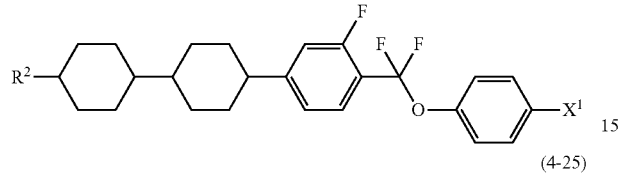
(4-25) 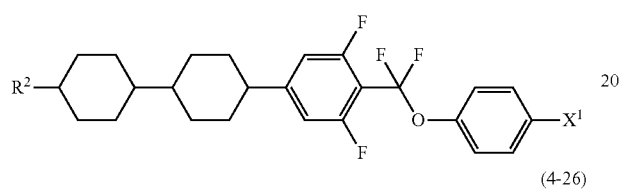
(4-26) 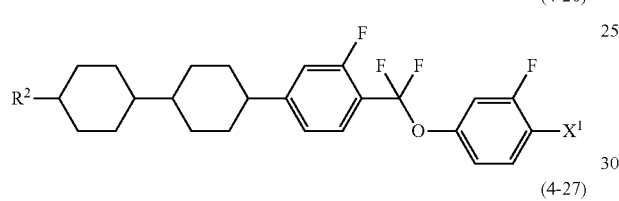
(4-27) 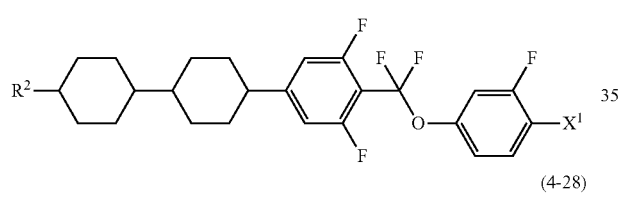
(4-28) 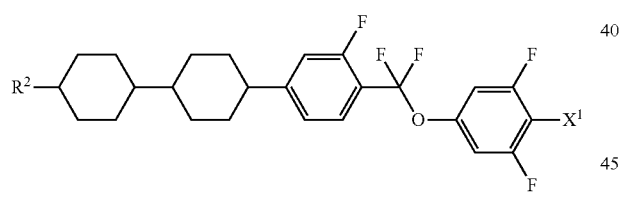
(4-29) 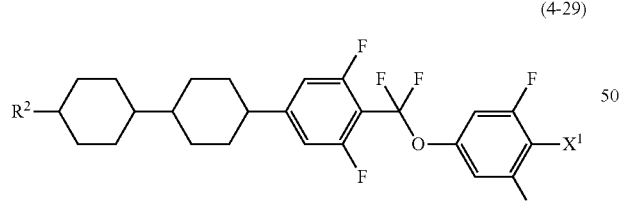
(4-30) 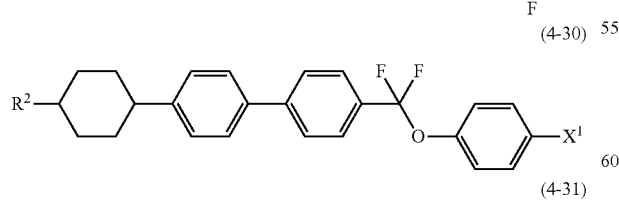
(4-31)
(4-32) 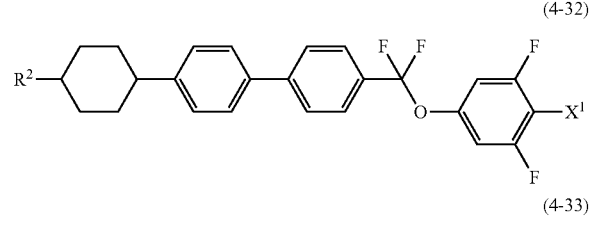
(4-33) 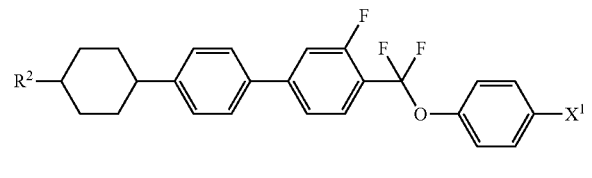
(4-34) 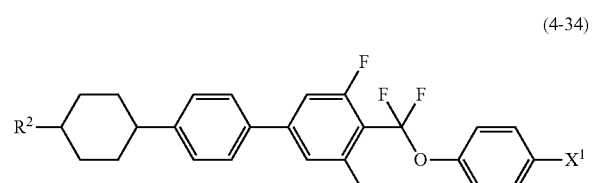
(4-35) 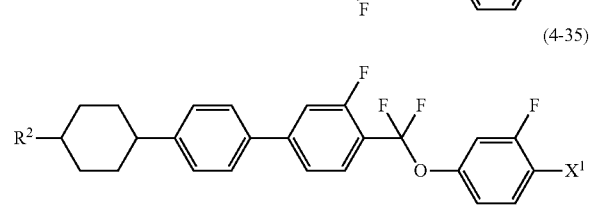
(4-36) 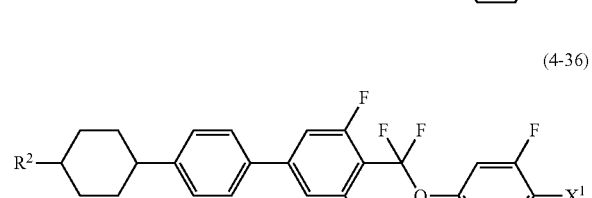
(4-37) 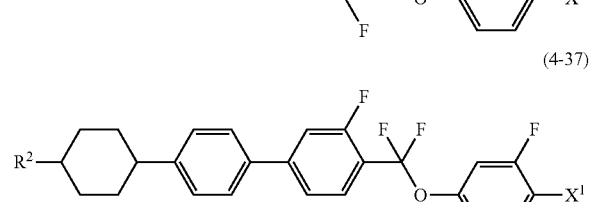
(4-38) 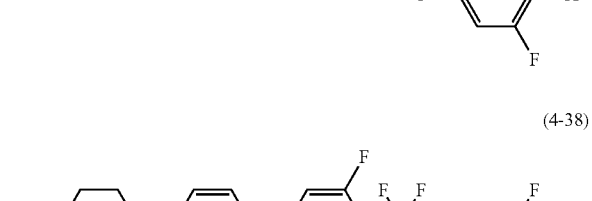
(4-39) 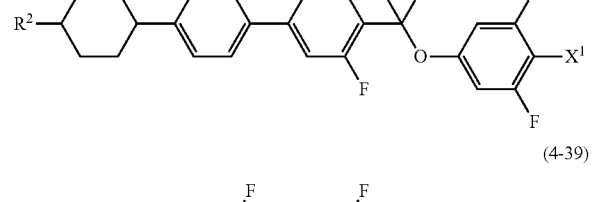

(4-40)
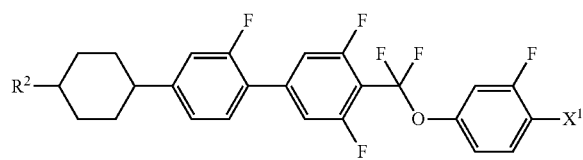

(4-41)
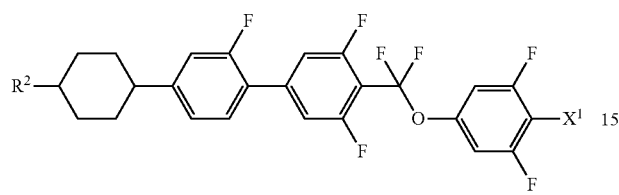

(4-42)
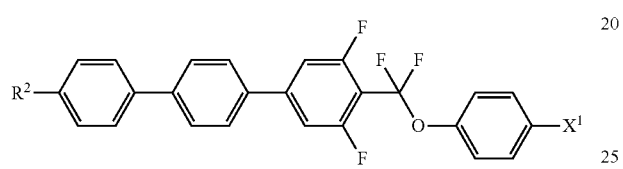

(4-43)
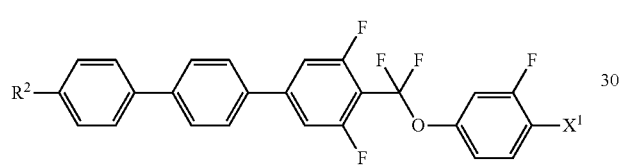

(4-44)
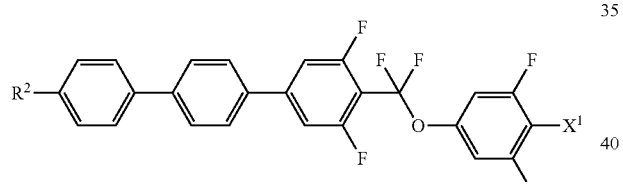

(4-45)
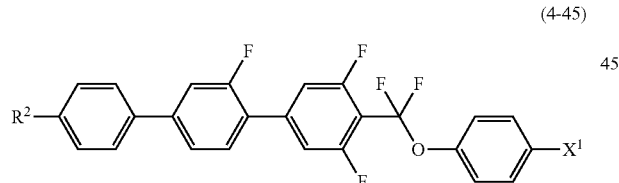

(4-46)
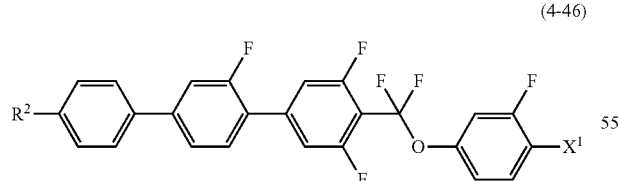

(4-47)
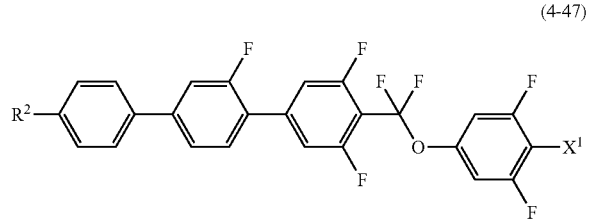

(4-48)
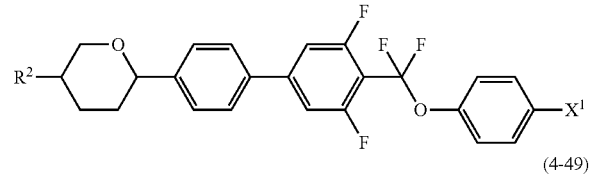

(4-49)
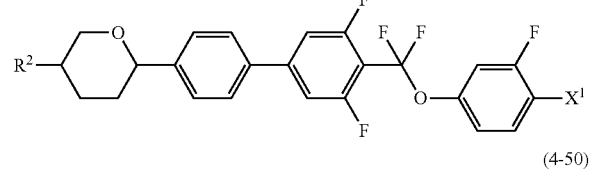

(4-50)
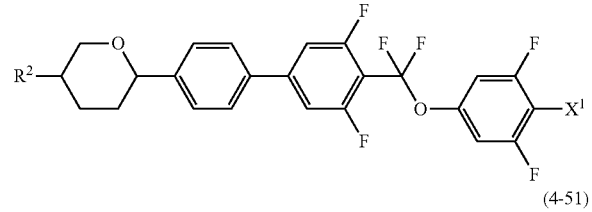

(4-51)
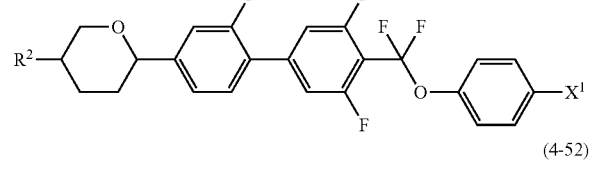

(4-52)
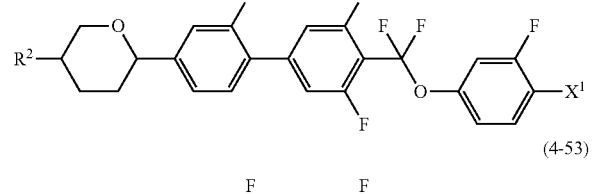

(4-53)
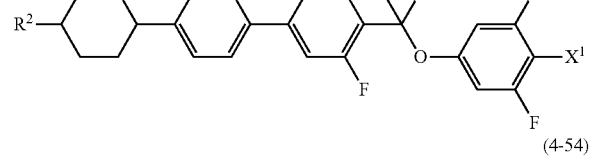

(4-54)
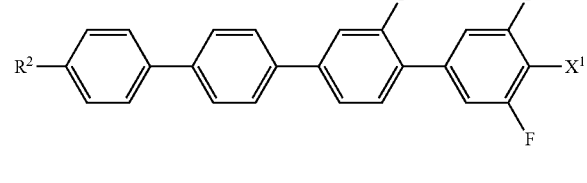

In these compounds (component B), $R^2$ and $X^1$ are defined as above.

As having a positive dielectric anisotropy and very good stability to heat and light, etc., compound B is used in cases of preparing a composition for use in the TFT mode or PSA mode. The content of compound B is suitably in the range of 1 to 99 wt %, preferably in the range of 10 to 97 wt %, and more preferably in the range of 40 to 95 wt %, based on the total weight of the composition. The composition can be further added with component E [including compounds (12), (13) and (14)] in order to adjust the viscosity.

Component C includes compounds of formula (5) having a right terminal group being —C≡N or —C≡C—C≡N (one of the terminals is a cyano-containing group bonded to the benzene ring). Preferred examples of component C may include compounds (5-1) to (5-64).
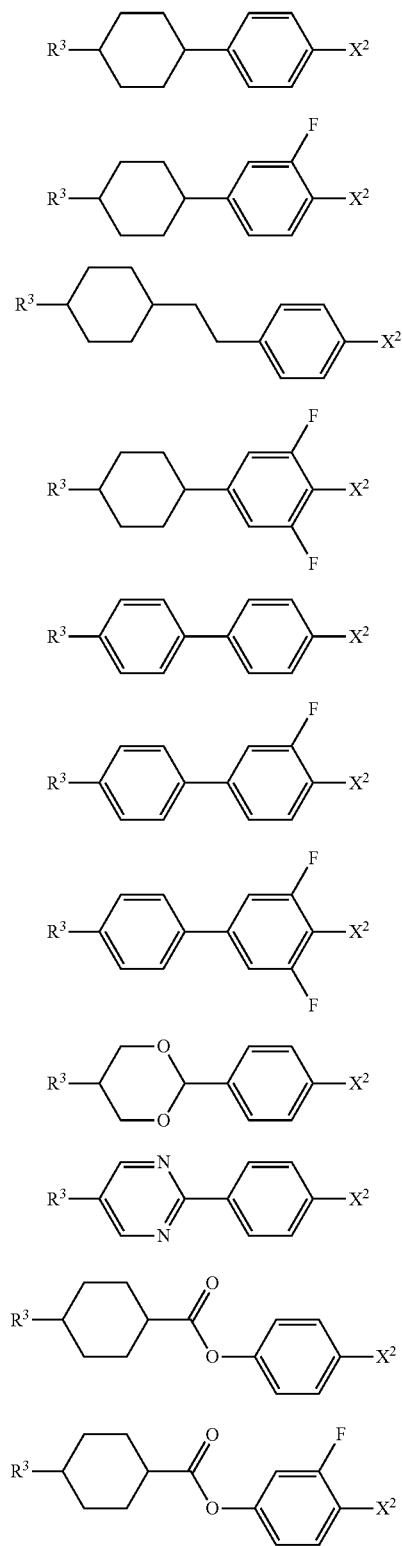
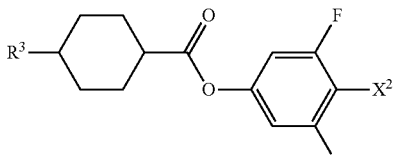  (5-12)
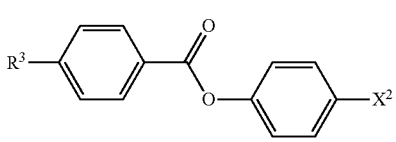  (5-13)
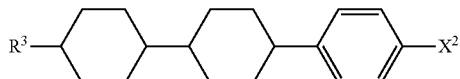  (5-28)
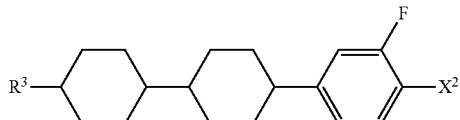  (5-29)
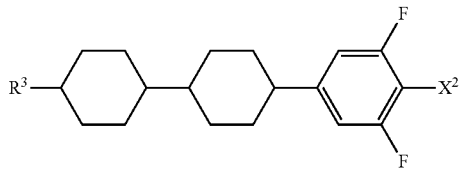  (5-30)
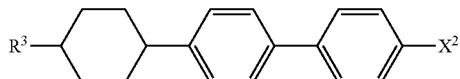  (5-31)
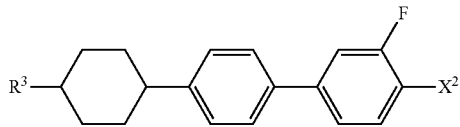  (5-32)
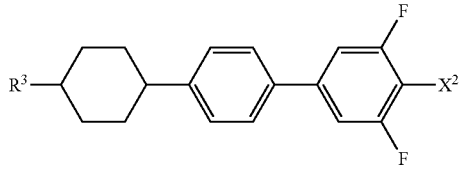  (5-33)
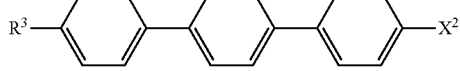  (5-34)
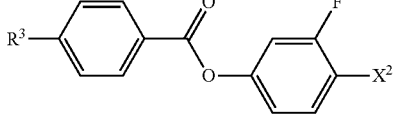  (5-14)
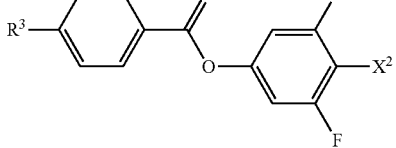  (5-15)

-continued
(5-16) 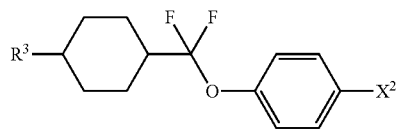
(5-17) 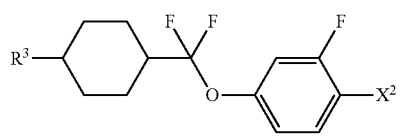
(5-18) 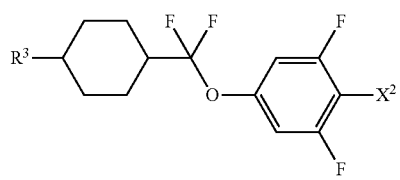
(5-19) 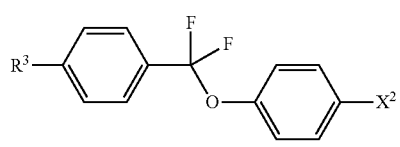
(5-20) 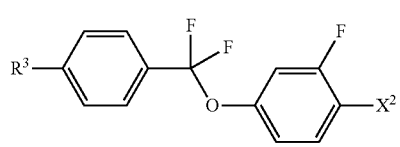
(5-21) 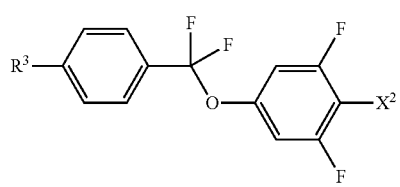
(5-22) 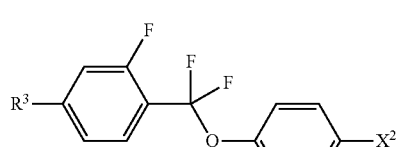
(5-23) 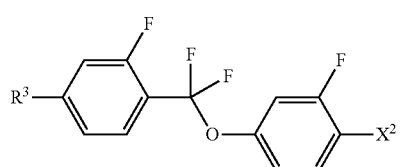
(5-24) 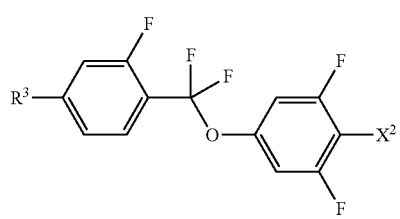
-continued
(5-25) 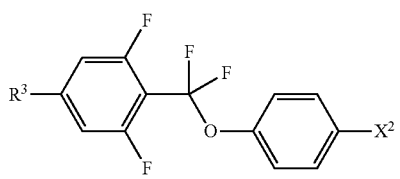
(5-26) 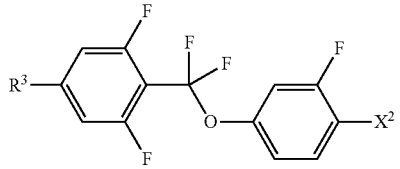
(5-27) 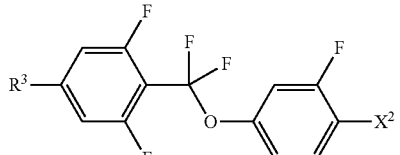
(5-38) 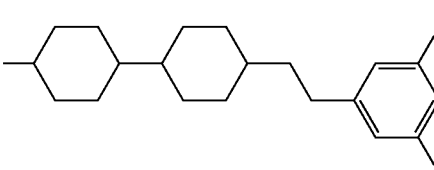
(5-39) 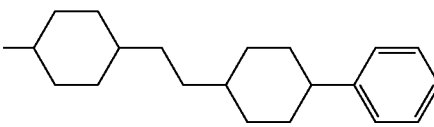
(5-40) 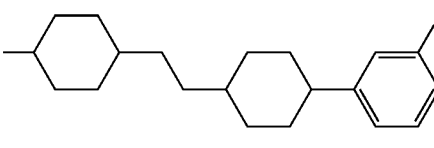
(5-41) 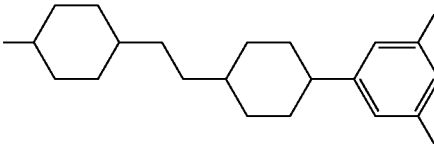
(5-42) 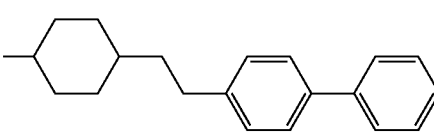
(5-43) 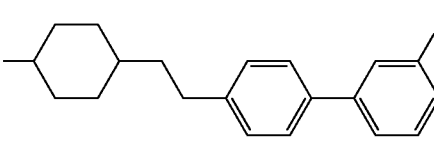

(5-44)
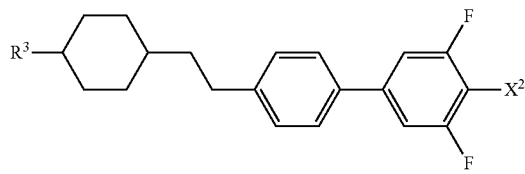
(5-35)
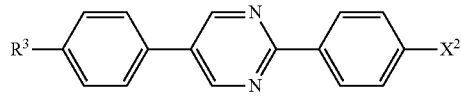
(5-36)
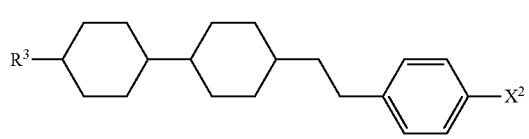
(5-37)
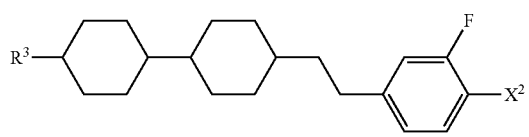
(5-50)
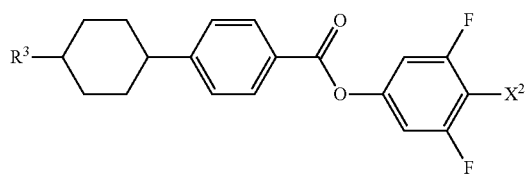
(5-51)
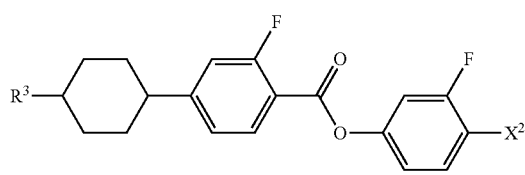
(5-52)
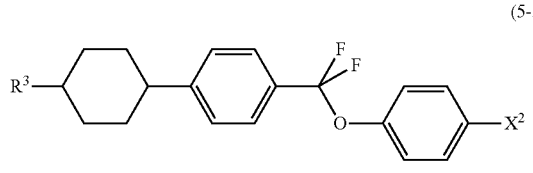
(5-53)
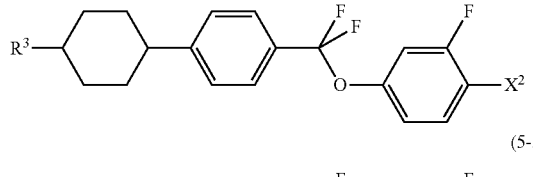
(5-54)
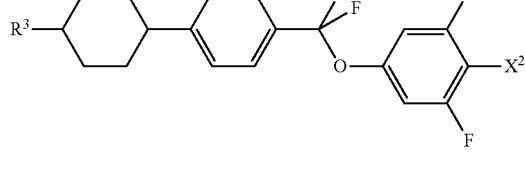
(5-55)
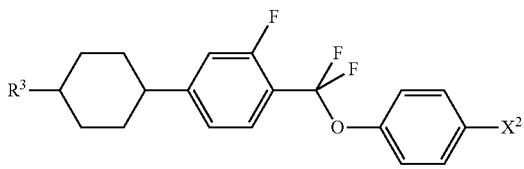
(5-56)
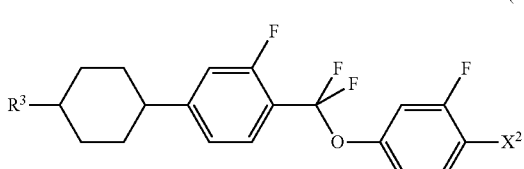
(5-57)
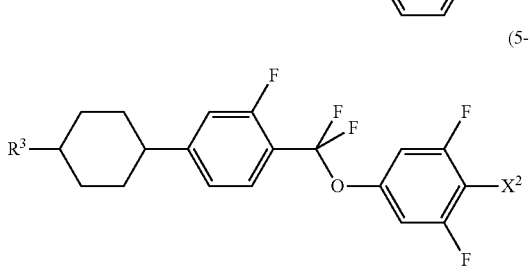
(5-45)
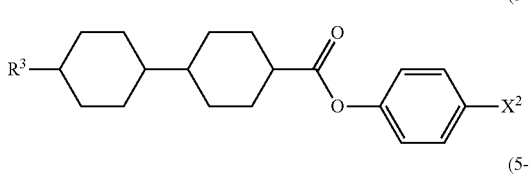
(5-46)
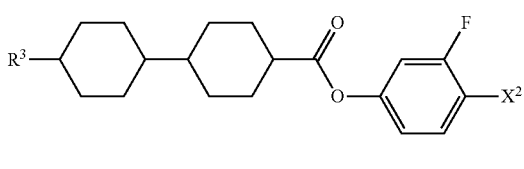
(5-47)
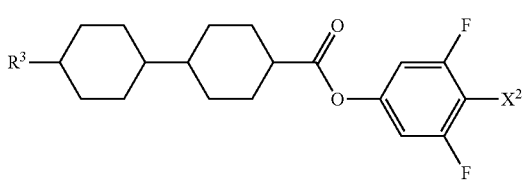
(5-48)
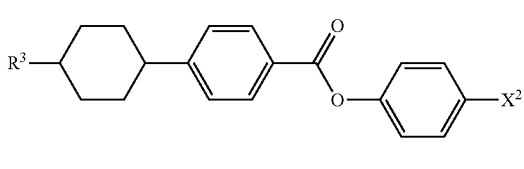
(5-49)
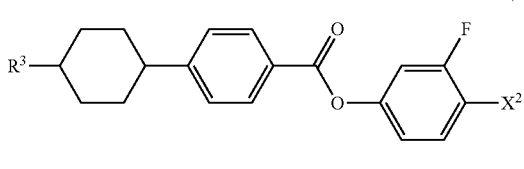

-continued

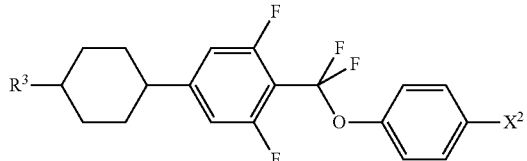
(5-58)

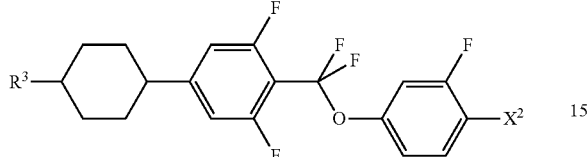
(5-59)

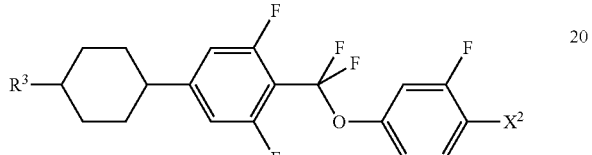
(5-60)

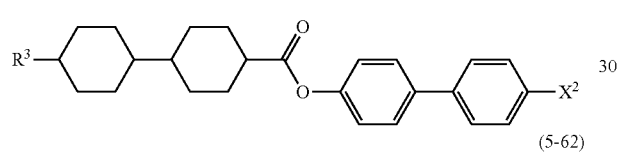
(5-61)

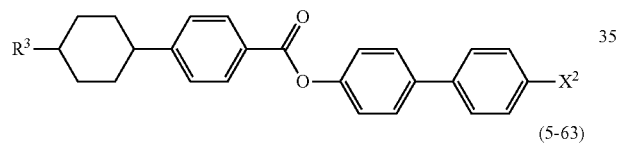
(5-62)

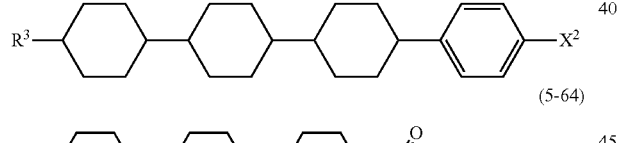
(5-63)

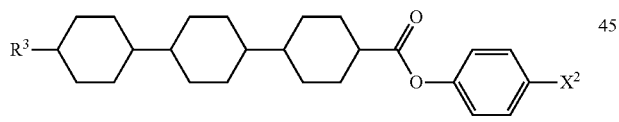
(5-64)

In these compounds (component C), $R^3$ and $X^2$ are defined as above.

As having a large positive dielectric anisotropy, compound C is used mainly in cases of preparing a composition for use in the STN mode, TN mode or PSA mode. By adding component C, the dielectric anisotropy of the composition can be increased. Component C has the effect of broadening the temperature range of liquid crystal phase, adjusting the viscosity, or adjusting the optical anisotropy. Component C is also useful in adjusting the voltage-transmittance curve of the element.

In preparing a composition for use in the STN mode or TN mode, the content of component C is suitably in the range of 1 to 99 wt %, preferably in the range of 10 to 97 wt %, and more preferably in the range of 40 to 95 wt %, based on the total weight of the composition. By adding component C in the composition, the temperature range of liquid crystal phase, viscosity, optical anisotropy, dielectric anisotropy and so on can be adjusted.

Component D includes compounds (6), (7), (8), (9), (10) and (11). These compounds have a benzene ring being halogen-substituted at two lateral positions, e.g., 2,3-difluoro-1,4-phenylene.

Preferred examples of component D include compounds (6-1) to (6-6), compounds (7-1) to (7-15), compound (8-1), compounds (9-1) to (9-3), compounds (10-1) to (10-11) and compounds (11-1) to (11-10).

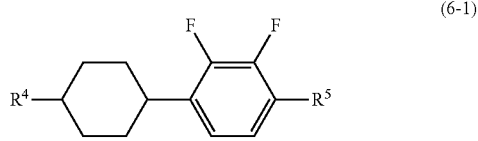
(6-1)

(6-2)

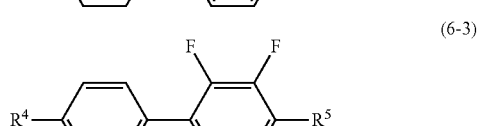
(6-3)

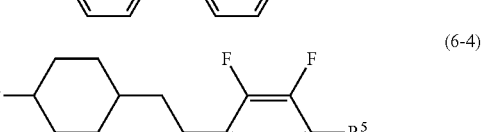
(6-4)

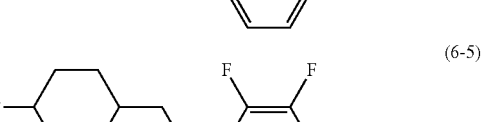
(6-5)

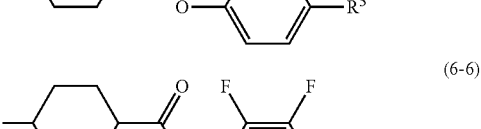
(6-6)

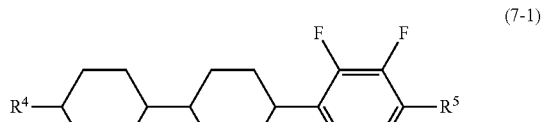
(7-1)

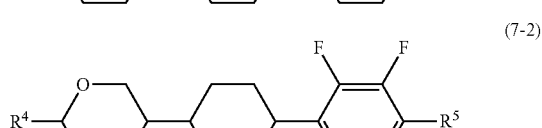
(7-2)

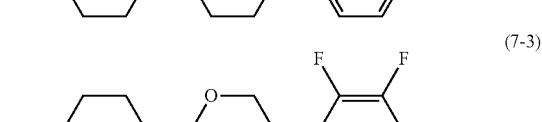
(7-3)

-continued
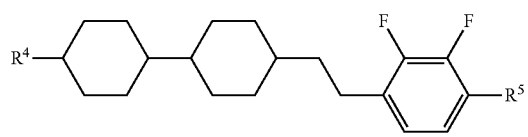 (7-4)
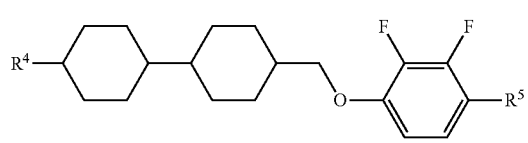 (7-5)
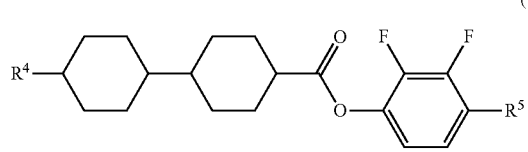 (7-6)
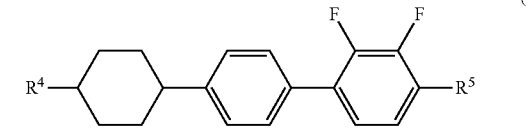 (7-7)
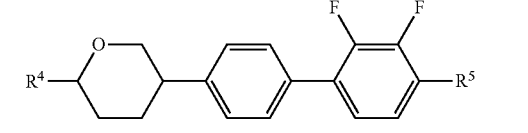 (7-8)
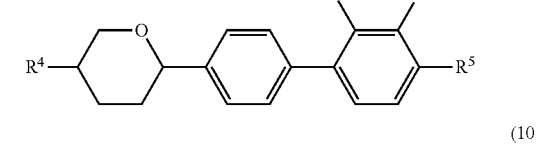 (7-9)
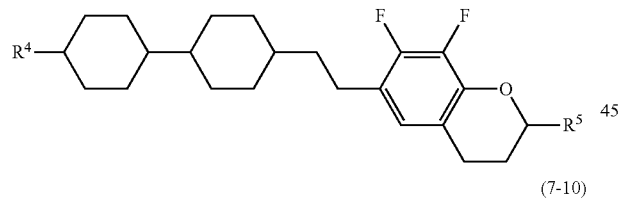 (10-5)
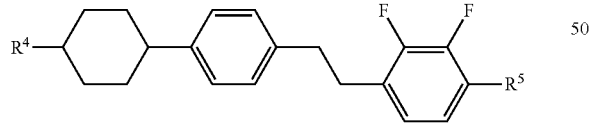 (7-10)
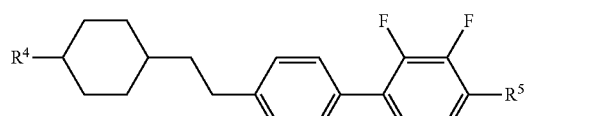 (7-11)
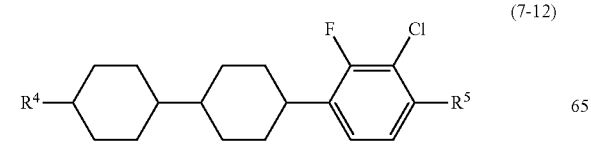 (7-12)
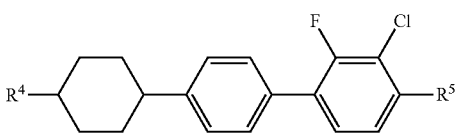 (7-13)
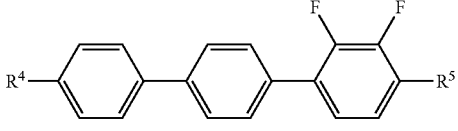 (7-14)
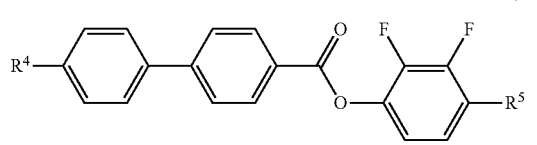 (7-15)
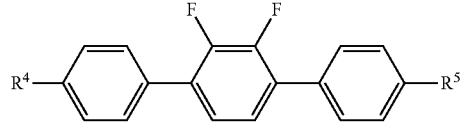 (8-1)
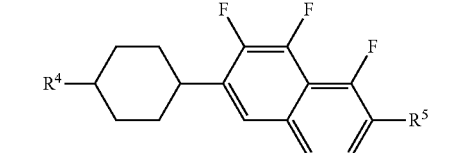 (9-1)
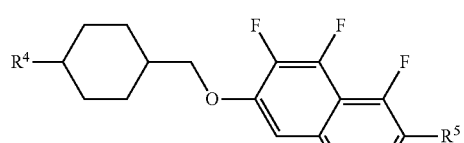 (9-2)
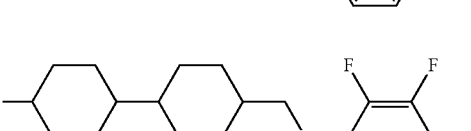 (9-3)
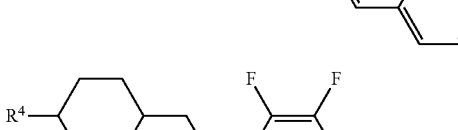 (10-1)
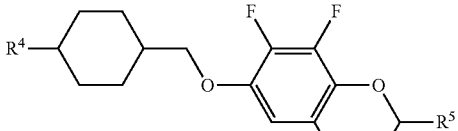 (10-2)
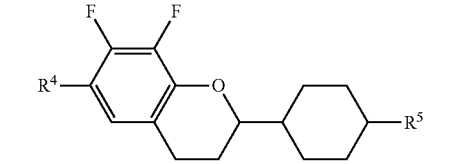 (10-3)

(10-4)
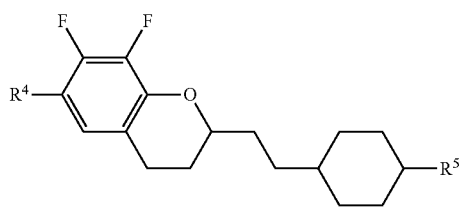
(11-2)
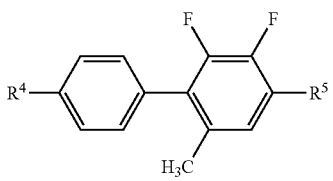
(11-1)
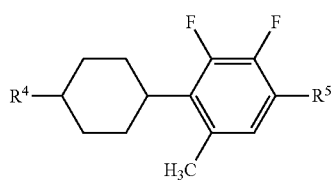
(11-3)
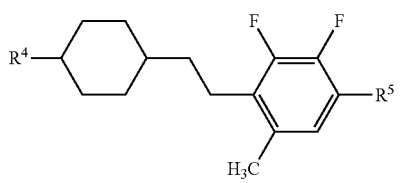
(10-6)
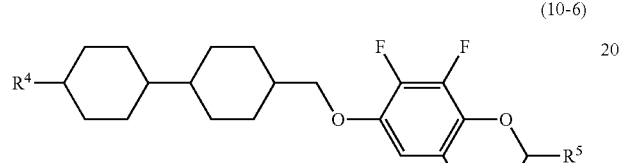
(11-4)
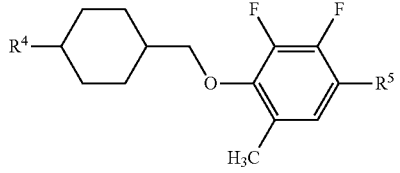
(10-7)
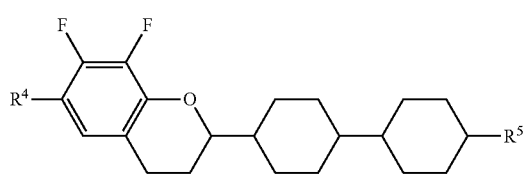
(11-5)
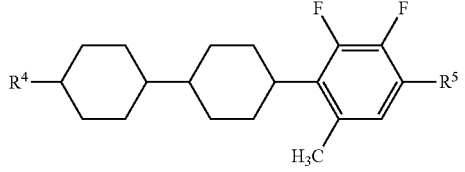
(10-8)
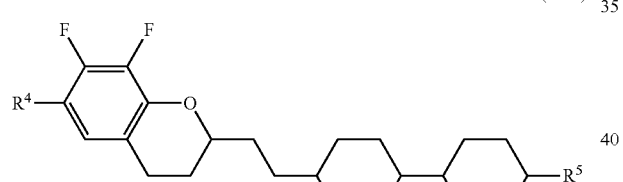
(11-6)
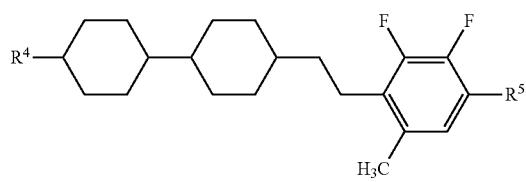
(10-9)
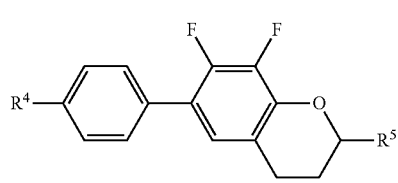
(11-7)
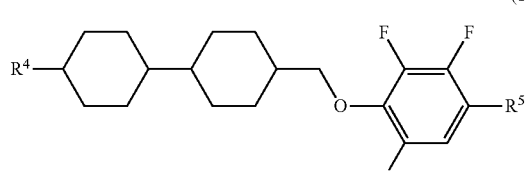
(10-10)
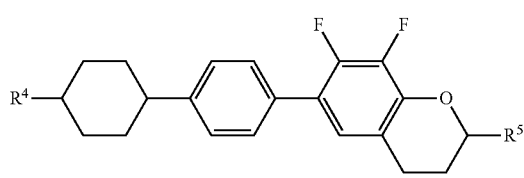
(11-8)
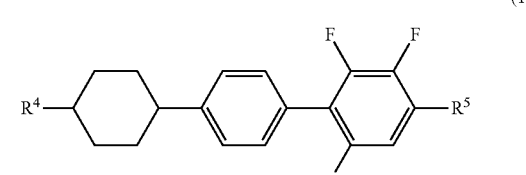
(10-11)
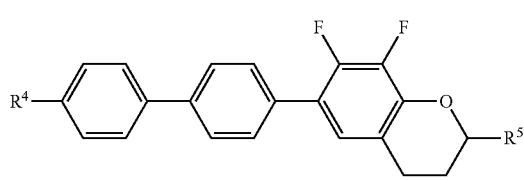
(11-9)
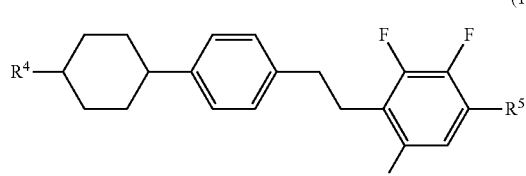

(11-10)

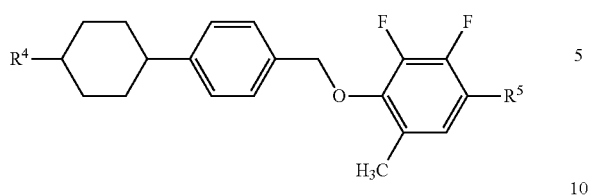

In these compounds (component D), $R^4$ and $R^5$ are defined as above.

A compound of component D has a negative dielectric anisotropy. Component D is used mainly in cases of preparing a composition for use in the VA mode or PSA mode. By increasing the content of component D, the dielectric anisotropy of the composition is increased, but the viscosity is increased. Hence, as long as the required value of the dielectric anisotropy is satisfied, component D is preferably contained in a less amount. Therefore, in consideration of allowing the absolute value of the dielectric anisotropy to reach about 5, the content is preferably not less than 40 wt % for sufficient voltage driving.

In component D, compound (6) is a 2-ring compound, and hence mainly has the effect of adjusting the viscosity, adjusting the optical anisotropy, or adjusting the dielectric anisotropy. Compound (7) and (8) are 3-ring compounds, and hence has the effect of raising the maximum temperature, increasing the optical anisotropy, or increasing the dielectric anisotropy. Compound (9), (10) and (11) have the effect of increasing the dielectric anisotropy.

In preparing a composition for use in the VA mode or PSA mode, the content of component D is preferably not less than 40 wt %, and more preferably in the range of 50 to 95 wt %, based on the total weight of the composition. By adding component D, it is possible to adjust the elastic constant of the composition or adjust the voltage-transmittance curve of the element. In cases where component D is added in a composition having a positive dielectric anisotropy, the content of component D is preferably not more than 30 wt % based on the total weight of the composition.

Component E includes compounds of which the two terminal groups being alkyl. Preferred examples of component E include compounds (12-1) to (12-11), compounds (13-1) to (13-19), and compounds (14-1) to (14-6).

(12-1)

(12-2)

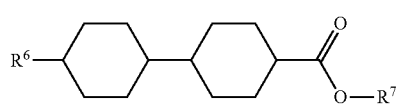

(12-3)

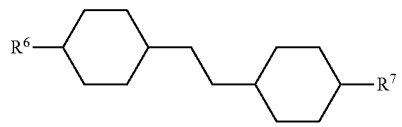

(12-4)

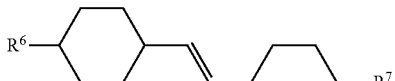

(12-5)

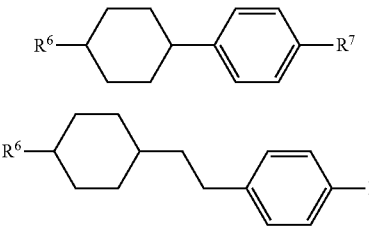

(12-6)

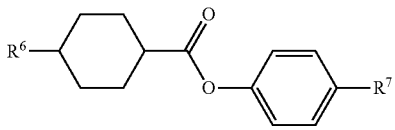

(12-7)

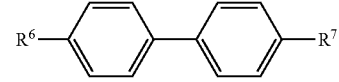

(12-8)

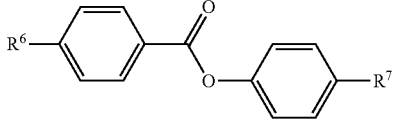

(12-9)

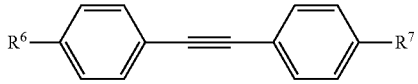

(12-10)

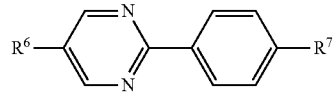

(12-11)

(13-1)

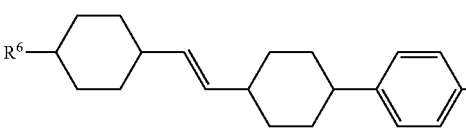

(13-2)

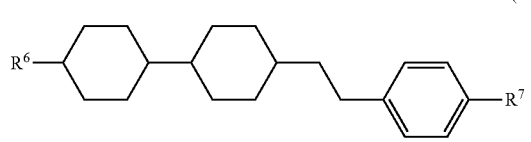

(13-3)

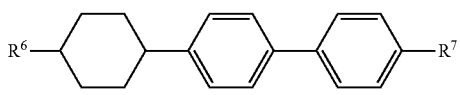

(13-4)

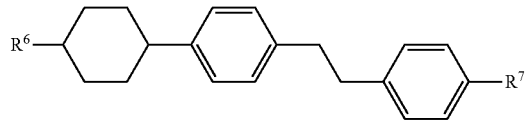

(13-5)

(13-6)
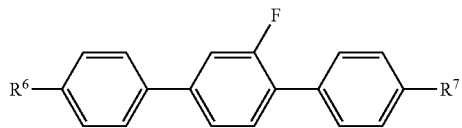
(13-7)
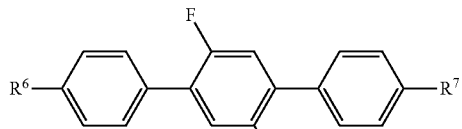
(13-8)
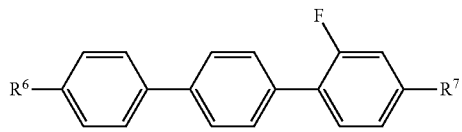
(13-9)
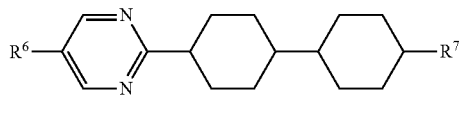
(13-10)
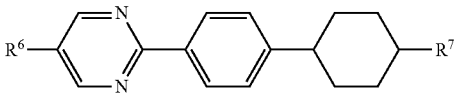
(13-11)
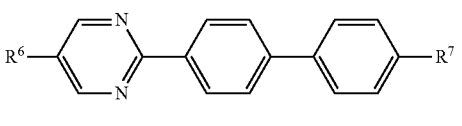
(13-12)
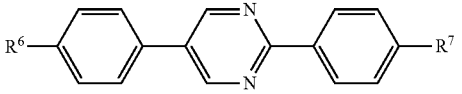
(13-13)
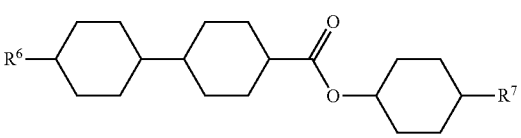
(13-14)
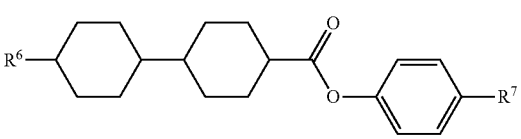
(13-15)
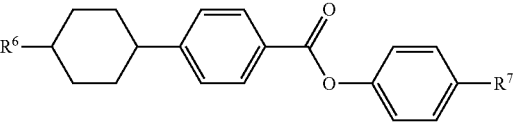
(13-16)
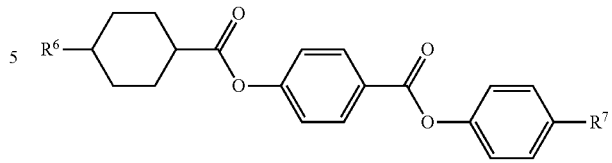
(13-17)
(13-18)
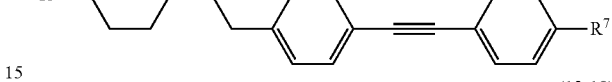
(13-19)
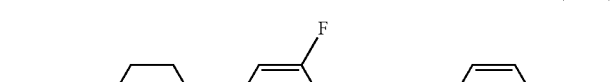
(14-1)
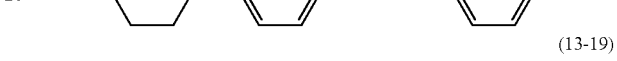
(14-2)
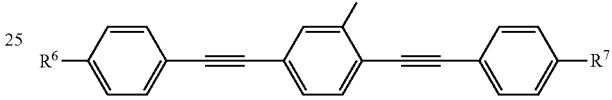
(14-3)
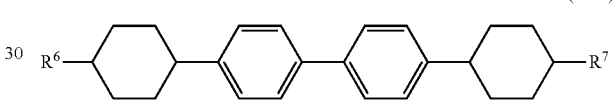
(14-4)
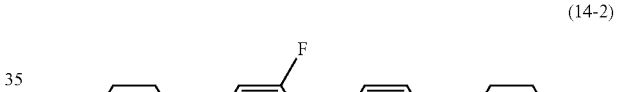
(14-5)
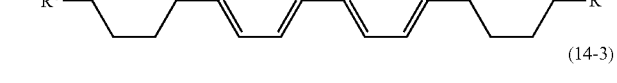
(14-6)
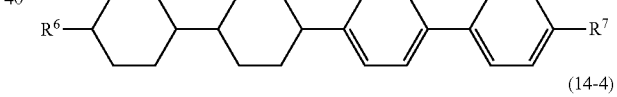
In these compounds (component E), $R^6$ and $R^7$ are defined as above.
Component E has a small absolute value of dielectric anisotropy, hence being a nearly neutral compound. Compound (12) is effective mainly in adjusting the viscosity or the optical anisotropy. Compounds (13) and (14) are effective in broadening the temperature range of the nematic phase by increasing the maximum temperature, or adjusting the optical anisotropy.

When the content of component E is increased, the viscosity of the composition is decreased, but the dielectric anisotropy is decreased. Hence, as long as a desired value of dielectric anisotropy is made, the content is preferably larger. Therefore, in a case where a composition for use in the VA mode or PSA mode is prepared, the content of component E is preferably not less than 30 wt %, and more preferably not less than 40 wt %, based on the total weight of the composition.

<Preparation of Liquid Crystal Composition>

Composition (1) is prepared by a method of dissolving necessary components at a high temperature, or the like.

According to the application, an additive may be added to the composition. Examples of the additive include an optically active compound, a polymerizable compound, a polymerization initiator, an antioxidant, and a UV absorbent, etc. Such additives are well known to those of ordinary skill in the art, and are described in literatures.

Composition (1) may further contain at least one optically active compound. A well-known chiral dopant could be added as an optically active compound. The chiral dopant is effective in inducing a helical structure in liquid crystal molecules to give a necessary twist angle, thereby preventing a reverse twist. Preferred examples of the chiral dopant include the following optically active compounds (Op-1) to (Op-18).

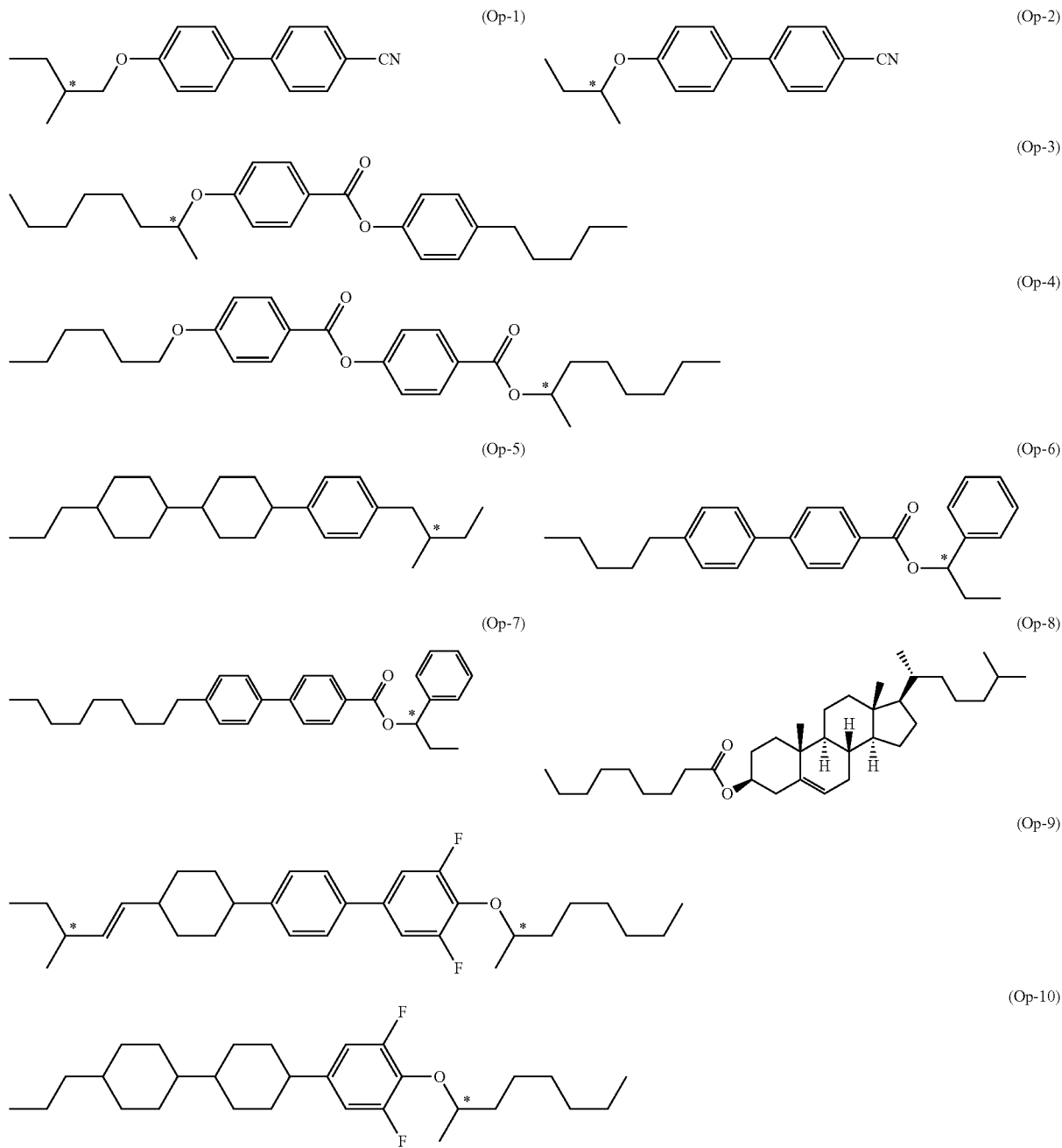

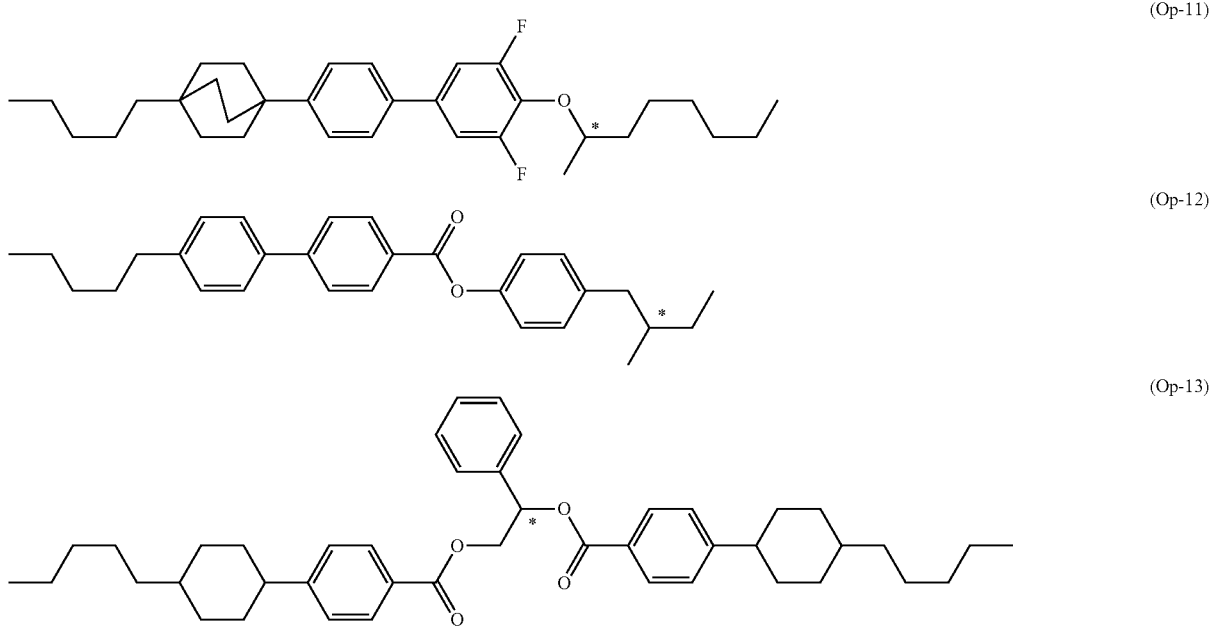

In composition (1), the helical pitch is adjusted by addition of such an optically active compound. The helical pitch is preferably adjusted to the range of 40-200 μm in a composition for the TFT mode and the TN mode. The helical pitch is preferably adjusted to the range of 6 to 20 μm in a composition for the STN mode. In the case of a composition for the BTN mode, the helical pitch is preferably adjusted to the range of 1.5 to 4 μm. Two or more optically active compounds may be added in order to adjust the temperature dependence of the helical pitch.

Composition (1) can also be used for the PSA mode by adding a polymerizable compound. Examples of the polymerizable compound include an acrylate, a methacrylate, a vinyl compound, a vinyloxy compound, propenyl ether, an epoxy compound, a vinyl ketone, and oxetane, etc. The polymerizable compound is preferably polymerized by UV-irradiation or the like in presence of a suitable initiator such as a photopolymerization initiator. Suitable conditions for the polymerization, suitable types of the initiator and suitable amounts thereof are known to those of ordinary skill in the art and are described in literatures.

The antioxidant is effective in maintaining a large voltage holding ratio. Preferred examples of the antioxidant include 2,6-di-t-butyl-4-alkylphenol, etc. The UV absorbeent is effective in preventing lowering of the maximum temperature. Preferred examples of the UV absorbent include a benzophenone derivative, a benzoate derivative and a triazole derivative, etc. A light stabilizer such as an amine having steric hindrance is also preferred.

Composition (1) can be used for a guest host (GH) mode by addition of a dichroic dye of merocyanine type, stylyl type, azo type, azomethine type, azoxy type, quinophthalone type, anthraquinone type, tetrazine type or the like.

The amounts of addition of the optically active compound, the polymerizable compound, the antioxidant, the UV absorbent and the dyes are not particularly limited.

An element containing the composition has a large voltage holding ratio. The composition is suitable for an AM element, especially a transmittive AM element. A composition having an optical anisotropy in the range of about 0.08 to about 0.25, and also a composition having an optical anisotropy in the range of about 0.10 to about 0.30 may be prepared by controlling the proportions of the component compounds or by mixing other liquid crystal compound. The composition can be used as a composition having a nematic phase, and can be used as an optically active composition by adding an optically active compound.

The minimum temperature of nematic phase of the liquid crystal composition of the invention is preferably about −20° C. or lower at least, more preferably about −30° C. or lower, and particularly preferably about −40° C. or lower. The maximum temperature of nematic phase of the liquid crystal composition of the invention is preferably about 70° C. or higher at least, more preferably about 80° C. or higher, and particularly preferably about 90° C. or higher. The optical anisotropy of the liquid crystal composition of the invention under 589 nm and 25° C. is preferably in the range of about 0.07 to about 0.20, more preferably in the range of about 0.07 to about 0.16, and particularly preferably in the range of about 0.08 to about 0.13. The dielectric anisotropy of the liquid crystal composition of the invention at 25° C. is preferably about 2 or more at least, more preferably about 3 or more, and particularly preferably about 3.5 or more.

3. LCD Element

Composition (1) can be used in a LCD element having an operation mode such as the PC mode, TN mode, STN mode, OCB mode or PSA mode and driven in an active matrix (AM) manner. Composition (1) can also be used in a LCD element having an operation mode such as the PC mode, TN mode, STN mode, OCB mode, VA mode or IPS mode and driven in an passive matrix (PM) manner. The AM element or PM element may be of a reflective type, a transmissive type, or a transflective type.

Composition (1) can also be used in a nematic curvilinear aligned phase (NCAP) element prepared by microencapsulating a nematic liquid crystal, a polymer dispersed LCD (PDLCD) element in which a 3D-network polymer is formed in the liquid crystal, and a polyer network LCD (PNLCD) element.

EXAMPLES

The invention will be explained in more details by way of Examples, but is not restricted by the Examples. Unless otherwise noted, "%" means "wt %".

The synthesized compounds were identified by a method such as an NMR analysis.

<NMR Analysis>

DRX-500 (made by Bruker BioSpin Corporation) was used as a measurement apparatus. In $^1$H-NMR measurement, the sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using CFCl$_3$ as an internal standard. In the explanation of nuclear magnetic resonance spectra, s, d, t, q, quin, sex, m and br stand for a singlet, a doublet, a triplet, a quartet, a quintet, a sextet, a multiplet and a broad peak, respectively.

[Sample for Measurement]

In measuring a phase structure and a transition temperature, a liquid crystal compound itself was used as a sample. In measuring physical properties such as the maximum temperature of nematic phase, viscosity, optical anisotropy and dielectric anisotropy, a composition prepared by mixing the compound in a base liquid crystal was used as a sample.

In a case where a sample prepared by mixing the compound with the base liquid crystal was used, the measurement was carried out as described below. A sample was prepared by mixing 15 wt % of the compound and 85 wt % of the base liquid crystal. An extrapolated value was calculated from the measured value of the sample, according to the extrapolation method based on the equation "(Extrapolated value)={100×(measured value of the sample)−(wt % of the base liquid crystal)×(measured value of the base liquid crystal)}/(wt % of the compound)."

When crystals (or a smectic phase) precipitated at 25° C. even at the above ratio of the compound to the base liquid crystal, the ratio of the compound to the base liquid crystal was changed in the order of 10 wt %:90 wt %, 5 wt %:95 wt % and 1 wt %:99 wt %, and the sample having a ratio at which crystals (or a smectic phase) did not precipitate at 25° C. was measured for physical properties thereof. In addition, unless otherwise noted, the ratio of the compound to the base liquid crystal is 15 wt %:85 wt %.

Base liquid crystal (i) shown below was used as the base liquid crystal. The proportions of the components of base liquid crystal (i) are expressed in terms of "wt %".

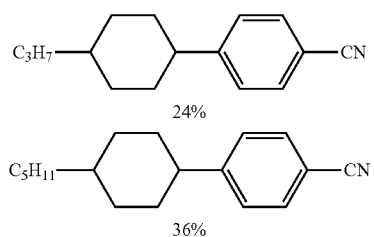

-continued

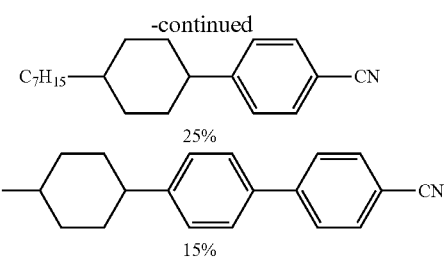

[Measurement Methods]

Physical properties were measured with the following methods. Most of them are applied as described in the standard EIAJ•ED-2521A in the Standard of Electronic Industries Association of Japan, or modified thereon. No TFT was attached to the TN element used for measurement.

1) Phase Structure

The sample was placed on a hot plate of a melting point apparatus (FP52 Hot Stage made by Mettler-Toledo International Inc.) equipped with a polarizing microscope, and the state of the phase and the change thereof were observed with the polarizing microscope while the sample was heated at a rate of 3° C./min, and the type of the phase was specified.

2) Phase Transition Temperatures (° C.)

A scanning calorimeter DSC-7 System or Diamond DSC System made by PerkinElmer, Inc. was used for the measurement. The temperature was increased or decreased at a rate of 3° C./min, and the starting point of an endothermic peak or exothermic peak caused by a change in the phase of the sample was determined by extrapolation to determine a phase transition temperature. The temperature at which the compound undergoes transition from a solid to a liquid crystal phase such as a smectic phase or a nematic phase may be abbreviated as "minimum temperature of the liquid crystal phase." The temperature at which the compound undergoes transition from a liquid crystal phase to a liquid may be abbreviated as "clearing point."

Crystal is expressed as C, and when types of the crystals are to be distinguished, each type is expressed as "C$_1$" or "C$_2$". A smectic phase and a nematic phase are expressed as "S" and "N", respectively. When smectic A phase, smectic B phase, smectic C phase or smectic F phase is distinguishable among the smectic phases, they are expressed as "S$_A$", "S$_B$", "S$_C$" or "S$_F$". A liquid (isotropic) is expressed as "I". A transition temperature is expressed as "C 50.0 N 100.0 I," for example. The expression indicates that the transition temperature from crystal to a nematic phase is 50.0° C. and that from the nematic phase to a liquid is 100.0° C.

3) Compatibility at Low Temperature

Samples in which the base liquid crystal and a compound were mixed with the compound taking 20 wt %, 15 wt %, 10 wt %, 5 wt %, 3 wt % and 1 wt %, respectively, were prepared and put in glass vials. The glass vials were kept in freezers at −10° C. or −20° C. for a predetermined period of time, and then whether or not crystals or a smectic phase precipitated was observed.

4) Maximum Temperature of Nematic Phase (T$_{NI}$ or NI; ° C.)

The sample was placed on a hot plate of a melting point apparatus equipped with a polarizing microscope and was heated at a rate of 1° C./min. The temperature at which a part of the sample began to change from a nematic phase to an isotropic liquid was measured. The maximum temperature of a nematic phase may be abbreviated as "maximum temperature."

5) Minimum Temperature of a Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as "$T_C \leq -20°$ C.". The minimum temperature of the nematic phase may be occasionally abbreviated as "minimum temperature."

6) Viscosity (Bulk Viscosity; η; Measured at 20° C.; mPa·s)

An E-type rotational viscometer was used for the measurement.

7) Viscosity (Rotational Viscosity; γ1; Measured at 25° C.; mPa·s)

The measurement was carried out with the method described in M. Imai et al., *Molecular Crystals and Liquid Crystals*, Vol. 259, p. 37 (1995). The sample was put in a TN element in which the twist angle was 0° and the distance (cell gap) between two glass substrates was 5 μm. Voltage was applied stepwise to the element in the range of 16 V to 19.5 V at an increment of 0.5 V. After a period of 0.2 sec with no voltage, voltage was applied repeatedly under the conditions of only one rectangular wave (rectangular pulse; 0.2 sec) and no voltage (2 sec). The peak current and the peak time of the transient current generated by the applied voltage were measured. The value of rotational viscosity was obtained from the measured values and Equation (8) on page 40 of the paper of M. Imai et al. The Δ∈ value required for the calculation was determined by using the element used for measuring the rotational viscosity and the method described below.

8) Optical Anisotropy (Refractive Index Anisotropy; Δn; Measured at 25° C.)

The measurement was carried out by an Abbe refractometer with a polarizing plate mounted on the ocular by using light at a wavelength of 589 nm. The surface of the main prism was rubbed in one direction, and then the sample was added dropwise onto the main prism. The refractive index $n_\parallel$ was measured when the direction of the polarized light was parallel to the direction of rubbing. The refractive index $n_\perp$ was measured when the direction of the polarized light was perpendicular to the direction of rubbing. The value of refractive index anisotropy was calculated from the equation "$\Delta n = n_\parallel - n_\perp$."

Dielectric Anisotropy (Δ∈; Measured at 25° C.)

The sample was put in a TN element in which the distance (cell gap) between two glass substrates was 9 μm and the twist angle was 80°. Sine waves (10 V, 1 kHz) were applied to the element, and after 2 sec, the dielectric constant $\in_\parallel$ in the major-axis direction of liquid crystal molecules was measured. Sine waves (0.5 V, 1 kHz) were applied to the element, and after 2 sec, the dielectric constant $\in_\perp$ in the minor-axis direction of the liquid crystal molecules was measured. The value of dielectric anisotropy was calculated using the equation "$\Delta \in = \in_\parallel - \in_\perp$."

10) Elastic Constant (K; Measured at 25° C.; pN)

A HP4284A-type LCR meter made by Yokogawa-Hewlett-Packard Company was used for the measurement. The sample was put in a horizontal alignment element in which the distance (cell gap) between two glass substrates was 20 μm. An electric charge of 0 to 20 V was applied to the element, and electrostatic capacity and applied voltage were measured. The measured values of electrostatic capacity (C) and applied voltage (V) were fitted to Equation (2.98) and Equation (2.101) on page 75 of the "Liquid Crystal Device Handbook" (Nikkan Kogyo Shimbun, Ltd.), and values of $K_{11}$ and $K_{33}$ were obtained using Equation (2.99). Next, $K_{22}$ was calculated using the previously obtained values of $K_{11}$ and $K_{33}$ and Equation (3.18) on page 171. The elastic constant was the mean value of $K_{11}$, $K_{22}$ and $K_{33}$ thus obtained.

11) Threshold Voltage (Vth; Measured at 25° C.; V)

A LCD-5100 luminance meter made by Otsuka Electronics Co., Ltd. was used for the measurement. The light source is a halogen lamp. The sample was put into a normally white mode TN element in which the distance (cell gap) between two glass substrates was about 0.45/Δn μm and the twist angle was 80°. Voltage (32 Hz, rectangular waves) applied to the element was increased stepwise from 0 V to 10 V at an increment of 0.02 V. On the occasion, the element was irradiated with light from a direction perpendicular to the element, and the amount of light transmitted through the element was measured. A voltage-transmittance curve was plotted in a manner that the maximum value of the amount of light corresponded to 100% transmittance and the minimum value of the amount of light corresponded to 0% transmittance. The threshold voltage is the voltage at 90% transmittance.

[Raw Materials]

Solmix™ A-11 was a mixture of 85.5% of ethanol, 13.4% of methanol, and 1.1% of isopropanol, and was purchased from Japan Alchohol Trading Co., Ltd. Tetrahydropyran is abbreviated as "THF". N-fluorobenzenesulfonimide is abbreviated as "NFSI."

Example 1

Synthesis of Compound No. (1-1-1)

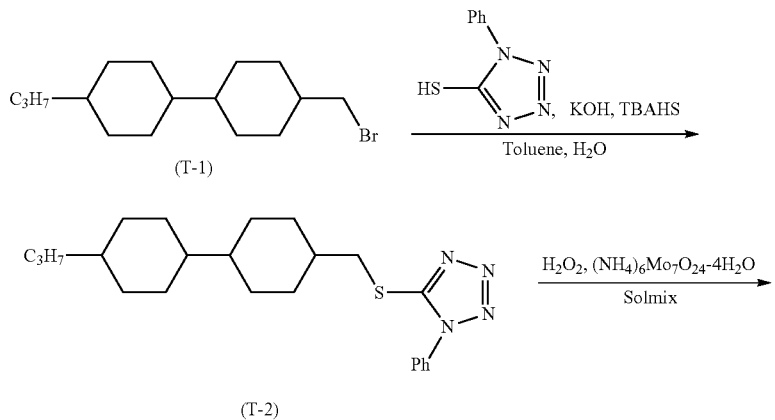

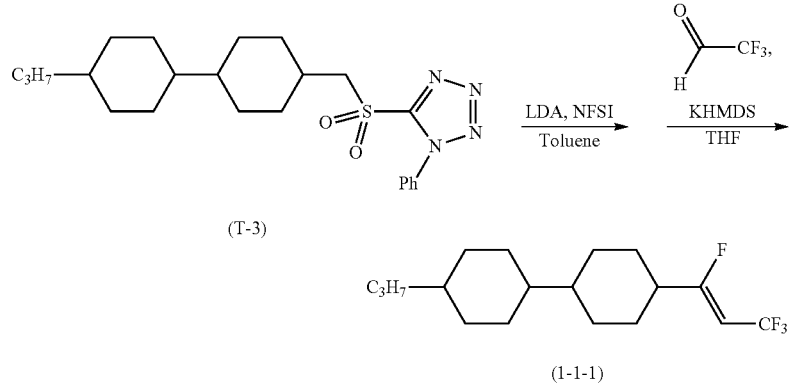

(T-3) → (1-1-1)

Step 1

In an $N_2$-atmosphere, 21.0 g of compound (T-1), 13.7 g of mercaptophenyltetrazole, and 1.18 g of TBAHS (tetrabutylammonium hydrogensulfate) were put in a reactor and dissolved in 80.0 ml of toluene. The resultant was slowly added with a solution of 5.56 g of potassium hydroxide in 40.0 ml of water, and was stirred at 70° C. for 8 hr. The reaction mixture was poured in ice water, and the water layer is extracted using toluene. The collected organic layer was washed using saline water and dried using anhydrous magnesium sulfate. The solution was concentrated under a reduced pressure to obtain 27.8 g of compound (T-2) (100%).

Step 2

In an $N_2$-atmosphere, 27.8 g of compound (T-2) was put in a reactor, dissolved in 400 ml of Solmix™ A-11, and cooled to 0° C. The resultant was slowly added with a solution of 8.62 g of hexaammonium heptamolybdate tetrahydrate in 67.8 g of 35% hydrogen peroxide water, and was stirred for 24 hr while returning to room temperature. The reaction mixture was pured in ice water, and the water layer was extracted using toluene. The collected organic layer was washed with a saturated aqueous solution of sodium hydrogensulfite and saline water in sequence, and was dried using anhydrous magnesium sulfate. The solution was concentrated under a reduced pressure, and the residue was refined by silica gel chromatography (toluene:ethyl acetate=9:1 in volume ratio) and further refined through recrystallization in toluene to obtain 17.0 g of compound (T-3) (56.6%).

Step 3

In an $N_2$-atmosphere, 8.49 g of compound (T-3) was put in a reactor, dissolved in 250 ml of toluene, and cooled to −70° C. The resultant was slowly added with a 24.6 ml THF solution of LDA (1.12 M), and stirred form 12 min. Next, the resultant was added with 9.32 g of NFSI, stirred for 50 min, and further stirred for 50 min while returning to room temperature. The reaction mixture was cooled to −70° C. again, slowly added with a 50.0 ml THF solution of 7.77 g of trifluoroacetaldehyde and a 39.4 ml THF solution of KHMDS (1.00 M), stirred for 1 hr, and further stirred for 3 hr while returning to room temperature. The trifluoroacetaldehyde used in the reaction was obtained by mixing 14.2 g of trifluoroacetaldehyde ethyl hemiacetal and 100 ml of concentrated sulfuric acid and stirring the mixture at 80° C. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in Solmix™ A-11 to obtain 1.74 g of compound no. (1-1-1) (27.5%).

Chemical shift δ (ppm; $CDCl_3$): 4.93 (dq, J=34.4 Hz, J=7.5 Hz, 1H), 2.16-2.04 (m, 1H), 1.98-1.91 (m, 2H), 1.86-1.66 (m, 6H), 1.35-1.19 (m, 4H), 1.19-1.10 (m, 3H), 1.10-0.91 (m, 6H), 0.91-0.79 (m, 5H).

The characteristic values of Compound no. (1-1-1) are as follows.

Phase transition temperatures: C 68.4 ($S_B$ 65.7) I.

$T_{NI}$=22.4° C.; Δ∈=13.2; Δn=0.050; η=16.2 mPa·s.

Example 2

Synthesis of Compound No. (1-2-3)

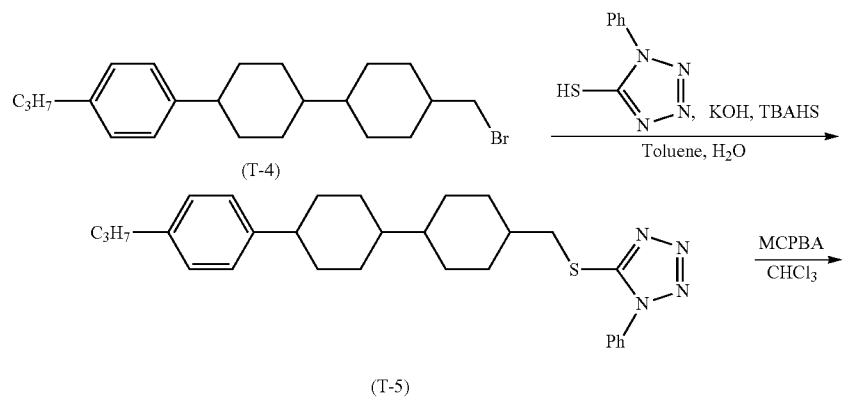

(T-4) → (T-5)

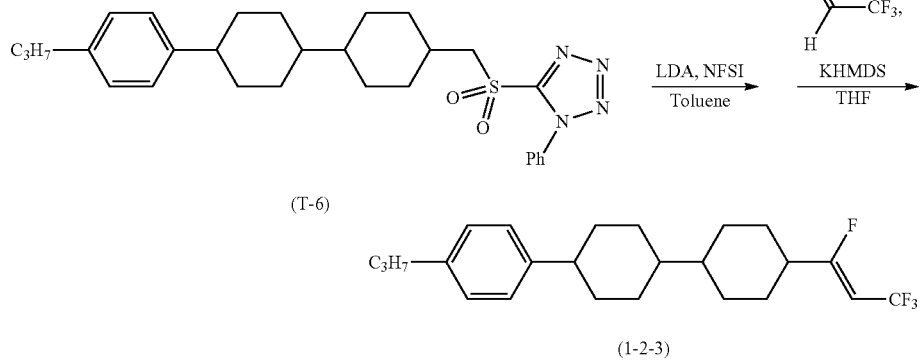

(T-6)

(1-2-3)

Step 1

In an $N_2$-atmosphere, 16.0 g of compound (T-4), 8.31 g of mercaptophenyltetrazole, and 0.720 g of TBAHS (tetrabutylammonium hydrogensulfate) were put in a reactor and dissolved in 80.0 ml of toluene. The resultant was slowly added with a solution of 3.39 g of potassium hydroxide in 40.0 ml of water, and stirred at 70° C. for 8 hr. The reaction mixture was poured in ice water, and the water layer was extracted using toluene. The collected organic layer was washed using saline water and dried using anhydrous magnesium sulfate. The solution was concentrated under a reduced pressure to obtain 20.1 g of compound (T-5) (100%).

Step 2

In an $N_2$-atmosphere, 21.6 g of compound (T-5) was put in a reactor, dissolved in 300 ml of chloroform, and cooled to −10° C. The resultant was slowly added with a solution of 23.6 g of MCPBA in 300 ml of chloroform, and was stirred for 24 hr while returning to room temperature. The reaction mixture was pured in a 2N aqueous solution of sodium hydroxide, and the water layer was extracted using dichloromethane. The collected organic layer was washed with a 2N aqueous solution of sodium hydroxide, a saturated aqueous solution of sodium hydrogensulfite, and saline water in sequence, and was dried using anhydrous magnesium sulfate. The solution was concentrated under a reduced pressure, and the residue was refined by silica gel chromatography (toluene) and further refined through recrystallization in toluene to obtain 18.2 g of compound (T-6) (78.8%).

Step 3

In an $N_2$-atmosphere, 10.0 g of compound (T-6) was put in a reactor, dissolved in 400 ml of toluene, and cooled to −70° C. The resultant was slowly added with a 24.6 ml THF solution of LDA (1.12M), and stirred for 12 min. Next, the resultant was added with 9.34 g of NFSI, stirred for 50 min, and further stirred for 50 min while returning to room temperature. The reaction mixture was cooled to −70° C. again, slowly added with a solution of 7.51 g of trifluoroacetaldehyde in 50.0 ml of THF and a 39.5 ml THF solution of KHMDS (1.00 M), stirred for 1 hr, and further stirred for 3 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in a mixed solvent of heptane and Solmix™ A-11 (volume ratio=1:1) to obtain 2.27 g of compound no. (1-2-3) (29.0%).

Chemical shift δ (ppm; CDCl$_3$): 7.13-7.03 (m, 4H), 4.95 (dq, J=34.4 Hz, J=7.5 Hz, 1H), 2.55 (t, J=7.6 Hz, 2H), 2.42 (tt, J=12.1 Hz, J=3.5 Hz, 1H), 2.18-2.05 (m, 1H), 2.01-1.78 (m, 8H), 1.68-1.57 (m, 2H), 1.49-1.36 (m, 2H), 1.33-1.21 (m, 2H), 1.21-1.12 (m, 6H), 0.94 (t, J=7.3 Hz, 3H).

The characteristic values of Compound no. (1-2-3) are as follows.

Phase transition temperatures: C 105 S$_B$ 134 N 147 I.

$T_{NI}$=100° C.; Δ∈=13.8; Δn=0.102; η=52.3 mPa·s.

Example 3

Synthesis of Compound No. (1-2-43)

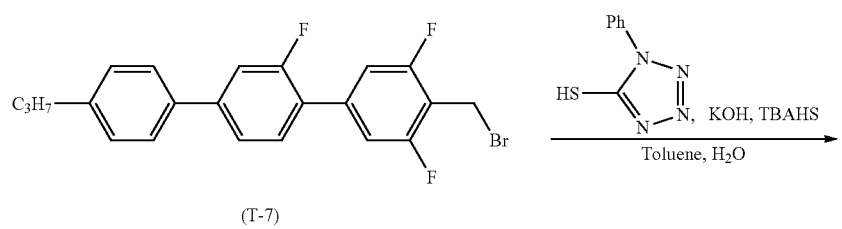

(T-7)

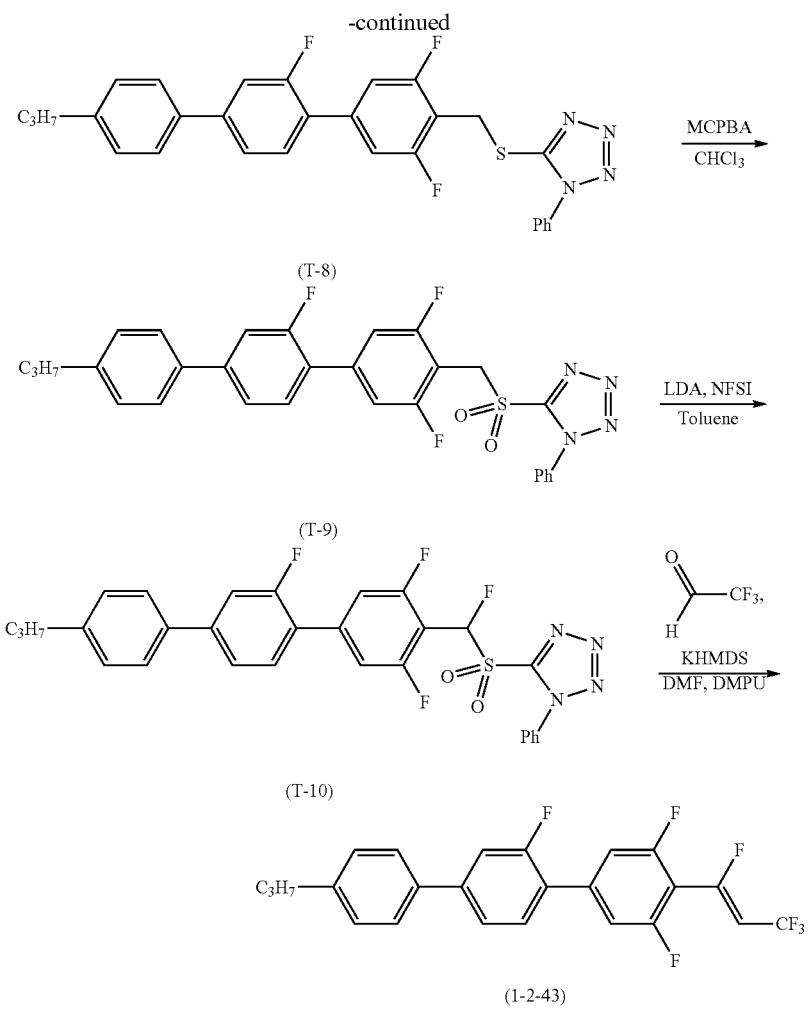

Step 1

18.2 g of compound (T-7) was used as a raw material, and the same operation as described in Step 1 of Example 1 was conducted to obtain 22.4 g of compound (T-8) (100%).

Step 2

22.4 g of compound (T-8) was used as a raw material, and the same operation as described in Step 2 of Example 2 was conducted to obtain 21.4 g of compound (T-9) (89.9%).

Step 3

In an $N_2$-atmosphere, 18.3 g of compound (T-9) was put in a reactor, dissolved in 730 ml of toluene, and cooled to −70° C. The resultant was slowly added with a 41.7 ml THF solution of LDA (1.12 M), and stirred for 12 min. Next, the resultant was added with 15.8 g of NFSI, stirred for 50 min, and further stirred for 50 min while returning to room temperature. The reaction mixture was poured in a saturated aqueous solution of ammonium chloride, and the water layer was extracted using ethyl acetate. The collected organic layer was washed using saline water and dried using anhydrous magnesium sulfate. The solution was concentrated under a reduced pressure, and the residue was refined by silica gel chromatography (toluene) and further refined through recrystallization in toluene to obtain 12.6 g of compound (T-10) (66.6%).

Step 4

In an $N_2$-atmosphere, 13.2 g of compound (T-10) was put in a reactor, dissolved in 200 ml of DMF (N,N-dimethylformamide) and 200 ml of DMPU (N,N'-dimethylpropyleneurea), and cooled to −70° C. The resultant was slowly added with a 46.6 ml THF solution of KHMDS (1.00 M) and a solution of 13.2 g of trifluoroacetaldehyde in 10.0 ml of THF, stirred for 1 hr, and further stirred for 3 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane:toluene=10:1 in volume ratio) and further refined through recrystallization in Solmix™ A-11 to obtain 1.68 g of compound no. (1-2-43) (16.5%).

Chemical shift δ (ppm; $CDCl_3$): 7.56-7.52 (m, 2H), 7.52-7.46 (m, 2H), 7.45-7.40 (m, 1H), 7.32-7.27 (m, 4H), 5.69 (dq, J=32.2 Hz, J=7.3 Hz, 1H), 2.65 (t, J=7.9 Hz, 2H), 1.75-1.65 (m, 2H), 0.98 (t, J=7.5 Hz, 3H).

The characteristic values of Compound no. (1-2-43) are as follows.

Phase transition temperatures: C 91.4 N 108 I.
$T_{NI}$=84.4° C.; $\Delta\varepsilon$=45.1; $\Delta n$=0.239; $\eta$=69.8 mPa·s.

Example 4

Synthesis of Compound No. (1-2-30)

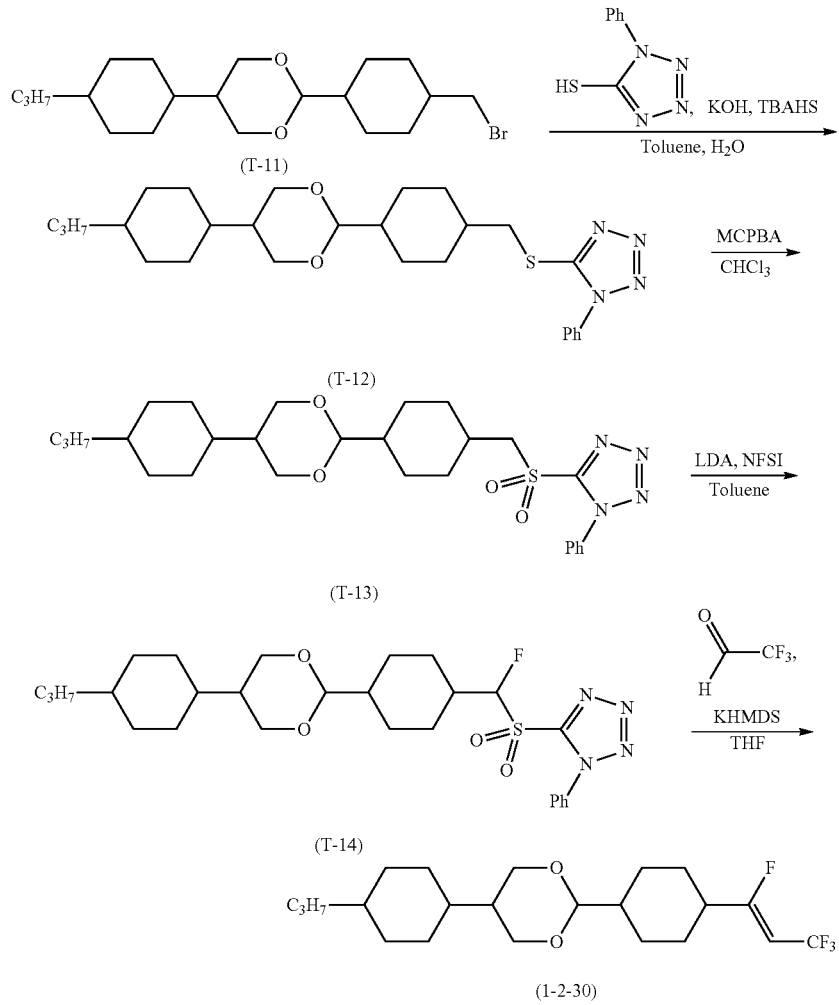

Step 1

17.6 g of compound (T-11) was used as a raw material, and the same operation as described in Step 1 of Example 1 was conducted to obtain 21.8 g of compound (T-12) (99.1%).

Step 2

20.3 g of compound (T-12) was used as a raw material, and the same operation as described in Step 2 of Example 2 was conducted to obtain 16.4 g of compound (T-13) (75.9%).

Step 3

15.4 g of compound (T-13) was used as a raw material, and the same operation as described in Step 3 of Example 3 was conducted to obtain 10.9 g of compound (T-14) (68.6%).

Step 4

In an $N_2$-atmosphere, 9.86 g of compound (T-14) was put in a reactor, dissolved in 400 ml of THF, and cooled to −70° C. The resultant was slowly added with a solution of 13.3 g of trifluoroacetaldehyde in 10.0 ml of THF and a 36.9 ml THF solution of KHMDS (1.00 M), stirred for 1 hr, and further stirred for 3 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane:ethyl acetate=10:1 in volume ratio) and further refined through recrystallization in a mixed solvent of isopropanol and ethyl acetate (volume ratio=1:1) to obtain 2.62 g of compound no. (1-2-30) (34.9%).

Chemical shift δ (ppm; $CDCl_3$): 4.94 (dq, J=34.3 Hz, J=7.4 Hz, 1H), 4.19-4.12 (m, 3H), 3.38 (dd, J=11.5 Hz, J=11.5 Hz, 2H), 2.18-2.05 (m, 1H), 2.00-1.89 (m, 4H), 1.78-1.60 (m, 5H), 1.55-1.46 (m, 1H), 1.33-1.09 (m, 9H), 1.02-0.90 (m, 3H), 0.90-0.76 (m, 5H).

Physical properties of compound no. (1-2-30) are given below. In the measurements of the maximum temperature, viscosity, optical anisotropy and dielectric anisotropy, a sample in which the compound to the base liquid crystal was 5 wt %:95 wt % was used.

Phase transition temperatures: C 74.4 $S_B$ 183 I.

$T_{NI}$=134° C.; Δ∈=14.1; Δn=0.103; η=80.0 mPa·s.

Example 5

Synthesis of Compound No. (1-2-71)

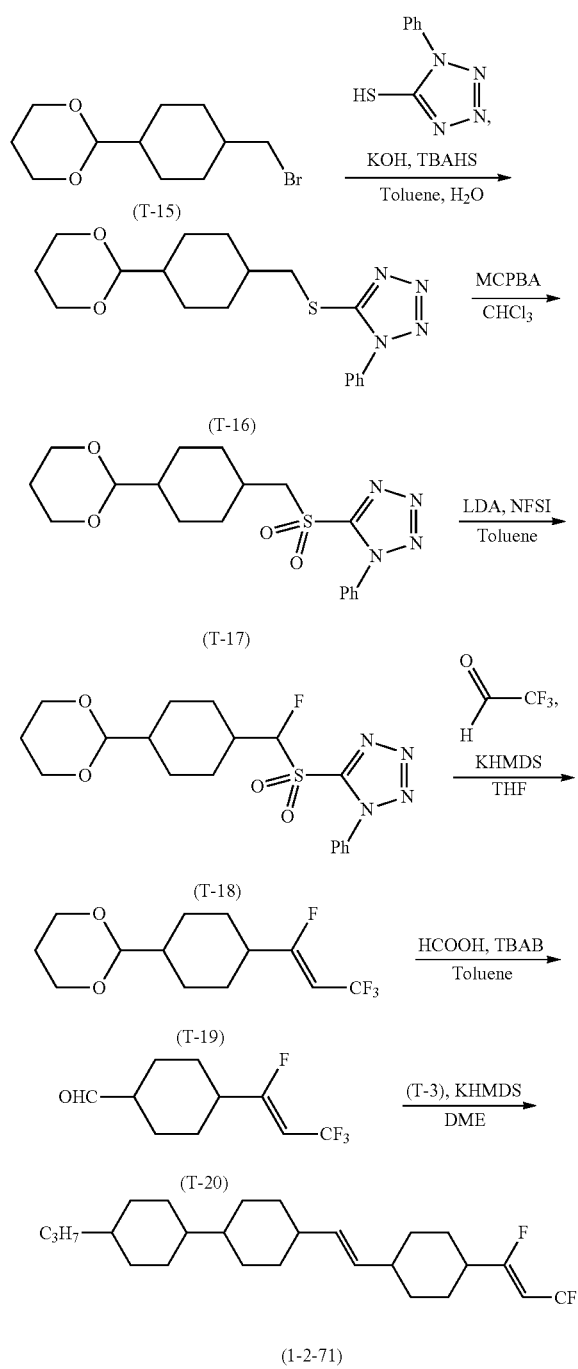

Step 1

18.1 g of compound (T-15) was used as a raw material, and the same operation as described in Step 1 of Example 1 was conducted to obtain 24.1 g of compound (T-16) (97.2%).

Step 2

24.1 g of compound (T-16) was used as a raw material, and the same operation as described in Step 2 of Example 2 was conducted to obtain 16.3 g of compound (T-17) (62.2%).

Step 3

16.3 g of compound (T-17) was used as a raw material, and the same operation as described in Step 3 of Example 3 was conducted to obtain 13.0 g of compound (T-18) (76.2%).

Step 4

13.0 g of compound (T-18) was used as a raw material, and the same operation as described in Step 4 of Example 4 was conducted to obtain 4.39 g of compound (T-19) (49.1%).

Step 5

In an $N_2$-atmosphere, 4.39 g of compound (T-19), 21.9 ml of formic acid, 1.50 g of TBAB (tetrabutylammonium bromide), and 45.0 ml of toluene were put in a reactor and stirred at room temperature for 12 hr. The reaction mixture was poured in water and neutralized using sodium hydrogencarbonate, and then the water layer was extracted using toluene. The collected organic layer was washed using water and dried using anhydrous magnesium sulfate. The solution was concentrated under a reduced pressure, and the residue was refined by silica gel chromatography (toluene) to obtain 2.76 g of compound (T-20) (79.1%).

Step 6

In an $N_2$-atmosphere, 1.56 g of compound (T-3) and 0.750 g of compound (T-20) were put in a reactor, dissolved in 60.0 ml of DME (ethylene glycol dimethyl ether), and cooled to −70° C. The resultant was slowly added with a 4.01 ml THF solution of KHMDS (1.00 M), stirred for 1 hr, and further stirred for 1 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in a mixed solvent of heptane and Solmix™ A-11 (volume ratio=1:1) to obtain 0.550 g of compound no. (1-2-71) (38.5%).

Chemical shift δ (ppm; $CDCl_3$): 5.37-5.23 (m, 2H), 4.94 (dq, J=34.3 Hz, J=7.5 Hz, 1H), 2.18-2.05 (m, 1H), 1.98-1.91 (m, 2H), 1.91-1.65 (m, 12H), 1.35-1.24 (m, 4H), 1.18-1.06 (m, 5H), 1.05-0.91 (m, 8H), 0.91-0.79 (m, 5H).

The characteristic values of compound no. (1-2-71) were as follows. In the measurements of the maximum temperature, viscosity, optical anisotropy and dielectric anisotropy, a sample in which the ratio of the compound to the base liquid crystal was 3 wt %:97 wt % was used.

Phase transition temperatures: C 78.3 $S_G$ 150 $S_B$ 172 N 229 I.

$T_{NI}$=168° C.; Δ∈=12.1; Δn=0.137; η=60.0 mPa·s.

Example 6

Synthesis of Compound No. (1-2-116)

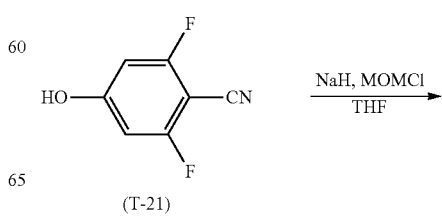

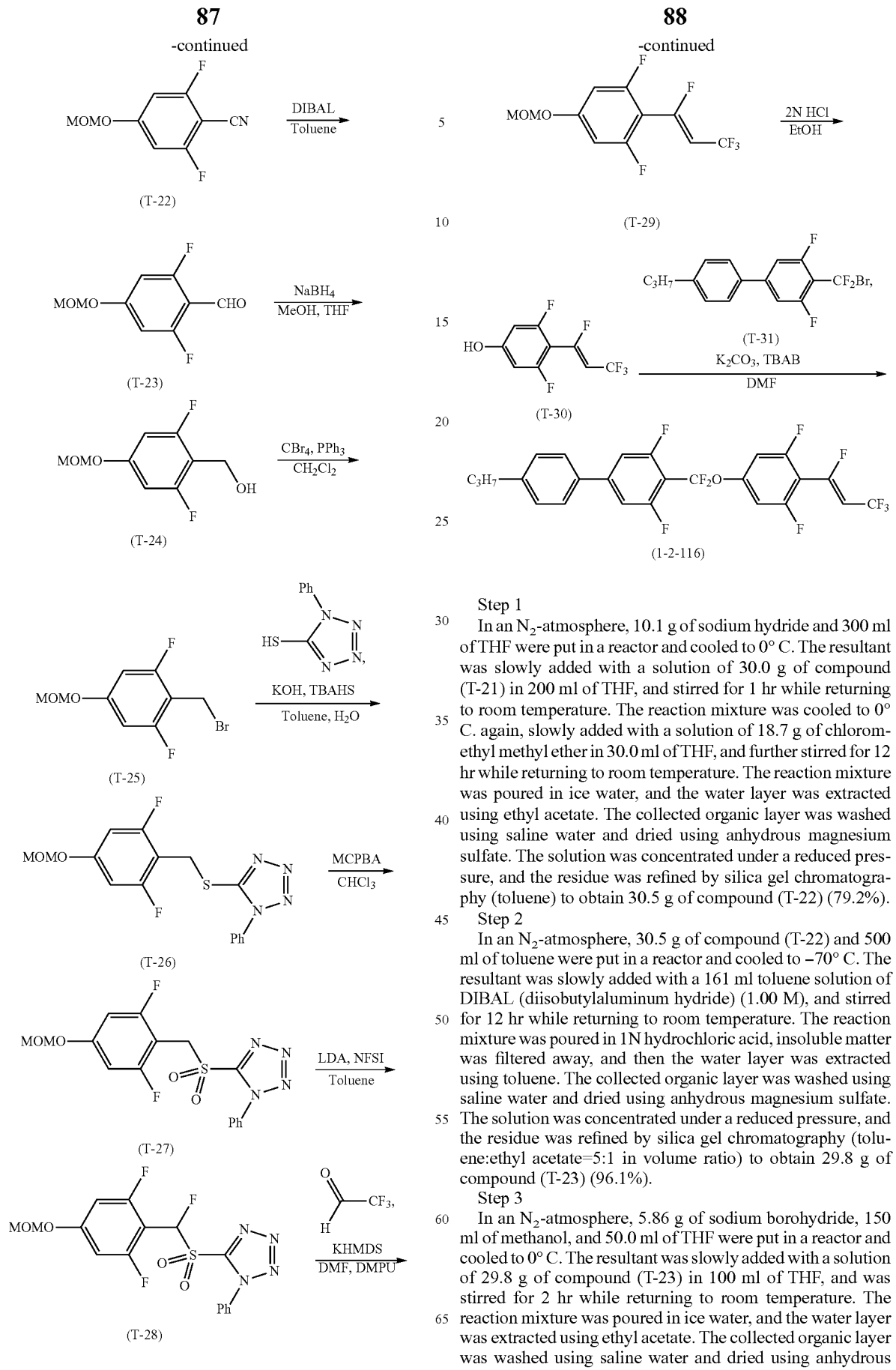

Step 1

In an $N_2$-atmosphere, 10.1 g of sodium hydride and 300 ml of THF were put in a reactor and cooled to 0° C. The resultant was slowly added with a solution of 30.0 g of compound (T-21) in 200 ml of THF, and stirred for 1 hr while returning to room temperature. The reaction mixture was cooled to 0° C. again, slowly added with a solution of 18.7 g of chloromethyl methyl ether in 30.0 ml of THF, and further stirred for 12 hr while returning to room temperature. The reaction mixture was poured in ice water, and the water layer was extracted using ethyl acetate. The collected organic layer was washed using saline water and dried using anhydrous magnesium sulfate. The solution was concentrated under a reduced pressure, and the residue was refined by silica gel chromatography (toluene) to obtain 30.5 g of compound (T-22) (79.2%).

Step 2

In an $N_2$-atmosphere, 30.5 g of compound (T-22) and 500 ml of toluene were put in a reactor and cooled to −70° C. The resultant was slowly added with a 161 ml toluene solution of DIBAL (diisobutylaluminum hydride) (1.00 M), and stirred for 12 hr while returning to room temperature. The reaction mixture was poured in 1N hydrochloric acid, insoluble matter was filtered away, and then the water layer was extracted using toluene. The collected organic layer was washed using saline water and dried using anhydrous magnesium sulfate. The solution was concentrated under a reduced pressure, and the residue was refined by silica gel chromatography (toluene:ethyl acetate=5:1 in volume ratio) to obtain 29.8 g of compound (T-23) (96.1%).

Step 3

In an $N_2$-atmosphere, 5.86 g of sodium borohydride, 150 ml of methanol, and 50.0 ml of THF were put in a reactor and cooled to 0° C. The resultant was slowly added with a solution of 29.8 g of compound (T-23) in 100 ml of THF, and was stirred for 2 hr while returning to room temperature. The reaction mixture was poured in ice water, and the water layer was extracted using ethyl acetate. The collected organic layer was washed using saline water and dried using anhydrous magnesium sulfate. The solution was concentrated under a reduced pressure to obtain 30.1 g of compound (T-24) (100%).

Step 4

In an $N_2$-atmosphere, 30.1 g of compound (T-24), 42.5 g of triphenylphosphine, and 300 ml of dichloromethane were put in a reactor and cooled to 0° C. The resultant was slowly added with a solution of 53.8 g of carbon tetrabromide in 280 ml of dichloromethane, and stirred for 3 hr while returning to room temperature. The reaction mixture was concentrated under a reduced pressure, and the residue was refined by silica gel chromatography (heptane:toluene=1:1 in volume ratio) to obtain 32.1 g of compound (T-25) (81.5%).

Step 5

32.1 g of compound (T-25) was used as a raw material, and the same operation as described in Step 1 of Example 1 was conducted to obtain 43.1 g of compound (T-26) (98.4%).

Step 6

43.1 g of compound (T-26) was used as a raw material, and the same operation as described in Step 2 of Example 2 was conducted to obtain 35.3 g of compound (T-27) (75.3%).

Step 7

33.5 g of compound (T-27) was used as a raw material, and the same operation as described in Step 3 of Example 3 was conducted to obtain 34.1 g of compound (T-28) (97.4%).

Step 8

31.0 g of compound (T-28) was used as a raw material, and the same operation as described in Step 4 of Example 3 was conducted to obtain 3.20 g of compound (T-29) (15.0%).

Step 9

In an $N_2$-atmosphere, 3.20 g of compound (T-29), 50.0 ml of ethanol, and 15.0 ml of 2N hydrochloric acid were put in a reactor, and stirred at 60° C. for 6 hr. The reaction mixture was poured in ice water, and the water layer was extracted using ethyl acetate. The collected organic layer was washed using saline water and dried using anhydrous magnesium sulfate. The solution was concentrated under a reduced pressure, and the residue was refined by silica gel chromatography (toluene:ethyl acetate=5:1 in volume ratio) to obtain 2.71 g of compound (T-30) (100%).

Step 10

In an $N_2$-atmosphere, 2.71 g of compound (T-30), 4.85 g of compound (T-31), 4.64 g of potassium carbonate, 0.722 g of TBAB, and 80.0 ml of DMF were put in a reactor, and stirred at 90° C. for 2 hr. The reaction mixture was poured in ice water, and the water layer was extracted using ethyl acetate. The collected organic layer was washed using saline water and dried using anhydrous magnesium sulfate. The solution was concentrated under a reduced pressure, and the residue was refined by silica gel chromatography (heptane:toluene=20:1 in volume ratio) and further refined through recrystallization in Solmix™ A-11 to obtain 3.26 g of compound no. (1-2-116) (55.7%).

Chemical shift δ (ppm; $CDCl_3$): 7.51-7.48 (m, 2H), 7.33-7.28 (m, 2H), 7.25-7.20 (m, 2H), 7.01-6.96 (m, 2H), 5.62 (dq, J=32.0 Hz, J=7.3 Hz, 1H), 2.65 (t, J=7.8 Hz, 2H), 1.74-1.65 (m, 2H), 0.97 (t, J=7.5 Hz, 3H).

The characteristic values of compound no. (1-2-116) are as follows.

Phase transition temperatures: C 59.4 I.

$T_{NI}$=23.7° C.; $\Delta\epsilon$=55.2; $\Delta n$=0.144; $\eta$=54.3 mPa·s.

Example 7

Synthesis of Compound No. (1-3-115)

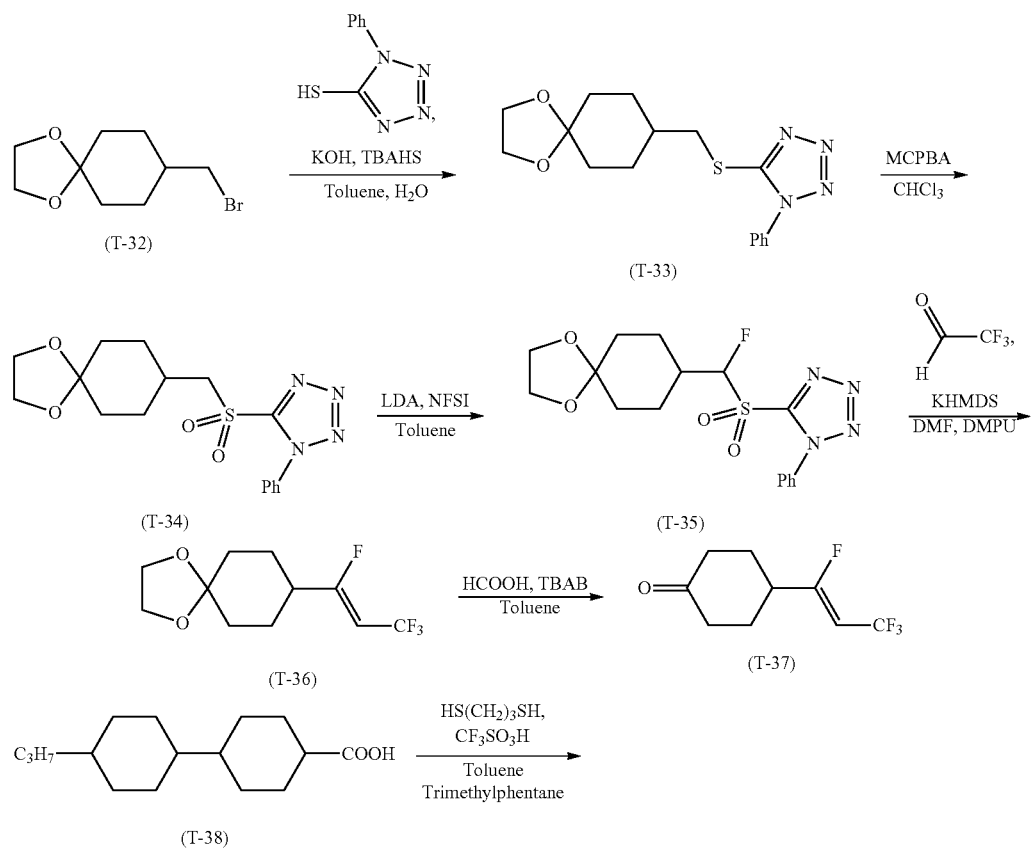

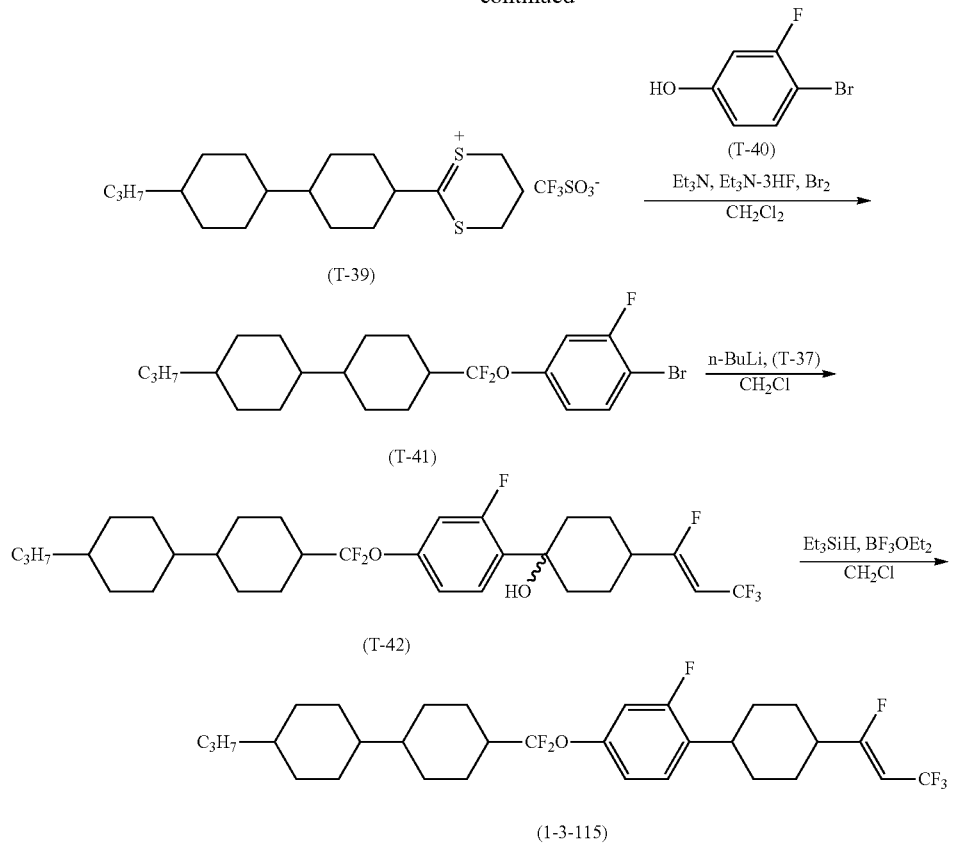

Step 1
24.2 g of compound (T-32) was used as a raw material, and the same operation as described in Step 1 of Example 1 was conducted to obtain 30.3 g of compound (T-33) (88.6%).

Step 2
30.3 g of compound (T-33) was used as a raw material, and the same operation as described in Step 2 of Example 2 was conducted to obtain 20.4 g of compound (T-34) (61.4%).

Step 3
20.4 g of compound (T-34) was used as a raw material, and the same operation as described in Step 3 of Example 3 was conducted to obtain 20.1 g of compound (T-35) (93.9%).

Step 4
20.1 g of compound (T-35) was used as a raw material, and the same operation as described in Step 4 of Example 4 was conducted to obtain 5.82 g of compound (T-36) (43.6%).

Step 5
5.82 g of compound (T-36) was used as a raw material, and the same operation as described in Step 5 of Example 5 was conducted to obtain 4.81 g of compound (T-37) (100%).

Step 6
In an $N_2$-atmosphere, 25.0 g of compound (T-38), 50.0 ml of toluene and 50.0 ml of 2,2,4-trimethylpentane were put in a reactor, and heated to 60° C. The resultant was added with 10.9 ml of propanedithiol and stirred for 1 hr, and was then slowly added with 19.4 ml of trifluoromethanesulfonic acid and stirred for 1 hr. Next, the resultant was heated under reflux for 2 hr while the distilled water was removed. The reaction mixture was cooled to room temperature and then concentrated under a reduced pressure, and the residue was refined through recrystallization in t-butyl methyl ether to obtain 40.8 g of compound (T-39) (86.8%).

Step 7
In an $N_2$-atmosphere, 2.41 g of compound (T-40), 1.91 ml of triethylamine and 150 ml of dichloromethane were put in a reactor and cooled to −70° C. The resultant was slowly added with a solution of 5.00 g of compound (T-39) in 150 ml of dichloromethane, and stirred for 1 hr. Next, the resultant was slowly added with 5.13 ml of hydrogen fluoride triethylamine complex, and stirred for 30 min. Next, the resultant was slowly added with 2.70 ml of bromine, and further stirred for 1 hr. The reaction mixture was poured in ice water and neutralized using sodium hydrogencarbonate, and the water layer was extracted using dichloromethane. The collected organic layer was washed using water and dried using anhydrous magnesium sulfate. The solution was concentrated under a reduced pressure, and the residue was refined by silica gel chromatography (heptane) to obtain 3.61 g of compound (T-41) (76.6%).

Step 8
In an $N_2$-atmosphere, 2.09 g of compound (T-41) and 60.0 ml of diethyl ether were put in a reactor and cooled to −70° C. The resultant was slowly added with a 3.12 ml n-hexane solution of n-butyl lithium (1.65 M), and stirred for 2 hr. Next, the resultant was slowly added with a solution of 1.18 g of compound (T-37) in 5.00 ml of diethyl ether, and stirred for 12 hr while returning to room temperature. The reaction mixture was poured in a saturated aqueous solution of ammonium chloride, and the water layer was extracted using ethyl acetate. The collected organic layer was washed using saline water and dried using anhydrous magnesium sulfate. The solution was concentrated under a reduced pressure, and the residue was refined by silica gel chromatography (toluene) to obtain 1.91 g of compound no. (T-42) (70.7%).

Step 9

In an N$_2$-atmosphere, 1.80 g of compound (T-42) and 16.0 ml of dichloromethane were put in a reactor and cooled to −70° C. The resultant was slowly added with 0.540 ml of triethylsilane and 0.430 ml of boron trifluoride diethyl ether complex, and stirred for 2 hr while being heated to 0° C. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in a mixed solvent of heptane and Solmix™ A-11 (volume ratio=1:1) to obtain 0.900 g of compound no. (1-3-115) (51.4%).

Chemical shift δ (ppm; CDCl$_3$): 7.16-7.10 (m, 1H), 6.93-6.85 (m, 2H), 5.00 (dq, J=34.3 Hz, J=7.4 Hz, 1H), 2.82 (tt, J=11.7 Hz, J=3.3 Hz, 1H), 2.33-2.22 (m, 1H), 2.10-1.95 (m, 7H), 1.89-1.80 (m, 2H), 1.80-1.68 (m, 4H), 1.57-1.45 (m, 4H), 1.40-1.26 (m, 4H), 1.20-1.11 (m, 3H), 1.10-0.92 (m, 6H), 0.92-0.80 (m, 5H).

The characteristic values of compound no. (1-3-115) were as follows. In the measurements of the maximum temperature, viscosity, optical anisotropy and dielectric anisotropy, a sample in which the ratio of the compound to the base liquid crystal was 10 wt %:90 wt % was used.

Phase transition temperatures: C 150 S$_B$ 159 N 276 I.

T$_{NI}$=174° C.; Δ∈=14.9; Δn=0.127; η=77.2 mPa·s.

Example 8

Synthesis of Compound No. (1-1-13)

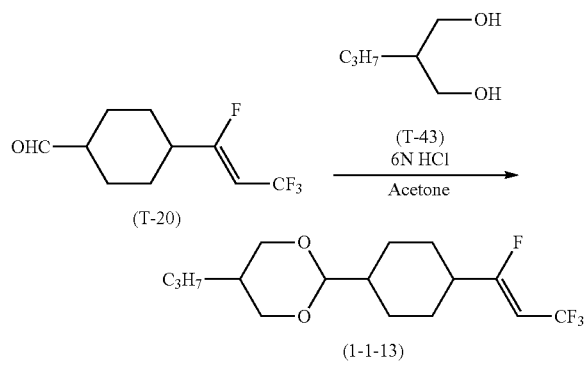

Step 1

In an N$_2$-atmosphere, 1.09 g of compound (T-20), 0.690 g of compound (T-43), 1.65 ml of 6N hydrochloric acid, and 5.00 ml of acetone were put in a reactor, and heated under reflux for 3 hr. The reaction mixture was poured in saline water, and the water layer was extracted using toluene. The collected organic layer was washed using a saturated aqueous solution of sodium hydrogencarbonate and saline water in sequence and dried using anhydrous magnesium sulfate. The solution was concentrated under a reduced pressure, and the residue was refined by silica gel chromatography (heptane:ethyl acetate=7:1 in volume ratio) and further refined through recrystallization in a mixed solvent of heptane and Solmix™ A-11 (volume ratio=1:1) to obtain 0.842 g of compound no. (1-1-13) (54.0%).

Chemical shift δ (ppm; CDCl$_3$): 4.94 (dq, J=34.3 Hz, J=7.5 Hz, 1H), 4.18 (d, J=5.1 Hz, 1H), 4.07 (dd, J=11.8 Hz, J=4.7 Hz, 2H), 3.28 (dd, J=11.5 Hz, J=11.5 Hz, 2H), 2.18-2.06 (m, 1H), 2.02-1.90 (m, 5H), 1.56-1.47 (m, 1H), 1.34-1.09 (m, 6H), 1.05-0.96 (m, 2H), 0.89 (t, J=7.4 Hz, 3H).

The characteristic values of compound no. (1-1-13) are as follows.

Phase transition temperatures: C 64.7 I.

T$_{NI}$=−26.3° C.; Δ∈=23.8; Δn=0.024; η=42.9 mPa·s.

Example 9

Synthesis of Compound No. (1-2-18)

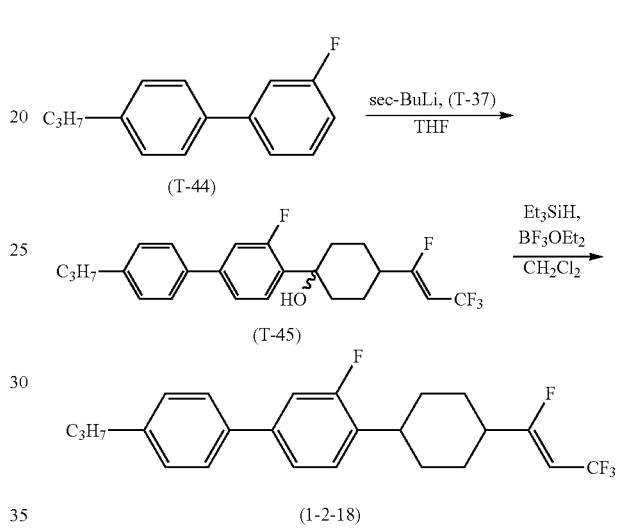

Step 1

In an N$_2$-atmosphere, 1.00 g of compound (T-44) and 15.0 ml of THF were put in a reactor and cooled to −70° C. The resultant was slowly added with a 4.75 ml cyclohexane/n-hexane solution of sec-butyl lithium (1.06 M), and stirred for 2 hr. Next, the resultant was slowly added with a solution of 1.18 g of compound (T-37) in 5.00 ml of THF, and stirred for 2 hr while returning to room temperature. The reaction mixture was poured in a saturated aqueous solution of ammonium chloride, and the water layer was extracted using ethyl acetate. The collected organic layer was washed using saline water and dried using anhydrous magnesium sulfate. The solution was concentrated under a reduced pressure, and the residue was refined by silica gel chromatography (toluene) to obtain 1.59 g of compound (T-45) (80.3%).

Step 2

1.59 g of compound (T-45) was used as a raw material, and the same operation as described in Step 9 of Example 7 to obtain 0.541 g of compound (1-2-18) (35.4%).

Chemical shill δ (ppm; CDCl$_3$): 7.49-7.45 (m, 2H), 7.34-7.30 (m, 1H), 7.26-7.21 (m, 4H), 5.02 (dq, J=34.2 Hz, J=7.4 Hz, 1H), 2.88 (tt, J=11.9 Hz, J=3.4 Hz, 1H), 2.62 (t, J=7.9 Hz, 2H), 2.35-2.24 (m, 1H), 2.13-2.00 (m, 4H), 1.73-1.45 (m, 6H), 0.97 (t, J=7.3 Hz, 3H).

The characteristic values of compound no. (1-2-18) were as follows.

Phase transition temperatures: C 128 I.

T$_{NI}$=76.4° C.; Δ∈=20.5; Δn=0.157; η=73.9 mPa·s.

Example 10

Synthesis of Compound No. (1-1-42)

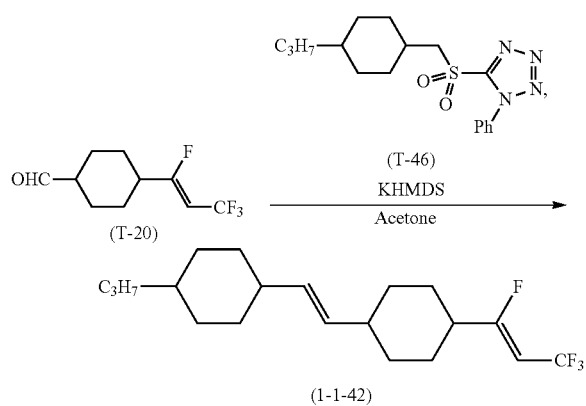

Step 1

In an $N_2$-atmosphere, 2.56 g of compound (T-46), 1.50 g of compound (T-20), and 30.0 ml of DME were put in a reactor and cooled to −70° C. The resultant was slowly added with a 8.03 ml THF solution of KHMDS (1.00 M), stirred for 1 hr, and further stirred for 1 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in Solmix™ A-11 to obtain 0.673 g of compound no. (1-1-42) (29.0%).

Chemical shift δ (ppm; $CDCl_3$): 5.37-5.24 (m, 2H), 4.95 (dq, J=34.5 Hz, J=7.5 Hz, 1H), 2.17-2.05 (m, 1H), 1.97-1.65 (m, 10H), 1.37-1.23 (m, 4H), 1.20-0.98 (m, 7H), 0.95-0.84 (m, 5H).

The characteristic values of compound no. (1-1-42) were as follows.

Phase transition temperatures: C 52.2 $S_B$ 65.7 I.
$T_{NI}$=24.4° C.; Δ∈=11.9; Δn=0.057; η=13.5 mPa·s.

Example 11

Synthesis of Compound No. (1-1-4)

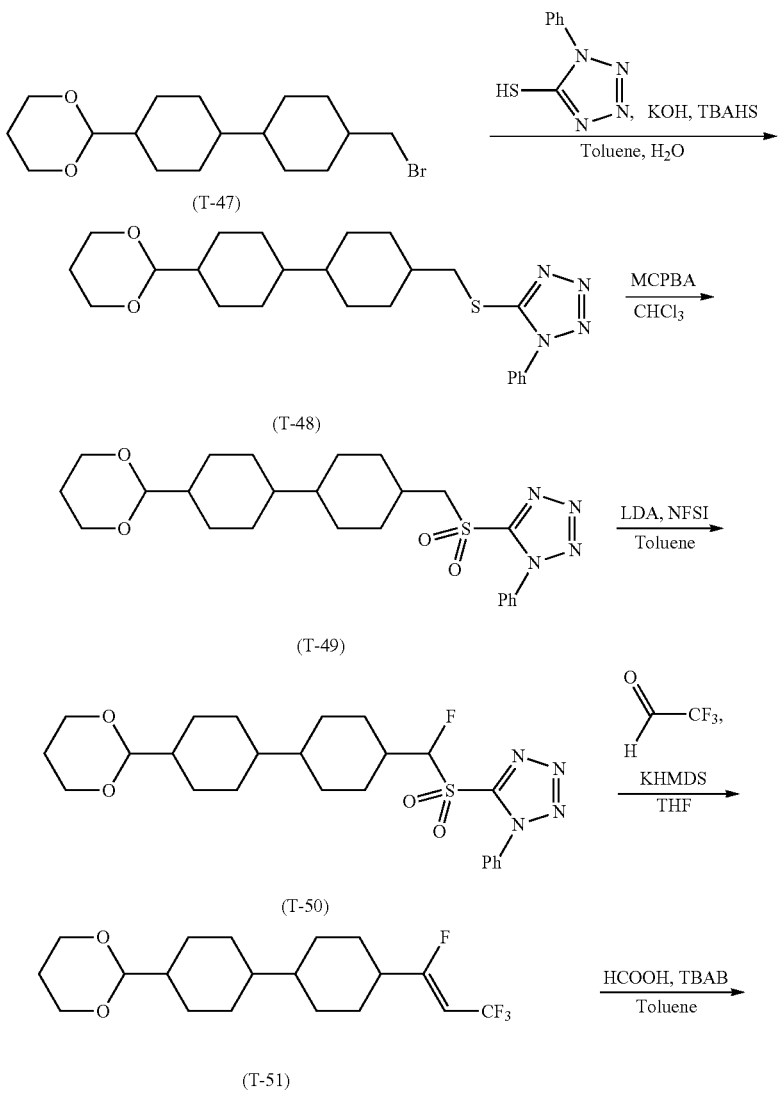

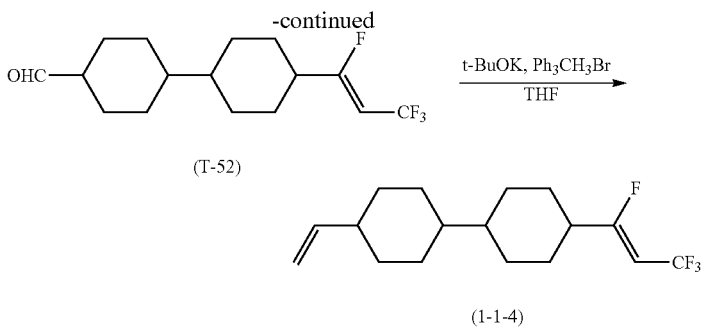

(T-52)

(1-1-4)

Step 1

17.8 g of compound (T-47) was used as a raw material, and the same operation as described in Step 1 of Example 1 was conducted to obtain 22.8 g of compound (T-48) (100%).

Step 2

22.8 g of compound (T-48) was used as a raw material, and the same operation as described in Step 2 of Example 2 was conducted to obtain 17.1 g of compound (T-49) (69.8%).

Step 3

17.1 g of compound (T-49) was used as a raw material, and the same operation as described in Step 3 of Example 3 was conducted to obtain 14.1 g of compound (T-50) (79.2%).

Step 4

13.0 g of compound (T-50) was used as a raw material, and the same operation as described in Step 4 of Example 4 was conducted to obtain 4.46 g of compound (T-51) (46.4%).

Step 5

4.64 g of compound (T-51) was used as a raw material, and the same operation as described in Step 5 of Example 5 was conducted to obtain 3.62 g of compound (T-52) (92.8%).

Step 6

In an $N_2$-atmosphere, 2.52 g of methyltriphenylphosphine bromide and 26.0 ml of THF were put in a reactor and cooled to −30° C. The resultant was slowly added with 0.760 g of potassium t-butoxide, and stirred for 30 min. Next, the resultant was slowly added with a solution of 1.80 g of compound (T-52) in 10.0 ml of THF, and stirred for 3 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in Solmix™ A-11 to obtain 0.657 g of compound no. (1-1-4) (36.7%).

Chemical shift δ (ppm; $CDCl_3$): 5.81-5.72 (m, 1H), 5.02-4.85 (m, 3H), 2.16-2.04 (m, 1H), 2.00-1.70 (m, 9H), 1.31-1.19 (m, 2H), 1.13-0.98 (m, 8H).

The characteristic values of compound no. (1-1-4) were as follows.

Phase transition temperatures: C 38.9 $S_B$ 47.7 I.

$T_{NI}$=0.4° C.; Δε=10.8; Δn=0.050; η=13.6 mPa·s.

Example 12

Synthesis of Compound No. (1-1-5)

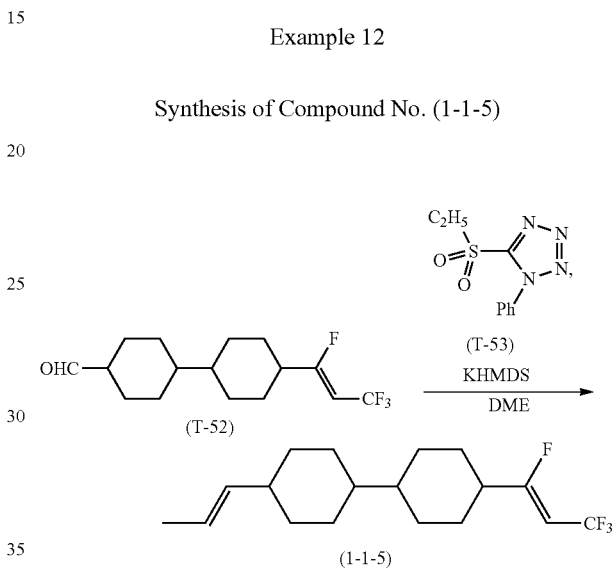

Step 1

In an $N_2$-atmosphere, 1.80 g of compound (T-52), 1.82 g of compound (T-53), and 36.0 ml of DME were put in a reactor and cooled to −70° C. The resultant was slowly added with a 7.64 ml THF solution of KHMDS (1.00 M), and stirred for 4 hr while returning to room temperature. The reaction mixture was poured in ice water, and the water layer was extracted using toluene. The collected organic layer was washed using saline water and dried using anhydrous magnesium sulfate. The solution was concentrated under a reduced pressure, and the residue was refined by silica gel chromatography (heptane) and further refined through recrystallization in Solmix™ A-11 to obtain 0.443 g of compound no. (1-1-5) (23.7%).

Chemical shift δ (ppm; $CDCl_3$): 5.43-5.32 (m, 2H), 4.93 (dq, J=34.4 Hz, J=7.5 Hz, 1H), 2.15-2.03 (m, 1H), 1.99-1.91 (m, 2H), 1.88-1.68 (m, 7H), 1.64 (d, 0.1=4.7 Hz, 3H), 1.30-1.19 (2H), 1.12-0.97 (m, 8H).

The characteristic values of compound no. (1-1-5) were as follows.

Phase transition temperatures: $S_B$ 101 I.

$T_{NI}$=33.7° C.; Δε=15.4; Δn=0.070; η=19.5 mPa·s.

With the same synthesis methods described in Examples 1 to 12, compound nos. (1-1-1) to (1-1-68), compound nos. (1-2-1) to (1-2-120) and compound nos. (1-3-1) to (1-3-140) as shown below could be synthesized.

| No. | |
|---|---|
| 1-1-1 | 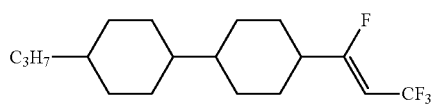<br>C68.4 (S_B 65.7) I<br>$T_{NI} = 22.4°$ C., $\Delta n = 0.050$, $\Delta\varepsilon = 13.2$,<br>$\eta = 16.2$ mPa·s |
| 1-1-2 | 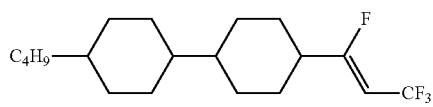 |
| 1-1-3 | 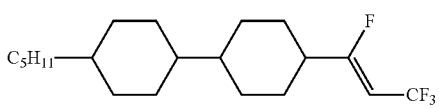 |
| 1-1-4 | 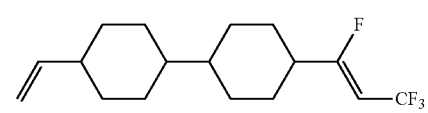<br>C 38.9 S_B 47.7 I<br>$T_{NI} = 0.4°$ C., $\Delta n = 0.050$, $\Delta\varepsilon = 10.8$,<br>$\eta = 13.6$ mPa·s |
| 1-1-5 | 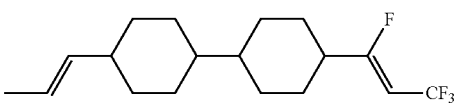<br>S_B 101 I<br>$T_{NI} = 33.7°$ C., $\Delta n = 0.070$, $\Delta\varepsilon = 15.4$,<br>$\eta = 19.5$ mPa·s |
| 1-1-6 | 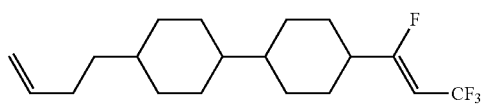 |
| 1-1-7 | 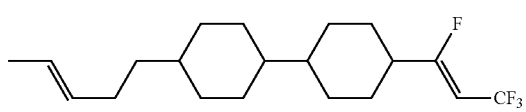 |
| 1-1-8 | 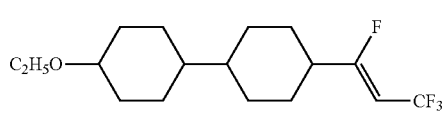 |
| 1-1-9 | 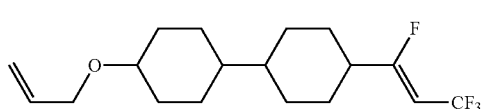 |
| 1-1-10 | 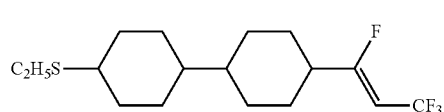 |
| 1-1-11 | 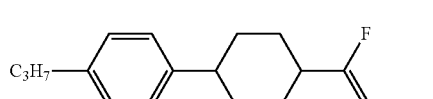 |

-continued
| No. | |
|---|---|
| 1-1-12 | 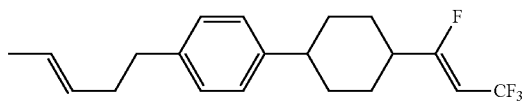 |
| 1-1-13 | 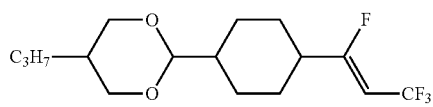<br>C 64.7 I<br>$T_{NI} = -26.3°$ C., $\Delta n = 0.024$, $\Delta \varepsilon = 23.8$,<br>$\eta = 42.9$ mPa · s |
| 1-1-14 | 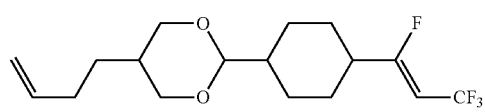 |
| 1-1-15 | 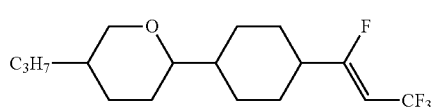 |
| 1-1-16 | 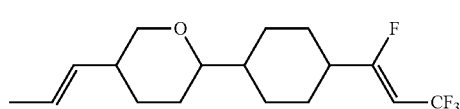 |
| 1-1-17 | 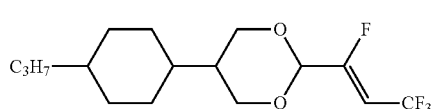 |
| 1-1-18 | 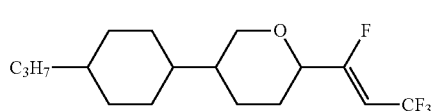 |
| 1-1-19 | 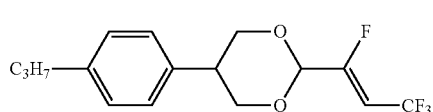 |
| 1-1-20 | 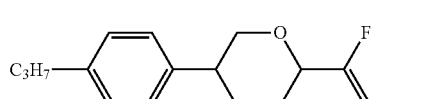 |
| 1-1-21 | 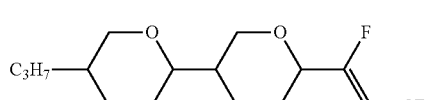 |
| 1-1-22 | 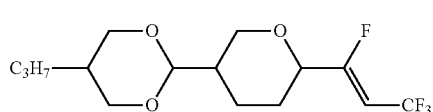 |
| 1-1-23 | 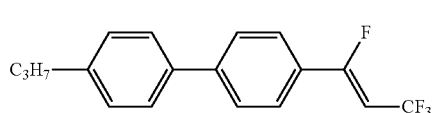 |
| 1-1-24 | 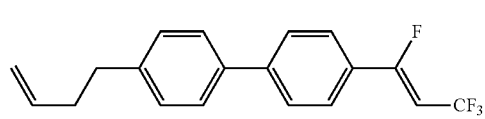 |

-continued
| No. | |
|---|---|
| 1-1-25 | 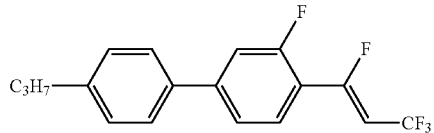 |
| 1-1-26 | 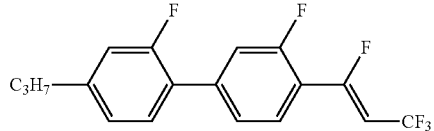 |
| 1-1-27 | 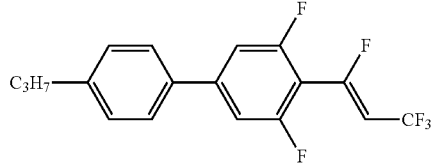 |
| 1-1-28 | 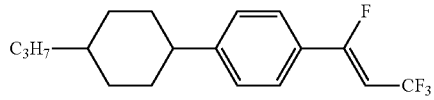 |
| 1-1-29 | 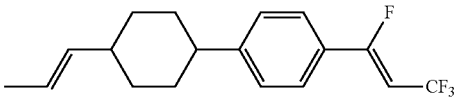 |
| 1-1-30 | 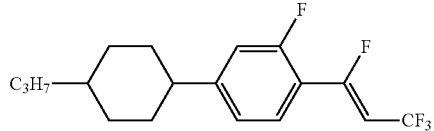 |
| 1-1-31 | 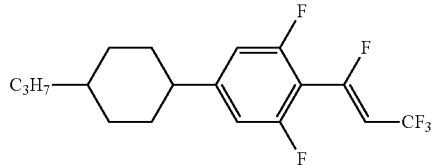 |
| 1-1-32 | 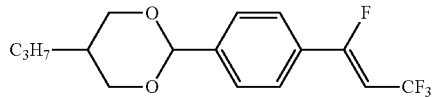 |
| 1-1-33 | 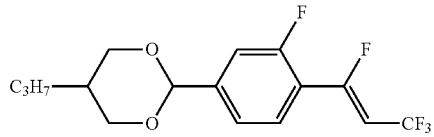 |
| 1-1-34 | 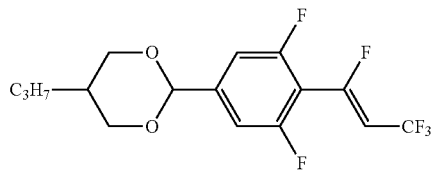 |
| 1-1-35 | 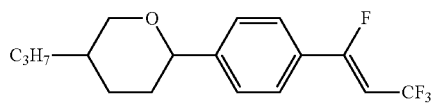 |

-continued
| No. | |
|---|---|
| 1-1-36 | 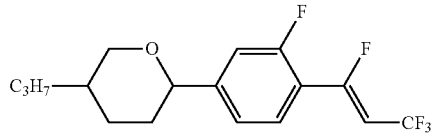 |
| 1-1-37 | 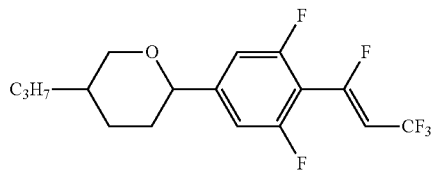 |
| 1-1-38 | 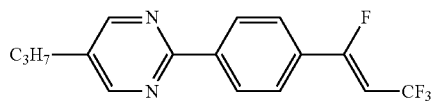 |
| 1-1-39 | 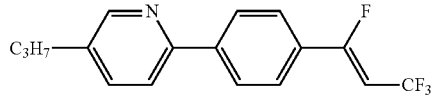 |
| 1-1-40 | 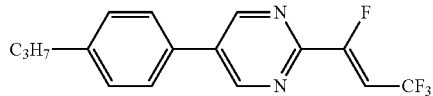 |
| 1-1-41 | 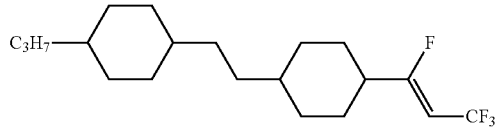 |
| 1-1-42 | 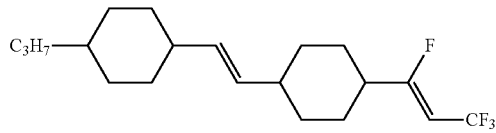<br>C 52.2 (S$_B$ 65.7) I<br>T$_{NI}$ = 24.4° C., Δn = 0.057, Δε = 11.9,<br>η = 13.5 mPa · s |
| 1-1-43 | 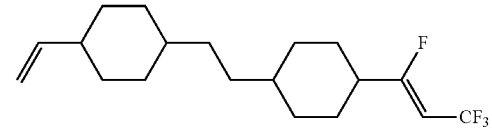 [SMILES: C=CC1CCC(CCC2CCC(/C(F)=C/C(F)(F)F)CC2)CC1] |
| 1-1-44 | 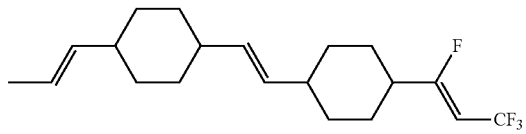 [SMILES: C/C=C/C1CCC(/C=C/C2CCC(/C(F)=C/C(F)(F)F)CC2)CC1] |
| 1-1-45 | 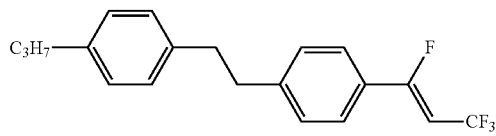 |

-continued
| No. | |
|---|---|
| 1-1-46 | 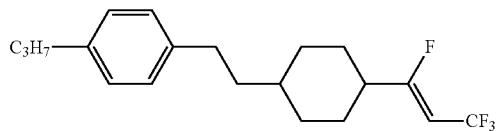 |
| 1-1-47 | 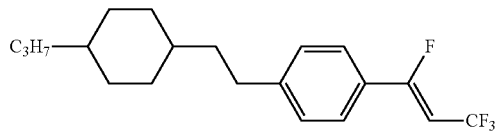 |
| 1-1-48 | 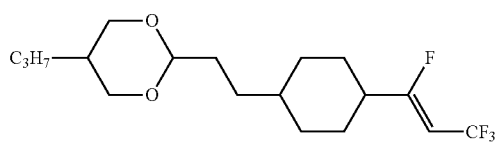 |
| 1-1-49 | 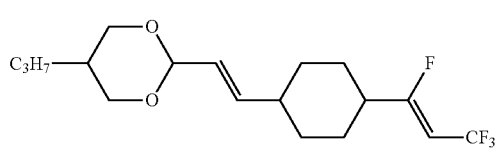 |
| 1-1-50 | 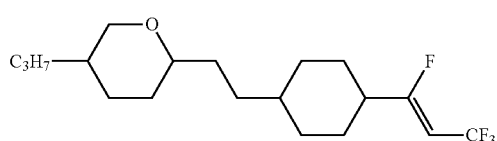 |
| 1-1-51 | 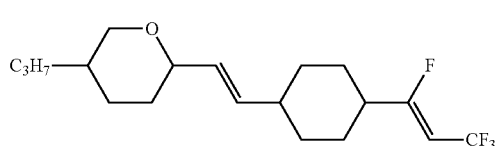 |
| 1-1-52 | 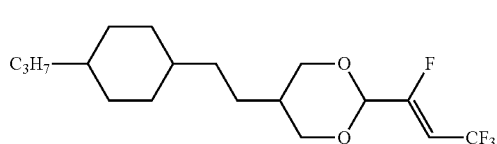 |
| 1-1-53 | 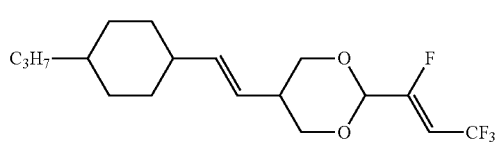 |
| 1-1-54 | 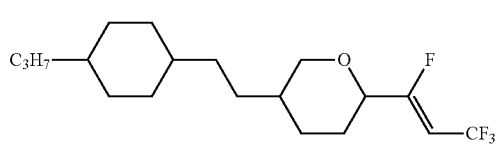 |
| 1-1-55 | 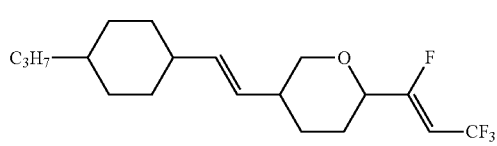 |
| 1-1-56 | 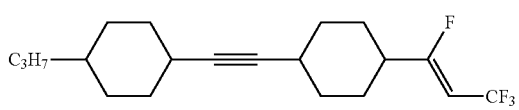 |

-continued
| No. | |
|---|---|
| 1-1-57 | 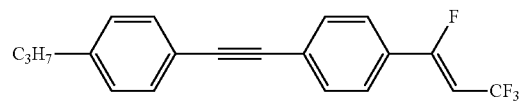 |
| 1-1-58 | 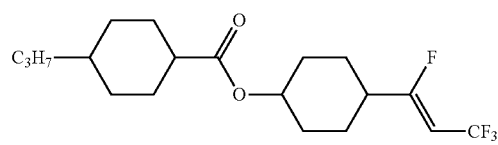 |
| 1-1-59 | 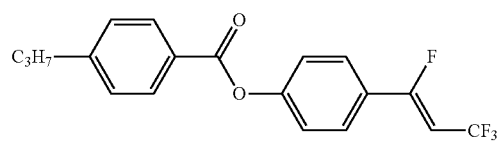 |
| 1-1-60 | 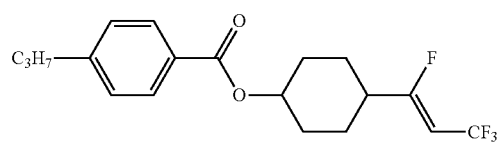 |
| 1-1-61 | 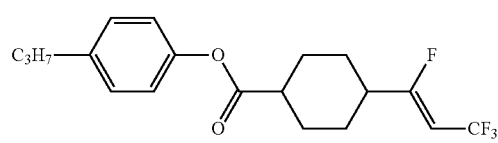 |
| 1-1-62 | 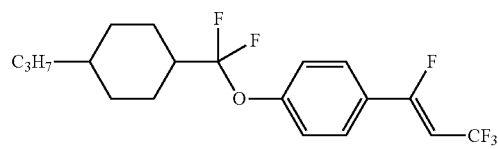 |
| 1-1-63 | 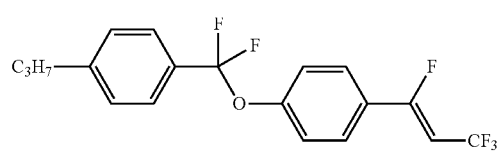 |
| 1-1-64 | 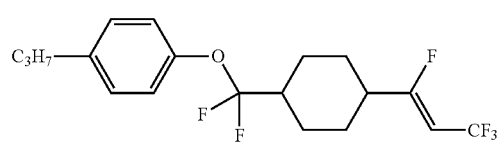 |
| 1-1-65 | 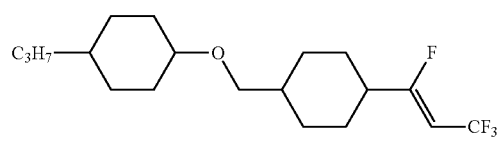 |
| 1-1-66 | 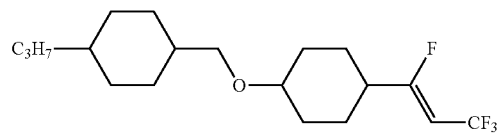 |
| 1-1-67 | 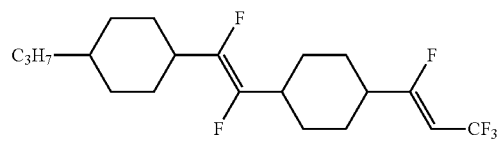 |

-continued
| No. | |
|---|---|
| 1-1-68 | 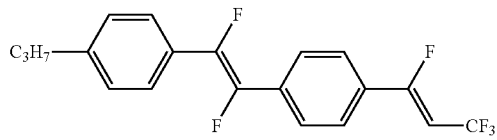 |
| 1-2-1 | 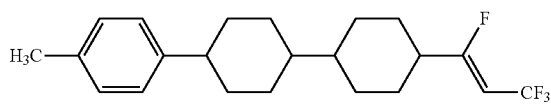 |
| 1-2-2 | 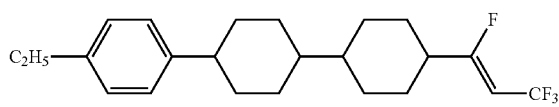 |
| 1-2-3 | 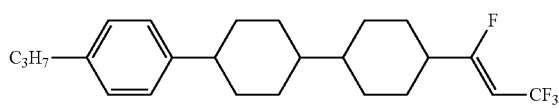 C 105 S$_B$ 134 N 147 I<br>T$_{NI}$ = 100° C., Δn = 0.102, Δε = 13.8,<br>η = 52.3 mPa · s |
| 1-2-4 | 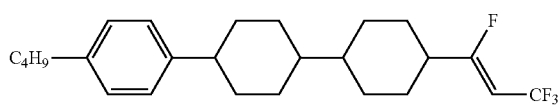 |
| 1-2-5 | 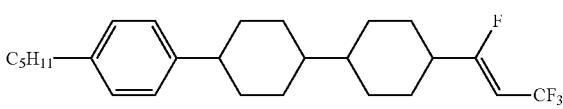 |
| 1-2-6 | 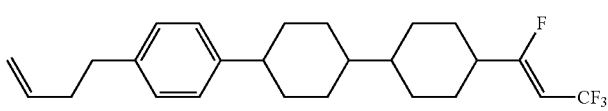 |
| 1-2-7 | 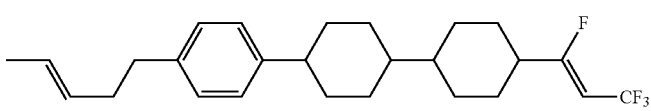 |
| 1-2-8 | 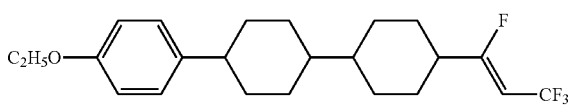 |
| 1-2-9 | 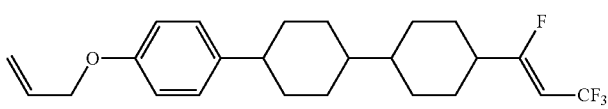 |
| 1-2-10 | 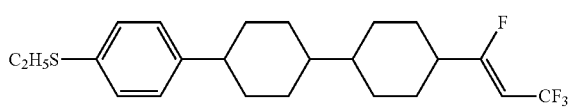 |
| 1-2-11 | 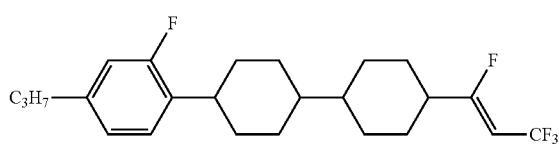 |

-continued
| No. | |
|---|---|
| 1-2-12 | 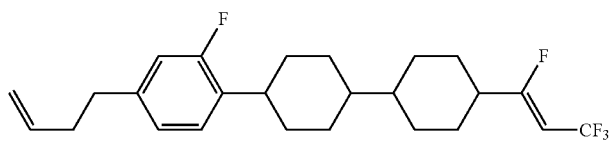 |
| 1-2-13 | 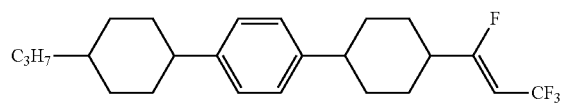 |
| 1-2-14 | 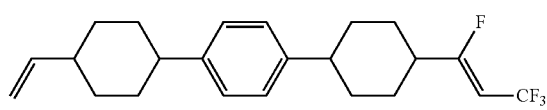 |
| 1-2-15 | 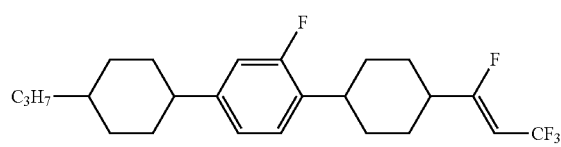 |
| 1-2-16 | 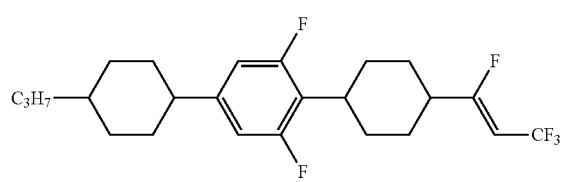 |
| 1-2-17 | 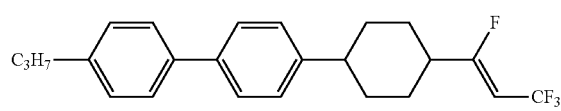 |
| 1-2-18 | 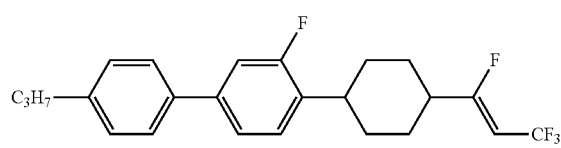<br>C 128 I<br>$T_{NI} = 76.4°$ C., $\Delta n = 0.157$, $\Delta \varepsilon = 20.5$,<br>$\eta = 73.9$ mPa·s |
| 1-2-19 | 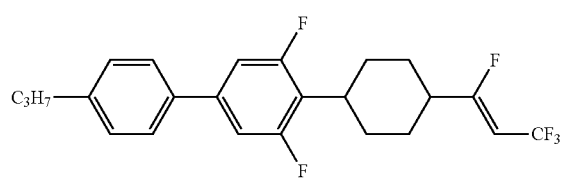 |
| 1-2-20 | 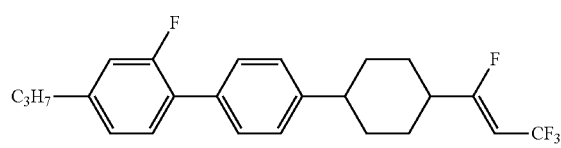 |
| 1-2-21 | 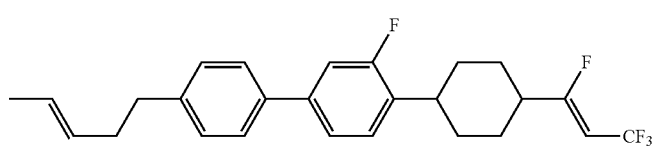 |

| No. | |
|---|---|
| 1-2-22 | 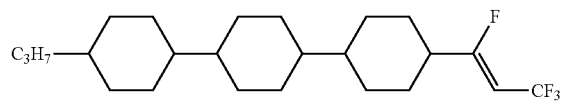 |
| 1-2-23 | 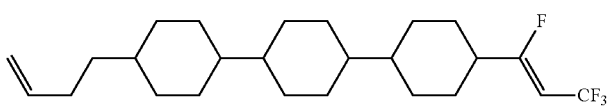 |
| 1-2-24 | 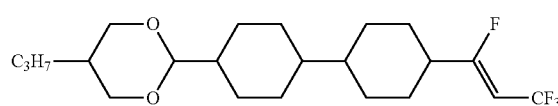 |
| 1-2-25 | 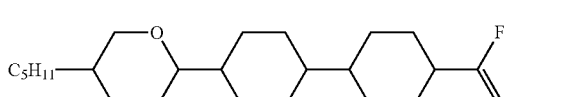 |
| 1-2-26 | 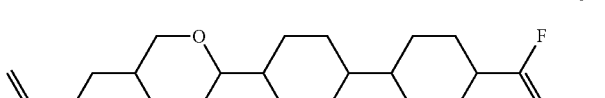 |
| 1-2-27 | 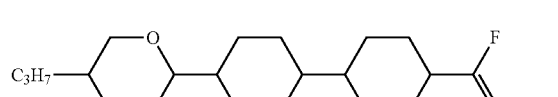 |
| 1-2-28 | 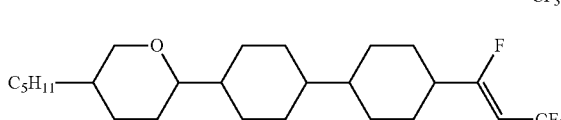 |
| 1-2-29 | 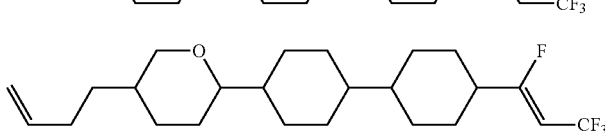 |
| 1-2-30 | 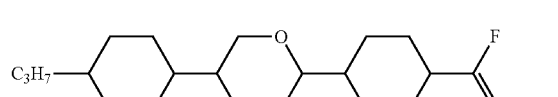<br>C 74.4 S$_B$ 183 I<br>T$_{NI}$ = 134° C., Δn = 0.103, Δε = 14.1,<br>η = 80.0 mPa · s |
| 1-2-31 | 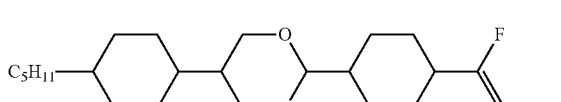 |
| 1-2-32 | 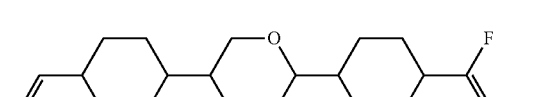 |
| 1-2-33 | 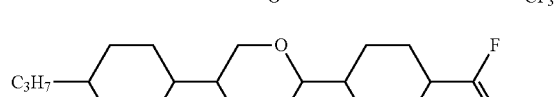 |
| 1-2-34 | 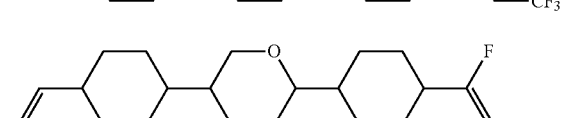 |

-continued
| No. | |
|---|---|
| 1-2-35 | 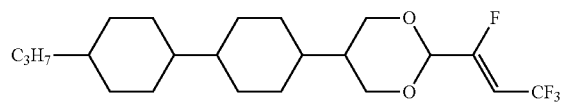 |
| 1-2-36 | 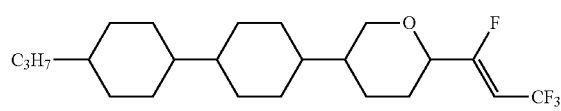 |
| 1-2-37 | 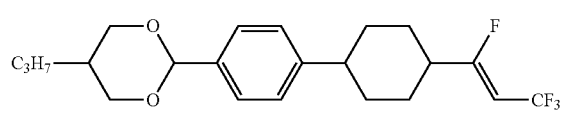 |
| 1-2-38 | 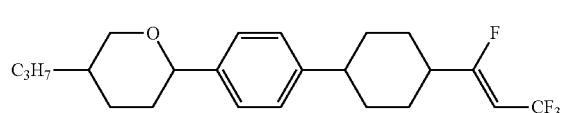 |
| 1-2-39 | 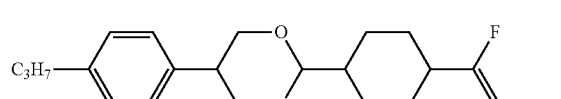 |
| 1-2-40 | 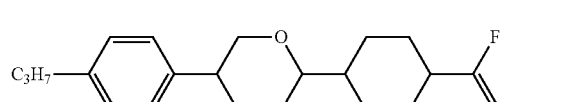 |
| 1-2-41 | 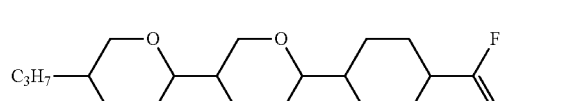 |
| 1-2-42 | 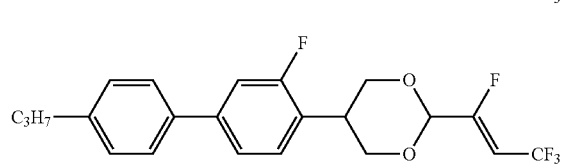 |
| 1-2-43 | 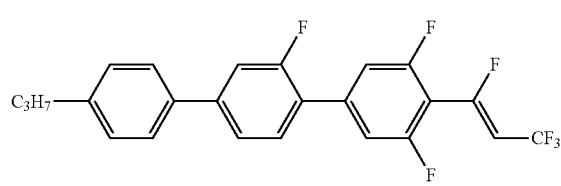<br>C 91.4 N 108 I<br>$T_{NI}$ = 84.4° C., $\Delta n$ = 0.239, $\Delta \varepsilon$ = 45.1,<br>$\eta$ = 69.8 mPa · s |
| 1-2-44 | 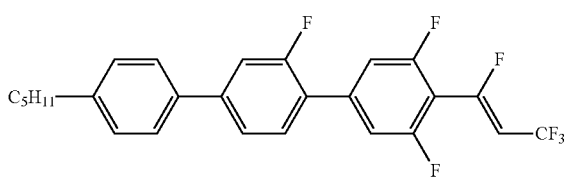 |
| 1-2-45 | 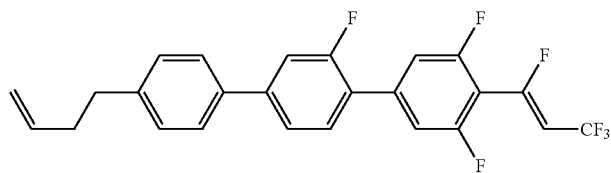 [SMILES: C=CCCc1ccc(-c2ccc(-c3cc(F)c(/C(F)=C/C(F)(F)F)c(F)c3)c(F)c2)cc1] |

-continued
| No. | |
|---|---|
| 1-2-46 | 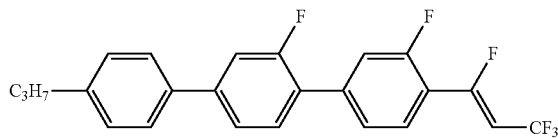 |
| 1-2-47 | 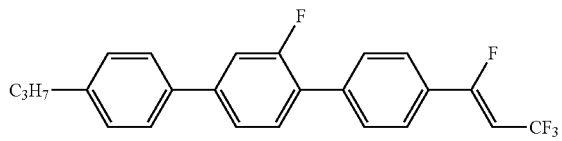 |
| 1-2-48 | 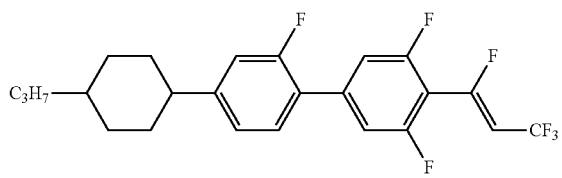 |
| 1-2-49 | 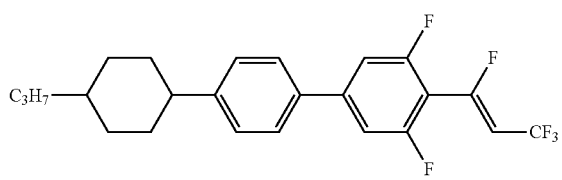 |
| 1-2-50 | 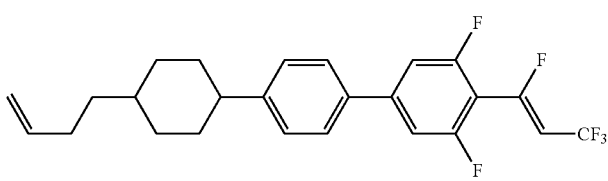 |
| 1-2-51 | 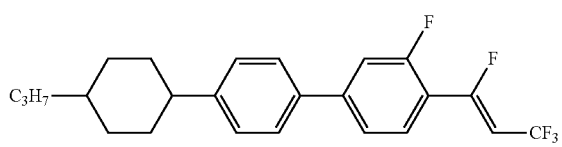 |
| 1-2-52 | 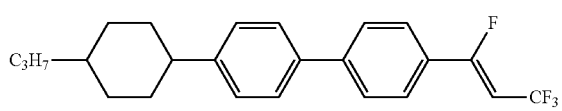 |
| 1-2-53 | 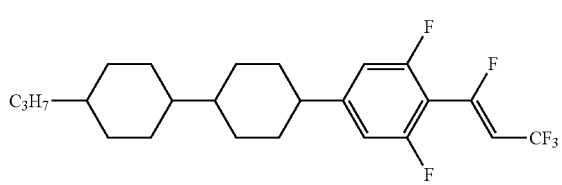 |
| 1-2-54 | 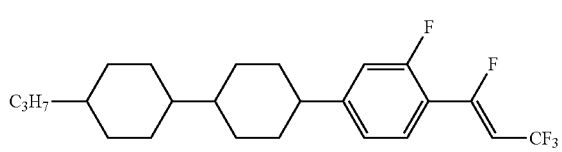 |
| 1-2-55 | 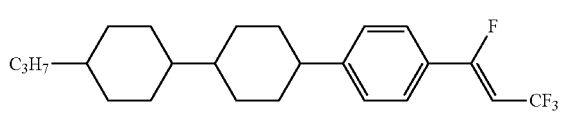 |

-continued
| No. | |
|---|---|
| 1-2-56 | 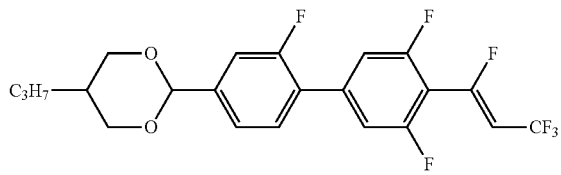 |
| 1-2-57 | 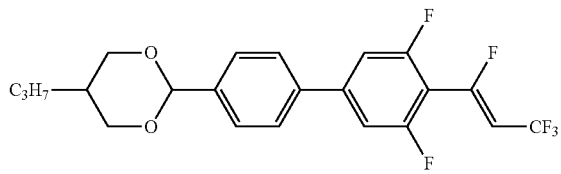 |
| 1-2-58 | 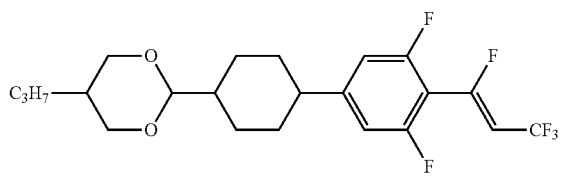 |
| 1-2-59 | 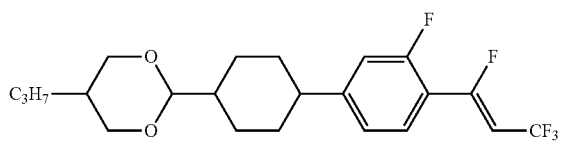 |
| 1-2-60 | 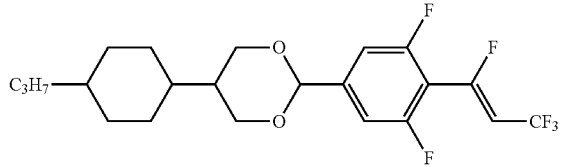 |
| 1-2-61 | 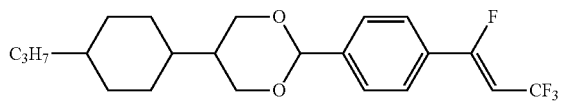 |
| 1-2-62 | 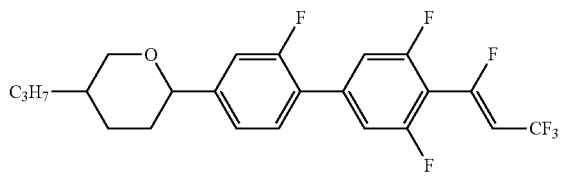 |
| 1-2-63 | 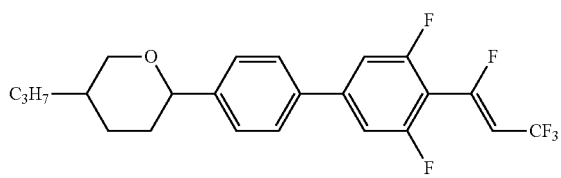 |
| 1-2-64 | 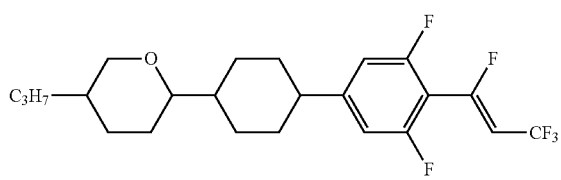 |

-continued
| No. | |
|---|---|
| 1-2-65 | 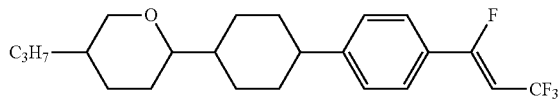 |
| 1-2-66 | 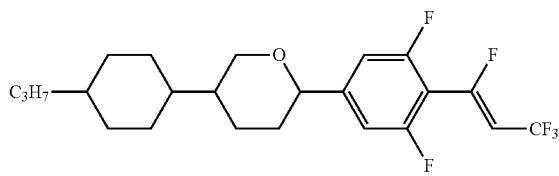 |
| 1-2-67 | 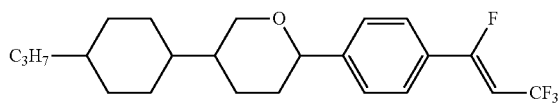 |
| 1-2-68 | 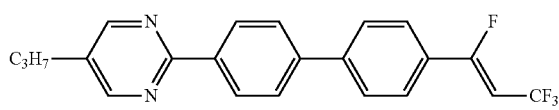 |
| 1-2-69 | 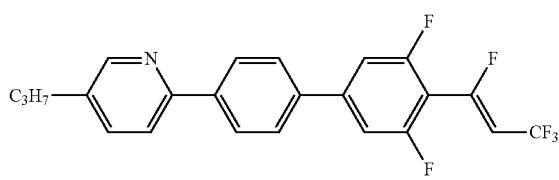 |
| 1-2-70 | 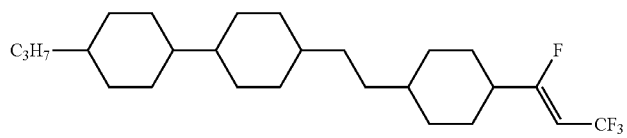 |
| 1-2-71 | 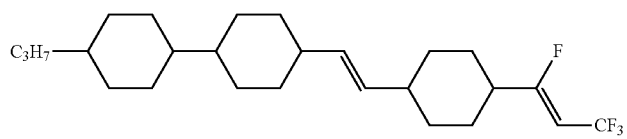
C 78.3 S$_G$ 150 S$_B$ 172 N 229 I
T$_{NI}$ = 168° C., Δn = 0.137, Δε = 12.1,
η = 60.0 mPa · s |
| 1-2-72 | 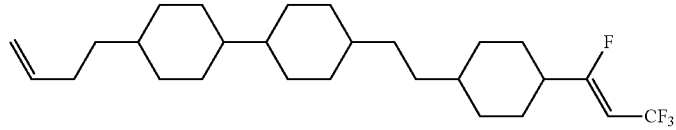 |
| 1-2-73 | 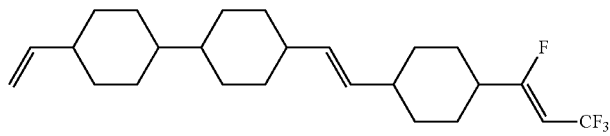 |
| 1-2-74 | 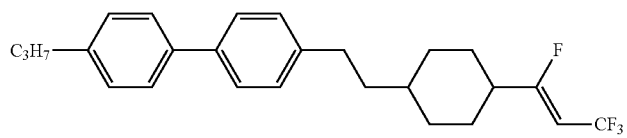 |

-continued
| No. | |
|---|---|
| 1-2-75 | 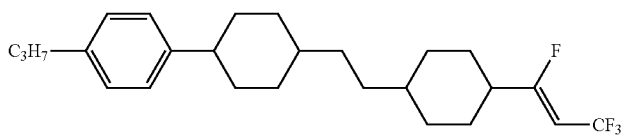 |
| 1-2-76 | 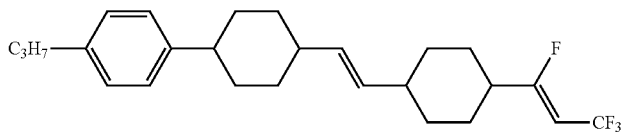 |
| 1-2-77 | 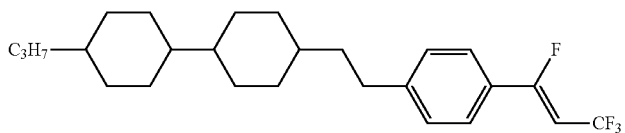 |
| 1-2-78 | 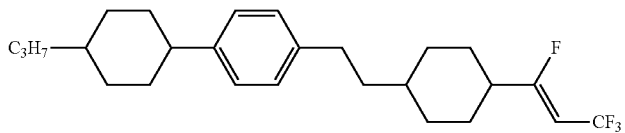 |
| 1-2-79 | 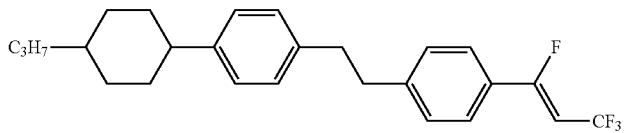 |
| 1-2-80 | 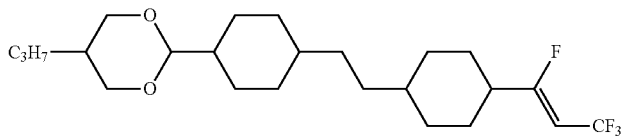 |
| 1-2-81 | 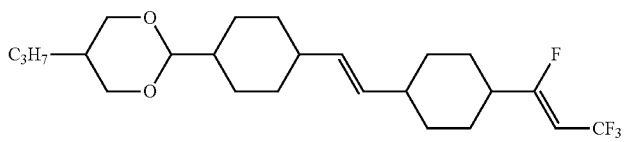 |
| 1-2-82 | 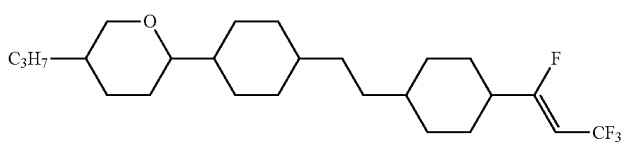 |
| 1-2-83 | 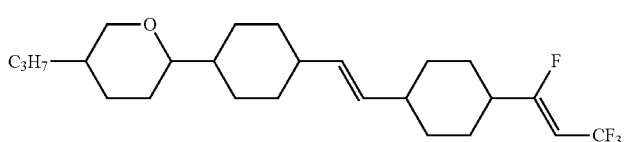 |
| 1-2-84 | 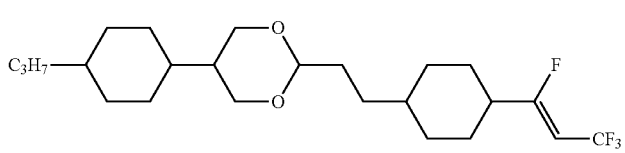 |

-continued
| No. | |
|---|---|
| 1-2-85 | 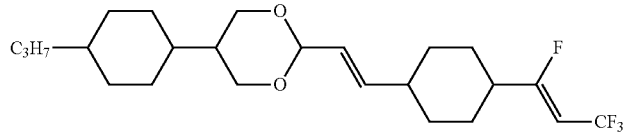 |
| 1-2-86 | 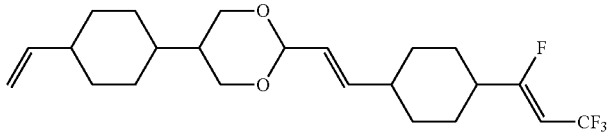 |
| 1-2-87 | 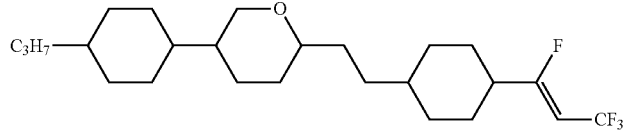 |
| 1-2-88 | 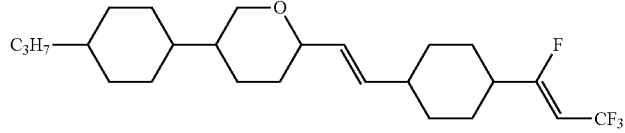 |
| 1-2-89 | 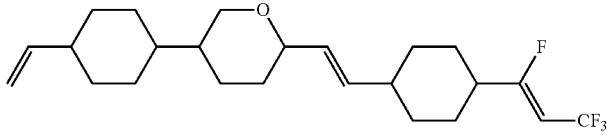 [SMILES: C=CC1CCC(C2CCC(/C=C/C3CCC(/C(F)=C/C(F)(F)F)CC3)OC2)CC1] |
| 1-2-90 | 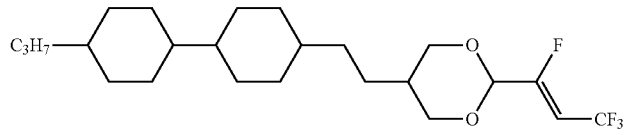 |
| 1-2-91 | 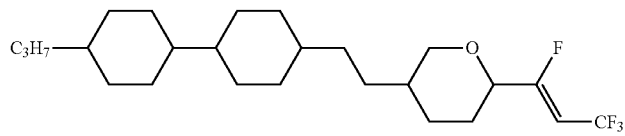 |
| 1-2-92 | 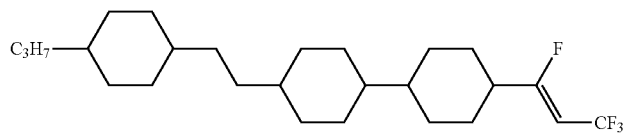 |
| 1-2-93 | 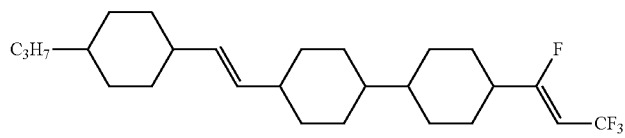 |
| 1-2-94 | 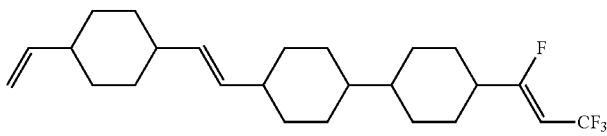 |

| No. | |
|---|---|
| 1-2-95 | 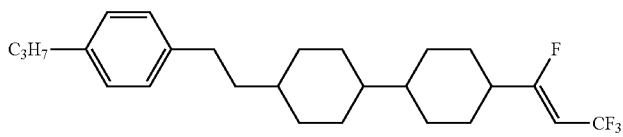 |
| 1-2-96 | 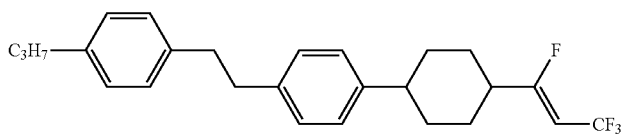 |
| 1-2-97 | 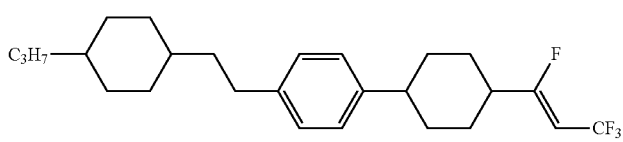 |
| 1-2-98 | 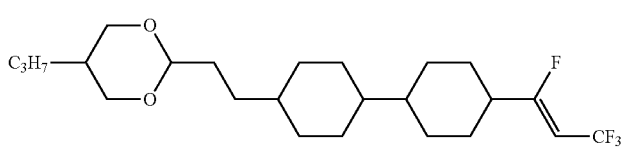 |
| 1-2-99 | 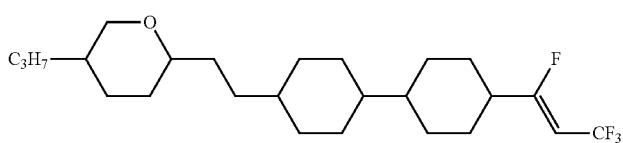 |
| 1-2-100 | 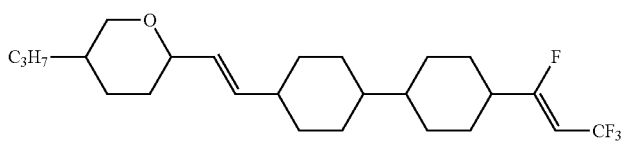 |
| 1-2-101 | 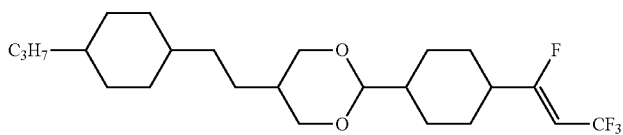 |
| 1-2-102 | 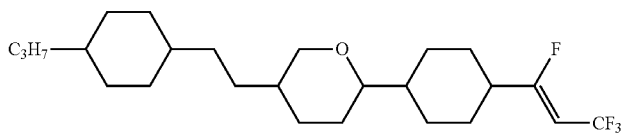 |
| 1-2-103 | 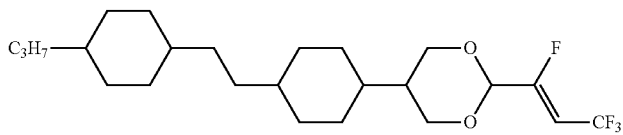 |
| 1-2-104 | 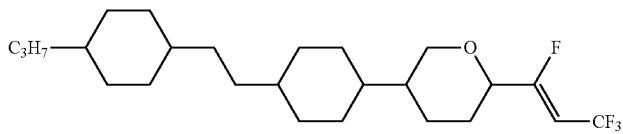 |
| 1-2-105 | 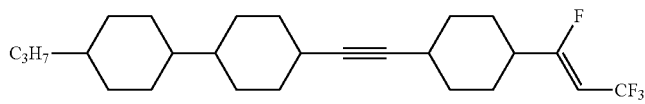 |

-continued
| No. | |
|---|---|
| 1-2-106 | 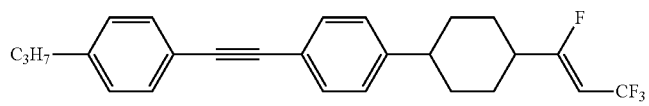 |
| 1-2-107 | 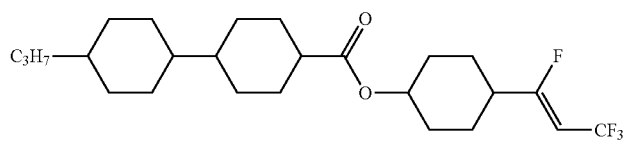 |
| 1-2-108 | 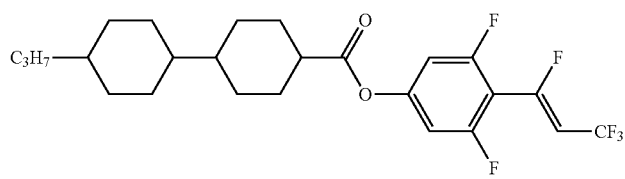 |
| 1-2-109 | 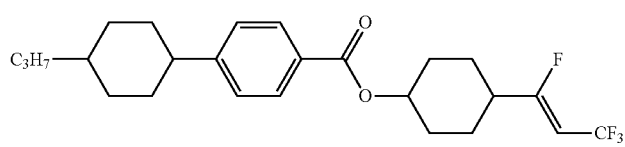 |
| 1-2-110 | 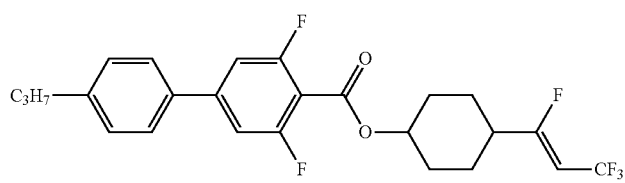 |
| 1-2-111 | 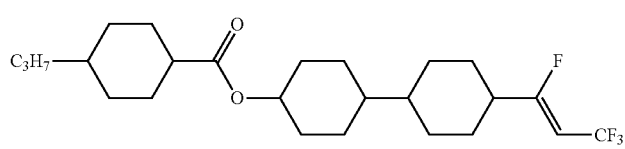 |
| 1-2-112 | 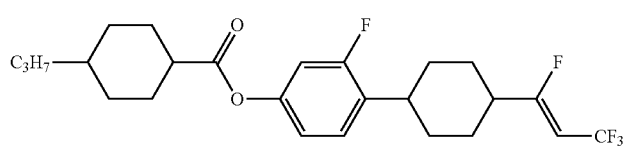 |
| 1-2-113 | 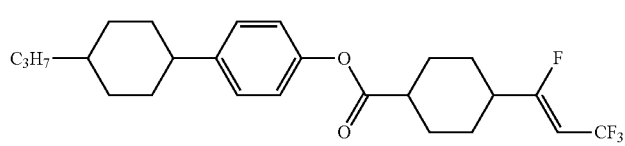 |
| 1-2-114 | 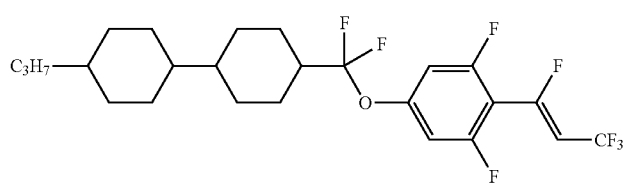 |
| 1-2-115 | 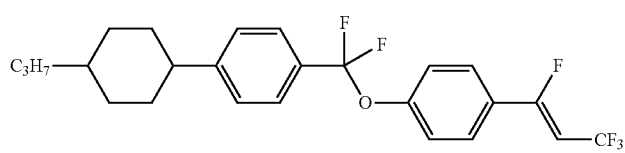 |

-continued
| No. | |
|---|---|
| 1-2-116 | 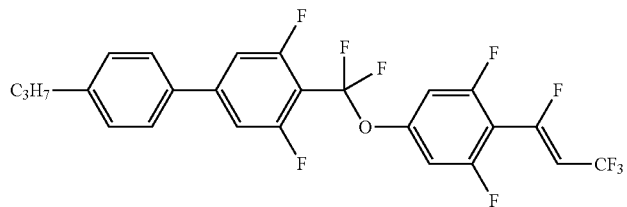<br>C 59.4 I<br>$T_{NI}$ = 23.7° C., $\Delta n$ = 0.144, $\Delta\epsilon$ = 55.2,<br>$\eta$ = 54.3 mPa·s |
| 1-2-117 | 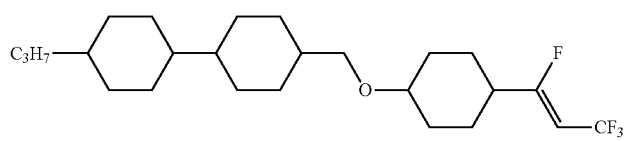 |
| 1-2-118 | 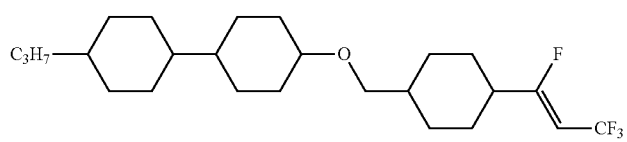 |
| 1-2-119 | 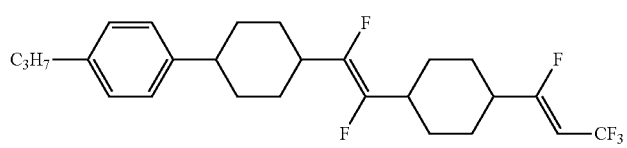 |
| 1-2-120 | 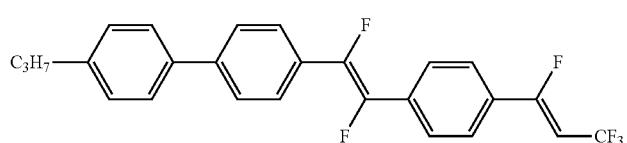 |
| 1-3-1 | 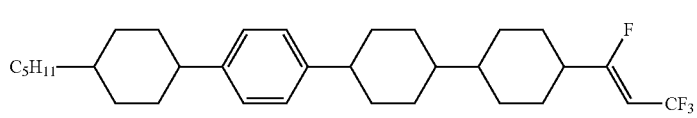 |
| 1-3-2 | 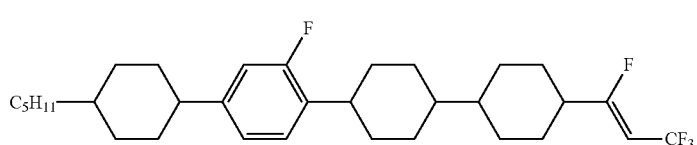 |
| 1-3-3 | 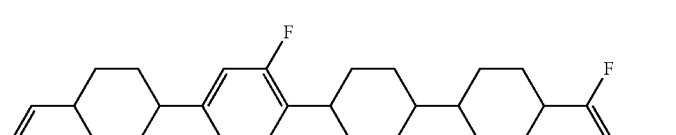 |
| 1-3-4 | 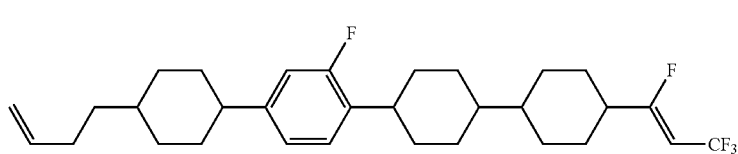 |
| 1-3-5 | 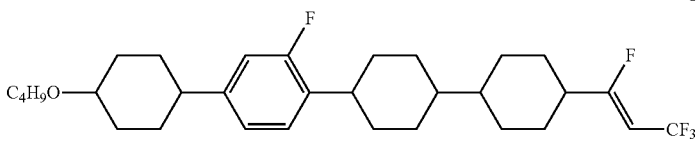 |

-continued
| No. |
|---|
| 1-3-6 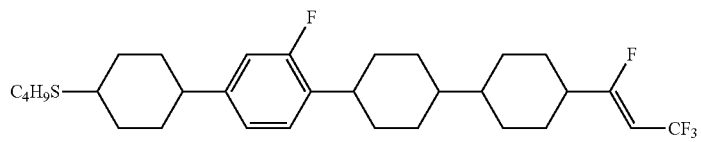 |
| 1-3-7 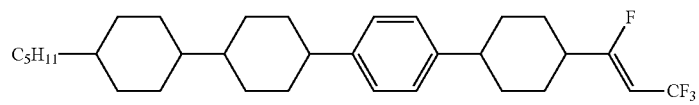 |
| 1-3-8 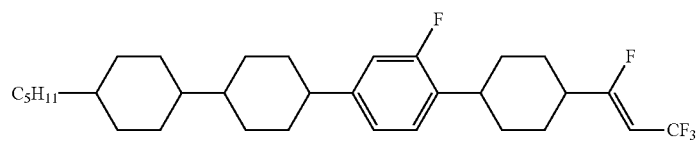 |
| 1-3-9 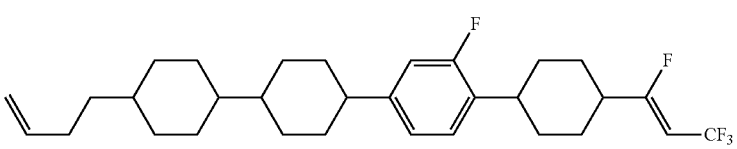 |
| 1-3-10 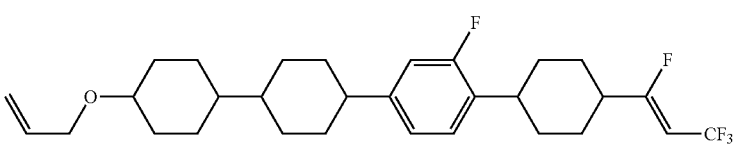 |
| 1-3-11 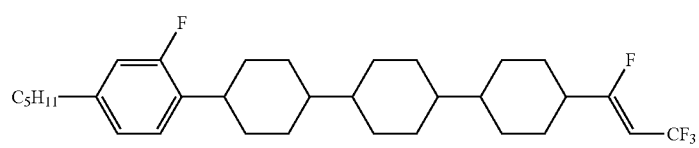 |
| 1-3-12 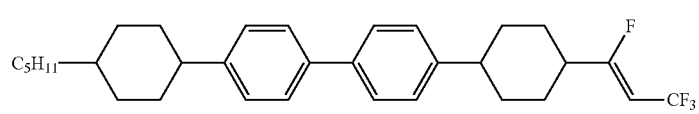 |
| 1-3-13 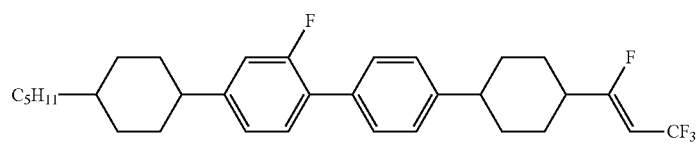 |
| 1-3-14 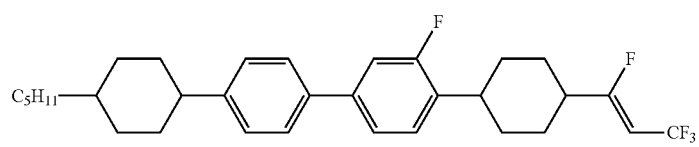 |
| 1-3-15 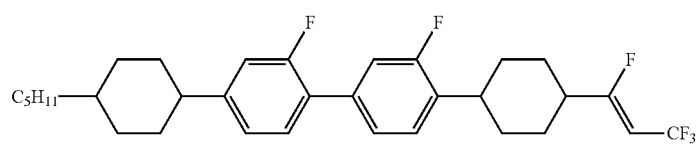 |
| 1-3-16 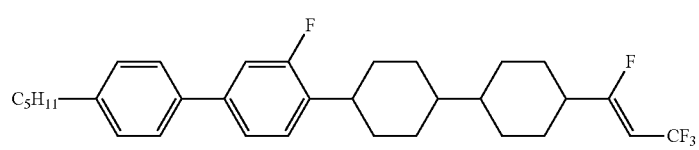 |

-continued
| No. | |
|---|---|
| 1-3-17 | 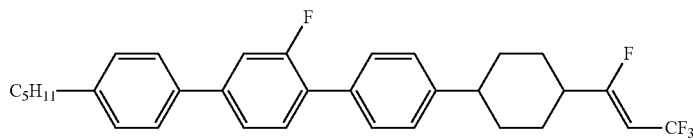 |
| 1-3-18 | 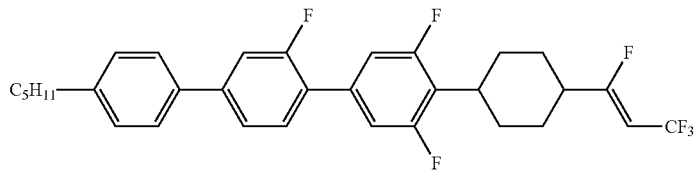 |
| 1-3-19 | 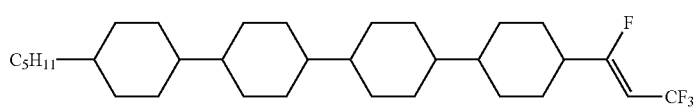 |
| 1-3-20 | 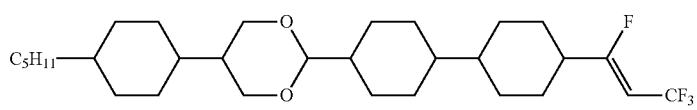 |
| 1-3-21 | 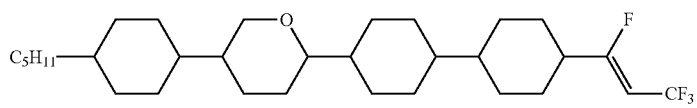 |
| 1-3-22 | 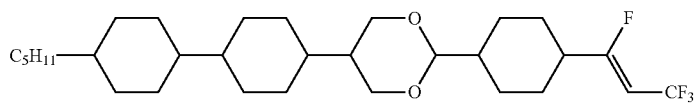 |
| 1-3-23 | 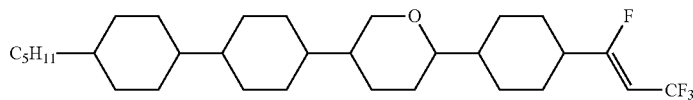 |
| 1-3-24 | 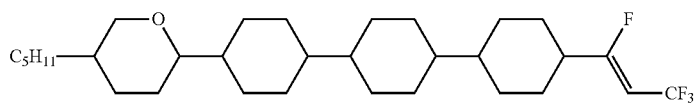 |
| 1-3-25 | 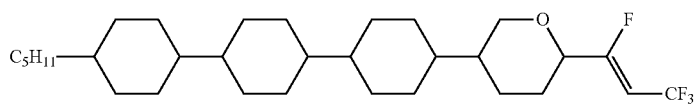 |
| 1-3-26 | 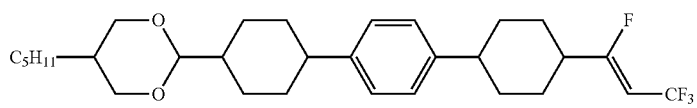 |
| 1-3-27 | 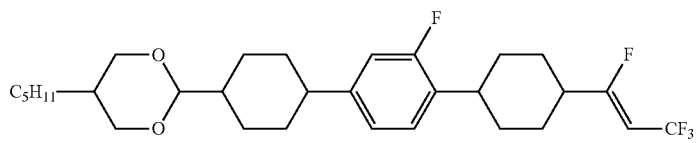 |
| 1-3-28 | 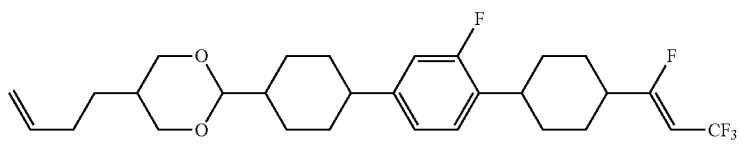 |

-continued
| No. | |
|---|---|
| 1-3-29 | 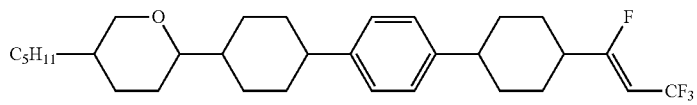 |
| 1-3-30 | 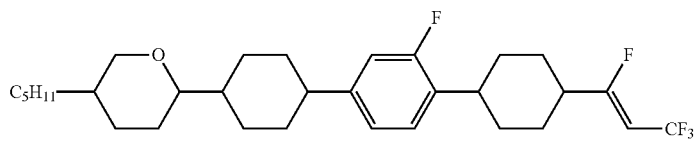 |
| 1-3-31 | 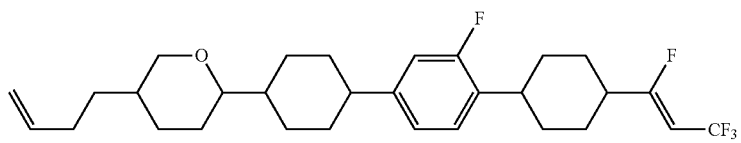 |
| 1-3-32 | 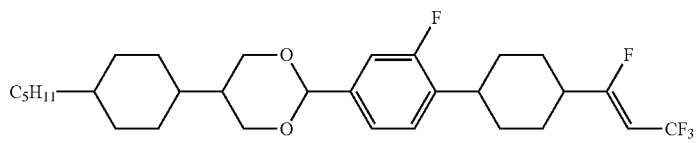 |
| 1-3-33 | 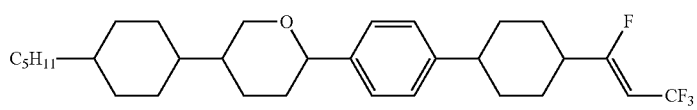 |
| 1-3-34 | 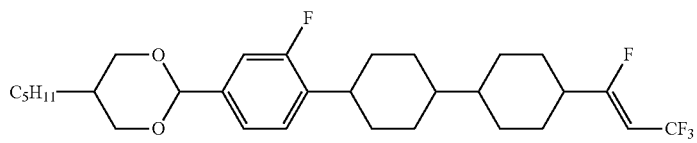 |
| 1-3-35 | 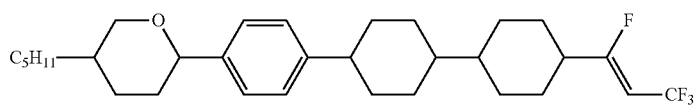 |
| 1-3-36 | 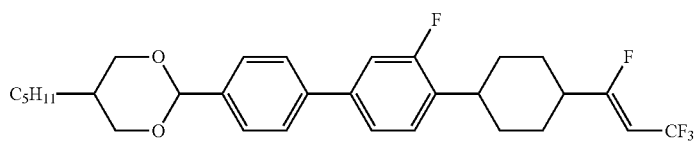 |
| 1-3-37 | 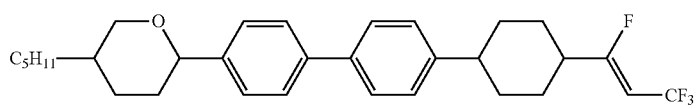 |
| 1-3-38 | 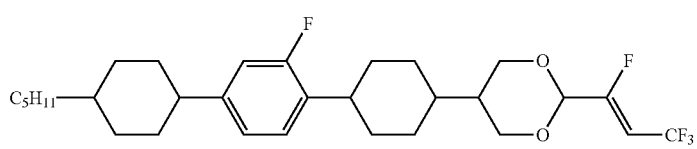 |
| 1-3-39 | 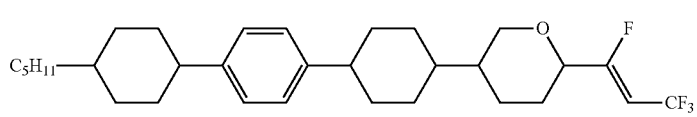 |

-continued
| No. | |
|---|---|
| 1-3-40 | 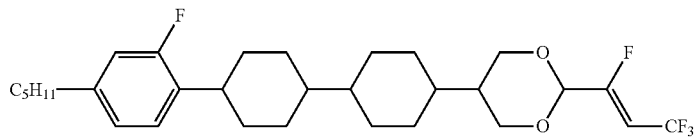 |
| 1-3-41 | 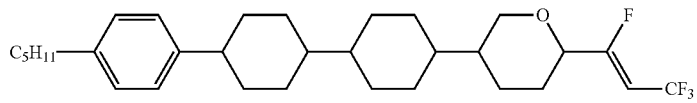 |
| 1-3-42 | 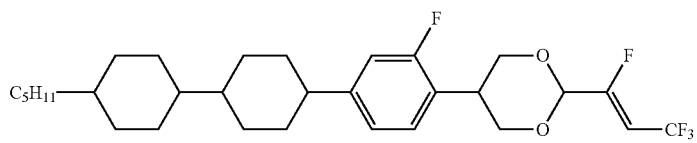 |
| 1-3-43 | 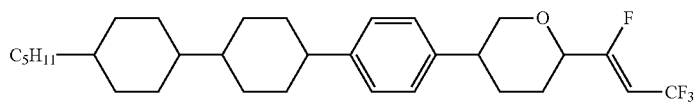 |
| 1-3-44 | 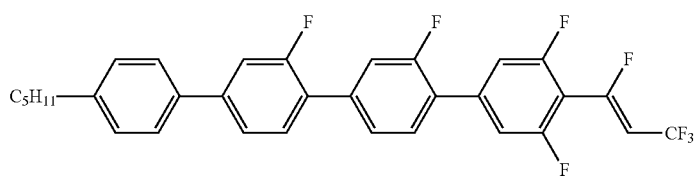 |
| 1-3-45 | 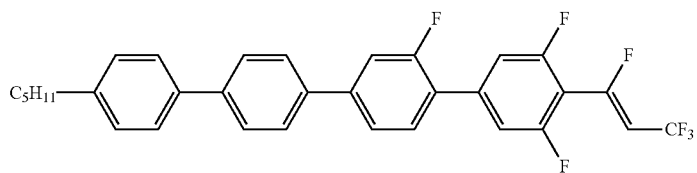 |
| 1-3-46 | 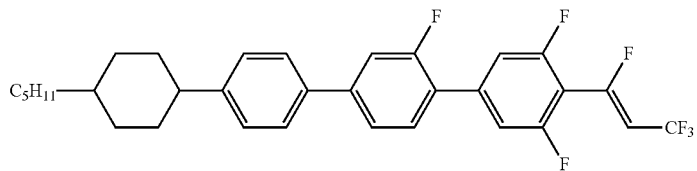 |
| 1-3-47 | 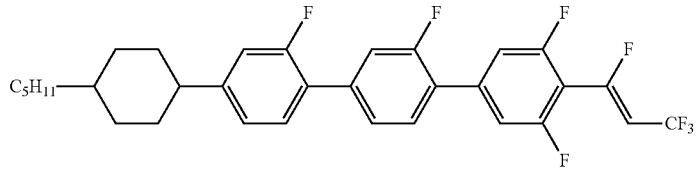 |
| 1-3-48 | 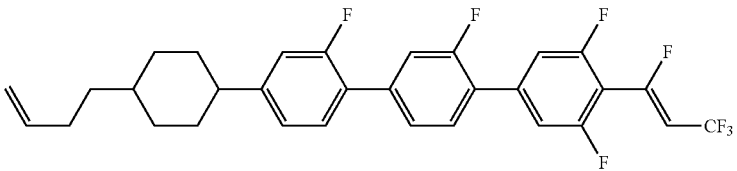 [SMILES: C=CCCC1CCC(c2ccc(-c3ccc(-c4cc(F)c(/C(F)=C/C(F)(F)F)c(F)c4)c(F)c3)c(F)c2)CC1] |

-continued
| No. | |
|---|---|
| 1-3-49 | 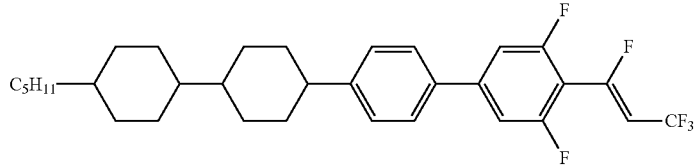 |
| 1-3-50 | 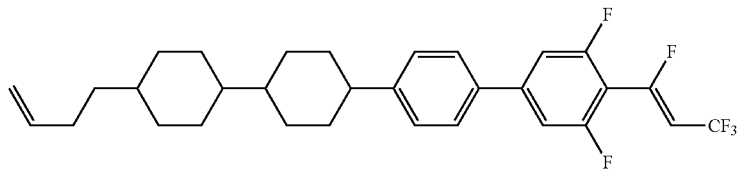 [SMILES: C=CCCC1CCC(C2CCC(c3ccc(-c4cc(F)c(/C(F)=C/C(F)(F)F)c(F)c4)cc3)CC2)CC1] |
| 1-3-51 | 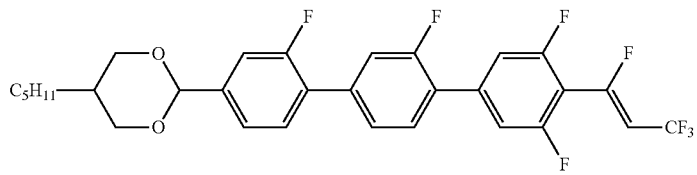 |
| 1-3-52 | 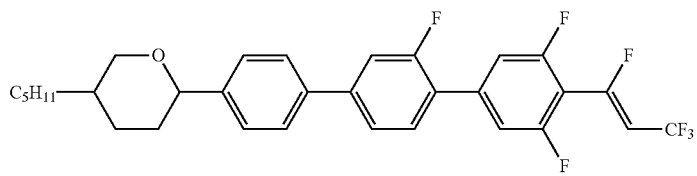 |
| 1-3-53 | 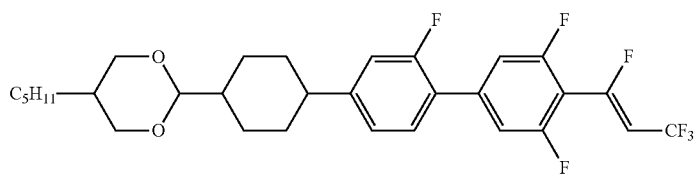 |
| 1-3-54 | 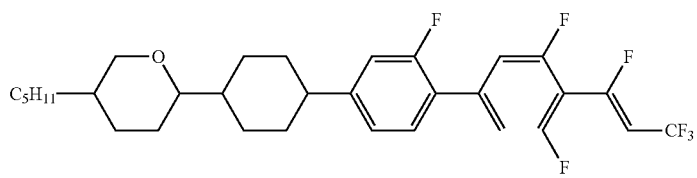 |
| 1-3-55 | 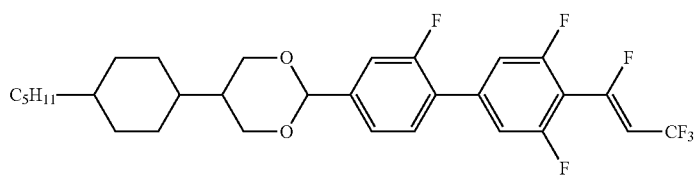 |
| 1-3-56 | 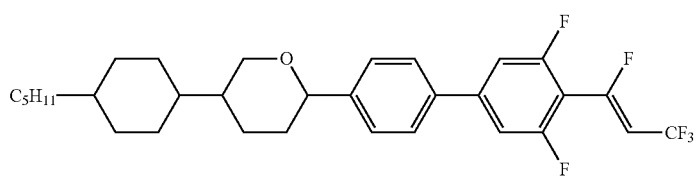 |

-continued
| No. | |
|---|---|
| 1-3-57 | 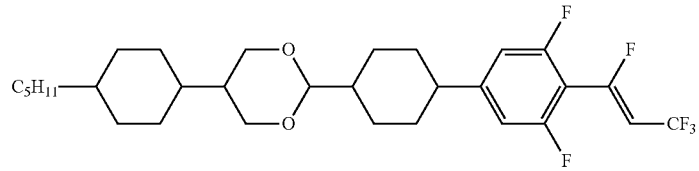 |
| 1-3-58 | 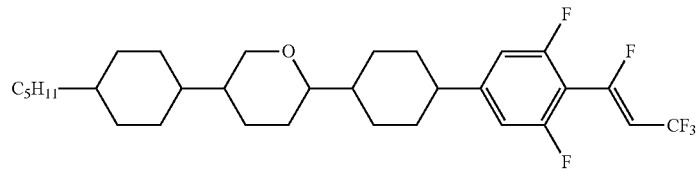 |
| 1-3-59 | 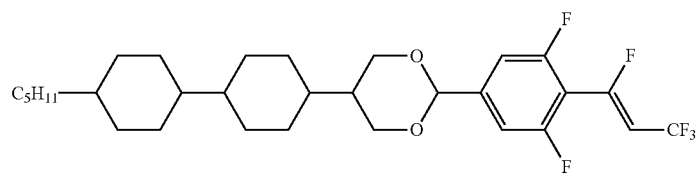 |
| 1-3-60 | 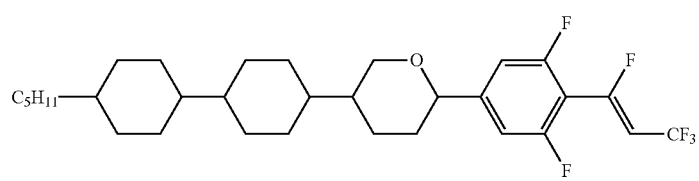 |
| 1-3-61 | 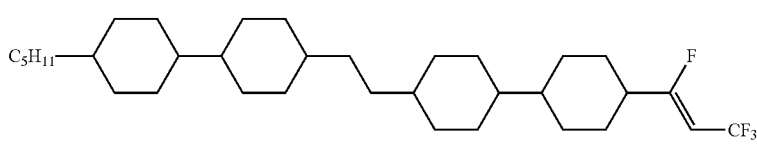 |
| 1-3-62 | 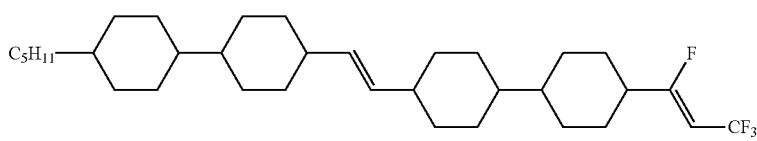 |
| 1-3-63 | 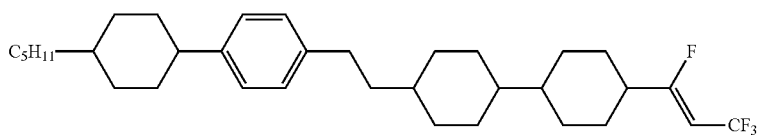 |
| 1-3-64 | 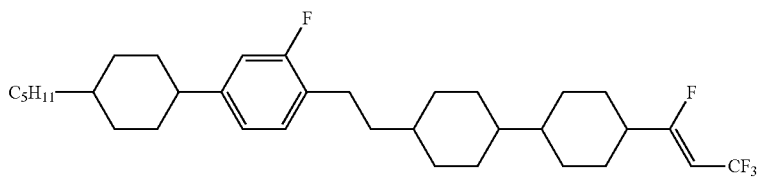 |
| 1-3-65 | 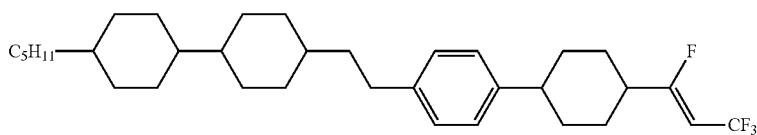 |

-continued
| No. | |
|---|---|
| 1-3-66 | 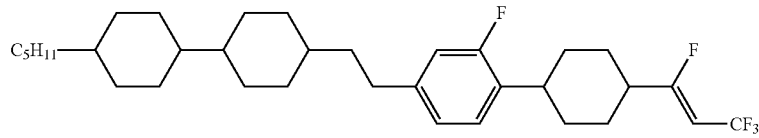 |
| 1-3-67 | 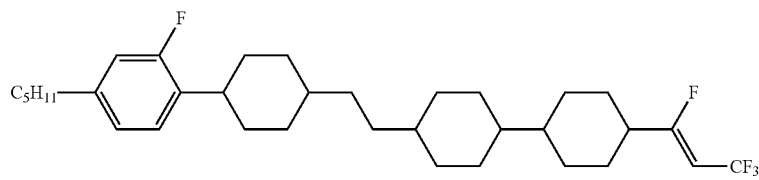 |
| 1-3-68 | 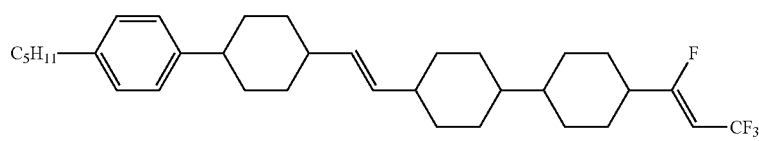 |
| 1-3-69 | 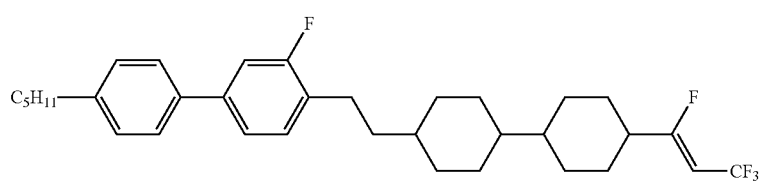 |
| 1-3-70 | 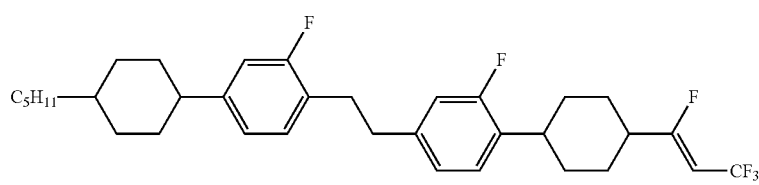 |
| 1-3-71 | 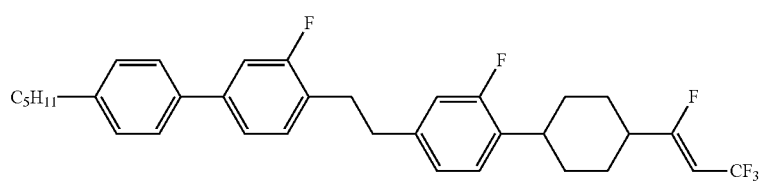 |
| 1-3-72 | 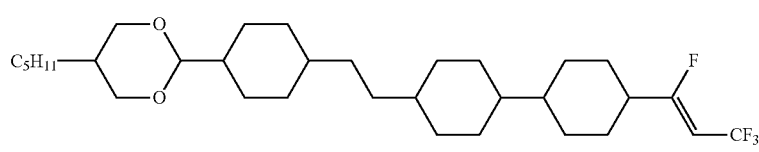 |
| 1-3-73 | 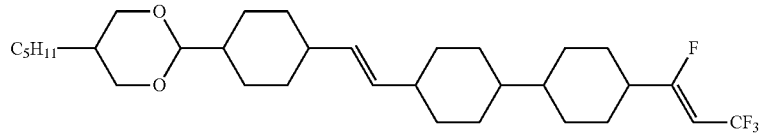 |
| 1-3-74 | 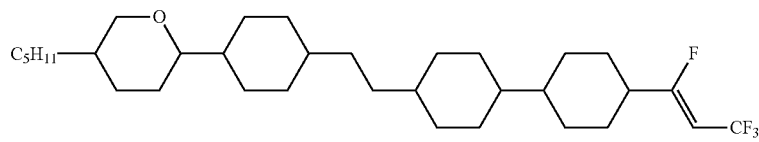 |

-continued
| No. | |
|---|---|
| 1-3-75 | 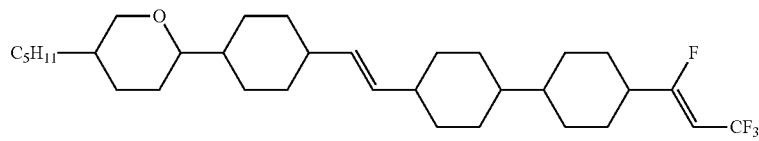 |
| 1-3-76 | 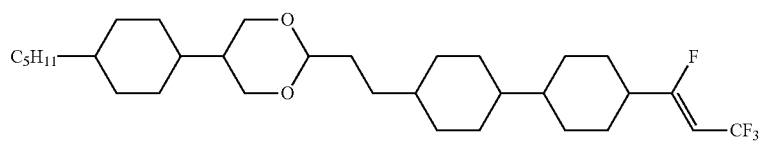 |
| 1-3-77 | 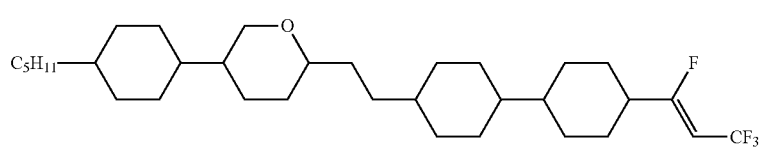 |
| 1-3-78 | 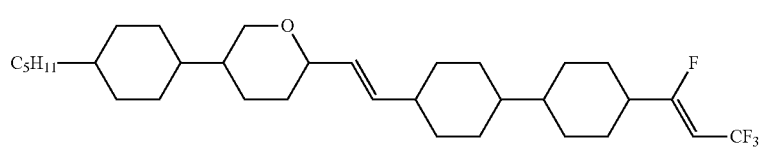 |
| 1-3-79 | 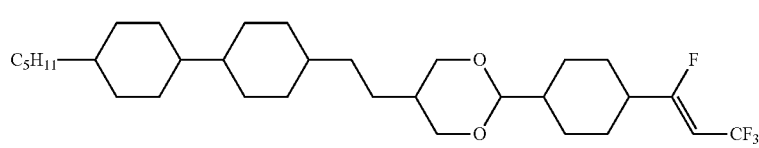 |
| 1-3-80 | 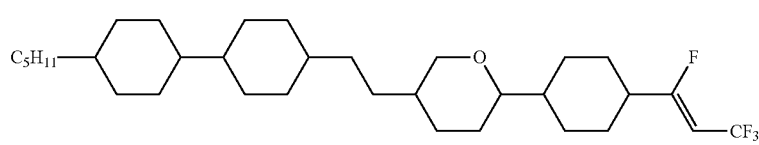 |
| 1-3-81 | 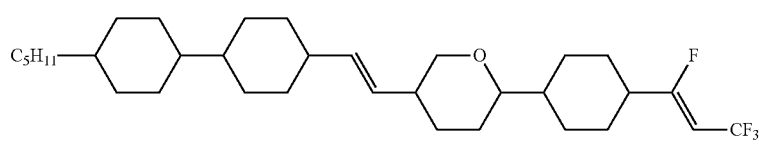 |
| 1-3-82 | 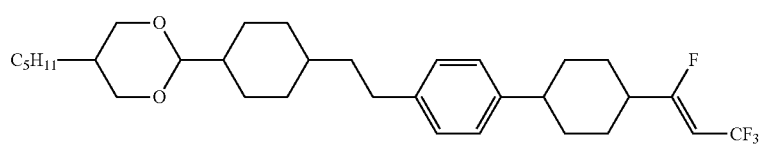 |
| 1-3-83 | 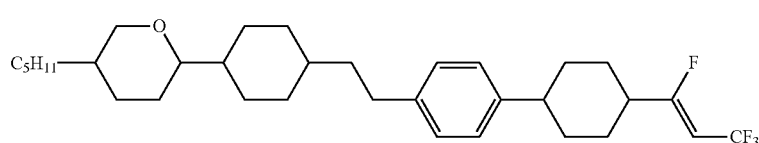 |
| 1-3-84 | 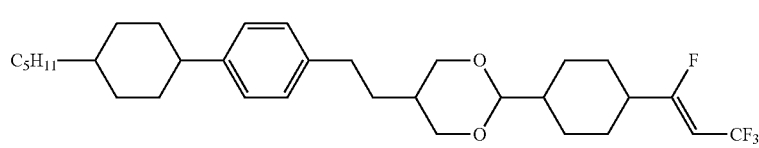 |

-continued
| No. | |
|---|---|
| 1-3-85 | 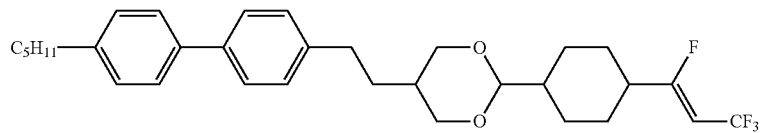 |
| 1-3-86 | 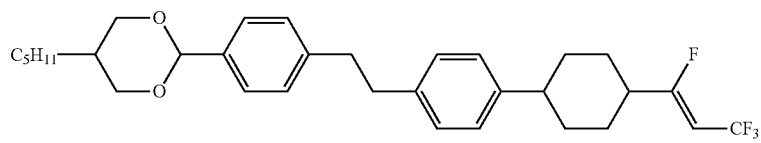 |
| 1-3-87 | 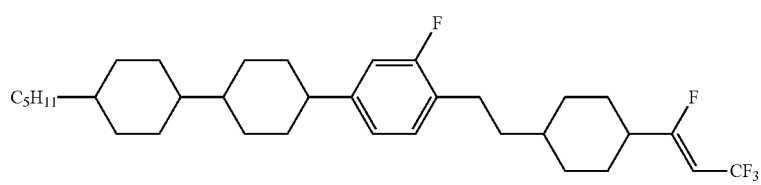 |
| 1-3-88 | 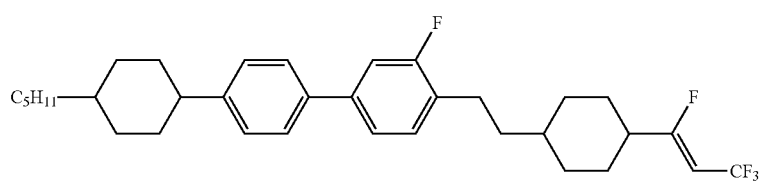 |
| 1-3-89 | 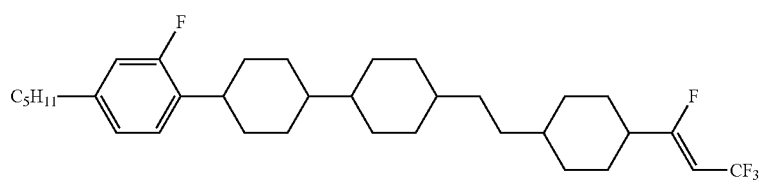 |
| 1-3-90 | 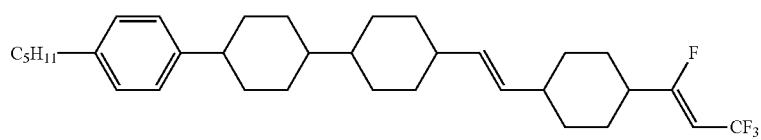 |
| 1-3-91 | 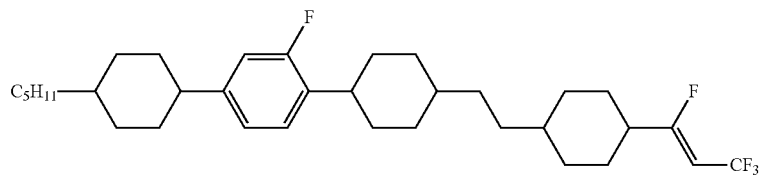 |
| 1-3-92 | 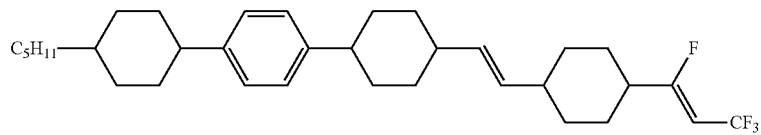 |
| 1-3-93 | 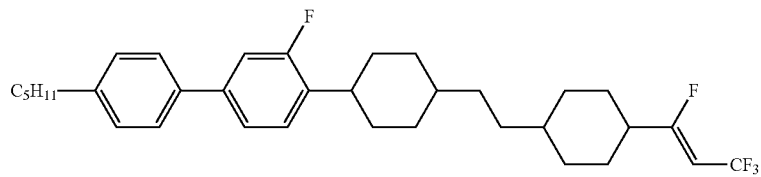 |

| No. | |
|---|---|
| 1-3-94 | 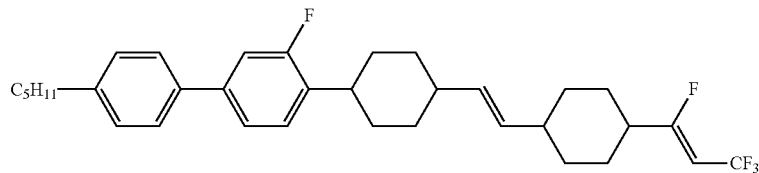 |
| 1-3-95 | 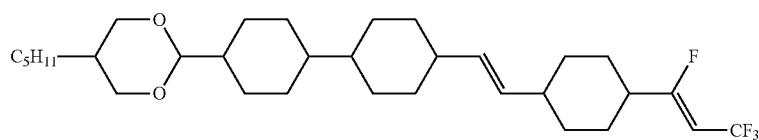 |
| 1-3-96 | 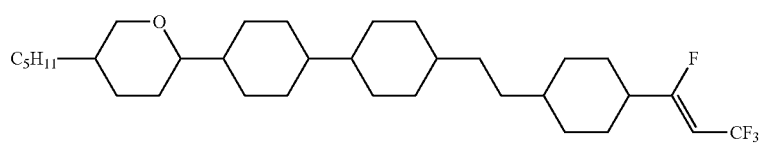 |
| 1-3-97 | 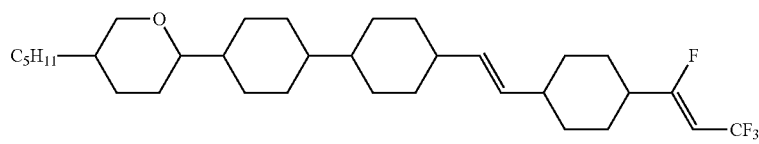 |
| 1-3-98 | 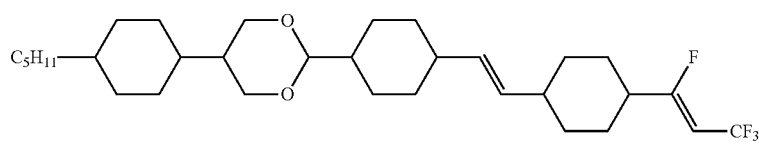 |
| 1-3-99 | 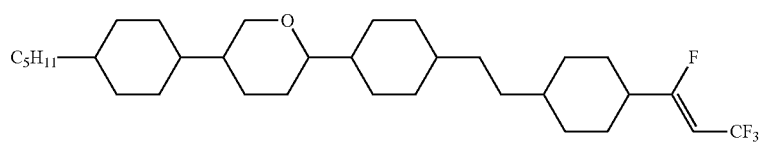 |
| 1-3-100 | 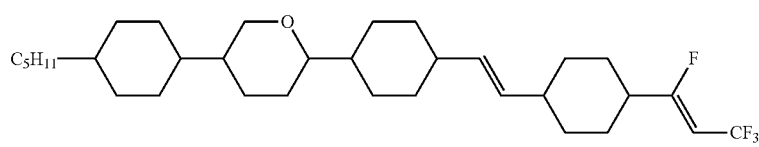 |
| 1-3-101 | 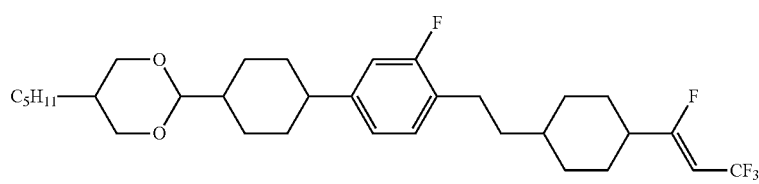 |
| 1-3-102 | 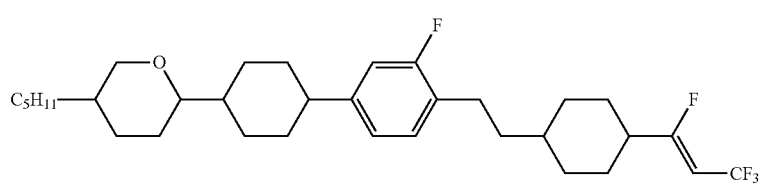 |
| 1-3-103 | 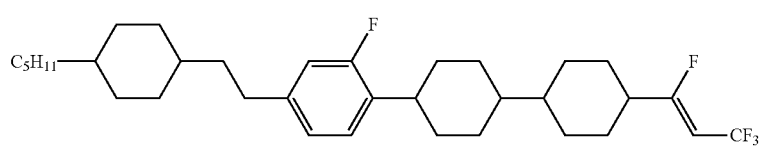 |

| No. | |
|---|---|
| 1-3-104 | 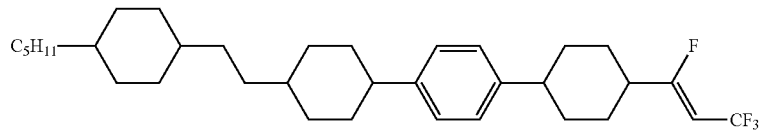 |
| 1-3-105 | 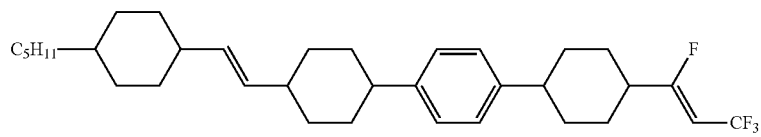 |
| 1-3-106 | 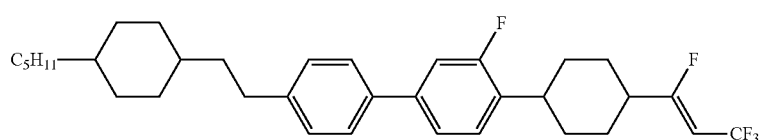 |
| 1-3-107 | 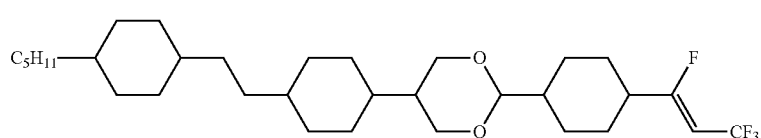 |
| 1-3-108 | 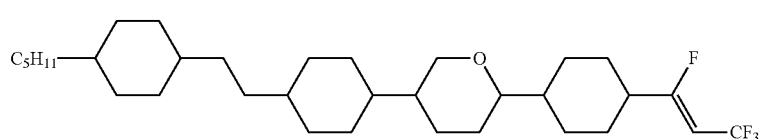 |
| 1-3-109 | 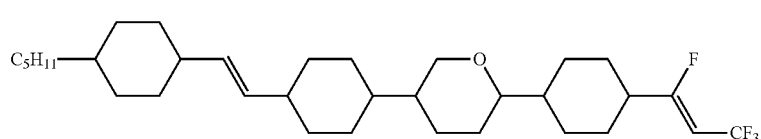 |
| 1-3-110 | 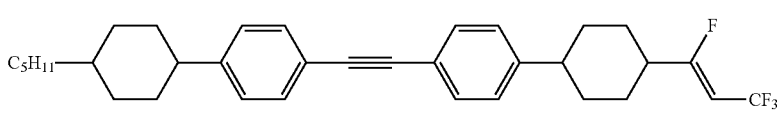 |
| 1-3-111 | 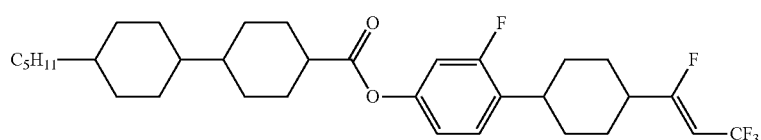 |
| 1-3-112 | 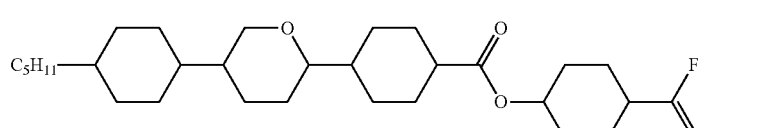 |
| 1-3-113 | 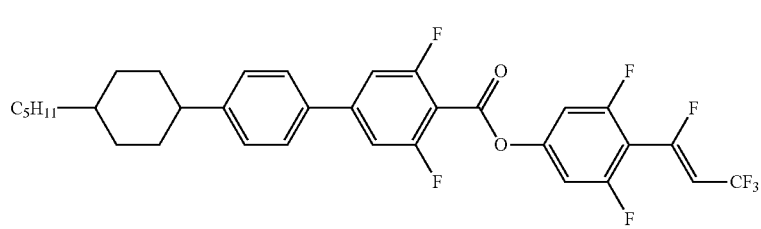 |

| No. | |
|---|---|
| 1-3-114 | 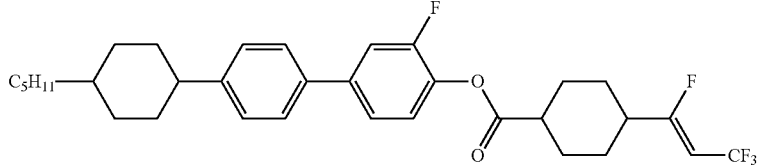 |
| 1-3-115 | 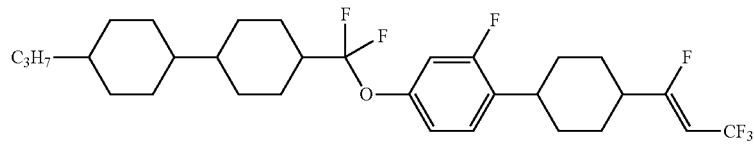
C 150 S$_B$ 159 N 276 I
T$_{NI}$ = 174° C., Δn = 0.127, Δε = 14.9,
η = 77.2 mPa·s |
| 1-3-116 | 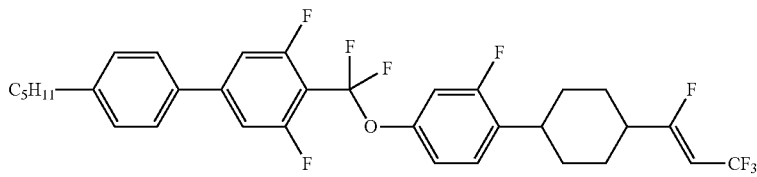 |
| 1-3-117 | 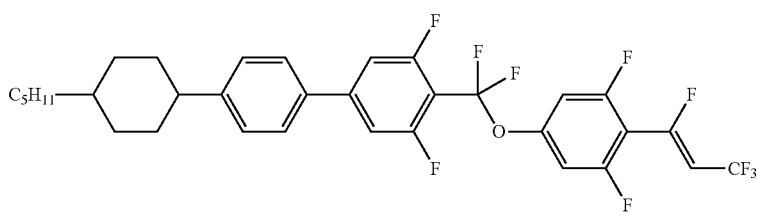 |
| 1-3-118 | 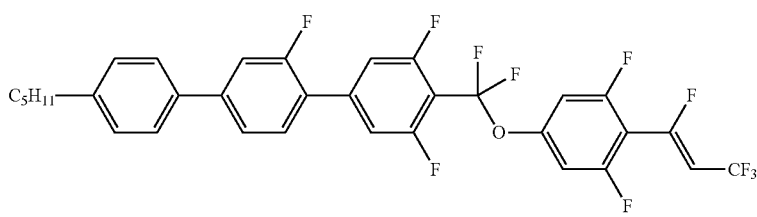 |
| 1-3-119 | 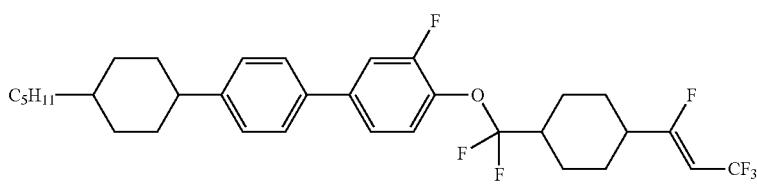 |
| 1-3-120 | 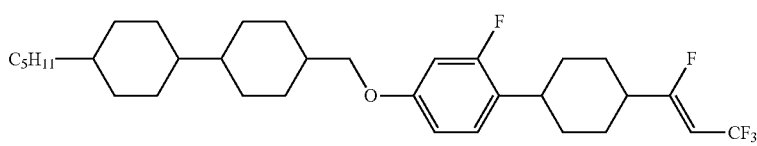 |
| 1-3-121 | 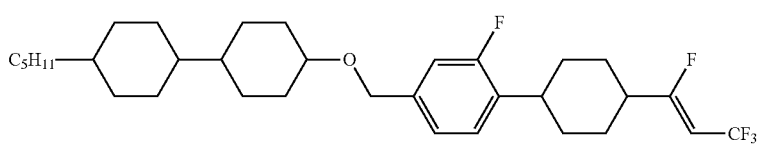 |

-continued
| No. |  |
|---|---|
| 1-3-122 | 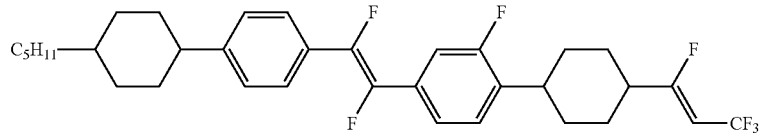 |
| 1-3-123 | 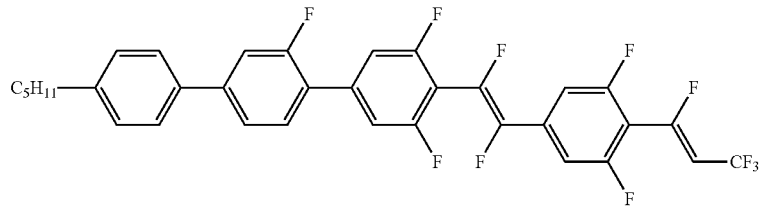 |
| 1-3-124 | 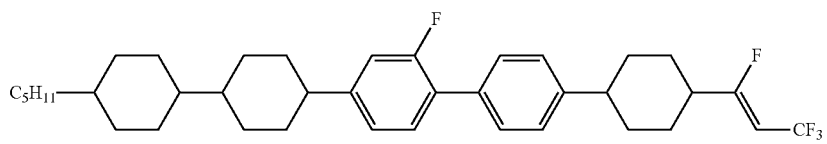 |
| 1-3-125 | 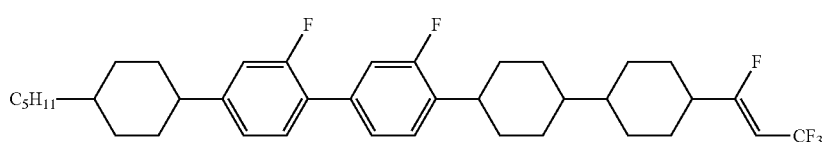 |
| 1-3-126 | 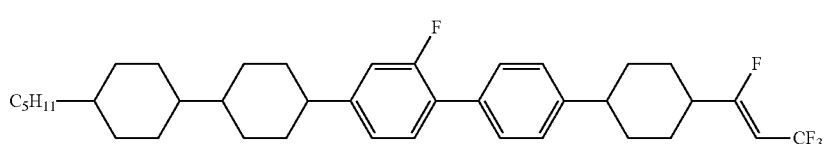 |
| 1-3-127 | 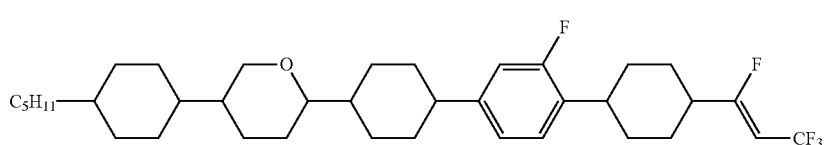 |
| 1-3-128 | 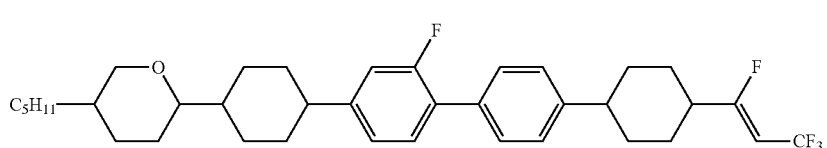 |
| 1-3-129 | 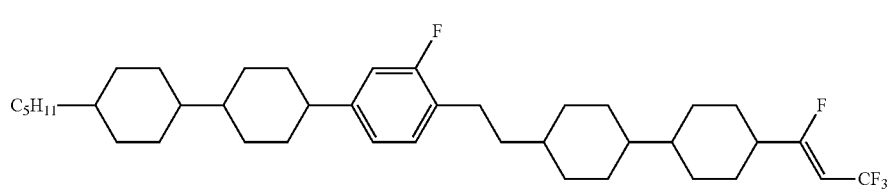 |
| 1-3-130 | 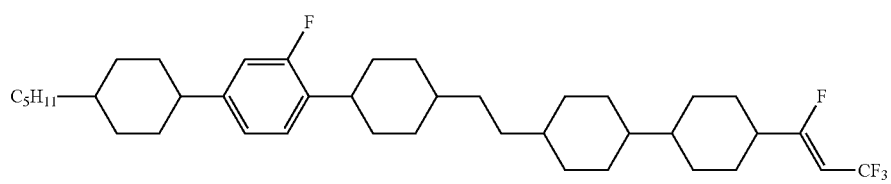 |

-continued
| No. | |
|---|---|
| 1-3-131 | 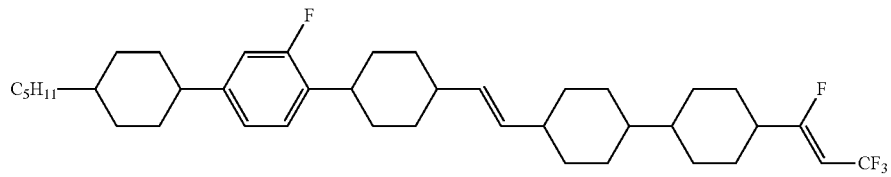 |
| 1-3-132 | 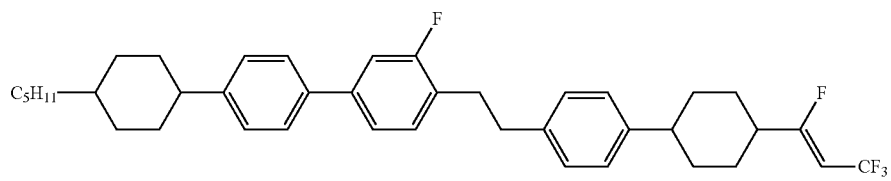 |
| 1-3-133 | 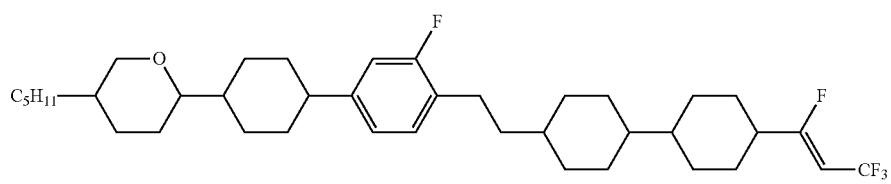 |
| 1-3-134 | 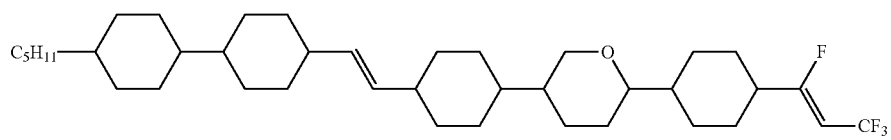 |
| 1-3-135 | 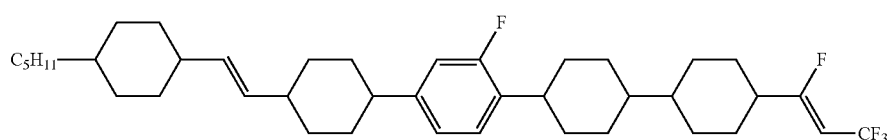 |
| 1-3-136 | 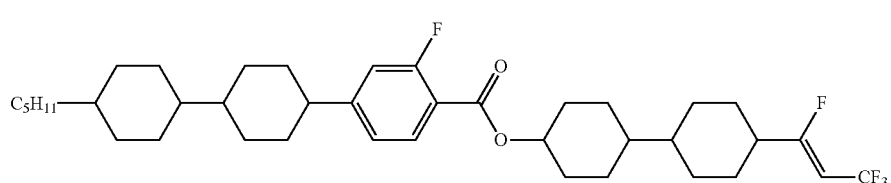 |
| 1-3-137 | 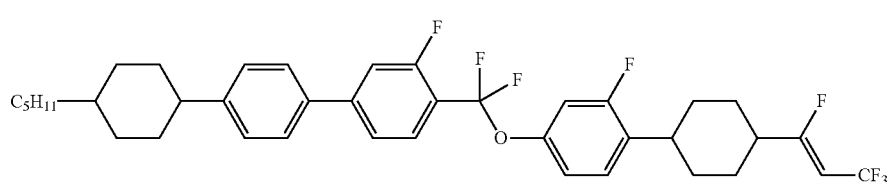 |
| 1-3-138 | 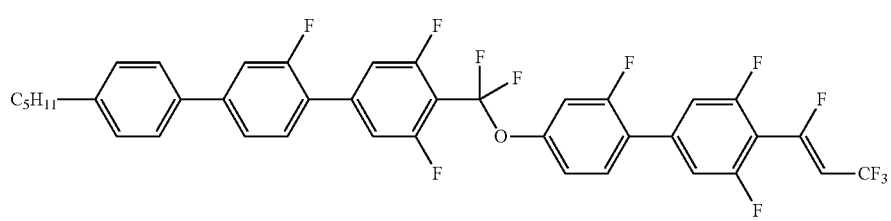 |

-continued

| No. | |
|---|---|
| 1-3-139 | 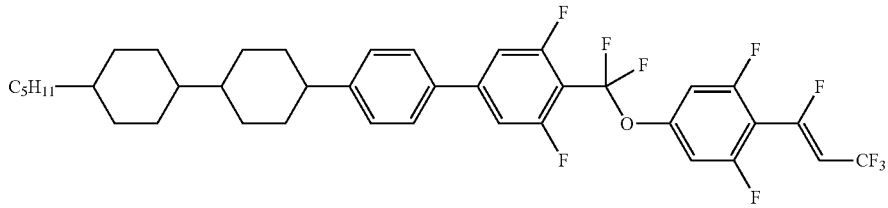 |
| 1-3-140 | 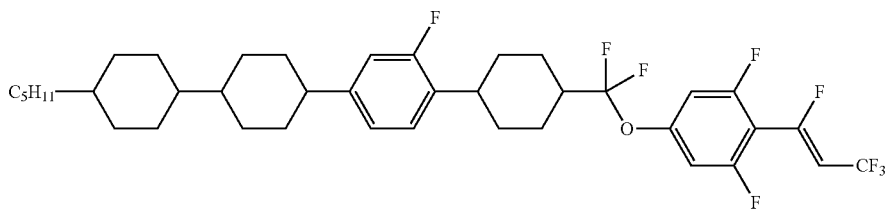 |

Comparative Example 1

Compound (S-1) was synthesized as a comparative compound. The compound is described in EP0480217A, and is a compound having trifluoromethylvinyl that is obtain by substituting one fluorine of the compound of the invention with hydrogen.

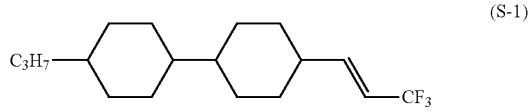

(S-1)

Chemical shift δ (ppm; CDCl$_3$): 6.31 (m, 1H), 5.53 (m, 1H), 2.04-1.95 (m, 1H), 1.84-1.65 (m, 9H), 1.35-1.26 (m, 2H), 1.20-0.91 (m, 10H), 0.91-0.80 (m, 5H).

The characteristic values of comparative compound (S-1) were as follows.

Phase transition temperatures: C 55.7 S$_B$ 62.8 I.
T$_{NI}$=25.0° C.; Δ∈=7.40; Δn=0.057; η=8.70 mPa·s.

Comparative Example 2

Physical properties of compound no. (1-1-1) obtained in Example 1 and comparative compound (S-1) are put together in Table 1. It is clear from Table 1 that compound no. (1-1-1) was superior to comparative compound (S-1) in having a larger dielectric anisotropy.

Compound (S-2) was synthesized as a comparative compound. The compound is described in JP 2005-298466A, and is a compound having perfluoropropenyl that is obtain by substituting one hydrogen of the compound of the invention with fluorine.

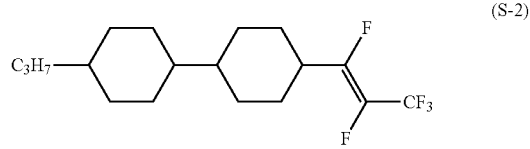

(S-2)

Chemical shift δ (ppm; CDCl$_3$): 2.65-2.50 (m, 1H), 1.90-1.67 (m, 8H), 1.55-1.44 (m, 2H), 1.35-1.28 (m, 2H), 1.20-0.80 (m, 14H).

Physical properties of comparative compound (S-2) were given below.

Phase transition temperatures: C 49.5 S$_B$ 62.6 I.
T$_{NI}$=27.7° C.; Δ∈=8.10; Δn=0.057; η=7.30 mPa·s.

TABLE 1

Characteristic values of compound no. (1-1-1) and comparative compound (S-1)

| | Compound no. (1-1-1) | Comparative compound (S-1) |
|---|---|---|
| Maximum temperature (T$_{NI}$) | 22.4° C. | 25.0° C. |
| Dielectric anisotropy (Δε) | 13.2 | 7.40 |
| Optical anisotropy (Δn) | 0.050 | 0.057 |
| Viscosity (η) | 16.2 mPa·s | 8.70 mPa·s |

TABLE 2

Characteristic values of compound no. (1-1-1) and comparative compound (S-2)

Compound no. (1-1-1)

Comparative compound (S-2)

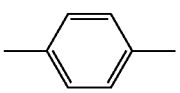

| | | |
|---|---|---|
| Maximum temperature ($T_{NI}$) | 22.4° C. | 27.7° C. |
| Dielectric anisotropy (Δε) | 13.2 | 8.10 |
| Optical anisotropy (Δn) | 0.050 | 0.057 |
| Viscosity (η) | 16.2 mPa·s | 7.30 mPa·s |

Physical properties of Compound no. (1-1-1) obtained in Example 1 and comparative compound (S-2) are put together in Table 2. It is clear from Table 2 that as compared with comparative compound (S-2), compound no. (1-1-1) had a larger dielectric anisotropy. It is particularly worth mentioning that though compound no. (1-1-1) had one less fluorine substituent than comparative compound (S-2), its dielectric anisotropy was larger than that of the latter.

Examples of Composition (1)

The liquid crystal composition of the invention will be explained in details by way of Examples. The invention is not limited by the Examples described below. The compounds in the Examples were expressed using symbols according to the definitions in Table 3 below. In Table 3, the configuration of 1,4-cyclohexylene is trans. A parenthesized number next to a symbolized compound in the Examples corresponds to the number of the compound. The symbol "(-)" means any other liquid crystal compound. The proportions (percent) of the liquid crystal compounds is presented in terms of weight percent (wt %) based on the total weight of the liquid crystal composition. The values of characteristics of the composition were summarized in the last part. The characteristics were measured with the methods described above, and were directly described without extrapolating the measured values.

TABLE 3

Method of expressing compounds using symbols
R—($A_1$)—$Z_1$— ... —$Z_n$—($A_n$)—R'

| 1) Left-terminal group R— | Symbol |
|---|---|
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |

| 2) Right-terminal group —R' | Symbol |
|---|---|
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |

TABLE 3-continued

Method of expressing compounds using symbols
R—($A_1$)—$Z_1$— ... —$Z_n$—($A_n$)—R'

| | |
|---|---|
| —Cl | —CL |
| —$OCF_3$ | —OCF3 |
| —$OCF_2H$ | —OCF2H |
| —$CF_3$ | —CF3 |
| —CF=CH—$CF_3$ | —FVCF3 |
| —C≡N | —C |

| 3) Linking group —$Z_n$— | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

| 4) Ring structure —$A_n$— | Symbol |
|---|---|
| 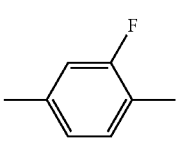 | H |
| 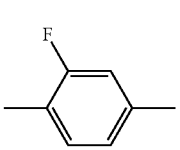 | B |
| 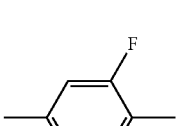 | B(F) |
| (2F structure) | B(2F) |
| (F,F structure) | B(F,F) |

TABLE 3-continued

Method of expressing compounds using symbols
R—(A₁)—Z₁—...—Zₙ—(Aₙ)—R'

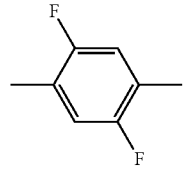 B(2F,5F)

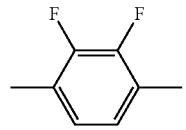 B(2F,3F)

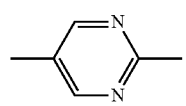 Py

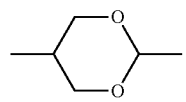 G

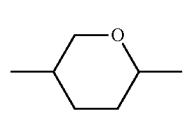 dh

5) Examples of Expression

Example 1 3-HH-FVCF3

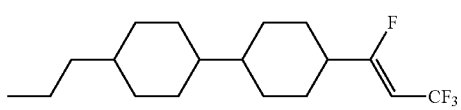

Example 2 3-BB(F)B(F,F)-FVCF3

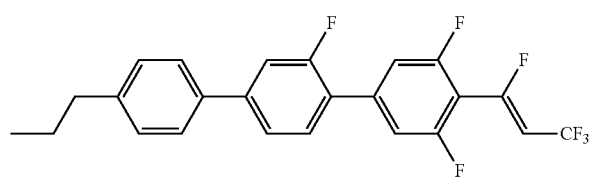 [SMILES: CCCc1ccc(-c2ccc(-c3cc(F)c(/C(F)=C/C(F)(F)F)c(F)c3)c(F)c2)cc1]

Example 3 3-HH-4

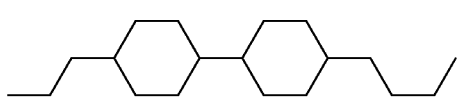 [SMILES: CCCCC1CCC(C2CCC(CCC)CC2)CC1]

Example 4 3-HBB(F,F)-F

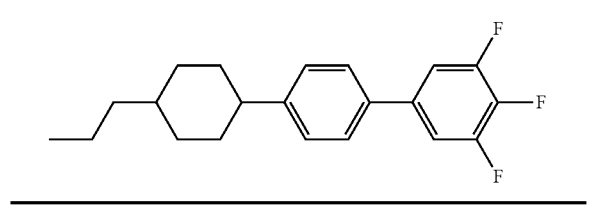

Example 13

| | | |
|---|---|---|
| 3-HH-FVCF3 | (1-1-1) | 3% |
| 5-HB-CL | (2-2) | 16% |
| 3-HH-4 | (12-1) | 12% |
| 3-HH-5 | (12-1) | 4% |
| 3-HHB-F | (3-1) | 4% |
| 3-HHB-CL | (3-1) | 3% |
| 4-HHB-CL | (3-1) | 4% |
| 3-HHB(F)-F | (3-2) | 10% |
| 4-HHB(F)-F | (3-2) | 7% |
| 5-HHB(F)-F | (3-2) | 8% |
| 7-HHB(F)-F | (3-2) | 8% |
| 5-HBB(F)-F | (3-23) | 4% |
| 1O1-HBBH-5 | (14-1) | 3% |
| 3-HHBB(F,F)-F | (4-6) | 2% |
| 4-HHBB(F,F)-F | (4-6) | 3% |
| 5-HHBB(F,F)-F | (4-6) | 3% |
| 3-HH2BB(F,F)-F | (4-15) | 3% |
| 4-HH2BB(F,F)-F | (4-15) | 3% |

NI = 112.6° C.; Δn = 0.090; Δ∈ = 4.0; Vth = 2.45 V; η = 19.2 mPa·s.

Example 14

| | | |
|---|---|---|
| 3-BHH-FVCF3 | (1-2-3) | 3% |
| 3-dhHH-FVCF3 | (1-2-27) | 3% |
| 3-HHB(F,F)-F | (3-3) | 8% |
| 3-H2HB(F,F)-F | (3-15) | 8% |
| 4-H2HB(F,F)-F | (3-15) | 8% |
| 5-H2HB(F,F)-F | (3-15) | 5% |
| 3-HBB(F,F)-F | (3-24) | 20% |
| 5-HBB(F,F)-F | (3-24) | 20% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (14-1) | 4% |
| 1O1-HBBH-5 | (14-1) | 3% |

Example 15

| | | |
|---|---|---|
| 1-BHH-FVCF3 | (1-2-1) | 3% |
| 3-GHH-FVCF3 | (1-2-24) | 3% |
| 5-HB-F | (2-2) | 12% |
| 6-HB-F | (2-2) | 9% |
| 7-HB-F | (2-2) | 7% |
| 2-HHB-OCF3 | (3-1) | 7% |
| 3-HHB-OCF3 | (3-1) | 7% |
| 4-HHB-OCF3 | (3-1) | 5% |
| 5-HHB-OCF3 | (3-1) | 5% |
| 3-HH2B-OCF3 | (3-4) | 4% |
| 3-HHB(F,F)-OCF2H | (3-3) | 4% |
| 3-HHB(F,F)-OCF3 | (3-3) | 5% |
| 3-HH2B(F)-F | (3-5) | 3% |
| 3-HBB(F)-F | (3-23) | 10% |
| 5-HBB(F)-F | (3-23) | 10% |
| 5-HBBH-3 | (14-1) | 3% |
| 3-HB(F)BH-3 | (14-2) | 3% |

Example 16

| | | |
|---|---|---|
| 3-HGH-FVCF3 | (1-2-30) | 3% |
| 3-BB(F)B(F,F)-FVCF3 | (1-2-43) | 5% |
| 5-HB-CL | (2-2) | 11% |

-continued

| | | |
|---|---|---|
| 3-HH-4 | (12-1) | 8% |
| 3-HHB-1 | (13-1) | 5% |
| 3-HHB(F,F)-F | (3-3) | 8% |
| 3-HBB(F,F)-F | (3-24) | 15% |
| 5-HBB(F,F)-F | (3-24) | 15% |
| 3-HHEB(F,F)-F | (3-12) | 10% |
| 4-HHEB(F,F)-F | (3-12) | 3% |
| 5-HHEB(F,F)-F | (3-12) | 3% |
| 2-HBEB(F,F)-F | (3-39) | 3% |
| 3-HBEB(F,F)-F | (3-39) | 5% |
| 5-HBEB(F,F)-F | (3-39) | 3% |
| 3-HHBB(F,F)-F | (4-6) | 3% |

NI = 72.0° C.; Δn = 0.092; Δ∈ = 7.7; Vth = 1.45 V; η = 18.5 mPa·s.

Example 17

| | | |
|---|---|---|
| 3-BB(F)B(F,F)-FVCF3 | (1-2-43) | 4% |
| 5-HB(F)HH-FVCF3 | (1-3-2) | 3% |
| 3-HB-CL | (2-2) | 6% |
| 5-HB-CL | (2-2) | 4% |
| 3-HHB-OCF3 | (3-1) | 5% |
| 3-H2HB-OCF3 | (3-13) | 5% |
| 5-H4HB-OCF3 | (3-19) | 10% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF3 | (3-21) | 8% |
| 5-H4HB(F,F)-CF3 | (3-21) | 10% |
| 5-H2HB(F,F)-F | (3-15) | 5% |
| 5-H4HB(F,F)-F | (3-21) | 5% |
| 2-H2BB(F)-F | (3-26) | 5% |
| 3-H2BB(F)-F | (3-26) | 10% |
| 3-HBEB(F,F)-F | (3-39) | 5% |

Example 18

| | | |
|---|---|---|
| 3-HH-FVCF3 | (1-1-1) | 3% |
| 3-BB(F)-FVCF3 | (1-1-25) | 4% |
| 5-HB-CL | (2-2) | 3% |
| 7-HB(F)-F | (2-3) | 6% |
| 3-HH-4 | (12-1) | 9% |
| 3-HH-EMe | (12-2) | 20% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 3% |
| 5-HGB(F,F)-F | (3-103) | 6% |
| 2-H2GB(F,F)-F | (3-106) | 4% |
| 3-H2GB(F,F)-F | (3-106) | 4% |
| 5-GHB(F,F)-F | (3-109) | 7% |

Example 19

| | | |
|---|---|---|
| 5-HH-FVCF3 | (1-1-3) | 3% |
| 5-HGH-FVCF3 | (1-2-31) | 3% |
| 2-HB-C | (5-1) | 5% |
| 3-HB-C | (5-1) | 10% |
| 3-HB-O2 | (12-5) | 15% |
| 2-BTB-1 | (12-10) | 3% |
| 3-HHB-1 | (13-1) | 7% |
| 3-HHB-F | (3-1) | 4% |
| 3-HHB-O1 | (13-1) | 5% |
| 3-HHB-3 | (13-1) | 12% |
| 3-HHEB-F | (3-10) | 4% |
| 5-HHEB-F | (3-10) | 4% |
| 2-HHB(F)-F | (3-2) | 7% |

-continued

| | | |
|---|---|---|
| 3-HHB(F)-F | (3-2) | 7% |
| 5-HHB(F)-F | (3-2) | 7% |
| 3-HHB(F,F)-F | (3-3) | 4% |

Example 20

| | | |
|---|---|---|
| 3-BHH-FVCF3 | (1-2-3) | 5% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 20% |
| 5-HBB(F,F)-F | (3-24) | 16% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (14-1) | 4% |
| 1O1-HBBH-5 | (14-1) | 4% |

NI = 100.1° C.; Δn = 0.115; Δ∈ = 9.1; Vth = 1.79 V; η = 35.6 mPa·s.

After 0.25 part of Op-05 was added to 100 parts of the above composition, the pitch was 62.3 μm.

Example 21

| | | |
|---|---|---|
| 3-HHVH-FVCF3 | (1-2-71) | 3% |
| 3-HB-O2 | (12-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 9% |
| 3-HBB(F)-F | (3-23) | 9% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

NI = 92.5° C.; Δn = 0.119; Δ∈ = 6.4; η = 26.4 mPa·s.

Example 22

| | | |
|---|---|---|
| 3-BB(F,F)XB(F,F)-FVCF3 | (1-2-116) | 5% |
| 1V2-BEB(F,F)-C | (5-15) | 6% |
| 3-HB-C | (5-1) | 18% |
| 2-BTB-1 | (12-10) | 10% |
| 5-HH-VFF | (12-1) | 30% |
| 3-HHB-1 | (13-1) | 4% |
| VFF-HHB-1 | (13-1) | 8% |
| VFF2-HHB-1 | (13-1) | 11% |
| 3-H2BTB-3 | (13-17) | 4% |
| 3-H2BTB-4 | (13-17) | 4% |

NI = 74.1° C.; Δn = 0.125; Δ∈ = 9.1; η = 13.6 mPa·s.

Example 23

| | | |
|---|---|---|
| 3-HHXB(F)H-FVCF3 | (1-3-115) | 3% |
| 3-HH-4 | (12-1) | 4% |
| 3-HBB(F,F)-F | (3-24) | 33% |

-continued

| | | |
|---|---|---|
| 5-HBB(F,F)-F | (3-24) | 32% |
| 3-H2HB(F,F)-F | (3-15) | 10% |
| 4-H2HB(F,F)-F | (3-15) | 10% |
| 5-H2HB(F,F)-F | (3-15) | 8% |

NI = 64.1° C.; Δn = 0.104; Δ∈ = 8.8; η = 30.2 mPa · s.

Example 24

| | | |
|---|---|---|
| 3-GH-FVCF3 | (1-1-13) | 5% |
| 7-HB(F,F)-F | (2-4) | 3% |
| 3-HB-O2 | (12-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 9% |
| 3-HBB(F)-F | (3-23) | 9% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 5-HBB(F,F)-F | (3-24) | 10% |

NI = 81.5° C.; Δn = 0.110; Δ∈ = 6.4; η = 25.2 mPa · s.

Example 25

| | | |
|---|---|---|
| 3-BB(F)H-FVCF3 | (1-2-18) | 5% |
| 1V2-BEB(F,F)-C | (5-15) | 6% |
| 3-HB-C | (5-1) | 18% |
| 2-BTB-1 | (12-10) | 10% |
| 5-HH-VFF | (12-1) | 30% |
| 3-HHB-1 | (13-1) | 4% |
| VFF-HHB-1 | (13-1) | 8% |
| VFF2-HHB-1 | (13-1) | 11% |
| 3-H2BTB-3 | (13-17) | 4% |
| 3-H2BTB-4 | (13-17) | 4% |

NI = 76.7° C.; Δn = 0.126; Δ∈ = 7.3; η = 14.6 mPa · s.

Example 26

| | | |
|---|---|---|
| 3-HVH-FVCF3 | (1-1-42) | 3% |
| 3-HH-4 | (12-1) | 4% |
| 3-HBB(F,F)-F | (3-24) | 30% |
| 5-HBB(F,F)-F | (3-24) | 32% |
| 3-H2HB(F,F)-F | (3-15) | 10% |
| 4-H2HB(F,F)-F | (3-15) | 10% |
| 5-H2HB(F,F)-F | (3-15) | 8% |
| 3-HHBB(F,F)-F | (4-6) | 3% |

NI = 63.9° C.; Δn = 0.103; Δ∈ = 8.7; η = 29.3 mPa · s.

Example 27

| | | |
|---|---|---|
| V-HH-FVCF3 | (1-1-4) | 5% |
| 7-HB(F,F)-F | (2-4) | 3% |
| 3-HB-O2 | (12-5) | 7% |
| 2-HHB(F)-F | (3-2) | 10% |
| 3-HHB(F)-F | (3-2) | 10% |
| 5-HHB(F)-F | (3-2) | 10% |
| 2-HBB(F)-F | (3-23) | 9% |
| 3-HBB(F)-F | (3-23) | 9% |
| 5-HBB(F)-F | (3-23) | 16% |

-continued

| | | |
|---|---|---|
| 2-HBB-F | (3-22) | 4% |
| 3-HBB-F | (3-22) | 4% |
| 5-HBB-F | (3-22) | 3% |
| 5-HBB(F,F)-F | (3-24) | 10% |

NI = 82.9° C.; Δn = 0.112; Δ∈ = 5.8; η = 23.7 mPa · s.

Example 28

| | | |
|---|---|---|
| 1V-HH-FVCF3 | (1-1-5) | 5% |
| 1V2-BEB(F,F)-C | (5-15) | 6% |
| 3-HB-C | (5-1) | 18% |
| 2-BTB-1 | (12-10) | 10% |
| 5-HH-VFF | (12-1) | 30% |
| 3-HHB-1 | (13-1) | 4% |
| VFF-HHB-1 | (13-1) | 8% |
| VFF2-HHB-1 | (13-1) | 11% |
| 3-H2BTB-3 | (13-17) | 4% |
| 3-H2BTB-4 | (13-17) | 4% |

NI = 74.6° C.; Δn = 0.121; Δ∈ = 7.1; η = 11.9 mPa · s.

The liquid crystal composition of any one of the above Examples was a liquid crystal composition having a low minimum temperature, a low viscosity, a suitable optical anisotropy and a large dielectric anisotropy.

INDUSTRIAL APPLICABILITY

The liquid crystal compound of this invention has high stability to heat and light, etc., a high clearing point, a low minimum temperature of liquid crystal phase, a low viscosity, a suitable optical anisotropy, a large dielectric anisotropy, a suitable elastic constant, and good compatibility with other liquid crystal compounds. The liquid crystal composition of this invention contains the compound, and has a high maximum temperature of liquid crystal phase, a low minimum temperature of liquid crystal phase, a low viscosity, a suitable optical anisotropy, a large dielectric anisotropy, and a suitable elastic constant. The composition has a balance between these characteristics. The LCD element of this invention contains the composition and has a broad temperature range for use, a short response time, a large voltage holding ratio, a large contrast ratio, and a long service life, and thus can be widely used for personal computers and televisions, etc.

The invention claimed is:

1. A compound represented by formula (1):

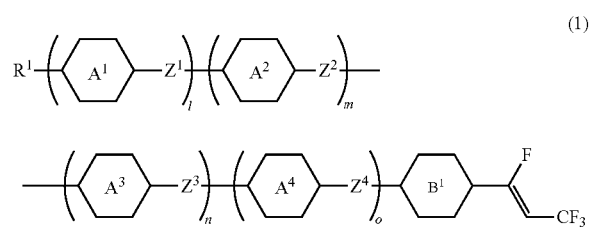

wherein in formula (1),
$R^1$ is $C_{1-15}$ alkyl, and in the alkyl, at least one —$CH_2$— is optionally replaced by —O— or —S—, at least one —(CH$_2$)$_2$— is optionally replaced by —CH═CH—, and at least one hydrogen is optionally substituted with halogen;

ring A$^1$, ring A$^2$, ring A$^3$, ring A$^4$ and ring B$^1$ are independently 1,4-cyclohexylene, 1,4-phenylene, 1,4-phenylene in which at least one hydrogen is substituted with halogen, 1,3-dioxane-2,5-diyl, tetrahydropyran-2,5-diyl, pyrimidine-2,5-diyl, or pyridine-2,5-diyl;

Z$^1$, Z$^2$, Z$^3$ and Z$^4$ are independently a single bond, —(CH$_2$)$_2$—, —CH═CH—, —C≡C—, —COO—, —OCO—, —CF$_2$O—, —OCF$_2$—, —CH$_2$O—, —OCH$_2$—, or —CF═CF—; and l, m, n and o are independently 0 or 1, and l+m+n+o≥1.

2. The compound of claim 1, wherein in formula (1), ring B$^1$ is 1,4-cyclohexylene, 1,4-phenylene, or 1,4-phenylene in which at least one hydrogen is substituted with halogen.

3. The compound of claim 1, wherein in formula (1), R$^1$ is C$_{1-15}$ alkyl, C$_{2-15}$ alkenyl, C$_{1-14}$ alkoxy, or C$_{2-14}$ alkenyloxy, and Z$^1$, Z$^2$, Z$^3$ and Z$^4$ are independently a single bond, —(CH$_2$)$_2$—, —CH═CH—, —COO—, —OCO—, —CF$_2$O—, —OCF$_2$—, or —CF═CF—.

4. The compound of claim 1, wherein in formula (1), R$^1$ is C$_{1-15}$ alkyl or C$_{2-15}$ alkenyl, and Z$^1$, Z$^2$, Z$^3$ and Z$^4$ are independently a single bond, —(CH$_2$)$_2$—, —CH═CH—, —COO—, or —CF$_2$O—.

5. The compound of claim 1, wherein in formula (1), R$^1$ is C$_{1-10}$ alkyl or C$_{2-10}$ alkenyl, ring A$^1$, ring A$^2$, ring A$^3$ and ring A$^4$ are independently 1,4-cyclohexylene, 1,4-phenylene, 1,4-phenylene in which at least one hydrogen is substituted with halogen, 1,3-dioxane-2,5-diyl, or tetrahydropyran-2,5-diyl, ring B$^1$ is 1,4-cyclohexylene, 1,4-phenylene, or 1,4-phenylene in which at least one hydrogen is substituted with halogen, and Z$^1$, Z$^2$, Z$^3$ and Z$^4$ are independently a single bond, —(CH$_2$)$_2$—, or —CH═CH—.

6. The compound of claim 1, which is represented by any one of formulae (1-1) to (1-3):

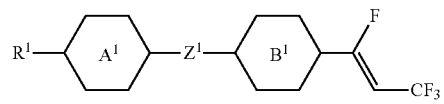
(1-1)

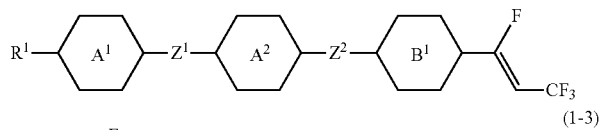
(1-2)

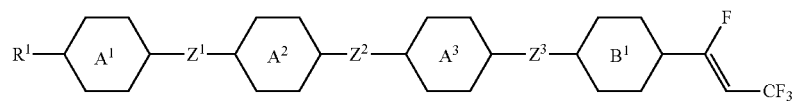
(1-3)

wherein in formulae (1-1) to (1-3),

R$^1$ is C$_{1-10}$ alkyl or C$_{2-10}$ alkenyl;

ring A$^1$, ring A$^2$ and ring A$^3$ are independently 1,4-cyclohexylene, 1,4-phenylene, 1,4-phenylene in which at least one hydrogen is substituted with halogen, 1,3-dioxane-2,5-diyl, or tetrahydropyran-2,5-diyl;

ring B$^1$ is 1,4-cyclohexylene, 1,4-phenylene, or 1,4-phenylene in which at least one hydrogen is substituted with halogen; and Z$^1$, Z$^2$ and Z$^3$ are independently a single bond, —(CH$_2$)$_2$—, or —CH═CH—.

7. The compound of claim 1, which is represented by any one of formulae (1-4) to (1-19):

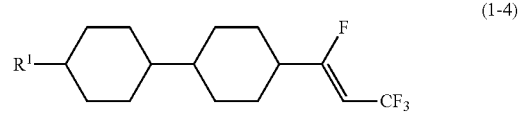
(1-4)

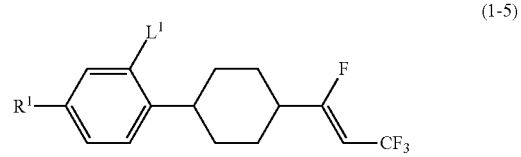
(1-5)

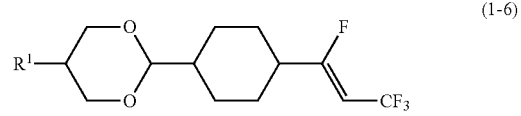
(1-6)

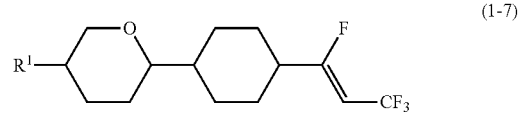
(1-7)

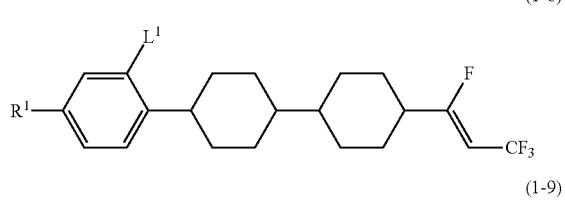
(1-8)

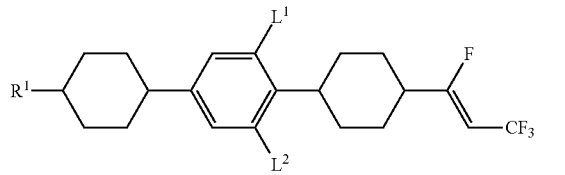
(1-9)

-continued

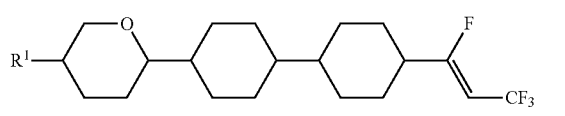
(1-12)

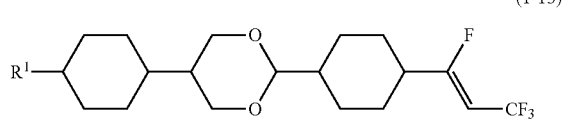
(1-13)

(1-14)
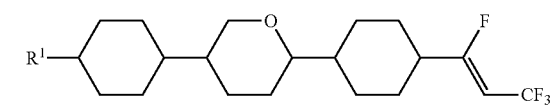
(1-15)
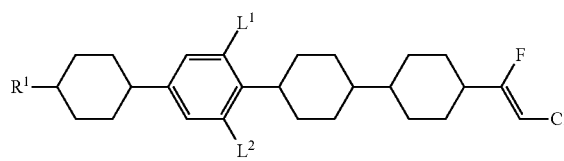
(1-16)
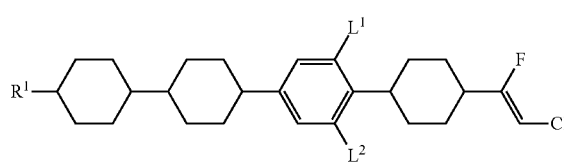
(1-17)
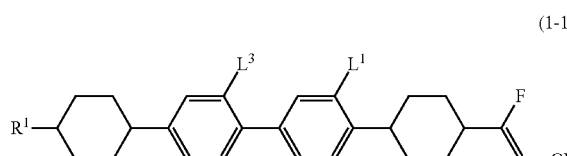
(1-10)
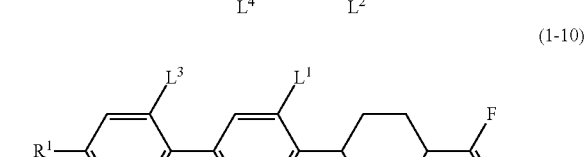
(1-11)
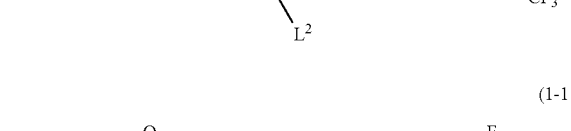
(1-18)
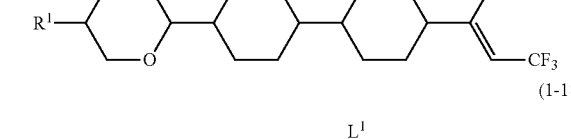
(1-19)
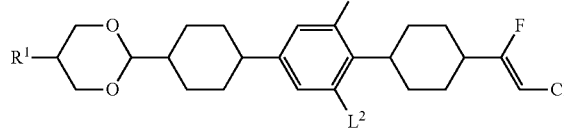
wherein in formulae (1-4) to (1-19), $R^1$ is $C_{1-10}$ alkyl or $C_{2-10}$ alkenyl, and $L^1$, $L^2$, $L^3$ and $L^4$ are hydrogen or fluorine.
8. The compound of claim 1, which is represented by any one of formulae (1-20) to (1-31):
(1-20)
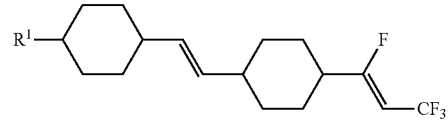
(1-21)
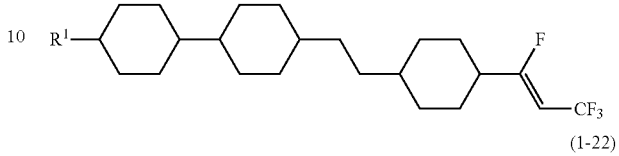
(1-22)
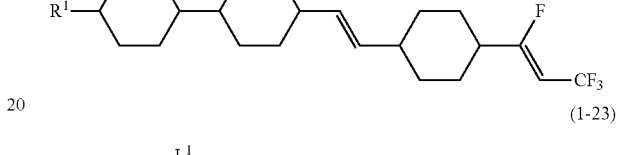
(1-23)
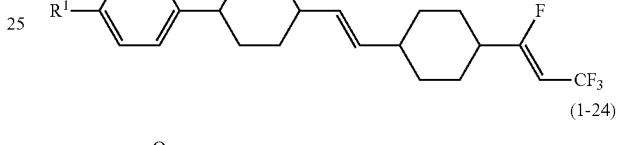
(1-24)
(1-25)
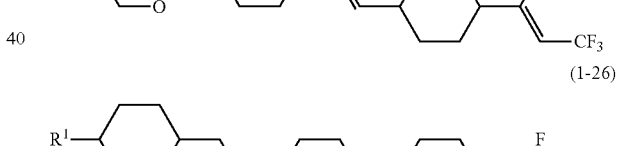
(1-26)
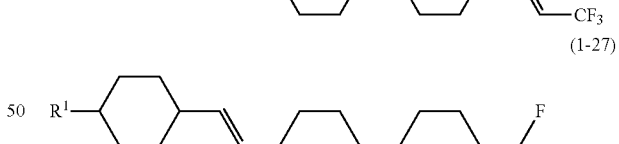
(1-27)
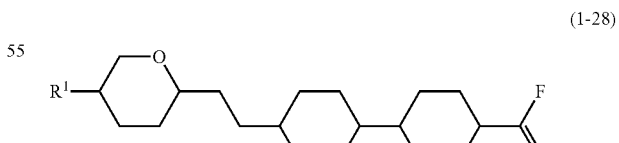
(1-28)
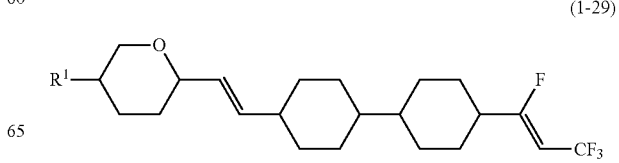
(1-29)

wherein in formulae (1-20) to (1-31), $R^1$ is $C_{1-10}$ alkyl or $C_{2-10}$ alkenyl, and $L^1$ is hydrogen or fluorine.

9. The compound of claim 1, which is represented by any one of formulae (1-32) to (1-39):

wherein in formulae (1-32) to (1-39), $R^1$ is $C_{1-10}$ alkyl or $C_{2-10}$ alkenyl, and $L^1$, $L^2$, $L^3$, $L^4$, $L^5$, $L^6$ and $L^7$ are independently hydrogen or fluorine.

10. The compound of claim 1, which is represented by any one of formulae (1-40) to (1-47):

-continued (1-45)
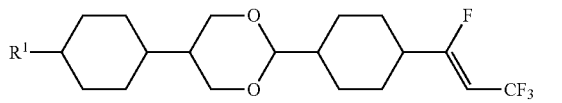

(1-46)

(1-47)
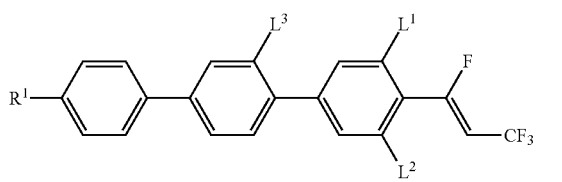

wherein in formulae (1-40) to (1-47), $R^1$ is $C_{1-10}$ alkyl, and $L^1$, $L^2$ and $L^3$ are independently hydrogen or fluorine.

11. A liquid crystal composition, containing at least one compound of claim 1.

12. The liquid crystal composition of claim 11, further containing at least one compound selected from the group consisting of compounds represented by formulae (2) to (4):

(2)
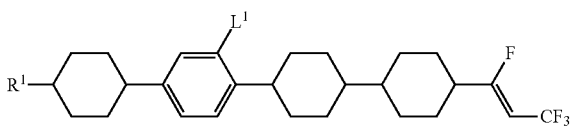

(3)
(4)
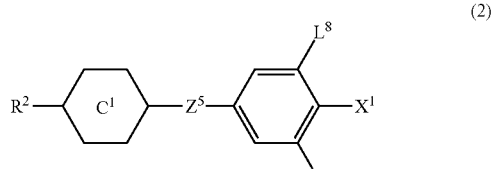

wherein in formulae (2) to (4), each $R^2$ is independently $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;

$X^1$ is fluorine, chlorine, —$OCF_3$, —$OCHF_2$, —$CF_3$, —$CHF_2$, —$CH_2F$, —CF=$F_2$, —$OCF_2CHF_2$, or —$OCF_2CHFCF_3$;

ring $C^1$, ring $C^2$ and ring $C^3$ are independently 1,4-cyclohexylene, 1,4-phenylene, 2-fluoro-1,4-phenylene, 2,6-difluoro-1,4-phenylene, 1,3-dioxane-2,5-diyl, tetrahydropyran-2,5-diyl, or pyrimidine-2,5-diyl;

$Z^5$ and $Z^6$ are independently a single bond, —$(CH_2)_2$—, —CH=CH—, —C≡C—, —COO—, —$CF_2O$—, —$OCF_2$—, —$CH_2O$—, or —$(CH_2)_4$—; and $L^8$ and $L^9$ are independently hydrogen or fluorine.

13. The liquid crystal composition of claim 11, further containing at least one compound selected from the group consisting of compounds represented by formula (5):

(5)
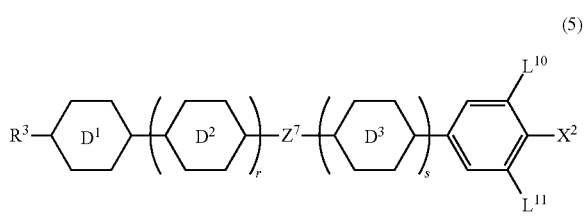

wherein in formula (5), $R^3$ is $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;

$X^2$ is —C≡N or —C≡C—C≡N;

ring $D^1$, ring $D^2$ and ring $D^3$ are independently 1,4-cyclohexylene, 1,4-phenylene in which at least one hydrogen is optionally substituted with fluorine, 1,3-dioxane-2,5-diyl, tetrahydropyran-2,5-diyl, or pyrimidine-2,5-diyl;

$Z^7$ is a single bond, —$(CH_2)_2$—, —C≡C—, —COO—, —$CF_2O$—, —$OCF_2$—, or —$CH_2O$—;

$L^{10}$ and $L^{11}$ are independently hydrogen or fluorine; and r is 0, 1 or 2, s is 0 or 1, and r+s is 0, 1, 2 or 3.

14. The liquid crystal composition of claim 11, further containing at least one compound selected from the group consisting of compounds represented by formulae (6) to (11):

(6)
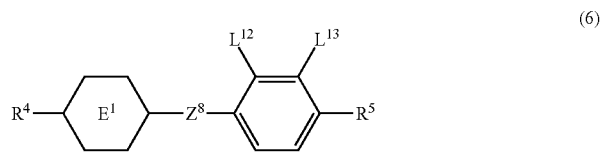

(7)
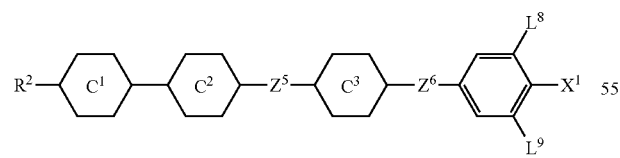

(8) 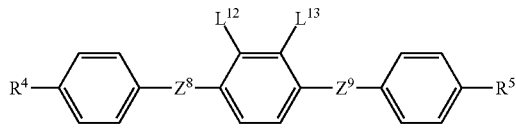

(9) 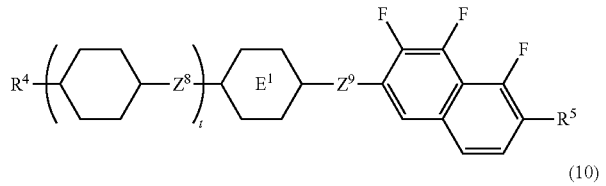

(10) 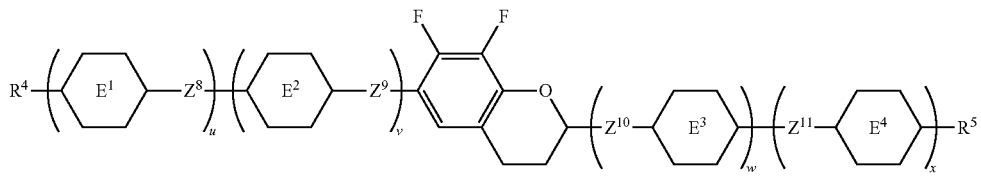

(11) 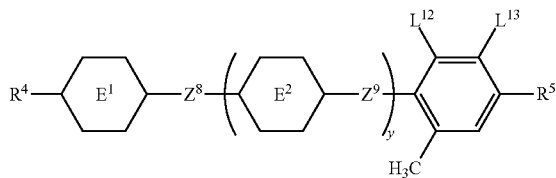

wherein in formulae (6) to (11),
$R^4$ and $R^5$ are independently $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;
ring $E^1$, ring $E^2$, ring $E^3$ and ring $E^4$ are independently 1,4-cyclohexylene, 1,4-cyclohexenylene, 1,4-phenylene in which at least one hydrogen is optionally substituted with fluorine, tetrahydropyran-2,5-diyl, or decahydronaphthalene-2,6-diyl;
$Z^8$, $Z^9$, $Z^{10}$ and $Z^{11}$ are independently a single bond, —$(CH_2)_2$—, —COO—, —$OCF_2$— or —$OCF_2(CH_2)_2$—;
$L^{12}$ and $L^{13}$ are independently fluorine or chlorine; and
t, u, v, w, x and y are independently 0 or 1, and u+v+w+x is 1 or 2.

15. The liquid crystal composition of claim 11, further containing at least one compound selected from the group consisting of compounds represented by formulae (12) to (14):

(12) 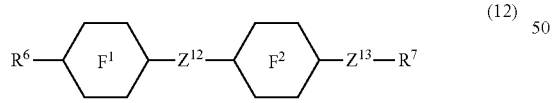

(13) 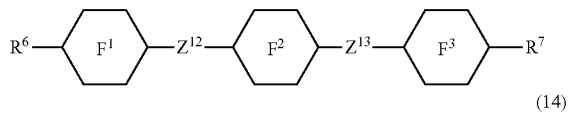

(14) 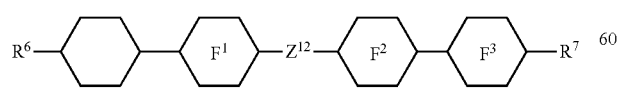

wherein in formulae (12) to (14),
$R^6$ and $R^7$ are independently $C_{1-10}$ alkyl or $C_{2-10}$ alkenyl, and in the alkyl and the alkenyl, at least one —$CH_2$— is optionally replaced by —O—;

ring $F^1$, ring $F^2$ and ring $F^3$ are independently 1,4-cyclohexylene, 1,4-phenylene, 2-fluoro-1,4-phenylene, 2,5-difluoro-1,4-phenylene, or pyrimidine-2,5-diyl; and
$Z^{12}$ and $Z^{13}$ are independently a single bond, —$(CH_2)_2$—, —CH=CH—, —C≡C—, or —COO—.

16. The liquid crystal composition of claim 12, further containing at least one compound selected from the group consisting of compounds represented by formula (5):

(5) 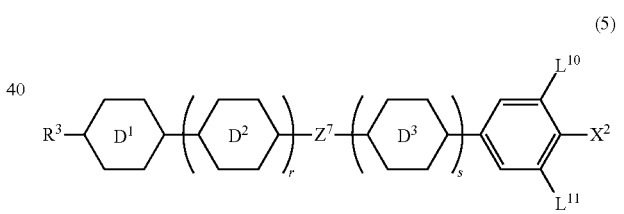

wherein in formula (5),
$R^3$ is $C_{1-10}$ alkyl or $C_{2-10}$ alkenyl, and in the alkyl and the alkenyl, at least one hydrogen is optionally substituted with fluorine, and at least one —$CH_2$— is optionally replaced by —O—;
$X^2$ is —C≡N or —C≡C—C≡N;
ring $D^1$, ring $D^2$ and ring $D^3$ are independently 1,4-cyclohexylene, 1,4-phenylene in which at least one hydrogen is optionally substituted with fluorine, 1,3-dioxane-2,5-diyl, tetrahydropyran-2,5-diyl, or pyrimidine-2,5-diyl;
$Z^7$ is a single bond, —$(CH_2)_2$—, —C≡C—, —COO—, —$CF_2O$—, —$OCF_2$—, or —$CH_2O$—;
$L^{10}$ and $L^{11}$ are independently hydrogen or fluorine; and
r is 0, 1 or 2, s is 0 or 1, and r+s is 0, 1, 2 or 3.

17. The liquid crystal composition of claim 12, further containing at least one compound selected from the group consisting of compounds represented by formulae (12) to (14):

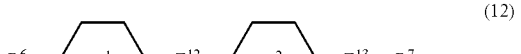
(12)

(13)

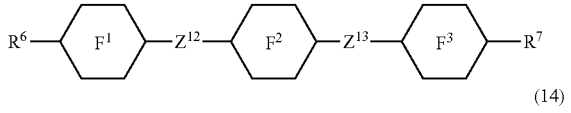
(14)

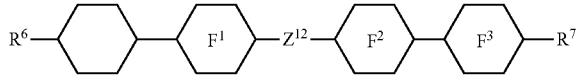

wherein in formulae (12) to (14), $R^6$ and $R^7$ are independently $C_{1-10}$ alkyl or $C_{2-10}$ alkenyl, and in the alkyl and the alkenyl, at least one —$CH_2$— is optionally replaced by —O—;

ring $F^1$, ring $F^2$ and ring $F^3$ are independently 1,4-cyclohexylene, 1,4-phenylene, 2-fluoro-1,4-phenylene, 2,5-difluoro-1,4-phenylene, or pyrimidine-2,5-diyl; and $Z^{12}$ and $Z^{13}$ are independently a single bond, —$(CH_2)_2$—, —CH=CH—, —C≡C—, or —COO—.

18. The liquid crystal composition of claim 13, further containing at least one compound selected from the group consisting of compounds represented by formulae (12) to (14):

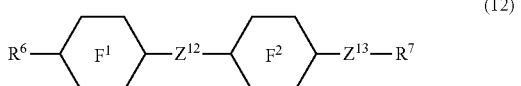
(12)

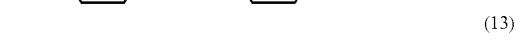
(13)

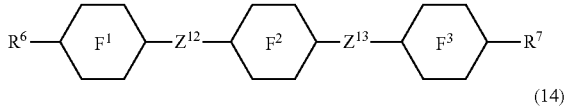
(14)

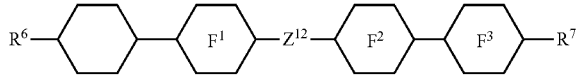

wherein in formulae (12) to (14), $R^6$ and $R^7$ are independently $C_{1-10}$ alkyl or $C_{2-10}$ alkenyl, and in the alkyl and the alkenyl, at least one —$CH_2$— is optionally replaced by —O—;

ring $F^1$, ring $F^2$ and ring $F^3$ are independently 1,4-cyclohexylene, 1,4-phenylene, 2-fluoro-1,4-phenylene, 2,5-difluoro-1,4-phenylene, or pyrimidine-2,5-diyl; and $Z^{12}$ and $Z^{13}$ are independently a single bond, —$(CH_2)_2$—, —CH=CH—, —C≡C—, or —COO—.

19. The liquid crystal composition of claim 14, further containing at least one compound selected from the group consisting of compounds represented by formulae (12) to (14):

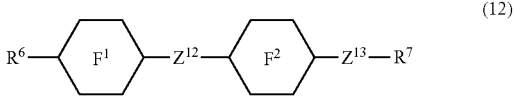
(12)

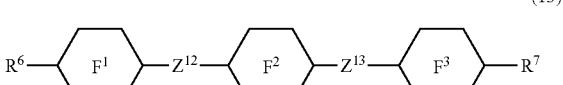
(13)

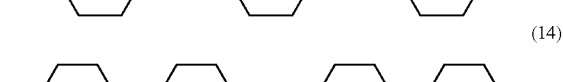
(14)

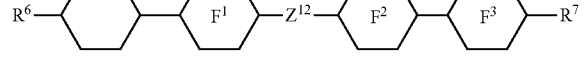

wherein in formulae (12) to (14), $R^6$ and $R^7$ are independently $C_{1-10}$ alkyl or $C_{2-10}$ alkenyl, and in the alkyl and the alkenyl, at least one —$CH_2$— is optionally replaced by —O—;

ring $F^1$, ring $F^2$ and ring $F^3$ are independently 1,4-cyclohexylene, 1,4-phenylene, 2-fluoro-1,4-phenylene, 2,5-difluoro-1,4-phenylene, or pyrimidine-2,5-diyl; and $Z^{12}$ and $Z^{13}$ are independently a single bond, —$(CH_2)_2$—, —CH=CH—, —C≡C—, or —COO—.

20. The liquid crystal composition of claim 11, further containing at least one optically active compound and/or at least one polymerizable compound.

21. The liquid crystal composition of claim 11, further containing at least one antioxidant and/or at least one UV absorbent.

22. A liquid crystal display element, including the liquid crystal composition of claim 11.

* * * * *